US012480960B2

(12) United States Patent
Noth

(10) Patent No.: US 12,480,960 B2
(45) Date of Patent: Nov. 25, 2025

(54) COMPOSITIONS AND METHODS FOR PREDICTING LUNG FUNCTION DECLINE IN IDIOPATHIC PULMONARY FIBROSIS

(71) Applicant: University of Virginia Patent Foundation, Charlottesville, VA (US)

(72) Inventor: Imre Noth, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 907 days.

(21) Appl. No.: 17/422,033

(22) PCT Filed: Jan. 13, 2020

(86) PCT No.: PCT/US2020/013367
§ 371 (c)(1),
(2) Date: Jul. 9, 2021

(87) PCT Pub. No.: WO2020/146887
PCT Pub. Date: Jul. 16, 2020

(65) Prior Publication Data

US 2022/0291231 A1 Sep. 15, 2022

Related U.S. Application Data

(60) Provisional application No. 62/849,630, filed on May 17, 2019, provisional application No. 62/791,083, filed on Jan. 11, 2019.

(51) Int. Cl.
*G01N 33/68* (2006.01)
*C12Q 1/68* (2018.01)

(52) U.S. Cl.
CPC ........... *G01N 33/6893* (2013.01); *C12Q 1/68* (2013.01); *G01N 33/68* (2013.01); *G01N 2800/12* (2013.01); *G01N 2800/52* (2013.01)

(58) Field of Classification Search
CPC ...... G01N 33/68; G01N 33/6893; C12Q 1/68; C12Q 1/6874
See application file for complete search history.

(56) References Cited

U.S. PATENT DOCUMENTS

| | | | |
|---|---|---|---|
| 3,974,281 | A | 8/1976 | Gadekar |
| 5,800,992 | A | 9/1998 | Fodor et al. |
| 6,004,755 | A | 12/1999 | Wang |
| 6,013,449 | A | 1/2000 | Hacia et al. |
| 6,020,135 | A | 2/2000 | Levine et al. |
| 6,033,860 | A | 3/2000 | Lockhart et al. |
| 6,040,138 | A | 3/2000 | Lockhart et al. |
| 6,177,248 | B1 | 1/2001 | Oliner et al. |
| 6,251,601 | B1 | 6/2001 | Bao et al. |
| 6,309,822 | B1 | 10/2001 | Fodor et al. |
| 6,762,180 | B1 | 7/2004 | Roth et al. |
| 7,824,856 | B2 | 11/2010 | Monforte |
| 8,592,462 | B2 | 11/2013 | Bradford et al. |
| 9,884,802 | B2 | 2/2018 | Gagnon et al. |
| 9,920,367 | B2 | 3/2018 | Bhargava et al. |
| 10,028,966 | B2 | 7/2018 | Surber |
| 10,105,365 | B2 | 10/2018 | Miller et al. |
| 10,227,584 | B2 | 3/2019 | Emerick et al. |
| 2010/0120097 | A1 | 5/2010 | Matz et al. |
| 2011/0189679 | A1 | 8/2011 | Kurn et al. |
| 2013/0116166 | A1* | 5/2013 | Desai .................. C12Q 1/6883 435/7.1 |
| 2014/0113333 | A1 | 4/2014 | Getts et al. |
| 2015/0133333 | A1 | 5/2015 | Garcia et al. |
| 2015/0307874 | A1 | 10/2015 | Jaitin et al. |
| 2016/0024583 | A1 | 1/2016 | Whitney et al. |
| 2018/0064695 | A1 | 3/2018 | Bradford et al. |
| 2018/0101642 | A1 | 4/2018 | Kaminski et al. |
| 2018/0169084 | A1 | 6/2018 | Bradford |
| 2018/0320234 | A1 | 11/2018 | Noth et al. |
| 2019/0030012 | A1 | 1/2019 | Surber |
| 2019/0282565 | A1 | 9/2019 | Liang |

FOREIGN PATENT DOCUMENTS

| | | | |
|---|---|---|---|
| EP | 2860525 | A1 | 4/2015 |
| EP | 3908668 | | 11/2021 |
| WO | WO 2013/148232 | A1 | 10/2013 |
| WO | WO 2016/042114 | A1 | 3/2016 |
| WO | WO 2020/146887 | A1 | 7/2020 |

OTHER PUBLICATIONS

Adams et al., Am. J. Respir. Crit. Care Med., 2016, vol. 194(3): 374-376.*
International Search Report and Written Opinion corresponding to International Patent Application No. PCT/US2020/013367 dated Apr. 1, 2020.
Communication of Publication corresponding to European Patent Application Serial No. 20738547.7 dated Oct. 20, 2021.
Search Report corresponding to EP Application No. 20738547.7 dated Oct. 7, 2022.
Bauer et al. (2015) "A Novel Genomic Signature with Translational Significance for Human Idiopathic Pulmonary Fibrosis," American Journal of Respiratory Cell and Molecular Biology, vol. 52, No. 2, pp. 217-231.

(Continued)

*Primary Examiner* — Xiaozhen Xie
(74) *Attorney, Agent, or Firm* — Jenkins, Taylor & Hunt, P.A.

(57) ABSTRACT

Provided are methods for generating prognostic signatures for subject diagnosed with Idiopathic Pulmonary Fibrosis (IPF) with respect to decline in lung Forced Vital Capacity (FVC). The methods can include determining first expression levels for one or more genes as set forth herein in a first biological sample obtained from a subject diagnosed with IPF, determining a second expression level for the same one or more genes in a second biological sample obtained from the subject, and comparing the first and second expression levels for the one or more genes to provide a prognostic signature. The first and second biological samples can include peripheral blood mononuclear cells (PBMCs) and/or nucleic acids extracted from PBMCs. Also provided are methods for classifying subjects with IPF as being at risk for FVC decline, for identifying and treating at risk subjects, and for monitoring the progress of treatments.

9 Claims, 15 Drawing Sheets

Specification includes a Sequence Listing.

(56) References Cited

OTHER PUBLICATIONS

Herazo-Maya et al. (2013) "Peripheral Blood Mononuclear Cell Gene Expression Profiles Predict Poor Outcome in Idiopathic Pulmonary Fibrosis," Science Translational Medicine, vol. 5, No. 205, pp. 1-23.
Herazo-Maya et al. (2017) "Validation of a 52-Gene Risk Profile for Outcome Prediction in Patients with Idiopathic Pulmonary Fibrosis: an International, Multicentre, Cohort Study," The Lancet, Respiratory Medicine, vol. 5, No. 11, pp. 857-868.
Office Action corresponding to European Patent Application No. 20738547.7-1111 dated Oct. 29, 2024, pp. 4.
Wirsdorfer & Jendrossek (2016) The Role of Lymphocytes in Radiotherapy-Induced Adverse Late Effects in the Lung. Front Immunol 7:591.
Trapnell et al. (2009) TopHat: discovering splice junctions with RNA-Seq. Bioinformatics 25:1105-1111.
Tibshirani et al. (2012) Strong rules for discarding predictors in lasso-type problems. J R Stat Soc Series B Stat Methodol 74:245-266.
Tajiri et al. (2015) Serum level of periostin can predict long-term outcome of idiopathic pulmonary fibrosis. Respir Investig 53:73-81.
Suykens & Vandewalle (1999) Least Squares Support Vector Machine Classifiers. Neural Processing Letters 9:293-300.
Subramanian et al. (2005)Gene set enrichment analysis: a knowledge-based approach for interpreting genome-wide expression profiles. Proc Natl Acad Sci US A 102:15545-15550.
Smyth (2004) Linear models and empirical Bayes methods for assesing differential expression in microarray experiments. Stat Appl Genet Mol Biol 3 :Article3.
Simon et al. (2011) Regularization Paths for Cox's Proportional Hazards Model via Coordinate Descent. J Stat Softw 3 9: 1-13.
Schmidt et al. (2014) Predicting pulmonary fibrosis disease course from past trends in pulmonary function. Chest 145:579-585.
Rosas et al. (2008) MMP1 and MMP7 as potential peripheral blood biomarkers in idiopathic pulmonary fibrosis. PLoS Med 5:e93.
Robinson et al. (2010) edgeR: a Bioconductor package for differential expression analysis of digital gene expression data. Bioinformatics 26:139-140.
Robinson & Oshlack (2010) A scaling normalization method for differential expression analysis of RNA-seg data. Genome Biol 11 :R25.
Robin et al. (2011) pROC: an open-source package for Rand S+ to analyze and compare ROC curves. BMC Bioinformatics 12:77.
Richeldi et al. (2014) Efficacy and safety ofnintedanib in idiopathic pulmonary fibrosis. N Engl J Med 370:2071-2082.
Richards et al. (2012) Plasma proteins for risk prediction in idiopathic pulmonary fibrosis. Am J Respir Crit Care Med 185:1329-1330.
Raghu et al. (2011) An official ATS/ERS/JRS/ALAT statement: idiopathic pulmonary fibrosis: evidence-based guidelines for diagnosis and management. Am J Respir Crit Care Med 183:788-824.
Prasse et al. (2009) Serum CC-chemokine ligand 18 concentration predicts outcome in idiopathic pulmonary fibrosis. Am J Respir Crit Care Med 179: 717-723.
Peljto et al. (2013) Association between the MUC5B promoter polymorphism and survival in patients with idiopathic pulmonary fibrosis. JAMA 309:2232-2239.
Pardo et al. (2016) Role of matrix metalloproteinases in the pathogenesis of idiopathic pulmonary fibrosis. Respir Res 17:23.
Ohta et al. (2017) The usefulness of monomeric periostin as a biomarker for idiopathic pulmonary fibrosis. PLoS One 12:e0174547.
O'Dwyer et al. (2017) The peripheral blood proteome signature of idiopathic pulmonary fibrosis is distinct from normal and is associated with novel immunological processes. Sci Rep 7:46560.
Noth et al. (2012) Idiopathic Pulmonary Fibrosis Clinical Research N. A placebo-controlled randomized trial of warfarin in idiopathic pulmonary fibrosis. Am J Respir Crit Care Med 186:88-95.
Neighbors et al. (2018) Prognostic and predictive biomarkers for patients with idiopathic pulmonary fibrosis treated with pirfenidone: post-hoc assessment of the Capacity and Ascend trials. Lancet Respir Med 6:615-626.
Naik et al. (2012) Periostin promotes fibrosis and predicts progression in patients with idiopathic pulmonary fibrosis. Am J Physiol Lung Cell Mol Physiol 303:L1046-1056.
Mortazavi et al. (2008) Mapping and quantifying mammalian transcriptomes by RNA-Seq. Nat Methods 5:621-628.
Miller et al. (2005b) Standardisation of spirometry. Eur Respir J 26:319-338.
Miller et al. (2005a) General considerations for lung function testing. Eur Respir J 26:153-161.
Masel & Siegal (2009) Robustness: mechanisms and consequences. Trends Genet 25:395-403.
Maher et al. (2017) An epithelial biomarker signature for idiopathic pulmonary fibrosis: an analysis from the multicentre Profile cohort study. LancetRespir Med 5:946-955.
Macintyre et al. (2005) Standardisation of the single-breath determination of carbon monoxide uptake in the lung. Eur Respir J 26:720-735.
Love et al. (2014) Moderated estimation of fold change and dispersion for RNA-Seq data with DESeq2. Genome Biol 15:550.
Li (2008) Automating dChip: toward reproducible sharing of microarray data analysis. BMC Bioinformatics 9:231.
Ley et al. (2016) Predictors of Mortality Poorly Predict Common Measures of Disease Progression in Idiopathic Pulmonary Fibrosis. Am J Respir Crit Care Med 194:711-718.
Ley et al. (20 14) Molecular biomarkers in idiopathic pulmonary fibrosis. Am J Physiol Lung Cell Mol Physiol307:L681-691.
Law et al. (2014) voom: Precision weights unlock linear model analysis tools for RNA-seq read counts. Genome Biol 15:R29.
King et al. (2014) A phase 3 trial of pirfenidone in patients with idiopathic pulmonary fibrosis. N Engl J Med 370:2083-2092.
Karlin & Altschul (1993) Applications and statistics for multiple high-scoring segments in molecular sequences. Proc Natl Acad Sci US A 90:5873-5877.
Karlin & Altschul (1990) Methods for assessing the statistical significance of molecular sequence features by using general scoring schemes. Proc Natl A cad Sci U S A 87:2264-2268.
Karimi-Shah & Chowdhury (2015) Forced vital capacity in idiopathic pulmonary fibrosis-FDA review of pirfenidone and nintedanib. N Engl J Med 372:1189-1191.
Kang et al. (2007) Transforming growth factor (TGF)-beta1 stimulates pulmonary fibrosis and inflammation via a Bax-dependent, bid-activated pathway that involves matrix metalloproteinase-12. J Biol Chern 282:7723-7732.
Kaner et al. (2019) Design of IPF Clinical Trials in the Era of Approved Therapies. Am J Respir Crit Care Med 200:133-139.
Kaimal et al. (2010) ToppCluster: a multiple gene list feature analyzer for comparative enrichment clustering and network-based dissection of biological systems. Nucleic Acids Res 38: W96-102.
Jegal et al. (2005) Physiology is a stronger predictor of survival than pathology in fibrotic interstitial pneumonia. Am J Respir Crit Care Med 171:639-644.
Irizarry et al. (2003) Exploration, normalization, and summanes of high density oligonucleotide array probe level data. Biostatistics 4:249-264.
Idiopathic Pulmonary Fibrosis Clinical Research Network et al. (2012) Prednisone, azathioprine, and N-acetylcysteine for pulmonary fibrosis. N Engl J Med 366:1968-1977.
Idiopathic Pulmonary Fibrosis Clinical Research Network et al. (2010) A controlled trial of sildenafil in advanced idiopathic pulmonary fibrosis. N Engl J Med 363:620-628.
Hyslop & White (2009) Estimating precision using duplicate measurements. J Air Waste Manag Assoc 59:1032-1039.
Huang et al. (2017) Microbes Are Associated with Host Innate Immune Response in Idiopathic Pulmonary Fibrosis. Am J Respir Crit Care Med 196:208-219.
Hoffmann-Vold et al. (2016) High Level of Chemokine CCL18 Is Associated With Pulmonary Function Deterioration, Lung Fibrosis Progression, and Reduced Survival in Systemic Sclerosis. Chest 150:299-306.

(56) References Cited

OTHER PUBLICATIONS

Hamai et al. (2016) Comparative Study of Circulating MMP-7, CCL18, KL-6, SP-A, and SP-D as Disease Markers of Idiopathic Pulmonary Fibrosis. Dis Markers 2016; 2016: 4759040.
Gu et al. (2016) Complex heatmaps reveal patterns and correlations in multidimensional genomic data. Bioinformatics 32:2847-2849.
Greene et al. (2002) Serum surfactant proteins-A and -D as biomarkers in idiopathic pulmonary fibrosis. Eur Respir J 19:439-446.
Gautier et al. (2004) affy—analysis of Affymetrix GeneChip data at the probe level. Bioinformatics 20:307-315.
Friedman et al. (2010) Regularization Paths for Generalized Linear Models via Coordinate Descent. J Stat Softw 33:1-22.
Flaherty et al. (2007) Idiopathic interstitial pneumonia: do community and academic physicians agree on diagnosis? Am J Respir Crit Care Med 175:1054-1060.
Flaherty et al. (2004) Idiopathic interstitial pneumoma: what is the effect of a multidisciplinary approach to diagnosis? Am J Respir Crit Care Med 170:904-910.
DuBois et al. (2011) Forced vital capacity in patients with idiopathic pulmonary fibrosis: test properties and minimal clinically important difference. Am J Respir Crit Care Med 184:1382-1389.
Dobin et al. (2013) STAR: ultrafast universal RNA-seq aligner. Bioinformatics 29:15-21.
Chilosi et al. (2002) Abnormal re-epithelialization and lung remodeling in idiopathic pulmonary fibrosis: the role of deltaN-p63. Lab Invest 82:1335-1345.
Benjamini & Hochberg (1995) Controlling the false discovery rate: a practical and powerful approach to multiple testing. J R Stat Soc 57:289-300.
Ballman et al. (2004) Faster cyclic loess: normalizing RNA arrays via linear models. Bioinformatics 20:2778-2786.
Armstrong et al. (2017) Serum Matrix Metalloproteinase-7, Respiratory Symptoms, and Mortality in Community-Dwelling Adults. MESA (Multi-Ethnic Study of Atherosclerosis). Am J Respir Crit Care Med 196:1311-1317.
Anders et al. (2014) HTSeq-a Python framework to work with high-throughput sequencing data. Bioinformatics 31:166-169.
American Thoracic Society & European Respiratory Society (2002) American Thoracic Society/European Respiratory Society International Multidisciplinary Consensus Classification of the Idiopathic Interstitial Pneumonias. This joint statement of the American Thoracic Society (ATS), and the European Respiratory Society (ERS) was adopted by the ATS board of directors, Jun. 2001 and by the ERS Executive Committee, Jun. 2001. Am J Respir Crit Care Med 165:277-304.
Altschul et al. (1997) Gapped BLAST and PSI-BLAST: a new generation of protein database search programs. Nucleic Acids Res 25:3389-3402.
Altschul et al. (1990b) Protein database searches for multiple alignments. Proc Natl Acad Sci US A 87:14:5509-5513.
Altschul et al. (1990a) Basic local alignment search tool. J Mol Biol 215:403-410.
Alexa et al. (2006) Improved scoring of functional groups from gene expression data by decorrelating GO graph structure. Bioinformatics 22:1600-1607.
Huang Y, Ma SF, Vij R, Oldham JM, Herazo-Maya J, Broderick SM, Strek ME, White SR, Hogarth DK, Sandbo NK, Lussier YA, Gibson KF, Kaminski N, Garcia JG, Noth I. A functional genomic model for predicting prognosis in idiopathic pulmonary fibrosis. BMC Pulm Med. Nov. 21, 2015;15:147.
Swigris JJ, Kuschner WG, Kelsey JL, Gould MK. Idiopathic pulmonary fibrosis: challenges and opportunities for the clinician and investigator. Chest. 2005;127(1):275-83.
Du Bois RM , Weycker D , Albera C , et al . Ascertainment of individual risk of mortality for patients with idiopathic pulmonary fibrosis . Am J Respir Crit Care.
Whitney AR, Diehn M, Popper SJ, Alizadeh AA, Boldrick JC, Relman DA, Brown PO. Individuality and variation in gene expression patterns in human blood. Proc Natl Acad Sci U S A. Feb. 18, 2003;100(4):1896-901.
Wright, F. A. et al. Heritability and genomics of gene expression in peripheral blood. Nat Genet 46, 430-437 (2014).
Hofmann T, Klenow S, Borowicki A, Gill CI, Pool-Zobel BL, Glei M. Gene expression profiles in human peripheral blood mononuclear cells as biomarkers for nutritional in vitro and in vivo investigations. Genes Nutr. Dec. 2010;5(4):309-19.
Kavcic P, Rojc B, Dolenc-Groselj L, Claustrat B, Fujs K, Poljak M. The impact of sleep deprivation and nighttime light exposure on clock gene expression in humans. Croat Med J. Oct. 15, 2011;52(5):594-603.
Eady JJ, Wortley GM, Wormstone YM, Hughes JC, Astley SB, Foxall RJ, Doleman JF, Elliott RM. Variation in gene expression profiles of peripheral blood mononuclear cells from healthy volunteers. Physiol Genomics. Aug. 11, 2005;22(3):402-11.
Tahira K, Ueno T, Fukuda N, Aoyama T, Tsunemi A, Matsumoto S, Nagura C, Matsumoto T, Soma M, Shimba S, Matsumoto Y. Obesity alters the expression profile of clock genes in peripheral blood mononuclear cells. Arch Med Sci. Dec. 31, 2011;7(6):933-40.
Debey-Pascher S, Eggle D, Schultze JL: RNA stabilization of peripheral blood and profiling by bead chip analysis. Methods Mol Biol 2009, 496:175-210.
Asare AL, Kolchinsky SA, Gao Z, Wang R, Raddassi K, Bourcier K, Seyfert-Margolis V: Differential gene expression profiles are dependent upon method of peripheral blood collection and RNA isolation. BMC Genomics 2008, 9:474.
Han MK, Swigris J, Liu L, Bartholmai B, Murray S, Giardino N, Thompson B, Frederick M, Li D, Schwarz M, Limper A, Flaherty K, Martinez FJ. Gender influences Health-Related Quality of Life in IPF. Respir Med. May 2010;104(5):724-30.
Moore BB, Fry C, Zhou Y, Murray S, Han MK, Martinez FJ, Flaherty KR; The COMET Investigators. Inflammatory leukocyte phenotypes correlate with disease progression in idiopathic pulmonary fibrosis. Front Med 2014;1:56.
De Boever P, Wens B, Forcheh AC, Reynders H, Nelen V, Kleinjans J, Van Larebeke N, Verbeke G, Valkenborg D, Schoeters G. Characterization of the peripheral blood transcriptome in a repeated measures design using a panel of healthy individuals. Genomics. Jan. 2014;103(1):31-9.
E.L. Meaburn, C. Fernandes, I.W. Craig, R. Plomin, L.C. Schalkwyk, Assessing individual differences in genome-wide gene expression in human whole blood:reliability over four hours and stability over 10 months, Twin Res. Hum. Genet. 12(2009) 372-380.
J.P. Radich, M. Mao, S. Stepaniants, M. Biery, J. Castle, T. Ward, G.Schimmack, S. Kobayashi, M. Carleton, J. Lampe, P.S. Linsley, Individual specific variation of gene expression in peripheral blood leukocytes, Genomics 83 (2004) 980-988.
Irizarry RA, Bolstad BM, Collin F, Cope LM, Hobbs B, Speed TP. (2003), Summaries of Affymetrix GeneChip probe level data Nucleic Acids Research 31(4):e15 Feb. 2003.
McCarthy, J. D, Chen, Yunshun, Smyth, K. G (2012). "Differential expression analysis of multifactor RNA-Seq experiments with respect to biological variation."

* cited by examiner

COMPOSITIONS AND METHODS FOR PREDICTING LUNG FUNCTION DECLINE IN IDIOPATHIC PULMONARY FIBROSIS

CROSS REFERENCE TO RELATED APPLICATIONS

This application is a national phase application of PCT International Patent Application PCT/US2020/013367, filed Jan. 13, 2020, which claims the benefit of U.S. Provisional Patent Application Ser. Nos. 62/791,083, filed Jan. 11, 2019; and 62/849,630, filed May 17, 2019; the disclosure of each of which is incorporated herein by reference in its entirety.

GOVERNMENT INTEREST

This invention was made with government support under grant number HL130796 awarded by The National Institutes of Health. The government has certain rights in the invention.

BACKGROUND

Idiopathic pulmonary fibrosis (IPF) is a deadly and progressive scarring lung disease of unknown etiology (Raghu et al., 2011). Prior to death, most patients experience progressive lung function decline, as measured by forced vital capacity (FVC). Longitudinal decline in FVC is a well-validated predictor of mortality and is often used as the primary efficacy endpoint in IPF clinical trials (du Bois et al., 2011; Schmidt et al., 2014; Karimi-Shah & Chowdhury, 2015). However, while most patients experience FVC decline, the rate is variable and periods of relative FVC stability are also often observed. Such heterogeneity hampers the development of effective therapies (Kaner et al., 2019), as many patients do not experience FVC decline during the clinical trial period (King et al., 2014; Richeldi et al., 2014).

Efforts to identify patients who will experience FVC decline have been met with frustration. Clinical prediction models reliably predict increased mortality risk, but fail to accurately predict FVC decline (Ley et al., 2016). Several genetic and plasma biomarkers have also been linked with mortality (Greene et al., 2002; Rosas et al., 2008; Richards et al., 2012; Herazo-Maya et al., 2013; Peljto et al., 2013; Ley et al., 2014; Herazo-Maya et al., 2017), but have less association with FVC decline. Even FVC decline itself fails to predict future FVC decline (Jegal et al., 2005; Schmidt et al., 2014). Such observations suggest that FVC reflects established fibrotic remodeling rather than ongoing, potentially modifiable processes leading to fibrosis. As such, markers of disease activity, rather than severity, would be of use in informing diagnoses.

The dynamic nature of the transcriptome has the potential to signal early indications of fibrosis activity. The great potential of this approach was previously demonstrated with a 52-gene signature that predicted IPF survival in cohorts around the world (Herazo-Maya et al., 2013; Herazo-Maya et al., 2017). This gene signature relied on cross-sectional data, which like clinical prediction models, may not account for critical gene expression changes that likely occur with disease activity. In accordance with the presently disclosed subject matter, it was investigated whether longitudinal within-patient gene expression changes would reflect disease activity, as measured by FVC decline. Using the presently disclosed results, a transcriptomic predictor of FVC decline was developed and validated in three independent IPF cohorts.

SUMMARY

This Summary lists several embodiments of the presently disclosed subject matter, and in many cases lists variations and permutations of these embodiments of the presently disclosed subject matter. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter pertains to methods for generating prognostic signatures for subjects diagnosed with Idiopathic Pulmonary Fibrosis (IPF) with respect to decline in lung Forced Vital Capacity (FVC). In some embodiments, the presently disclosed methods comprise determining a first expression level for one or more genes selected from the group consisting of ALDH4A1, APTX, ATP6AP1L, CCNB1, CNR2, DNAJC17, DTWD1, FAM111B, GABRR1, GPR39, GYPA, HBB, HLA-DPB1, IGLC1, ITLN1, LINC00319, MAZ, MRPL35, MSR1, NT5E, PAWR, PCDHB15, PLA2G4A, PLCL1, PNMA5, RAB3C, RBM43, RLBP1, SESN3, SLC25A37, SSU72P8, TP63, WDR17, ZNF252P, and ZNF582 in a first biological sample obtained from the subject diagnosed with IPF to establish a baseline expression level for the one or more genes; determining a second expression level for the one or more genes in a second biological sample obtained from the subject, wherein the first and second biological samples comprise peripheral blood mononuclear cells (PBMCs) and/or nucleic acids extracted from PBMCs; and comparing the first and second expression levels for the one or more genes, wherein the comparing provides a prognostic signature for the subject with respect to decline in lung FVC within two years from the time that the first biological sample was obtained from the subject. In some embodiments, the presently disclosed methods comprise determining first and second expression levels for a set of genes selected from the group consisting of (a) APTX, CNR2, GYPA, ITLN1, MAZ, MSR1, NT5E, PAWR, PLA2G4A, and PNMA5; (b) APTX, ATP6AP1L, ITLN1, LINC00319, MAZ, MSR1, NT5E, PCDHB15, RAB3C, SSU72P8, and TP62; (c) APTX, CNR2, GABRR1, GPR39, GYPA, HBB, ITLN1, MAZ, MSR1, NT5E, PAWR, PCDHB15, PLA2G4A, PNMA5, RLBP1, and SSU72P8; and (d) APTX, ATP6AP1L, CNR2, FAM111B, GABRR1, GPR39, GYPA, HBB, IGLC1, ITLN1, LINC00319, MAZ, MSR1, NT5E, PAWR, PCDHB15, PLA2G4A, PLCL1, PNMA5, RAB3C, RBM43, RLBP1, SSU72P8, TP63, and ZNF252P. In some embodiments, the presently disclosed methods compriss determining first and second expression levels for each of APTX, ATP6AP1L, CNR2, FAM111B, GABRR1, GPR39, GYPA, HBB, IGLC1, ITLN1, LINC00319, MAZ, MSR1, NT5E, PAWR, PCDHB15, PLA2G4A, PLCL1, PNMA5, RAB3C, RBM43, RLBP1, SSU72P8, TP63, and ZNF252P.

In some embodiments, the second biological sample is obtained from the subject at a time from about 4 to about 12 months subsequent to when the first biological sample was obtained from the subject.

In some embodiments, the subject is a human.

In some embodiments, one or both determining steps comprise a technique selected from the group consisting of RNA-seq analysis, quantitative polymerase chain reaction (PCR) including quantitative reverse transcription PCR (qRT-PCR), and the use of a nucleic acid or protein array, or any combination thereof.

In some embodiments, the comparing step comprises comparing a normalized expression level for each gene in the first biological sample to a normalized expression level for each gene in the second biological sample to generate a fold-increase and/or a fold-decrease in the second biological sample relative to the first biological sample for each gene.

In some embodiments, the comparing step comprises summing each fold-increase and/or fold-decrease to produce an FVC-gene predictor score for the subject.

In some embodiments, the summing is performed after multiplying each fold-increase and/or fold-decrease by a weighting value to produce a weighted FVC-gene predictor score for the subject.

The presently disclosed subject matter also related in some embodiments to methods for classifying subjects diagnosed with IPF as being at risk for FVC decline. In some embodiments, the methods comprise determining a first expression level for one or more genes selected from the group consisting ofALDH4A1, APTX, ATP6AP1L, CCNB1, CNR2, DNAJC17, DTWD1, FAM111B, GABRR1, GPR39, GYPA, HBB, HLA-DPB1, IGLC1, ITLN1, LINC00319, MAZ, MRPL35, MSR1, NT5E, PAWR, PCDHB15, PLA2G4A, PLCL1, PNMA5, RAB3C, RBM43, RLBP1, SESN3, SLC25A37, SSU72P8, TP63, WDR17, ZNF252P, and ZNF582 in a first biological sample obtained from the subject diagnosed with IPF to establish a baseline expression level for the one or more genes; determining a second expression level for the one or more genes in a second biological sample obtained from the subject, wherein the first and second biological samples comprise peripheral blood mononuclear cells (PBMCs) and/or nucleic acids extracted from PBMCs; and comparing the first and second expression levels for the one or more genes to create an FVC-gene predictor score, wherein if the FVC-gene predictor score is greater than or equal to a pre-selected value, the patient is classified as being at risk for a decline in lung FVC within two years from the time that the first biological sample was obtained from the subject. In some embodiments, the comparing comprises comparing a normalized expression level for each gene in the first biological sample to a normalized expression level for each gene in the second biological sample to generate a fold-increase and/or a fold-decrease in the second biological sample relative to the first biological sample for each gene. In some embodiments, the comparing further comprises summing each fold-increase and/or fold-decrease to produce an FVC-gene predictor score for the subject. In some embodiments, the summing is performed after multiplying each fold-increase and/or fold-decrease by a weighting value to produce a weighted FVC-gene predictor score for the subject. In some embodiments, the presently disclosed subject matter methods comprise determining first and second expression levels for a set of genes selected from the group consisting of (a) APTX, CNR2, GYPA, ITLN1, MAZ, MSR1, NT5E, PAWR, PLA2G4A, and PNMA5; (b) APTX, ATP6AP1L, ITLN1, LINC00319, MAZ, MSR1, NT5E, PCDHB15, RAB3C, SSU72P8, and TP62; (c) APTX, CNR2, GABRR1, GPR39, GYPA, HBB, ITLN1, MAZ, MSR1, NT5E, PAWR, PCDHB15, PLA2G4A, PNMA5, RLBP1, and SSU72P8; and (d) APTX, ATP6AP1L, CNR2, FAM111B, GABRR1, GPR39, GYPA, HBB, IGLC1, ITLN1, LINC00319, MAZ, MSR1, NT5E, PAWR, PCDHB15, PLA2G4A, PLCL1, PNMA5, RAB3C, RBM43, RLBP1, SSU72P8, TP63, and ZNF252P. In some embodiments, the presently disclosed subject matter methods comprise determining first and second expression levels for each of APTX, ATP6AP1L, CNR2, FAM111B, GABRR1, GPR39, GYPA, HBB, IGLC1, ITLN1, LINC00319, MAZ, MSR1, NT5E, PAWR, PCDHB15, PLA2G4A, PLCL1, PNMA5, RAB3C, RBM43, RLBP1, SSU72P8, TP63, and ZNF252P.

In some embodiments, the second biological sample is obtained from the subject at a time from about 4 to about 12 months subsequent to when the first biological sample was obtained from the subject.

In some embodiments, the subject is a human.

In some embodiments, one or both determining steps comprises a technique selected from the group consisting of RNA-seq analysis, quantitative polymerase chain reaction (PCR) including quantitative reverse transcription PCR (qRT-PCR), and the use of a nucleic acid or protein array, or any combination thereof.

The presently disclosed subject matter also relates in some embodiments to methods for identifying and treating subjects diagnosed with IPF and/or who are at risk for a decline in lung Forced Vital Capacity (FVC). In some embodiments, the methods comprise determining a first expression level for one or more genes selected from the group consisting of ALDH4A1, APTX, ATP6AP1L, CCNB1, CNR2, DNAJC17, DTWD1, FAM111B, GABRR1, GPR39, GYPA, HBB, HLA-DPB1, IGLC1, ITLN1, LINC00319, MAZ, MRPL35, MSR1, NT5E, PAWR, PCDHB15, PLA2G4A, PLCL1, PNMA5, RAB3C, RBM43, RLBP1, SESN3, SLC25A37, SSU72P8, TP63, WDR17, ZNF252P, and ZNF582 in a first biological sample obtained from the subject diagnosed with IPF to establish a baseline expression level for the one or more genes; determining a second expression level for the one or more genes in a second biological sample obtained from the subject, wherein the first and second biological samples comprise peripheral blood mononuclear cells (PBMCs) and/or nucleic acids extracted from PBMCs; comparing the first and second expression levels for the one or more genes to create an FVC-gene predictor score; and if the FVC-gene predictor score is greater than or equal to a pre-selected value, treating the subject with a treatment selected from the group consisting of lung transplantation and a drug therapy. In some embodiments, the drug therapy comprises administering to the subject a pharmaceutical composition comprising pirfenidone, nintedanib, or a combination thereof in an amount and via a route of administration effective to delay or prevent the development of FVC decline in the subject. In some embodiments, the comparing comprises comparing a normalized expression level for each gene in the first biological sample to a normalized expression level for each gene in the second biological sample to generate a fold-increase and/or a fold-decrease in the second biological sample relative to the first biological sample for each gene.

In some embodiments, the comparing further comprises summing each fold-increase and/or fold-decrease to produce an FVC-gene predictor score for the subject. In some embodiments, the summing is performed after multiplying each fold-increase and/or fold-decrease by a weighting value to produce a weighted FVC-gene predictor score for the subject. In some embodiments, the presently disclosed methods comprise determining first and second expression levels for a set of genes selected from the group consisting of (a) APTX, CNR2, GYPA, ITLN1, MAZ, MSR1, NT5E, PAWR, PLA2G4A, and PNMA5; (b) APTX, ATP6AP1L, ITLN1, LINC00319, MAZ, MSR1, NT5E, PCDHB15, RAB3C, SSU72P8, and TP62; (c) APTX, CNR2, GABRR1, GPR39, GYPA, HBB, ITLN1, MAZ, MSR1, NT5E, PAWR, PCDHB15, PLA2G4A, PNMA5, RLBP1, and SSU72P8; and (d) APTX, ATP6AP1L, CNR2, FAM111B, GABRR1, GPR39, GYPA, HBB, IGLC1, ITLN1, LINC00319, MAZ, MSR1, NT5E, PAWR, PCDHB15, PLA2G4A, PLCL1, PNMA5, RAB3C, RBM43, RLBP1, SSU72P8, TP63, and ZNF252P. In some embodiments, the presently disclosed methods comprise determining first and second expression levels for each of APTX, ATP6AP1L, CNR2, FAM111B, GABRR1, GPR39, GYPA, HBB, IGLC1, ITLN1, LINC00319, MAZ, MSR1, NT5E, PAWR, PCDHB15, PLA2G4A, PLCL1, PNMA5, RAB3C, RBM43, RLBP1, SSU72P8, TP63, and ZNF252P.

In some embodiments, the second biological sample is obtained from the subject at a time from about 4 to about 12 months subsequent to when the first biological sample was obtained from the subject.

In some embodiments, the subject is a human.

In some embodiments, one or both determining steps comprise a technique selected from the group consisting of RNA-seq analysis, quantitative polymerase chain reaction (PCR) including quantitative reverse transcription PCR (qRT-PCR), and the use of a nucleic acid or protein array, or any combination thereof.

In some embodiments, the presently disclosed subject matter also relates to methods for monitoring the progress of a treatment in an IPF patient whose is experiencing a decline in lung Forced Vital Capacity FVC. In some embodiments, the method comprises determining a first expression level for one or more genes selected from the group consisting of ALDH4A1, APTX, ATP6AP1L, CCNB1, CNR2, DNAJC17, DTWD1, FAM111B, GABRR1, GPR39, GYPA, HBB, HLA-DPB1, IGLC1, ITLN1, LINC00319, MAZ, MRPL35, MSR1, NT5E, PAWR, PCDHB15, PLA2G4A, PLCL1, PNMA5, RAB3C, RBM43, RLBP1, SESN3, SLC25A37, SSU72P8, TP63, WDR17, ZNF252P, and ZNF582 in a first biological sample obtained from the patient to establish a baseline expression level for the one or more genes; determining a second expression level for the one or more genes in a second biological sample obtained from the patient at a subsequent time point, wherein the first and second biological samples comprise peripheral blood mononuclear cells (PBMCs) and/or nucleic acids extracted from PBMCs; and comparing the first and second expression levels for the one or more genes, wherein the comparing step is indicative of the progress of the treatment in the patient. In some embodiments, the treatment comprises administering to the patient a pharmaceutical composition comprising pirfenidone, nintedanib, or a combination. In some embodiments, the comparing comprises comparing a normalized expression level for each gene in the first biological sample to a normalized expression level for each gene in the second biological sample to generate a fold-increase and/or a fold-decrease in the second biological sample relative to the first biological sample for each gene. In some embodiments, the comparing further comprises summing each fold-increase and/or fold-decrease to produce an FVC-gene predictor score for the patient. In some embodiments, the summing is performed after multiplying each fold-increase and/or fold-decrease by a weighting value to produce a weighted FVC-gene predictor score for the patient. In some embodiments, the presently disclosed methods comprise determining first and second expression levels for a set of genes selected from the group consisting of (a) APTX, CNR2, GYPA, ITLN1, MAZ, MSR1, NT5E, PAWR, PLA2G4A, and PNMA5; (b) APTX, ATP6AP1L, ITLN1, LINC00319, MAZ, MSR1, NT5E, PCDHB15, RAB3C, SSU72P8, and TP62; (c) APTX, CNR2, GABRR1, GPR39, GYPA, HBB, ITLN1, MAZ, MSR1, NT5E, PAWR, PCDHB15, PLA2G4A, PNMA5, RLBP1, and SSU72P8; and (d) APTX, ATP6AP1L, CNR2, FAM111B, GABRR1, GPR39, GYPA, HBB, IGLC1, ITLN1, LINC00319, MAZ, MSR1, NT5E, PAWR, PCDHB15, PLA2G4A, PLCL1, PNMA5, RAB3C, RBM43, RLBP1, SSU72P8, TP63, and ZNF252P. In some embodiments, the presently disclosed methods comprise determining first and second expression levels for each of APTX, ATP6AP1L, CNR2, FAM111B, GABRR1, GPR39, GYPA, HBB, IGLC1, ITLN1, LINC00319, MAZ, MSR1, NT5E, PAWR, PCDHB15, PLA2G4A, PLCL1, PNMA5, RAB3C, RBM43, RLBP1, SSU72P8, TP63, and ZNF252P.

In some embodiments, the second biological sample is obtained from the patient at a time subsequent to when the first biological sample was obtained from the patient selected from the group consisting of about 1 week, about 2 weeks, about 4 weeks, about 6 weeks, about 2 months, about 3 months, about 4 months, about 5 months, about 6 months, or longer than six months.

In some embodiments, the patient is a human.

In some embodiments, one or both determining steps comprise a technique selected from the group consisting of RNA-seq analysis, quantitative polymerase chain reaction (PCR) including quantitative reverse transcription PCR (qRT-PCR), and the use of a nucleic acid or protein array, or any combination thereof.

In some embodiments, the presently disclosed methods further comprise determining a one or more subsequent expression levels for one or more genes selected from the group consisting of ALDH4A1, APTX, ATP6AP1L, CCNB1, CNR2, DNAJC17, DTWD1, FAM111B, GABRR1, GPR39, GYPA, HBB, HLA-DPB1, IGLC1, ITLN1, LINC00319, MAZ, MRPL35, MSR1, NT5E, PAWR, PCDHB15, PLA2G4A, PLCL1, PNMA5, RAB3C, RBM43, RLBP1, SESN3, SLC25A37, SSU72P8, TP63, WDR17, ZNF252P, and ZNF582 in one or more subsequently isolated biological samples obtained from the patient; and comparing the first, second, and one or more subsequent expression levels for the one or more genes, wherein the comparing step is indicative of the progress of the treatment in the patient.

Accordingly, it is an object of the presently disclosed subject matter to provide compositions and methods for predicting lung function decline in patients with idiopathic pulmonary fibrosis. This and other objects are achieved in whole or in part by the presently disclosed subject matter. Further, objects of the presently disclosed subject matter having been stated above, other objects and advantages of the presently disclosed subject matter will become apparent to those skilled in the art after a study of the following description, Figures, and EXAMPLES. Additionally, various aspects and embodiments of the presently disclosed subject matter are described in further detail below.

BRIEF DESCRIPTION OF THE FIGURES

FIG. 1A. Flowchart of the COMET training cohort: The left panel summarized exemplary steps for identifying the 25-gene FVC-gene predictor predictive of FVC event status using short-term (0-4 month) within-patient ΔGE. The right panel shows gene pathways analyses applied to entire annotated gene set and to 25 genes that constituted the predictor. FIG. 1B. COMET subsets and independent validation cohorts with different transcriptome assay platforms: Steps of testing varied transcriptome sampling timepoints and durations in COMET subsets (left) and testing in external independent cohorts (right) using overlapping Gene ID in differing transcriptome assay platforms. Scores were determined as continuous values using the CV weights for each FVC predictor gene in each patient.

FIG. 2A. Hierarchical clustering of the 74 IPF patients in COMET. Below the clustering are three sets of data, with individual patients depicted as a horizontal line in FIG. 2A. The first group of vertical lines show the gender of the patient, with females in gray and males in black. The second group of vertical lines show the FVC status of each patient, with FVC stable patients in light gray (green in the color version of FIG. 2A) and FVC decline patients in dark gray (blue in the color version of FIG. 2A). The third group of vertical lines how the DLCO status of each patient, with DLCO stable patients in white (yellow in the color version of FIG. 2A) and DLCO decline patients in light gray (light blue in the color version of FIG. 2A). All of the 16 FVC progressor (FVC=1) patients (blue in the color version of FIG. 2A; dark gray in the black and white version of FIG. 2A) were enriched in the bottom cluster, while the upper cluster only contained FVC stable (FVC=0) patients (green in the color version of FIG. 2A; light gray in the black and white version of FIG. 2A). Red, white, and blue color in the color version of FIG. 2A indicate ΔGE values above, at, and below, respectively, the average ΔGE of the corresponding gene. FIGS. 2B and 2C. PCA of COMET training cohort based on the FVC-gene predictor using R/CRAN package "FactoMineR". Individual factor map with confidence ellipses around FVC progressor (blue in color version of FIG. 2B; black in black and white version of FIG. 2B) or stable (green in color version of FIG. 2B; gray in black and white version of FIG. 2B) status is shown in FIG. 2B. Variables factor map with predictor genes is shown in FIG. 2C. The projection of the arrow head of each variable (i.e., gene) onto each dimension represents the component loadings of the corresponding gene.

FIG. 3A. Independent validation cohorts. At anchored specificity of −75%, the sensitivities are 75.0%, 66.7% and 80.0%, for UChicago, UPMA and Imperial cohorts, respectively. FIG. 3B. Training and subset the COMET cohort (I) with increasing transcriptome sampling durations for determination of ΔGE. At anchored specificity of −75%, sensitivities are 100%, 92.3% and 78.6%, for 0-4 month, 0-8 month, and 0-12 month, respectively. FVC-gene predictor performance modestly diminished moving from 4 month to 8 months and 12 months. FIG. 3C. Training and subsets of the COMET cohort (II) with 4 month transcriptome sampling but varying baselines for ΔGE determination. At anchored specificity of −75%, sensitivities are 100%, 69.2% and 36.4% for 0-4 month, 4-8 month, and 8-12 month, respectively. Performance diminishes more dramatically and use of months 8-12 are ineffective. Detailed ROC/AUC analyses results can be found in Tables 5 and 6.

FIG. 4A. University of Chicago (UChicago); FIG. 4B. University of Pittsburgh Medical Center (UPMC); FIG. 4C. Imperial College London (Imperial). 1-specificity and sensitivity are displayed on upper left, total number of patients (FVC stable/FVC progressive) and AUC with 95% confidence intervals in parenthesis are displayed on lower right of each graph.

FIG. 6A. baseline FVC predicted percentage; FIG. 6B. Baseline peripheral plasma MM7 (Matrix metalloproteinase-7); FIG. 6C. Baseline peripheral plasma POSTN (Periostin); FIG. 6D. Baseline peripheral plasma CCL18 (C-C motif chemokine ligand 18).

FIG. 7A. Enrichment plot of 27 hallmark genes in TGF-beta signaling pathway. These genes demonstrated significant larger magnitude of changes from baseline to 4 month in progressive FVC patients than those remaining stable. FIG. 7B. Enrichment plot of 10 genes in Glycan degradation activity demonstrating larger magnitude of changes from baseline to 4 month in progressive FVC patients than stable FVC patients. Core Enrichment genes in each pathway are displayed in Tables 7 and 8.

FIGS. 8A and 8B. Minus versus Average plot between the CoV of baseline GE (CoV1) and the training ΔGE (CoV2) in FVC stable (FIG. 8A) and FVC progressor group (FIG. 8B). FIG. 8C. Power estimation based on postulated sample sizes of PBMC transcriptome using R/CRAN package "sizepower". Horizontal dotted line indicated power of 0.9, at an alpha of 0.05 whereas the corresponding sample size is 63 for baseline GE, and 16 for ΔGE. FIG. 8D. Intra-subject CoV analysis across different PBMC sampling time in COMET. Black bar: Intra-Subject CoV is larger in progressor than in stable patients in COMET ΔGE data; Grey bar. Intra-Subject CoV is larger in stable patients than in progressors in COMET ΔGE data.

DETAILED DESCRIPTION

Figure 1A:
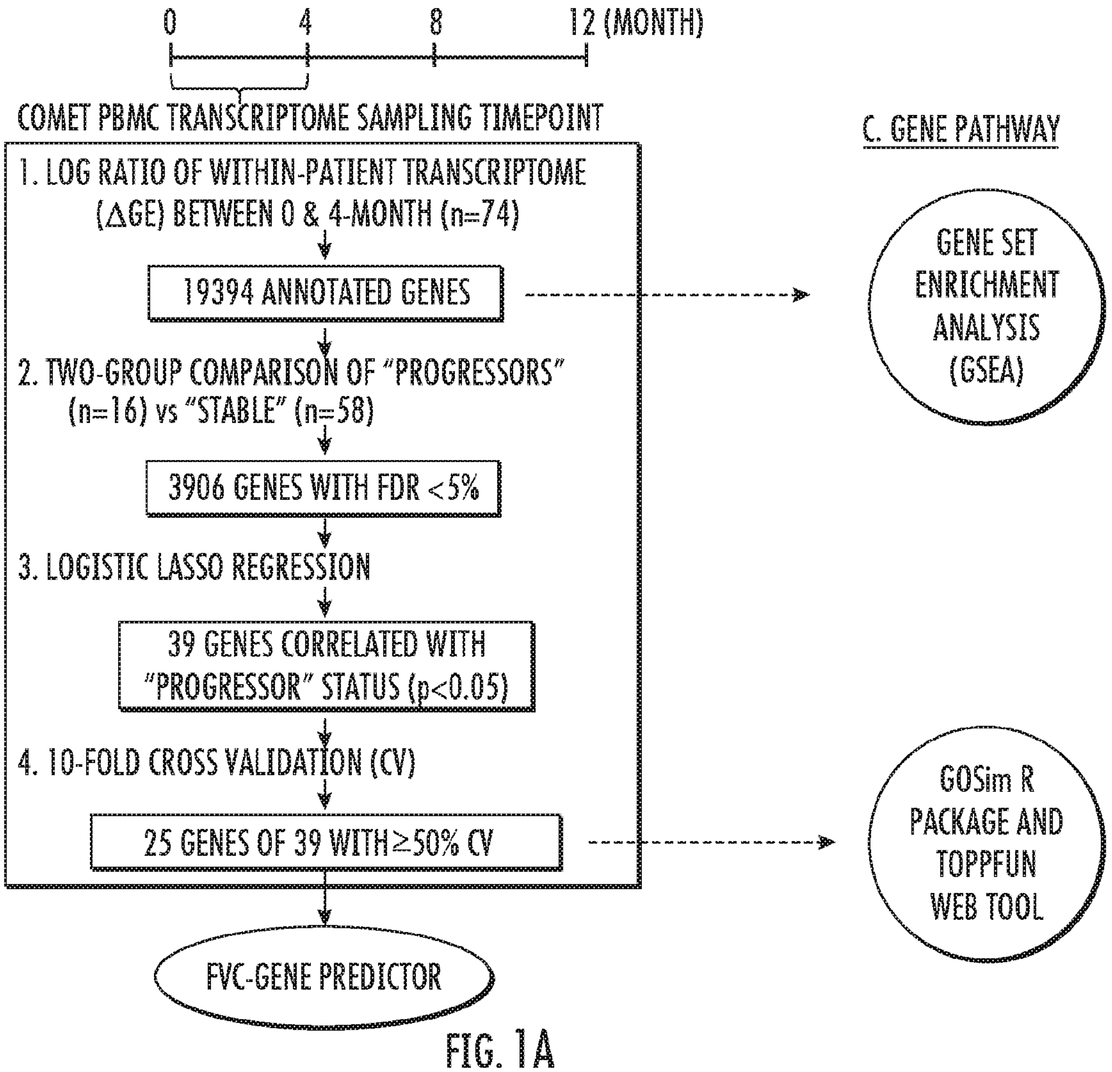
FIGS. 1A and 1B. Summary of the development and validation of the FVC-gene predictor.

Headings are included herein for reference and to aid in locating certain sections. These headings are not intended to limit the scope of the concepts described therein under, and these concepts may have applicability in other sections throughout the entire specification.

I. Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

The articles "a" and "an" are used herein to refer to one or to more than one (i.e., to at least one) of the grammatical object of the article. By way of example, "an element" means one element or more than one element.

The term "about", as used herein, means approximately, in the region of, roughly, or around. When the term "about" is used in conjunction with a numerical range, it modifies that range by extending the boundaries above and below the numerical values set forth. For example, In some embodiments, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about".

The terms "additional therapeutically active compound" or "additional therapeutic agent", as used in the context of the presently disclosed subject matter, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated. Disease and disorders being treated by the additional therapeutically active agent include, for example, hypertension and diabetes. The additional compounds may also be used to treat symptoms associated with the injury, disease, or disorder, including, but not limited to, pain and inflammation.

The term "adult" as used herein, is meant to refer to any non-embryonic or non-juvenile subject. For example, the term "adult adipose tissue stem cell", refers to an adipose stem cell, other than that obtained from an embryo or juvenile subject.

As used herein, an "agonist" is a composition of matter which, when administered to a mammal such as a human, enhances or extends a biological activity attributable to the level or presence of a target compound or molecule of interest in the subject.

A disease or disorder is "alleviated" if the severity of a symptom of the disease, condition, or disorder, or the frequency with which such a symptom is experienced by a subject, or both, are reduced.

As used herein, an "analog" of a chemical compound is a compound that, by way of example, resembles another in structure but is not necessarily an isomer (e.g., 5-fluorouracil is an analog of thymine).

An "antagonist" is a composition of matter which when administered to a mammal such as a human, inhibits a biological activity attributable to the level or presence of a compound or molecule of interest in the subject.

The term "antibody", as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the presently disclosed subject matter may exist in a variety of forms including, for example, polyclonal antibodies, monoclonal antibodies, Fv, Fab and $F(ab)_2$, as well as single chain antibodies and humanized antibodies.

The term "autologous", as used herein, refers to something that occurs naturally and normally in a certain type of tissue or in a specific structure of the body. In transplantation, it refers to a graft in which the donor and recipient areas are in the same individual, or to blood that the donor has previously donated and then receives back, usually during surgery.

The term "biological sample", as used herein, refers to samples obtained from a living organism, including skin, hair, tissue, blood, plasma, cells, sweat, and urine.

The term "bioresorbable", as used herein, refers to the ability of a material to be resorbed in vivo. "Full" resorption means that no significant extracellular fragments remain. The resorption process involves elimination of the original implant materials through the action of body fluids, enzymes, or cells. Resorbed calcium carbonate may, for example, be redeposited as bone mineral, or by being otherwise re-utilized within the body, or excreted. "Strongly bioresorbable", as the term is used herein, means that at least 80% of the total mass of material implanted is resorbed within one year.

The term "clearance", as used herein refers to the physiological process of removing a compound or molecule, such as by diffusion, exfoliation, removal via the bloodstream, and excretion in urine, or via sweat or other fluid.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

A "compound", as used herein, refers to any type of substance or agent that is commonly considered a drug, or a candidate for use as a drug, combinations, and mixtures of the above, as well as polypeptides and antibodies of the presently disclosed subject matter.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" means an amount sufficient to produce a selected effect. A "therapeutically effective amount" means an effective amount of an agent being used in treating or preventing a disease or disorder.

As used herein, a "functional" molecule is a molecule in a form in which it exhibits a property or activity by which it is characterized.

As used herein, a "functional biological molecule" is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'-ATTGCC-3' and 5'-TATGGC-3' share 50% homology.

As used herein, "homology" is used synonymously with "identity".

The determination of percent identity between two nucleotide or amino acid sequences can be accomplished using a mathematical algorithm. For example, a mathematical algorithm useful for comparing two sequences is the algorithm of Karlin & Altschul, 1990, modified as in Karlin & Altschul, 1993). This algorithm is incorporated into the NBLAST and XBLAST programs (see Altschul et al., 1990a; Altschul et al., 1990b), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al., 1997. Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

The term "ingredient" refers to any compound, whether of chemical or biological origin, that can be used in cell culture media to maintain or promote the proliferation, survival, or differentiation of cells. The terms "component", "nutrient", "supplement", and ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins, and the like. Other ingredients that promote or maintain cultivation of cells ex vivo can be selected by those of skill in the art, in accordance with the particular need.

The term "inhibit", as used herein, refers to the ability of a compound, agent, or method to reduce or impede a described function, level, activity, rate, etc., based on the context in which the term "inhibit" is used. In some embodiments, inhibition is by at least 10%, in some embodiments by at least 25%, in some embodiments by at least 50%, and in some embodiments, the function is inhibited by at least 75%. The term "inhibit" is used interchangeably with "reduce" and "block".

The term "inhibitor" as used herein, refers to any compound or agent, the application of which results in the inhibition of a process or function of interest, including, but not limited to, differentiation and activity. Inhibition can be inferred if there is a reduction in the activity or function of interest.

As used herein "injecting or applying" includes administration of a compound of the presently disclosed subject matter by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, "injury" generally refers to damage, harm, or hurt; usually applied to damage inflicted on the body by an external force.

Used interchangeably herein are the terms "isolate" and "select".

The term "isolated", when used in reference to cells, refers to a single cell of interest, or population of cells of interest, at least partially isolated from other cell types or other cellular material with which it naturally occurs in the tissue of origin (e.g., adipose tissue). A sample of stem cells is "substantially pure" when it is in some embodiments at least 60%, in some embodiments at least 75%, in some embodiments at least 90%, and, in certain cases, in some embodiments at least 99% free of cells other than cells of interest. Purity can be measured by any appropriate method, for example, by fluorescence-activated cell sorting (FACS), or other assays, which distinguish cell types.

An "isolated nucleic acid" refers to a nucleic acid segment or fragment, which has been separated from sequences, which flank it in a naturally occurring state, e.g., a DNA fragment that has been removed from the sequences, which are normally adjacent to the fragment, e.g., the sequences adjacent to the fragment in a genome in which it naturally occurs. The term also applies to nucleic acids, which have been substantially purified, from other components, which naturally accompany the nucleic acid, e.g., RNA or DNA, or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, a "ligand" is a compound that specifically binds to a target compound. A ligand (e.g., an antibody) "specifically binds to" or "is specifically immunoreactive with" a compound when the ligand functions in a binding reaction which is determinative of the presence of the compound in a sample of heterogeneous compounds. Thus, under designated assay (e.g., immunoassay) conditions, the ligand binds preferentially to a particular compound and does not bind to a significant extent to other compounds present in the sample. For example, an antibody specifically binds under immunoassay conditions to an antigen bearing an epitope against which the antibody was raised. A variety of immunoassay formats may be used to select antibodies specifically immunoreactive with a particular antigen. For example, solid-phase ELISA immunoassays are routinely used to select monoclonal antibodies specifically immunoreactive with an antigen. See Harlow & Lane, 1988 for a description of immunoassay formats and conditions that can be used to determine specific immunoreactivity.

A "receptor" is a compound that specifically or selectively binds to a ligand.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to either a molecule that joins two other molecules covalently or non-covalently, e.g., through ionic or hydrogen bonds or van der Waals interactions.

The terms "gene product" or "expression product" are used herein interchangeably to refer to the RNA transcription products (RNA transcript) of a gene, including mRNA, and the polypeptide translation product of such RNA transcripts. A gene product may be, for example, a polynucleotide gene expression product (e.g., an unspliced RNA, an mRNA, a splice variant mRNA, a microRNA, a fragmented RNA, and the like) or a protein expression product (e.g., a mature polypeptide, a post-translationally modified polypeptide, a splice variant polypeptide, and the like). In some embodiments the gene expression product may be a sequence variant including mutations, fusions, loss of heterozygoxity (LOH), and/or biological pathway effects.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

A "reference expression level" as applied to a gene expression product refers to an expression level for one or more reference (or "control") gene expression products. A "reference normalized expression level" as applied to a gene expression product refers to a normalized expression level value for one or more reference (or control) gene expression products (i.e., a normalized reference expression level). In some embodiments, a reference expression level is an expression level for one or more gene product in normal sample, as described herein. In some embodiments, a reference expression level is determined experimentally. In some embodiments, a reference expression level is a historical expression level, e.g., a database value of a reference expression level in a normal sample, which sample indicates a single reference expression level, or a summary of a plurality of reference expression levels (such as, e.g., (i) an average of two or more, in some embodiments three or more reference expression levels from replicate analysis of the reference expression level from a single sample; (ii) an average of two or more, in some embodiments three or more reference expression levels from analysis of the reference expression level from a plurality of different samples (e.g., normal samples); (iii) and a combination of the above mentioned steps (i) and (ii) (i.e., average of reference expression levels analyzed from a plurality of samples, wherein at least one of the reference expression levels are analyzed in replicate). In some embodiments, the "reference expression level" is an expression level of sequence variants, for example, in a sample that has been definitively determined to be UIP or non-UIP by other approaches (i.e. confirmed pathological diagnosis).

A "reference expression level value" as applied to a gene expression product refers to an expression level value for one or more reference (or control) gene expression products. A "reference normalized expression level value" as applied to a gene expression product refers to a normalized expression level value for one or more reference (or control) gene expression products.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature that may be used. As a result, it follows that higher relative temperatures may tend to make the reaction conditions more stringent, while lower temperatures less so. For additional details and explanation of stringency of hybridization reactions, see Ausubel et al., 1995.

"Stringent conditions" or "high stringency conditions", as defined herein, typically: (1) employ low ionic strength solutions and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., 1989, and include the use of washing solution and hybridization conditions (e.g., temperature, ionic strength and % SDS) less stringent that those described above. An example of moderately stringent condition is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

"Sensitivity" as used herein refers to the proportion of true positives of the total number tested that actually have the target disorder (i.e., the proportion of patients with the target disorder who have a positive test result). "Specificity" as used herein refers to the proportion of true negatives of all the patients tested who actually do not have the target disorder (i.e., the proportion of patients without the target disorder who have a negative test result).

In the context of the present disclosure, reference to "at least one," "at least two," "at least five," etc. of the genes listed in any particular gene set means any one or any and all combinations of the genes listed.

The term "modulate", as used herein, refers to changing the level of an activity, function, or process. The term "modulate" encompasses both inhibiting and stimulating an activity, function, or process. The term "modulate" is used interchangeably with the term "regulate" herein.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil).

As used herein, the term "nucleic acid" encompasses RNA as well as single and double stranded DNA and cDNA. Furthermore, the terms, "nucleic acid", "DNA", "RNA" and similar terms also include nucleic acid analogs, i.e. analogs having other than a phosphodiester backbone. For example, the so called "peptide nucleic acids", which are known in the art and have peptide bonds instead of phosphodiester bonds in the backbone, are considered within the scope of the presently disclosed subject matter. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences".

The term "nucleic acid construct", as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T".

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

The term "prevent", as used herein, means to stop something from happening, or taking advance measures against something possible or probable from happening. In the context of medicine, "prevention" generally refers to action taken to decrease the chance of getting a disease or condition.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

A "prophylactic" treatment is a treatment administered to a subject who does not exhibit signs of a disease or injury or exhibits only early signs of the disease or injury for the purpose of decreasing the risk of developing pathology associated with the disease or injury.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross & Mienhofer, 1981 for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl, or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell". A gene which is expressed in a recombinant host cell wherein the gene comprises a recombinant polynucleotide, produces a "recombinant polypeptide".

A "recombinant polypeptide" is one which is produced upon expression of a recombinant polynucleotide.

The term "regulate" refers to either stimulating or inhibiting a function or activity of interest.

As used herein, term "regulatory elements" is used interchangeably with "regulatory sequences" and refers to promoters, enhancers, and other expression control elements, or any combination of such elements.

A "sample", as used herein, refers in some embodiments to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

A "significant detectable level" is an amount of contaminate that would be visible in the presented data and would need to be addressed/explained during analysis of the forensic evidence.

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In some embodiments, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

The terms "solid support", "surface" and "substrate" are used interchangeably and refer to a structural unit of any size, where said structural unit or substrate has a surface suitable for immobilization of molecular structure or modification of said structure and said substrate is made of a material such as, but not limited to, metal, metal films, glass, fused silica, synthetic polymers, and membranes.

By the term "specifically binds", as used herein, is meant a molecule which recognizes and binds a specific molecule, but does not substantially recognize or bind other molecules in a sample, or it means binding between two or more molecules as in part of a cellular regulatory process, where said molecules do not substantially recognize or bind other molecules in a sample.

The term "standard", as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. "Standard" can also refer to an "internal standard", such as an agent or compound which is added at known amounts to a sample and which is useful in determining such things as purification or recovery rates when a sample is processed or subjected to purification or extraction procedures before a marker of interest is measured. Internal standards are often but are not limited to, a purified marker of interest which has been labeled, such as with a radioactive isotope, allowing it to be distinguished from an endogenous substance in a sample.

The term "stimulate" as used herein, means to induce or increase an activity or function level such that it is higher relative to a control value. The stimulation can be via direct or indirect mechanisms. In some embodiments, the activity or function is stimulated by at least 10% compared to a control value, in some embodiments by at least 25%, and in some embodiments by at least 50%. The term "stimulator" as used herein, refers to any composition, compound or agent, the application of which results in the stimulation of a process or function of interest, including, but not limited to, wound healing, angiogenesis, bone healing, osteoblast production and function, and osteoclast production, differentiation, and activity.

The term "subject," as used herein, generally refers to a mammal. Typically, the subject is a human. However, the term embraces other species, e.g., pigs, mice, rats, dogs, cats, or other primates. In certain embodiments, the subject is an experimental subject such as a mouse or rat. The subject may be a male or female. The subject may be an infant, a toddler, a child, a young adult, an adult or a geriatric. The subject may exhibit one or more symptoms of IPF. For example, the subject may exhibit shortness of breath (generally aggravated by exertion) and/or dry cough), and, in some cases may have obtained results of one or more of an imaging test (e.g., chest X-ray, computerized tomography (CT)), a pulmonary function test (e.g., spirometry, oximetry, exercise stress test), lung tissue analysis (e.g., histological and/or cytological analysis of samples obtained by bronchoscopy, bronchoalveolar lavage, surgical biopsy) that is indicative of the potential presence of IPF. A subject under the care of a physician or other health care provider may be referred to as a "patient".

A "subject" of diagnosis or treatment is an animal, including a human. It also includes pets and livestock.

As used herein, a "subject in need thereof" is a patient, animal, mammal, or human, who will benefit from the method of the presently disclosed subject matter.

As used herein, "substantially homologous amino acid sequences" includes those amino acid sequences which have at least about 95% homology, in some embodiments at least about 96% homology, more in some embodiments at least about 97% homology, in some embodiments at least about 98% homology, and most in some embodiments at least about 99% or more homology to an amino acid sequence of a reference sequence. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the presently disclosed subject matter.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. In some embodiments, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M $NaPO_4$, 1 mM EDTA at 50° C. with washing in 2× standard saline citrate (SSC), 0.1% SDS at 50° C.; in some embodiments in 7% (SDS), 0.5 M $NaPO_4$, 1 mM EDTA at 50° C. with washing in 1×SSC, 0.1% SDS at 50° C.; in some embodiments 7% SDS, 0.5 M $NaPO_4$, 1 mM EDTA at 50° C. with washing in 0.5×SSC, 0.1% SDS at 50° C.; and more in some embodiments in 7% SDS, 0.5 M $NaPO_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984), and the BLASTN or FASTA programs (Altschul et al., 1990a; Altschul et al., 1990b; Altschul et al., 1997). The default settings provided with these programs are suitable for determining substantial similarity of nucleic acid sequences for purposes of the presently disclosed subject matter.

The term "substantially pure" describes a compound, e.g., a protein or polypeptide which has been separated from components which naturally accompany it. Typically, a compound is substantially pure when at least 10%, more in some embodiments at least 20%, more in some embodiments at least 50%, more in some embodiments at least 60%, more in some embodiments at least 75%, more in some embodiments at least 90%, and most in some embodiments at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

A "surface active agent" or "surfactant" is a substance that has the ability to reduce the surface tension of materials and enable penetration into and through materials.

The term "symptom", as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse, and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

"Tissue" means (1) a group of similar cell united perform a specific function; (2) a part of an organism consisting of an aggregate of cells having a similar structure and function; or (3) a grouping of cells that are similarly characterized by their structure and function, such as muscle or nerve tissue.

The term "topical application", as used herein, refers to administration to a surface, such as the skin. This term is used interchangeably with "cutaneous application" in the case of skin. A "topical application" is a "direct application".

By "transdermal" delivery is meant delivery by passage of a drug through the skin or mucosal tissue and into the bloodstream. Transdermal also refers to the skin as a portal for the administration of drugs or compounds by topical application of the drug or compound thereto. "Transdermal" is used interchangeably with "percutaneous".

The term "transfection" is used interchangeably with the terms "gene transfer", "transformation", and "transduction", and means the intracellular introduction of a polynucleotide. "Transfection efficiency" refers to the relative amount of the transgene taken up by the cells subjected to transfection. In practice, transfection efficiency is estimated by the amount of the reporter gene product expressed following the transfection procedure.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "treating" may include prophylaxis of the specific injury, disease, disorder, or condition, or alleviation of the symptoms associated with a specific injury, disease, disorder, or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease. "Treating" is used interchangeably with "treatment" herein.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

As used herein "wound" or "wounds" may refer to any detectable break in the tissues of the body, such as injury to skin or to an injury or damage, or to a damaged site associated with a disease or disorder. As used herein, the term "wound" relates to a physical tear, break, or rupture to a tissue or cell layer. A wound may occur by any physical insult, including a surgical procedure or as a result of a disease, disorder condition. Although the terms "wound" and "injury" are not always defined exactly the same way, the use of one term herein, such as "injury", is not meant to exclude the meaning of the other term.

III. Methods and Uses of the Presently Disclosed Subject Matter

The presently disclosed subject matter relates in some embodiments to methods for identifying, classifying, and treating patients with Idiopathic Pulmonary Fibrosis (IPF) as suffering from or being at risk for developing a longitudinal decline in forced vital capacity (FVC).

As used herein, the phrase "forced vital capacity" (FVC) refers to that amount of air that can be forcibly exhaled from the lungs after taking one's deepest breath. FVC is typically measured by spirometry. It can be employed to distinguish between obstructive versus restrictive lung diseases. In Idiopathic Pulmonary Fibrosis (IPF), a longitudinal decline in FVC is a well-validated predictor of mortality and is often used as the primary efficacy endpoint in IPF clinical trials. With respect to FVC decline, IPF patients can be categorized as being stable (referred to herein as FVC-stable or FVC-S) or can have and/or be at risk for progressive disease. In some embodiments, an FVC-S patient is a patient who would not be predicted to suffer a ≥10% relative decline in FVC over the next 12 months. In some embodiments, an FVC-S patient is a patient who would not be predicted to suffer a ≥5% relative decline in FVC over the next 12 months. Thus, in some embodiments, as used herein, progressive disease is defined as a ≥10% relative decline in FVC over the next 12 months, and in some embodiments progressive disease is defined as a ≥5% relative decline in FVC over the next 12 months. Accordingly, an FVC-D patient is a patient who the presently disclosed methods would be predicted to suffer a ≥10% relative decline in FVC over the next 12 months, and in some embodiments an FVC-D patient is a patient who would be predicted to suffer a ≥5% relative decline in FVC over the next 12 months. As used herein, the term "decline" as employed in the context of FVC is synonymous with the term "progressor".

As disclosed in more detail herein below, the methods of the methods of the presently disclosed subject matter can be employed to identify, classify, and treat IPF patients suffering from and/or being at risk for developing progressive disease as defined herein as a longitudinal decline in FVC if in some embodiments ≥5% and in some embodiments ≥10% in the 12 months subsequent to testing.

III.A. Methods for Generating Prognostic Signatures

In order to identify patients (in some embodiments, human patients) suffering from or at risk for suffering progressive disease, in some embodiments the presently disclosed subject matter provides methods for generating prognostic signatures for IPF subjects with respect to a decline in FVC. In some embodiments, the methods comprise performing gene expression analysis with respect to one or more of the gene products disclosed herein at an initial and at a subsequent timepoint and comparing the first and second expression levels for the one or more genes, wherein the comparing provides a prognostic signature for the subject with respect to decline in lung FVC within a pre-determined time period subsequent to the later timepoint.

In some embodiments, the initial timepoint serves as to provide baseline values for the expression levels of the genes for the patient. In some embodiments, the subsequent timepoint provides later gene expression values for the patient, and when compared to the initial baseline values, can provide a prognostic signature that predicts whether or not the patient is likely to suffer from progressive disease within a pre-determined time period subsequent to the subsequent timepoint. In some embodiments, the initial (e.g., first) and subsequent (e.g., second) timepoints are separated by one or several months, which in some embodiments can be from about 1, 2, 3, 4, 5, 6, 7, 8, 9, 10, or about 12 months.

As disclosed herein, various genes have been identified as being relevant to the production of a prognostic signature with respect to patients suffering from or at risk for suffering progressive disease. These genes are listed below in Table 1.

TABLE 1

Exemplary Human Genes Employed in Generating Prognostic Signatures

| GENE | Description | Nucleic Acid* | Amino Acid** |
|---|---|---|---|
| ALDH4A1 | aldehyde dehydrogenase 4 family member A1 | NM_003748.4 (SEQ ID NO: 1) | NP_003739.2 (SEQ ID NO: 2) |
| APTX | Aprataxin | NM_175073.2 (SEQ ID NO: 3) | NP_778243.1 (SEQIDNO: 4) |
| ATP6AP1L | ATPase H+ transporting accessory protein 1 like | NM_001349372.2 (SEQ ID NO: 5) | NP_001336301.1 (SEQIDNO: 6) |
| CCNB1 | cyclin B1 | NM_031966.4 (SEQ ID NO: 7) | NP_114172.1 (SEQIDNO: 8) |

TABLE 1-continued

Exemplary Human Genes Employed in Generating Prognostic Signatures

| GENE | Description | Nucleic Acid* | Amino Acid** |
|---|---|---|---|
| CNR2 | Cannabinoid receptor 2 | NM_001841.3 (SEQ ID NO: 9) | NP_001832.1 (SEQIDNO: 10) |
| DNAJC17 | DnaJ heat shock protein family (Hsp40) member C17 | NM_018163.3 (SEQ ID NO: 11) | NP_060633.1 (SEQ ID NO: 12) |
| DTWD1 | DTW domain containing 1 | NM_020234.6 (SEQ ID NO: 13) | NP_064619.2 (SEQ ID NO: 14) |
| FAM111B | Family with sequence similarity 111 member B | NM_198947.4 (SEQ ID NO: 15) | NP_945185.1 (SEQIDNO: 16) |
| GABRRI | γ-aminobutyric acid type A receptor rho1 subunit | NM_002042.5 (SEQ ID NO: 17) | NP_002033.2 (SEQIDNO: 18) |
| GPR39 | G protein-coupled receptor 39 | NM_001508.3 (SEQ ID NO: 19) | NP_001499.1 (SEQ ID NO: 20) |
| GYPA | Glycophorin A (MNS blood group) | NM_002099.8 (SEQ ID NO: 21) | NP_002090.4 (SEQ ID NO: 22) |
| HBB | Hemoglobin subunit beta | NM_000518.5 (SEQ ID NO: 23) | NP_000509.1 (SEQ ID NO: 24) |
| HLA-DPB1 | major histocompatibility complex, class II, DP beta 1 | NM_002121.6 (SEQ ID NO: 25) | NP_002112.3 (SEQ ID NO: 26) |
| IGLC1 | Immunoglobulin lambda constant 1 | BCO12159.1 (SEQ ID NO: 27) | AAH12159.1 (SEQ ID NO: 28) |
| ITLN1 | Intelectin 1 | NM_017625.3 (SEQ ID NO: 29) | NP_060095.2 (SEQ ID NO: 30) |
| LINC00319 | Long intergenic non-protein coding RNA 319 | NR_152722.1 (SEQ ID NO: 31) | N/A |
| MAZ | MYC associated zinc finger protein | NM_002383.4 (SEQ ID NO: 32) | NP_002374.2 (SEQ ID NO: 33) |
| MRPL35 | mitochondrial ribosomal protein L35 | NM_016622.4 (SEQ ID NO: 34) | NP_057706.2 (SEQ ID NO: 35) |
| MSR1 | Macrophage scavenger receptor 1 | NM_138715.3 (SEQ ID NO: 36) | NP_619729.1 (SEQ ID NO: 37) |
| NT5E | 5'-nucleotidase ecto | NM_002526.4 (SEQ ID NO: 38) | NP_002517.1 (SEQ ID NO: 39) |
| PAWR | Pro-apoptotic WT1 regulator | NM_002583.4 (SEQ ID NO: 40) | NP_002574.2 (SEQ ID NO: 41) |
| PCDHB15 | Protocadherin beta 15 | NM_018935.4 (SEQ ID NO: 42) | NP_061758.1 (SEQ ID NO: 43) |
| PLA2G4A | Phospholipase A2 group IVA | NM_024420.2 (SEQ ID NO: 44) | NP_077734.1 (SEQ ID NO: 45) |
| PLCL1 | Phospholipase C like 1 (inactive) | NM_006226.4 (SEQ ID NO: 46) | NP_006217.3 (SEQ ID NO: 47) |
| PNMA5 | PNMA family member 5 | NM_001103151.1 (SEQ ID NO: 48) | NP_001096621.1 (SEQ ID NO: 49) |
| RAB3C | RAB3C, RAS oncogene family | NM_138453.4 (SEQ ID NO: 50) | NP_612462.1 (SEQ ID NO: 51) |
| RBM43 | RNA binding motif protein 43 | NM_198557.3 (SEQ ID NO: 52) | NP_940959.1 (SEQ ID NO: 53) |
| RLBP1 | Retinaldehyde binding protein 1 | NM_000326.5 (SEQ ID NO: 54) | NP_000317.1 (SEQ ID NO: 55) |
| SESN3 | sestrin 3 | NM_144665.4 (SEQ ID NO: 56) | NP_653266.2 (SEQ ID NO: 57) |
| SLC25A37 | solute carrier family 25 member 37 | NM_016612.4 (SEQ ID NO: 58) | NP_057696.2 (SEQ ID NO: 59) |
| SSU72P8 | SSU72 pseudogene 8 | NG_012760.1 | N/A |
| TP63 | Tumor protein p63 | NM_003722.5 (SEQ ID NO: 60) | NP_003713.3 (SEQ ID NO: 61) |
| WDR17 | WD repeat domain 17 | NM_170710.5 (SEQ ID NO: 62) | NP_733828.2 (SEQ ID NO: 63) |
| ZNF252P | Zinc finger protein 252, pseudogene | NR_023392.1 (SEQ ID NO: 64) | N/A |
| ZNF582 | zinc finger protein 582 | NM_001320371.2 (SEQ ID NO: 65) | NP_001307300.1 (SEQ ID NO: 66) |

*Accession No. for a representative human nucleic acid gene product in the GENBANK ® biosequence database.
**Accession No. for a representative human amino acid gene product in the GENBANK ® biosequence database that is encoded by the corresponding nucleic acid Accession No. It is noted that certain nucleic acid gene products are non-coding, and they are listed identified in this column with N/A (not applicable).

In some embodiments, the presently disclosed methods comprising determining a first expression level for one or more genes selected from the group consisting of ALDH4A1, APTX, ATP6AP1L, CCNB1, CNR2, DNAJC17, DTWD1, FAM111B, GABRR1, GPR39, GYPA, HBB, HLA-DPB1, IGLC1, ITLN, LINC00319, MAZ, MRPL35, MSR1, NT5E, PAWR, PCDHB15, PLA2G4A, PLCL1, PNMA5, RAB3C, RBM43, RLBP1, SESN3, SLC25A37, SSU72P8, TP63, WDR17, ZNF252P, and ZNF582 in a first biological sample obtained from the subject diagnosed with IPF to establish a baseline expression level for the one or more genes; determining a second expression level for the same one or more genes in a second biological sample obtained from the subject, wherein the first and second biological samples comprise peripheral blood mononuclear cells (PBMCs) and/or nucleic acids extracted from PBMCs; and comparing the first and second expression levels for the one or more genes, wherein the comparing provides a prognostic signature for the subject with respect to decline in lung FVC within a pre-determined timeframe (e.g., 12 months) from the time that the first biological sample was obtained from the subject. In some embodiments, the presently disclosed methods comprising determining first and second expression levels for the genes APTX, CNR2, GYPA, ITLN, MAZ, MSR1, NT5E, PAWR, PLA2G4A, and PNMA5. In some embodiments, the presently disclosed methods comprising determining first and second expression levels for the genes APTX, ATP6AP1L, ITLN1, LINC00319, MAZ, MSR1, NT5E, PCDHB15, RAB3C, SSU72P8, and TP62. In some embodiments, the presently disclosed methods comprising determining first and second expression levels for the genes APTX, CNR2, GABRR1, GPR39, GYPA, HBB, ITLN1, MAZ, MSR1, NT5E, PAWR, PCDHB15, PLA2G4A, PNMA5, RLBP1, and SSU72P8. In some embodiments, the presently disclosed methods comprising determining first and second expression levels for the genes APTX, ATP6AP1L, CNR2, FAM111B, GABRR1, GPR39, GYPA, HBB, IGLC1, ITLN1, LINC00319, MAZ, MSR1, NT5E, PAWR, PCDHB15, PLA2G4A, PLCL1, PNMA5, RAB3C, RBM43, RLBP1, SSU72P8, TP63, and ZNF252P.

Any technique that permits determination of a level of expression of a gene can be employed within the methods of the presently disclosed subject matter. In some embodiments, the gene expression levels for the selected genes are determined by employing a technique selected from the group consisting of RNA-seq analysis, quantitative polymerase chain reaction (PCR) including quantitative reverse transcription PCR (qRT-PCR), the use of a nucleic acid or protein array, or any combination thereof. In some embodiments, assaying the expression level is accomplished using RT-PCR, nucleic acid microarray hybridization, RNASeq, or a combination thereof. In some embodiments, the expression level is assayed by detecting a nucleotide expressed in the test sample or synthesized from a nucleotide expressed in the test sample. In some embodiments, the method comprises synthesizing cDNA from RNA expressed in the test sample prior to assaying the expression level. In some embodiments, the method comprises synthesizing double-stranded cDNA from the cDNA prior to assaying the expression level. In some embodiments, the method comprises synthesizing non-natural RNA from the double-stranded cDNA prior to assaying the expression level. In some embodiments, the non-natural RNA is cRNA. In some embodiments, the non-natural RNA is labeled. In some embodiments, the label comprises a sequencing adaptor or a biotin molecule. In some embodiments, the method comprises amplification of the nucleotide prior to assaying the expression level. Techniques for assaying gene expression levels using RT-PCR, nucleic acid and/or protein microarray hybridization, and RNA-Seq are known in the art (see e.g., U.S. Pat. Nos. 5,800,992; 6,004,755; 6,013,449; 6,020,135; 6,033,860; 6,040,138; 6,177,248; 6,251,601; 6,309,822; 7,824,856; 9,920,367; 10,227,584; each of which is incorporated by reference in its entirety. See also U.S. Patent Application Publication Nos. 2010/0120097; 2011/0189679; 2014/0113333; 2015/0307874; each of which is incorporated by reference in its entirety. See also Mortazaavi et al., 2008.

In some embodiments, the presently disclosed methods comprise comparing a normalized expression level for each gene in the first biological sample to a normalized expression level for each gene in the second biological sample to generate a fold-increase and/or a fold-decrease in the second biological sample relative to the first biological sample for each gene. As used herein, the phrase "normalized expression level" as applied to a gene expression product refers in some embodiments to a level of the gene product normalized relative to one or more reference (or control) gene expression products. Exemplary reference gene expression products include the so-called "housekeeping genes", which are genes for which expression does not vary significantly over time, with respect to different cell types, and/or under different disease conditions. Prototypical reference genes include, but are not limited to glyceraldehyde 3-phosphate dehydrogenase (GAPDH) and β-actin. In some embodiments, an average value within an individual cohort is employed as a normalization metric, such that fold increase and fold decrease values are expressed relative to that average.

Normalized gene expression data from two different samples can be compared to each other to determine changes in gene expression between the two different samples. In some embodiments, gene expression changes are calculated as "fold differences" between the samples. Fold differences include both fold increases (which can in some embodiments be expressed as a positive number) and fold decreases (which can in some embodiments be expressed as a negative number rather than as a fractional number between 0 and 1).

A "gene signature" of a "prognostic signature" is a gene expression pattern (i.e., expression levels of one or more genes) that is indicative of some characteristic or phenotype (such as but not limited to FVC decline within a pre-determined time period). In some embodiments, a prognostic signature refers to the expression (and/or lack of expression) of a gene, a plurality of genes, a fragment of a gene or a plurality fragments of one or more genes, which expression and/or lack of expression is indicative of status of a subject as being FVC-S or as being FVC-D.

The prognostic signature can thus be in some embodiments an overall depiction of all genes assayed or, in some embodiments, a depiction of a subset of genes (such as but not limited to informative genes).

Various other software and/or hardware modules or processes may be implemented. In certain methods, feature selection and model estimation may be performed by logistic regression with lasso penalty using glmnet (Friedman et al. 2010). Raw reads may be aligned using TopHat (Trapnell et al., 2009). Gene counts may be obtained using HTSeq (Anders et al., 2014) and normalized using DESeq (Love et al., 2014). In methods, top features (N ranging from 10 to 200) were used to train a linear support vector machine (SVM; Suykens & Vandewalle, 1999) using the e1071 library (Meyer, 2014). Confidence intervals may be computed using the pROC package (Robin et al., 2011).

In addition, data may be filtered to remove data that may be considered suspect. In some embodiments, data deriving from microarray probes that have fewer than about 4, 5, 6, 7 or 8 guanosine and cytosine nucleotides may be considered to be unreliable due to their aberrant hybridization propensity or secondary structure issues. Similarly, data deriving from microarray probes that have more than about 12, 13, 14, 15, 16, 17, 18, 19, 20, 21, or 22 guanosine and cytosine nucleotides may be considered unreliable due to their aberrant hybridization propensity or secondary structure issues.

In some cases, unreliable probe sets may be selected for exclusion from data analysis by ranking probe-set reliability against a series of reference datasets. For example, RefSeq or Ensembl (EMBL) are considered very high quality reference datasets. Data from probe sets matching RefSeq or Ensembl sequences may in some cases be specifically included in microarray analysis experiments due to their expected high reliability. Similarly data from probe-sets matching less reliable reference datasets may be excluded from further analysis, or considered on a case by case basis for inclusion. In some cases, the Ensembl high throughput cDNA (HTC) and/or mRNA reference datasets may be used to determine the probe-set reliability separately or together. In other cases, probe-set reliability may be ranked. For example, probes and/or probe-sets that match perfectly to all reference datasets such as for example RefSeq, HTC, HTSeq, and mRNA, may be ranked as most reliable (1). Furthermore, probes and/or probe-sets that match two out of three reference datasets may be ranked as next most reliable (2), probes and/or probe-sets that match one out of three reference datasets may be ranked next (3) and probes and/or probe sets that match no reference datasets may be ranked last (4). Probes and or probe-sets may then be included or excluded from analysis based on their ranking. For example, one may choose to include data from category 1, 2, 3, and 4 probe-sets; category 1, 2, and 3 probe-sets; category 1 and 2 probe-sets; or category 1 probe-sets for further analysis. In another example, probe-sets may be ranked by the number of base pair mismatches to reference dataset entries. It is understood that there are many methods understood in the art for assessing the reliability of a given probe and/or probe-set for molecular profiling and the methods of the present disclosure encompass any of these methods and combinations thereof.

III.B. Methods for Classifying IPF Subjects as Being at Risk for FVC Decline

The presently disclosed subject matter also provides in some embodiments methods for classifying subjects diagnosed with Idiopathic Pulmonary Fibrosis (IPF) as being at risk for a decline in lung Forced Vital Capacity (FVC). In some embodiments, the methods comprise determining a first expression level for one or more genes selected from the group consisting of ALDH4A1, APTX, ATP6AP1L, CCNB1, CNR2, DNAJC17, DTWD1, FAM111B, GABRR1, GPR39, GYPA, HBB, HLA-DPB1, IGLC1, ITLN1, LINC00319, MAZ, MRPL35, MSR1, NT5E, PAWR, PCDHB15, PLA2G4A, PLCL1, PNMA5, RAB3C, RBM43, RLBP1, SESN3, SLC25A37, SSU72P8, TP63, WDR17, ZNF252P, and ZNF582 in a first biological sample obtained from the subject diagnosed with IPF to establish a baseline expression level for the one or more genes; determining a second expression level for the one or more genes in a second biological sample obtained from the subject, wherein the first and second biological samples comprise peripheral blood mononuclear cells (PBMCs) and/or nucleic acids extracted from PBMCs; and comparing the first and second expression levels for the one or more genes to create an FVC-gene predictor score, wherein if the FVC-gene predictor score is greater than or equal to a pre-selected value, the patient is classified as being at risk for a decline in lung FVC within a pre-determined time period (e.g., 12 months) from the time that the first biological sample was obtained from the subject. With respect to the presently disclosed classifying methods, the methods comprise the same gene expression approaches disclosed herein above with respect to generating a prognostic signature for a given subject, When expression levels for only one gene is being compared, the fold increase or fold decrease can be reported as a score. However, when expression levels for more than one gene are being compared, a synthesis of the various gene expression levels can be employed to generate an overall score. In some embodiments, a simple sum of the normalized fold increases (e.g., values ≥0) and normalized fold decreases (e.g., values ≤0) are employed to generate an overall score.

In some embodiments, the overall score is reported as a simple sum of the normalized fold increases and decreases, which in some embodiments can be referred to as a "raw score". In some embodiments, however, the overall score is reported as a weighted sum of the normalized fold increases and decreases. Values that can be employed for weighting can be pre-determined and can include, for example, using regression coefficients and assessed using area under the curve (AUC) analysis as described herein below. By way of example and not limitation, a score can be generated by multiplying normalized fold increase(s) and fold decrease(s) by a logistic LASSO regression coefficient derived from analyzing expression of any given gene(s) in normal controls and/or FVC-S patients, and summing the weighted values to produce an FVC-gene predictor score for a given subject.

Scores can vary based in some embodiments on the number of genes employed, in some embodiments on the assay technique employed, in some embodiments the time between the first and second sample isolations (e.g., between an initial isolation and an isolate 4 months later), and in some embodiments on a pre-selected minimum sensitivity. In some embodiments, a raw score of at least 5, 6, 7, or 8 can be indicative of a subject being in FVC decline when all 25 of APTX, ATP6AP1L, CNR2, FAM111B, GABRR1, GPR39, GYPA, HBB, IGLC1, ITLN1, LINC00319, MAZ, MSR1, NT5E, PAWR, PCDHB15, PLA2G4A, PLCL1, PNMA5, RAB3C, RBM43, RLBP1, SSU72P8, TP63, and ZNF252P are employed. In some embodiments, a score of at least 7.5 provides a 75% sensitivity when these 25 genes are employed and a microassay technique is employed for gene expression analysis. It is noted, however, that the technique employed for assaying gene expression changes and the time between first and second sample isolations can affect the values of the fold increases and decreases. As such, in some embodiments the same technique is employed for assaying gene expression at all times for both the control subjects and for the test subjects in order to minimize cross-testing variability, and the time between first and second sample isolations is fixed at four months. In some embodiments, when RNA-seq is employed to determine gene expression levels for the genes APTX, CNR2, GABRR1, GPR39, GYPA, HBB, ITLN1, MAZ, MSR1, NT5E, PAWR, PCDHB15, PLA2G4A, PNMA5, RLBP1, and SSU72P8, a score of −1.73 provides 75% sensitivity to the identification of FVC-D subjects.

III.C. Methods for Identifying and Treating IPF Subjects at Risk for FVC Decline In some embodiments of the presently disclosed subject matter, once a patient is classified as being in or at risk for FVC-D, that patient can be identified as being appropriate for treatment, whereas if a patient is classified as not being in or at risk for FVC-D (i.e., is classified as FVC-S), that patient can be identified as being appropriate for further monitoring but not treatment.

Accordingly, in some embodiments the presently disclosed subject matter relates to methods for identifying and treating IPF subjects at risk for or experience a decline in lung FVC. In some embodiments, the methods comprise determining a first expression level for one or more genes selected from the group consisting of ALDH4A1, APTX, ATP6AP1L, CCNB1, CNR2, DNAJC17, DTWD1, FAM111B, GABRR1, GPR39, GYPA, HBB, HLA-DPB1, IGLC1, ITLN1, LINC00319, MAZ, MRPL35, MSR1, NT5E, PAWR, PCDHB15, PLA2G4A, PLCL1, PNMA5, RAB3C, RBM43, RLBP1, SESN3, SLC25A37, SSU72P8, TP63, WDR17, ZNF252P, and ZNF582 in a first biological sample obtained from the subject diagnosed with IPF to establish a baseline expression level for the one or more genes; determining a second expression level for the one or more genes in a second biological sample obtained from the subject, wherein the first and second biological samples comprise peripheral blood mononuclear cells (PBMCs) and/or nucleic acids extracted from PBMCs; comparing the first and second expression levels for the one or more genes to create an FVC-gene predictor score; and if the FVC-gene predictor score is greater than or equal to a pre-selected value, treating the subject with a treatment selected from the group consisting of lung transplantation and a drug therapy. Appropriate treatments for patients in need of treatment include in some embodiments administering to the subject a pharmaceutical composition comprising pirfenidone, nintedanib, or a combination thereof in an amount and via a route of administration effective to delay or prevent the development of FVC decline in the subject. See U.S. Pat. Nos. 3,974,281; 6,762,180; 8,592,462; 9,884,802; 10,028,966; and 10,105,365, each of which is incorporated herein by reference in its entirety. See also U.S. Patent Application Publication Nos. 2018/0064695, 2018/0169084; 2019/0030012; and 2019/0282565, each of which is incorporated herein by reference in its entirety.

As with other methods disclosed herein, in some embodiments the method comprise determining first and second expression levels for a set of genes selected from the group consisting of (a) APTX, CNR2, GYPA, ITLN1, MAZ, MSR1, NT5E, PAWR, PLA2G4A, and PNMA5; (b) APTX, ATP6AP1L, ITLN1, LINC00319, MAZ, MSR1, NT5E, PCDHB15, RAB3C, SSU72P8, and TP62; (c) APTX, CNR2, GABRR1, GPR39, GYPA, HBB, ITLN1, MAZ, MSR1, NT5E, PAWR, PCDHB15, PLA2G4A, PNMA5, RLBP1, and SSU72P8; and (d) APTX, ATP6AP1L, CNR2, FAM111B, GABRR1, GPR39, GYPA, HBB, IGLC1, ITLN1, LINC00319, MAZ, MSR1, NT5E, PAWR, PCDHB15, PLA2G4A, PLCL1, PNMA5, RAB3C, RBM43, RLBP1, SSU72P8, TP63, and ZNF252P.

The presently disclosed subject matter is also directed to methods of administering the compounds of the presently disclosed subject matter to a subject.

Pharmaceutical compositions comprising the present compounds are administered to a subject in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal approaches.

In accordance with one embodiment, a method for treating a subject in need of such treatment is provided. The method comprises administering a pharmaceutical composition comprising at least one composition of the presently disclosed subject matter to a subject in need thereof. Compositions provided by the methods of the presently disclosed subject matter can be administered with known compounds or other medications as well.

The pharmaceutical compositions useful for practicing the presently disclosed subject matter may be administered to deliver a dose of between 1 ng/kg/day and 100 mg/kg/day.

The presently disclosed subject matter encompasses the preparation and use of pharmaceutical compositions comprising a compound useful for treatment of the diseases and disorders disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The compositions of the presently disclosed subject matter may comprise at least one active polypeptide, one or more acceptable carriers, and optionally other polypeptides or therapeutic agents.

For in vivo applications, the compositions of the presently disclosed subject matter may comprise a pharmaceutically acceptable salt. Suitable acids which are capable of forming such salts with the compounds of the presently disclosed subject matter include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, anthranilic acid, cinnamic acid, naphthalene sulfonic acid, sulfanilic acid and the like.

Pharmaceutically acceptable carriers include physiologically tolerable or acceptable diluents, excipients, solvents, or adjuvants. The compositions are in some embodiments sterile and nonpyrogenic. Examples of suitable carriers include, but are not limited to, water, normal saline, dextrose, mannitol, lactose or other sugars, lecithin, albumin, sodium glutamate, cysteine hydrochloride, ethanol, polyols (propylene glycol, polyethylene glycol, glycerol, and the like), vegetable oils (such as olive oil), injectable organic esters such as ethyl oleate, ethoxylated isosteraryl alcohols, polyoxyethylene sorbitol and sorbitan esters, microcrystalline cellulose, aluminum methahydroxide, bentonite, kaolin, agar-agar and tragacanth, or mixtures of these substances, and the like.

The pharmaceutical compositions may also contain minor amounts of nontoxic auxiliary pharmaceutical substances or excipients and/or additives, such as wetting agents, emulsifying agents, pH buffering agents, antibacterial and antifungal agents (such as parabens, chlorobutanol, phenol, sorbic acid, and the like). Suitable additives include, but are not limited to, physiologically biocompatible buffers (e.g., tromethamine hydrochloride), additions (e.g., 0.01 to 10 mole percent) of chelants (such as, for example, DTPA or DTPA-bisamide) or calcium chelate complexes (as for example calcium DTPA or CaNaDTPA-bisamide), or, optionally, additions (e.g., 1 to 50 mole percent) of calcium or sodium salts (for example, calcium chloride, calcium ascorbate, calcium gluconate or calcium lactate). If desired, absorption enhancing or delaying agents (such as liposomes, aluminum monostearate, or gelatin) may be used. The compositions can be prepared in conventional forms, either as liquid solutions or suspensions, solid forms suitable for solution or suspension in liquid prior to injection, or as emulsions. Pharmaceutical compositions according to the presently disclosed subject matter can be prepared in a manner fully within the skill of the art.

The compositions of the presently disclosed subject matter or pharmaceutical compositions comprising these compositions may be administered so that the compositions may have a physiological effect. Administration may occur enterally or parenterally; for example, orally, rectally, intracisternally, intravaginally, intraperitoneally, locally (e.g., with powders, ointments or drops), or as a buccal or nasal spray or aerosol. Parenteral administration is an approach. Particular parenteral administration methods include intravascular administration (e.g., intravenous bolus injection, intravenous infusion, intra-arterial bolus injection, intra-arterial infusion and catheter instillation into the vasculature), peri- and intra-target tissue injection, subcutaneous injection or deposition including subcutaneous infusion (such as by osmotic pumps), intramuscular injection, and direct application to the target area, for example by a catheter or other placement device.

Where the administration of the composition is by injection or direct application, the injection or direct application may be in a single dose or in multiple doses. Where the administration of the compound is by infusion, the infusion may be a single sustained dose over a prolonged period of time or multiple infusions.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the presently disclosed subject matter is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

A pharmaceutical composition of the presently disclosed subject matter may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the presently disclosed subject matter will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the presently disclosed subject matter may further comprise one or more additional pharmaceutically active agents. Particularly contemplated additional agents include anti-emetics and scavengers such as cyanide and cyanate scavengers.

Controlled- or sustained-release formulations of a pharmaceutical composition of the presently disclosed subject matter may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the presently disclosed subject matter are known in the art and described, for example in Gennaro, 1990 and/or Gennaro, 2003, each of which is incorporated herein by reference.

Typically, dosages of the compound of the presently disclosed subject matter which may be administered to an animal, in some embodiments a human, range in amount from 1 μg to about 100 g per kilogram of body weight of the animal. While the precise dosage administered will vary depending upon any number of factors, including but not limited to, the type of animal and type of disease state being treated, the age of the animal and the route of administration. In some embodiments, the dosage of the compound will vary from about 1 mg to about 10 g per kilogram of body weight of the animal. In another aspect, the dosage will vary from about 10 mg to about 1 g per kilogram of body weight of the animal.

The compositions may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type of cancer being diagnosed, the type and severity of the condition or disease being treated, the type and age of the animal, etc.

Suitable preparations include injectables, either as liquid solutions or suspensions, however, solid forms suitable for solution in, suspension in, liquid prior to injection, may also be prepared. The preparation may also be emulsified, or the compositions encapsulated in liposomes. The active ingredients are often mixed with excipients which are pharmaceutically acceptable and compatible with the active ingredient. Suitable excipients are, for example, water saline, dextrose, glycerol, ethanol, or the like and combinations thereof. In addition, if desired, the preparation may also include minor amounts of auxiliary substances such as wetting or emulsifying agents, pH buffering agents, and/or adjuvants.

Various aspects and embodiments of the presently disclosed subject matter are described in further detail below.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

The compounds of the presently disclosed subject matter may be administered to, for example, a cell, a tissue, or a subject by any of several methods described herein and by others which are known to those of skill in the art.

The relative amounts of the active ingredient, the pharmaceutically acceptable carrier, and any additional ingredients in a pharmaceutical composition of the presently disclosed subject matter will vary, depending upon the identity, sex, age, size, and condition of the subject treated and further depending upon the route by which the composition is to be administered.

In addition to the active ingredient, a composition of the presently disclosed subject matter may further comprise one or more additional pharmaceutically active or therapeutic agents. Particularly contemplated additional agents include anti-emetics and scavengers such as cyanide and cyanate scavengers.

Controlled- or sustained-release formulations of a composition of the presently disclosed subject matter may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the presently disclosed subject matter are known in the art and described, for example in Gennaro, 1990 and/or Gennaro, 2003, each of which is incorporated herein by reference.

Other components such as preservatives, antioxidants, surfactants, absorption enhancers, viscosity enhancers or film forming polymers, bulking agents, diluents, coloring agents, flavoring agents, pH modifiers, sweeteners or taste-masking agents may also be incorporated into the composition. Suitable coloring agents include red, black, and yellow iron oxides and FD&C dyes such as FD&C Blue No. 2, FD&C Red No. 40, and the like. Suitable flavoring agents include mint, raspberry, licorice, orange, lemon, grapefruit, caramel, vanilla, cherry grape flavors, combinations thereof, and the like. Suitable pH modifiers include citric acid, tartaric acid, phosphoric acid, hydrochloric acid, maleic acid, sodium hydroxide, and the like. Suitable sweeteners include aspartame, acesulfame K, thaumatic, and the like. Suitable taste-masking agents include sodium bicarbonate, ion-exchange resins, cyclodextrin inclusion compounds, adsorbates, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the presently disclosed subject matter is contemplated include, but are not limited to, humans and other primates, mammals including commercially relevant mammals such as cattle, pigs, horses, sheep, cats, and dogs, and birds including commercially relevant birds such as chickens, ducks, geese, and turkeys.

The pharmaceutical compositions of the presently disclosed subject matter can be administered in any suitable formulation, by any suitable means, and by any suitable route of administration. Formulations suitable for topical administration include, but are not limited to, liquid or semi-liquid preparations such as liniments, lotions, oil in water or water in oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

An alternative standard of care treatment for patients diagnosed with FVC-D and/or who are at risk for developing FVC-D within a pre-determined time period is lung transplantation. Thus, in some embodiments a patient classified and/or identified with FVC-D and/or who is at risk for developing FVC-D within a pre-determined time period (e.g., within 12 months) is an appropriate candidate for lung transplantation.

III.D. Methods for Monitoring the Progress of a Treatment

The basic techniques described herein can also be employed to monitor the progress of a treatment. As used herein, the phrase "progress of a treatment" refers to the ability of a treatment to reduce FVC decline over time, particularly with respect to reducing the rate at which FVC decline occurs in a patient.

As such, in some embodiments the presently disclosed subject matter relates to methods for monitoring the progress of a treatment in an IPF patient whose is experiencing a decline in lung Forced Vital Capacity (FVC) comprising determining a first expression level for one or more genes selected from the group consisting of ALDH4A1, APTX, ATP6AP1L, CCNB1, CNR2, DNAJC17, DTWD1, FAM111B, GABRR1, GPR39, GYPA, HBB, HLA-DPB1, IGLC1, ITLN1, LINC00319, MAZ, MRPL35, MSR1, NT5E, PAWR, PCDHB15, PLA2G4A, PLCL1, PNMA5, RAB3C, RBM43, RLBP1, SESN3, SLC25A37, SSU72P8, TP63, WDR17, ZNF252P, and ZNF582 in a first biological sample obtained from the patient to establish a baseline expression level for the one or more genes; determining a second expression level for the one or more genes in a second biological sample obtained from the patient at a subsequent time point, wherein the first and second biological samples comprise peripheral blood mononuclear cells (PBMCs) and/or nucleic acids extracted from PBMCs; and comparing the first and second expression levels for the one or more genes, wherein the comparing step is indicative of the progress of the treatment in the patient.

As set forth herein above, an exemplary treatment for FVC-decline comprises administering to the patient an effective amount of pirfenidone, nintedanib, or a combination thereof. At a first time point (including but not limited to a time point at or before initiation of the treatment), a normalized expression level for each gene in first biological sample can be determined. Thereafter, at a subsequent timepoint of interest (e.g., one or more weeks or months subsequent to the initial timepoint), the same genes can again be assayed and a normalized expression level for each gene in the second, subsequent biological sample can be determined. In some embodiments, the first and second normalized expression level for each gene assays are compared to generate a fold-increase and/or a fold-decrease in the second biological sample relative to the first biological sample for each gene. As before, the comparing can comprise summing each fold-increase and/or fold-decrease to produce an FVC-gene predictor score for the patient, wherein the FVC-gene predictor score produced can be a raw or a weighted score.

Also as before, the set of genes for which first and second expression levels are determined can be selected from the group consisting of: (a) APTX, CNR2, GYPA, ITLN1, MAZ, MSR1, NT5E, PAWR, PLA2G4A, and PNMA5; (b) APTX, ATP6AP1L, ITLN1, LINC00319, MAZ, MSR1, NT5E, PCDHB15, RAB3C, SSU72P8, and TP62; (c) APTX, CNR2, GABRR1, GPR39, GYPA, HBB, ITLN1, MAZ, MSR1, NT5E, PAWR, PCDHB15, PLA2G4A, PNMA5, RLBP1, and SSU72P8; and (d) APTX, ATP6AP1L, CNR2, FAM111B, GABRR1, GPR39, GYPA, HBB, IGLC1, ITLN1, LINC00319, MAZ, MSR1, NT5E, PAWR, PCDHB15, PLA2G4A, PLCL1, PNMA5, RAB3C, RBM43, RLBP1, SSU72P8, TP63, and ZNF252P. In some embodiments, first and second expression levels for each of APTX, ATP6AP1L, CNR2, FAM111B, GABRR1, GPR39, GYPA, HBB, IGLC1, ITLN1, LINC00319, MAZ, MSR1, NT5E, PAWR, PCDHB15, PLA2G4A, PLCL1, PNMA5, RAB3C, RBM43, RLBP1, SSU72P8, TP63, and ZNF252P are compared.

In some embodiments, the second biological sample is obtained from the patient at a time subsequent to when the first biological sample was obtained from the patient selected from the group consisting of about 1 week, about 2 weeks, about 4 weeks, about 6 weeks, about 2 months, about 3 months, about 4 months, about 5 months, about 6 months, or longer than six months.

In some embodiments, the presently disclosed monitoring method can further comprise determining a one or more subsequent expression levels for one or more genes selected from the group consisting of ALDH4A1, APTX, ATP6AP1L, CCNB1, CNR2, DNAJC17, DTWD1, FAM111B, GABRR1, GPR39, GYPA, HBB, HLA-DPB1, IGLC1, ITLN1, LINC00319, MAZ, MRPL35, MSR1, NT5E, PAWR, PCDHB15, PLA2G4A, PLCL1, PNMA5, RAB3C, RBM43, RLBP1, SESN3, SLC25A37, SSU72P8, TP63, WDR17, ZNF252P, and ZNF582 in one or more subsequently isolated biological samples obtained from the patient; and (e) comparing the first, second, and one or more subsequent expression levels for the one or more genes, wherein the comparing step is indicative of the progress of the treatment in the patient.

In accordance with the presently disclosed subject matter, as described above or as discussed in the EXAMPLES below, there can be employed conventional chemical, cellular, histochemical, biochemical, molecular biology, microbiology, recombinant DNA, and clinical techniques which are known to those of skill in the art. Such techniques are explained fully in the literature. See for example, Sambrook et al., 1989; Glover, 1985; Gait, 1984; Harlow & Lane, 1988; Roe et al., 1996; and Ausubel et al., 1995.

The presently disclosed subject matter may be embodied in other specific forms without departing from the spirit or essential attributes thereof. The presently disclosed subject matter encompasses all combinations of the different aspects of the presently disclosed subject matter noted herein. It is understood that any and all embodiments of the presently disclosed subject matter may be taken in conjunction with any other embodiment or embodiments to describe additional representative embodiments. It is also to be understood that each individual element of the disclosed embodiments is intended to be taken individually as its own independent representative embodiment. Furthermore, any element of an embodiment is meant to be combined with any and all other elements from any embodiment to describe an additional embodiment.

Typically, dosages of the compounds of the presently disclosed subject matter which may be administered to an animal, in some embodiments a human, range in amount from about 1.0 μg to about 100 g per kilogram of body weight of the animal. The precise dosage administered will vary depending upon any number of factors, including but not limited to, the type of animal and type of disease state being treated, the age of the animal and the route of administration. In some embodiments, the dosage of the compound will vary from about 1 mg to about 10 g per kilogram of body weight of the animal. In some embodiments, the dosage will vary from about 10 mg to about 1 g per kilogram of body weight of the animal.

The compounds may be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

EXAMPLES

The presently disclosed subject matter will be now be described more fully hereinafter with reference to the accompanying EXAMPLES, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

Materials and Methods

IPF Cohorts Generally. The training cohort was comprised of patients participating in the prospective COMET study (Huang et al., 2017; NCT01071707). Validation cohorts included prospectively enrolled patients at the University of Chicago (UChicago); University of Pittsburgh Medical Center (UPMC; Herazo-Maya et al., 2013); and Imperial College London (Imperial; Herazo-Maya et al., 2017). All patients were diagnosed with IPF according to international guidelines (American Thoracic Society & European Respiratory Society, 2002; Raghu et al., 2011). Patients in each cohort were stratified according to the presence of progressive disease, defined as ≥10% relative decline in FVC over the study timeframe. Additional cohort-specific detailed are provided in the online supplement.

COMET Training Cohort. Subjects included in this analysis were participants in COMET-IPF (Correlating Outcomes with biochemical Markers to Estimate Time-progression in Idiopathic Pulmonary Fibrosis), a prospective, observational study correlating biomarkers with disease progression (NCT01071707; Naik et al., 2012). This multicenter investigation recruited subjects at nine clinical centers in the US. Inclusion criteria required diagnosis of IPF was confirmed using a multidisciplinary diagnostic approach per international guidelines (Raghu et al., 2011) using expertise from clinicians, radiologists, and pathologists at the local, enrolling clinical center (Flaherty et al., 2004; Flaherty et al., 2007) and age 35-80 years. Subjects were excluded if the diagnosis of IPF was >4 years prior to screening or if there was a diagnosis of collagen-vascular disorder, FEV1/FVC<0.60, evidence of active infection at screening, or comorbid conditions other than IPF likely to result in death within one year. Subjects underwent protocol-directed visits every 4 months after the baseline (0 visit) for a minimum of 1 year, establishing four transcriptome sampling timepoints with PFTs and blood draws performed every 4 months. Registry patients with peripheral blood mononuclear cells (PBMC) gene expression (GE) sampling over at least two time points were included in training (1-4 month) and each subset cohort (i.e., 0-8 month; 0-12 month; 4-8 month; 4-12 month). Forced vital capacity (FVC) and diffusion capacity for carbon monoxide (DLCO) were obtained per ATS guidelines (Macintyre et al., 2005; Miller et al., 2005a; Miller et al., 2005b). Subjects in COMET experiencing a relative reduction <10% or ≥10% in FVC % predicted from baseline visit to follow-up visit at month 12 were defined as FVC-S (stable) or FVC-D (decline), respectively. DLCO-S (stable) or DLCO-D (decline) were defined as <15% or ≥15% of relative reduction in DLCO % predicted from the baseline visit to follow-up at month 12, respectively. Informed consent was obtained from all participants. The study protocol was reviewed by the institutional review board of each participating center.

UChicago Validation Cohort. Study populations were collected from the University of Chicago Medical Center and was approved by the institutional review board and informed consent was provided by all study subjects. All patients with IPF met American Thoracic Society/European Respiratory Society (ATS/ERS) diagnosis criteria (American Thoracic Society & European Respiratory Society, 2002). Demographic information, clinical characteristics, and pulmonary function tests were collected from all patients with IPF. Spirometry testing, including forced vital capacity percent predicted (FVC % predicted), diffusion capacity for carbon monoxide percent predicted (DLCO % predicted) as well as lung volumes by plethysmography were obtained per ATS guidelines (Macintyre et al., 2005; Miller et al., 2005a; Miller et al., 2005b). The prognosis of IPF subjects was dichotomously categorized as FVC stable (FVC-S) or FVC decline (FVC-D) defined by < or ≥10% reduction in FVC % predicted from the baseline to over 2 years of follow-up.

UPMC validation cohort. Patients were recruited from the University of Pittsburgh. IPF diagnosis was established by a multidisciplinary group at each institution with the American Thoracic Society/European Respiratory Society criteria (American Thoracic Society & European Respiratory Society, 2002) and was consistent with recent guidelines (Raghu et al., 2011). Patients were excluded in the study if they had evidence of autoimmune syndromes, malignancies, infections, drugs, or occupational exposures known to cause lung fibrosis. The studies were approved by the institutional review boards at the two institutions, and informed consent was obtained from all patients. Demographic and clinical information were collected in all patients at the time of blood draw. Spirometric data and diffusion capacity of the lung for carbon monoxide (DLCO) were obtained within 3 months of blood draw, with the exception of four IPF patients of the replication cohort who did not have DLCO values available within this time range. The prognosis of IPF subjects was dichotomously categorized as FVC stable (FVC-S) or FVC decline (FVC-D) defined by < or ≥10% relative reduction in FVC % of predicted from the baseline to about 12 month follow-up.

Imperial Validation Cohort. Patients were prospectively recruited from the Interstitial Lung Disease Unit at the Royal Brompton Hospital, London, United Kingdom, between November 2010 and January 2013. Diagnoses of IPF were made according to international guidelines (Raghu et al., 2011) after multidisciplinary team discussion. Subjects were excluded if they had a history of self-reported upper or lower respiratory tract infection, antibiotic use in the prior 3 months, acute IPF exacerbation, or other respiratory disorders. Written informed consent was obtained from all subjects, and the study was approved by the local research ethics committee (reference numbers 10/110720/12 and 12/LO/1034). At baseline and at each subsequent visit, pulmonary function test was performed and peripheral blood were collected into PAXgene RNA tubes (PreAnalytiX, Hombrechtikon, Switzerland). at baseline and at 6 and 12 months. The prognosis of IPF subjects was dichotomously categorized as FVC stable (FVC-S) or FVC decline (FVC-D) defined by < or ≥10% relative reduction in FVC % of predicted from the baseline to about 12 month follow-up.

Gene Expression Data. Information regarding gene expression (GE) assays, raw data processing and normalization, pathway analyses, and sample classification were as follows.

COMET Cohort. PBMC sample collection, RNA isolation, microarray hybridization, and data processing. Peripheral blood mononuclear cells (PBMCs) from IPF patients were isolated from whole blood collected in Lavender top tubes containing EDTA by Ficoll-Paque Plus (GE Healthcare Life Science, Pittsburgh, Pennsylvania, United States of America) as described in Eppendorf Application Note No. 372 dated June 2016 (available from the Eppendorf website) and lysed with TRIzol reagent (Thermo Fisher Sci., Waltham, Massachusetts, United States of America) for RNA extraction following manufacturer's protocol. Sodium acetate/ethanol was used to re-precipitate RNA to increase the purity prior to Affymetrix PRIMEVIEW™ brand array assay (Affymetrix, Santa Clara, California) according to manufacturer's manual (available from the Affymetric website). RNA quality and integrity were confirmed by Nanodrop ($A_{260}/A_{280}$ ratios between 1.7 and 2.2) and Bio-Analyzer mini-gel assay, respectively. One hundred fifty ng RNA per sample was reverse transcribed to single stranded cDNA, and then amplified to cRNA using Affymetrix GeneChip WT cDNA Synthesis Kit. Qualities and yields (exceeding 25 μg/ml and 1000 μg/ml, respectively) of cRNA after the first and second amplifications were all satisfactory prior to hybridization and scanning. The Affymetrix microarray raw data in ".cel" format were processed using R/Bioconductor package "affy" (Gautier et al., 2004). Background correction and gene expression intensities were summarized and normalized using "rma" algorithm (Irizarry et al., 2003). The complete data sets are available in the Gene Expression Omnibus database under platform No. GSE132607 (see the website of the National Center for Biotechnology Infor of the United States National Institutes of Health; Accession No. GSE132607).

UChicago Cohort. PBMC sample collection, RNA isolation, RNA-Seq library preparation and sequencing. PBMC samples were obtained by density centrifugation. RNA was extracted with TRIzol (Invitrogen) and was re-precipitated by sodium acetate/ethanol. RNA quality and integrity were confirmed by Nanodrop ($A_{260}/A_{280}$ ratios between 1.7 and 2.2) and Bio-Analyzer mini-gel assay (Agilent, Santa Clara, California, United States of America). All RNA samples displayed a RNA Integrity Number (RIN)>7 were proceeded to cDNA library preparation at the Genomics Core Facility of the University of Chicago. Total RNA in the amount of 1 μg per sample was depleted of ribosomal RNA using the Ribo-Zero kit (Epicentre, Madison, Wisconsin, United States of America). The directional (first strand) cDNA libraries were prepared following the guide of TruSeq Stranded Total RNA Sample Preparation kit. RNA was fragmented at 94° C. for 6 minutes, followed by the first strand cDNA generation. Deoxy-UTP was incorporated in second strand synthesis in order to effectively quench the second strand during PCR amplification. After adenylation of the 3' end and ligation of adapters, fragments were selected and enriched with 10 cycles of PCR amplification. Clusters were generated by bridge amplification within paired-end flow cells using Illumina HiSeq PE Cluster Kit v4 cBot according to manufacturer's instructions (Illumina, San Diego, California, United States of America). The clusters on flow cells were then sequenced on the Illumina HiSeq4000 using HiSeq SBS Kit. A total of 1 Tbase reads were generated for cDNA libraries prepared from 54 samples using high output mode of 100 bp paired-end (PE) sequencing. Around 94% sequences passed quality checked (>Q30), yielding about 87M passing filter clusters per sample, and 4.7G clusters in total. Raw sequencing data in fastq format were processed using RNA-seq aligner STAR v2 (Dobin et al., 2013). GenCode v24 was used for transcriptome annotation. The abundance of transcripts was summarized into CPM (Counts per Million mapped reads). Genes with a value of CPM>0.5 in at least two samples were included for downstream analysis. The filtered raw read data were transformed to log 2-counts per million (log CPM) and normalized with the associated precision weights using "voom" (Law et al., 2014) and "TMM" (Robinson & Oshlack, 2010) normalization implemented in R/Bioconductor packages, including "limma" (Smyth, 2004) and "edgeR" (Robinson et al., 2010). Given the different technologies of gene expression assay used in COMET (Affymetrix PrimeView) and the three independent validation cohorts (Agilent 4×44K, Affymetrix Human Gene 1.1 ST and RNA-seq), the Gene ID was matched across different platforms.

UPMC Cohort. PBMC sample collection, RNA isolation, microarray hybridization, and data processing. Peripheral blood was collected in a cell preparation tube, followed by centrifugation to isolate PBMCs. These cells were suspended in QIAzol (Qiagen) and stored at −80° C. Total RNA was extracted and purified using the miRNeasy Mini Kit (Qiagen) and QIAcube device (Qiagen), following the manufacturer's protocols. After extraction, total RNA yield and quality were evaluated using NanoDrop at 260 nm and the 2100 Bioanalyzer (Agilent Technologies). Labeling reactions were performed using Agilent Quick Amp labeling kit, one-color (Agilent Technologies). Briefly, an initial cDNA strand was synthesized using 400 ng of total RNA and a T7-oligo(dT) primer containing a phage T7 RNA Polymerase promoter sequence at its 5'-end. This cDNA was then used as a template to generate Cy3-labeled cRNA by a reverse transcriptase enzyme. The cRNA was fragmented, hybridized to Whole Human Genome Oligo Microarray, 4×44K (G4112F, Agilent Technologies), and scanned using an Agilent Microarray Scanner. For array readout, Agilent Feature Extraction software version 10.7 was used. To normalize the gProcessed signal, cyclic-LOESS was performed using the bioconductor package as described previously (Ballman et al., 2004). The average of the gene expression signal was used in the case of replicated probes for the same gene with different expression values. The complete data sets are available in the Gene Expression Omnibus database under Accession No. GSE28221 via the website of the National Center for Biotechnology Information of the United States National Institutes of Health.

Imperial cohort. PBMC sample collection, RNA isolation, microarray hybridization, and data processing. Whole blood was collected using PAXgene blood RNA tubes (PreAnalytiX) and stored in −80° C. Total RNA extraction was performed using the PAXgene Blood RNA Kit, following the manufacturer's protocol. Total RNA was quantified using the NanoDrop ND 1000 UV-Vis spectrophotometer (Thermo Scientific, Wilmington, DE), and the quality and integrity were assessed using the 2100 Bioanalyzer (Agilent Technologies, Santa Clara, California, United States of America) by ratio comparison of the 18S and 28S rRNA bands. Thirty nanograms of each RNA sample was used to synthesize double-stranded complementary DNA (dscDNA) using the Ovation Pico WTA System V2 Kit (NuGEN, San Carlos, California, United States of America). Exogenous poly(A)-positive control subjects were added to monitor the efficiency of the synthesis of the dscDNA and target-labeling process. The Encore Biotin Module Kit (NuGEN) was used to fragment 2.8 μg of the purified cDNA template, which was then hybridized, washed, and scanned on the GeneTitan system (Affymetrix, Santa Clara, CA) using Human Gene 1.1 ST 16- or 24-sample array plates (Affymetrix). The complete data sets are available in the Gene Expression Omnibus database under Accession No. GSE93606 via the website of the National Center for Biotechnology Information of the United States National Institutes of Health.

Gene ID was matched across cohorts to account for differing GE assay platforms.

FVC-gene Predictor Training and Validation. Gene expression changes (ΔGE) between baseline and 4 month visit were compared between stable and progressive groups in the COMET training cohort using empirical Bayesian moderated t-test implemented in R/Bioconductor package "limma" (Smyth, 2004). P-values were adjusted for multiple comparisons using the Benjamini-Hochberg method (Benjamini & Hochberg, 1995). The R package 'glmet' (Friedman et al., 2010; Simon et al., 2011; Tibshirani et al., 2012) was then used to perform Logistic Least Absolute Shrinkage and Selection Operator (LASSO) to enhance the prediction accuracy via variable selection and regularization. Ten-fold Cross-Validation was performed in conjunction with logistic LASSO regression to evaluate correct classification rate.

Genes predictive of FVC decline by this approach were used to generate an FVC-gene predictor score, defined as the sum of each ΔGE value multiplied by the corresponding logistic LASSO regression coefficient. Receiver operator analysis was performed using R-CRAN package "pROC" (Robin et al., 2011) and "OptimalCutpoints" (López-Ratón et al., 2014) to identify the optimal threshold for cohort stratification. Scores above that threshold were considered to have a positive FVC-gene predictor. The FVC-gene predictor score was then calculated for patients in each validation cohort using the subset of overlapping genes from each platform weighted by the cohort-specific cross-validation coefficient to identify those with a positive FVC-gene predictor. FVC-gene predictor test performance characteristics were then assessed in each cohort.

Comparative Analysis between FVC-gene Predictor and Cross-sectional Biomarkers. The test performance for predicting FVC decline was then compared between the FVC-gene predictor and prior plasma biomarkers of IPF mortality, including circulating plasma MMP7, periostin (POSTN), and CCL18. Additional information about this analysis is detailed in the online supplement.

Comparison of Cross-sectional and Longitudinal Gene Expression Modeling. The Coefficient of Variation (CoV) was compared between two different approaches utilizing gene expression data to determine impact on development and performance of an FVC-gene predictor. The CoV was calculated for each gene by dividing the gene-specific standard deviation by the mean. Intra-subject CoV for each gene was then computed using the root mean square method, where d is the difference between two paired measurements and m is the mean of paired measurements (Hyslop & White, 2009).

Sample Classification. Sample and gene clustering based on a priori selected genes was performed using dChip software (Li, 2008) or R/Bioconductor package 'Complex-Heatmap' (Gu et al., 2016). Principle Component Analysis (PCA) was performed using R package 'FactoMine' (Husson et al., 2010).

Pathway Analyses. Gene expression changes (ΔGE) between baseline and 4 month visit were compared between FVC-D and FVC-S groups. Gene set enrichment analysis (GSEA; Subramanian et al., 2005) of ΔGE was conducted at whole transcriptome level to identify significant canonical pathways with the criterion of false discover rate (FDR) <10%. Positive enrichment scores (ES) represented longitudinal decrease of gene expressions from baseline to 4 month follow-up, while negative ES represented longitudinal increase in gene expressions in COMET training cohort.

Genes constituting the FVC-gene predictor were analyzed using R package "GOSim" (Alexa et al., 2006) with the criterion of q-value (Benjamini-Yekutieli adjusted p-value) <0.01 for biological process enrichment. Alternatively, ToppFun web application (Kaimal et al., 2010) was used for functional enrichment analysis of FVC-gene predictor.

Peripheral Plasma Proteomics. The COMET baseline plasma samples had previously been subjected to a proteomic aptmer-based assay (O'Dwyer et al., 2017). Levels of MMP7 (Rosas et al., 2008), CCL18 (PARC; Prasse et al., 2009; Hoffmann-Vold et al., 2016), and Periostin (POSTN; Naik et al., 2012; Tajiri et al., 2015; Ohta et al., 2017) and their predictive/prognostic performance of absolute change in FVC % predicted were extracted (Neighbors et al., 2018) and conducted as comparators for ROC/AUC analyses of the FVC-gene predictor. Peripheral blood was collected in EDTA-containing vacutainers at study centers and samples were prepared as described before (O'Dwyer et al., 2017). The SOMASCAN® proteomic assay has been described. In brief, each of the listed proteins is measured using a modified aptamer reagent and measured quantitatively in relative fluorescence units (RFU's) using a custom Agilent hybridization chip. Normalization and inter-run calibration were performed according to SOMASCAN® v3 assay data quality-control procedures as defined in the SomaLogic good laboratory practice quality system. A complete list of SOMASCAN® analytes can be found online via the website of Somalogic).

Example 1

Study Cohort Characteristics

Demographics, median follow-up time, median transcriptomic sampling timepoints and interquartile range (IQR), PFT, and outcomes for the COMET and validation cohorts are shown in Table 2. Twenty-two percent (16/74) of patients experienced FVC decline in the COMET training cohort and ranged from 30-63% in the validation cohorts, with the Imperial cohort having the highest prevalence of progressors. No significant differences were noted in the COMET training cohort with regard to demographics or lung function when stratifying by FVC decline (Table 3). The mean time from 2nd blood draw to the PFT follow-up was 12.1 months in UChicago, 6.5 months in UPMC, and 10.7 months in Imperial.

TABLE 2

Clinical Demographics in IPF Cohorts

| | COMET Cohort | | | | | | |
|---|---|---|---|---|---|---|---|
| Clinical | 0-4 | 0-8 | 4-8 | 0-12 | Independent Validation | | |
| Demographics | mo | mo | mo | mo | UChicago | UPMC | Imperial |
| Sample Size | 74 | 67 | 67 | 59 | 27 | 35 | 24 |
| GE sampling duration Median (IRQ) | 4 mo (n/a) | 8 mo (n/a) | 4 mo (n/a) | 12 mo (n/a) | 16.6 mo (9.3-25.9) | 6 mo (2-8) | 6 mo (n/a) |
| FVC follow-up Median (IRQ) | 12 mo (n/a) | 12 mo (n/a) | 12 mo (n/a) | 12 mo (n/a) | 28 mo (20.2-35.8) | 13 mo (10-16) | 12 mo (7.8-16.2) |
| Sex (M/F) | 52/22 | 47/20 | 47/20 | 44/15 | 19/8 | 2114 | 18/6 |
| Caucasian (%) | 94.6 | 94.0 | 94.0 | 94.9 | 85.2 | 92.3 | 94.3 |
| Smokers (%) | 66.2 | 67.2 | 70.1 | 67.8 | 48.1 | 73.1 | 57.1 |
| Age (average) | 66.6 | 67.0 | 67.5 | 65.9 | 66.7 | 68.3 | 66.8 |
| FVC (Stable/Progressor) | 58/16 | 54/13 | 54/13 | 45/14 | 19/8 | 23/12 | 9/15 |
| DLCO (Stable/Progressor) | 48/26 | 42/25 | 43/24 | 40/19 | 9/14 | 15/20 | 5/17 |

TABLE 3

Stratification of COMET Training Cohort by FVC Status

| FVC Status* | Sex (M/F) | Race[#] (C/O) | Smoker (Y/N) | Age (Mean) | Baseline[1] FVC_pp | Baseline[2] DLCO_pp |
|---|---|---|---|---|---|---|
| Stable | 41/17 | 55/3 | 38/20 | 67.4 | 71.6 | 46.4 |
| Progressive | 11/5 | 15/1 | 10/6 | 63.7 | 62.6 | 42.7 |

*FVC status was defined as relative decline of FVC % of predicted over 12 months from baseline.
[#]Race (C/O): Caucasian or Others; [1]FVC_pp: FVC percent of predicted; [2]DLCO_pp: DLCO percent of predicted.

Example 2

FVC-Gene Predictor Training

Figure 1B:
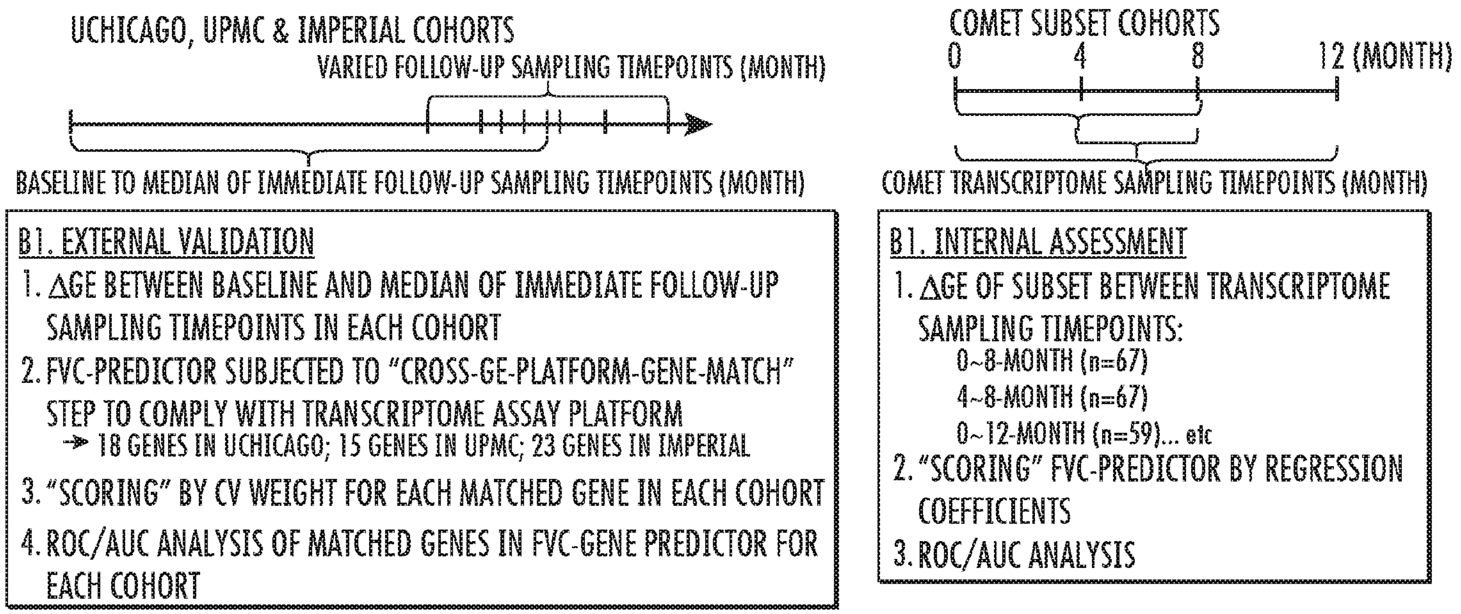
Figure 2A:
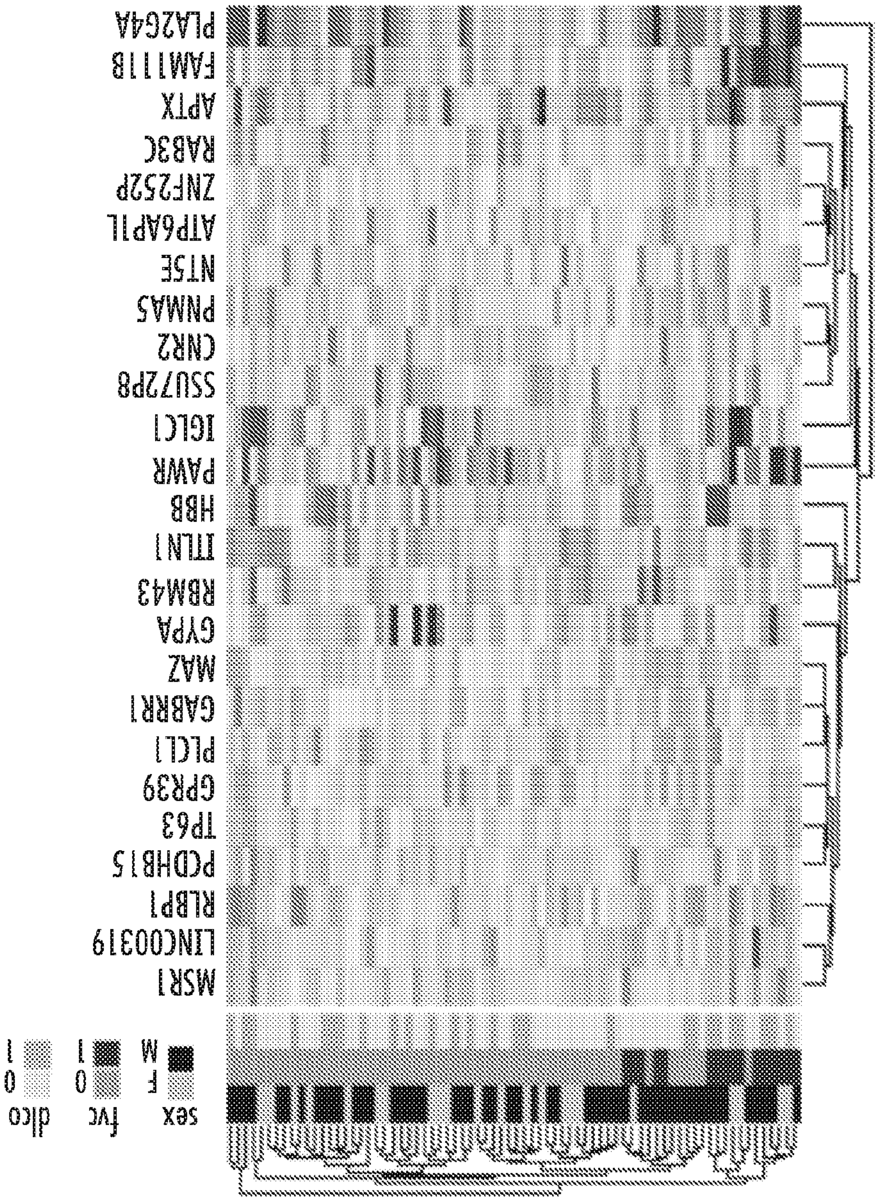
FIGS. 2A-2C. Classification of COMET training cohort using the genes constituted FVC-gene predictor.
Figure 2B:
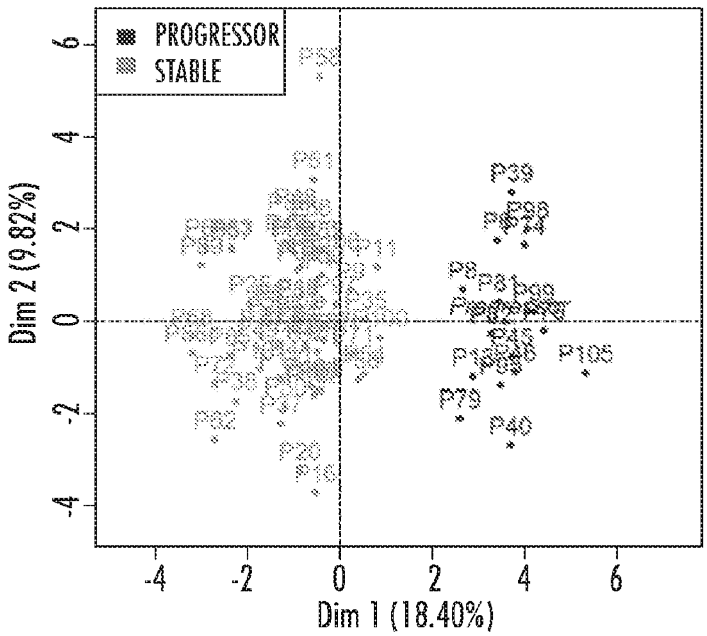
Figure 2C:
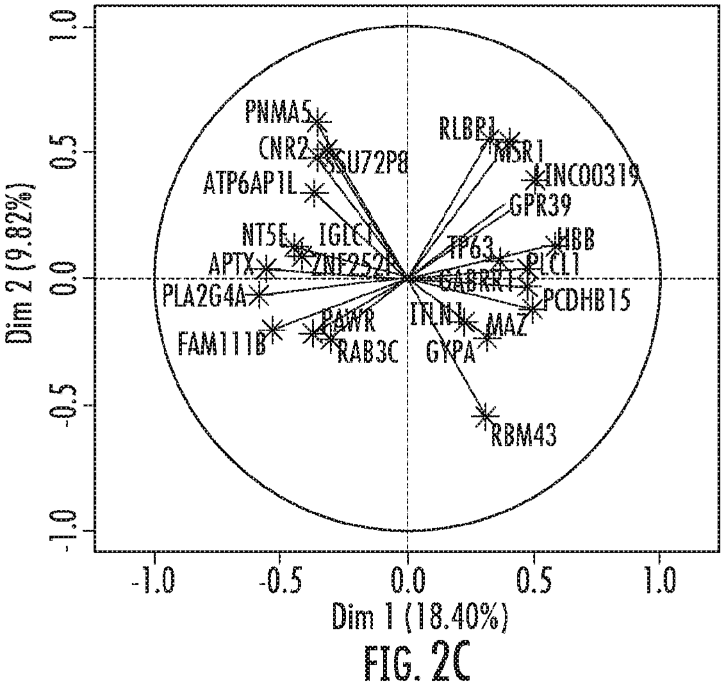

A flowchart of study design and data analysis processes is illustrated in FIGS. 1A and 1B. An empirical Bayes moderated t-test identified 3906 probe-sets at FDR<0.05 predictive of FVC decline using ΔGE training data (FIG. 1A-2). LASSO regression further reduced this to 39 genes identified, which correctly classified 88% (n=65/74) of patients in the training set. 25 out of the 39 genes displaying ≥500 cross-validation support were prioritized (FIGS. 1A-4) and these genes were employed to develop the FVC-gene predictor score based on LASSO regression coefficients (Table 4). Hierarchical clustering discriminated FVC decline, while having no association with DLCO decline (FIG. 2A). PCA map of the training data confirmed the distinct separation of stable and progressive patients (FIG. 2B). The PCA variables factor map aligned the direction of association of individual genes with these groups (FIG. 2C).

TABLE 4

List of 25 Genes, LASSO Regression Coefficient and Percent of 10-Fold Cross Validation (CV) Support of Each Gene Consists of the FVC-classifier

| Gene Symbol* | Gene Description | LASSO Regression Coefficient | % CV Support |
|---|---|---|---|
| APTX | Aprataxin | −1.38 | 60 |
| ATP6AP1L | ATPase H+ transporting accessory protein 1 like | −2.08 | 70 |
| CNR2 | Cannabinoid receptor 2 | −1.066 | 100 |
| FAM111B | Family with sequence similarity 111 member B | −0.601 | 50 |
| GABRR1 | γ-aminobutyric acid type A receptor rho1 subunit | 0.058 | 50 |
| GPR39 | G protein-coupled receptor 39 | 0.706 | 50 |
| GYPA | Glycophorin A (MNS blood group) | 0.029 | 60 |
| HBB | Hemoglobin subunit beta | 0.037 | 60 |
| IGLC1 | Immunoglobulin lambda constant 1 | $4.9 \times 10^{-4}$ | 70 |
| ITLN1 | Intelectin 1 | 3.44 | 100 |
| LINC00319 | Long intergenic non-protein coding RNA 319 | 4.758 | 100 |
| MAZ | MYC associated zinc finger protein | 2.188 | 80 |
| MSR1 | Macrophage scavenger receptor 1 | 2.157 | 90 |
| NT5E | 5'-nucleotidase ecto | −3.361 | 80 |
| PAWR | Pro-apoptotic WT1 regulator | −0.515 | 50 |
| PCDHB15 | Protocadherin beta 15 | 3.521 | 100 |
| PLA2G4A | Phospholipase A2 group IVA | −0.542 | 80 |
| PLCL1 | Phospholipase C like 1 (inactive) | 0.617 | 50 |
| PNMA5 | PNMA family member 5 | −0.942 | 60 |
| RAB3C | RAB3C, RAS oncogene family | −2.218 | 100 |
| RBM43 | RNA binding motif protein 43 | 0.284 | 50 |
| RLBP1 | Retinaldehyde binding protein 1 | 0.038 | 60 |

TABLE 4-continued

List of 25 Genes, LASSO Regression Coefficient and Percent of 10-Fold Cross Validation (CV) Support of Each Gene Consists of the FVC-classifier

| Gene Symbol* | Gene Description | LASSO Regression Coefficient | % CV Support |
|---|---|---|---|
| SSU72P8 | SSU72 pseudogene 8 | −1.367 | 90 |
| TP63 | Tumor protein p63 | 1.71 | 70 |
| ZNF252P | Zinc finger protein 252, pseudogene | −0.289 | 70 |

*FVC-classifier genes were prioritized from COMET training cohort as described in FIGS. 1A and 1B.

Example 3

FVC-Gene Predictor Validation

A "cross-platform-gene-match" step to account for transcriptome assay platform differences yielded an overlap of 72% (18/25), 60% (15/25), and 92% (23/25) genes in UChicago, UPMC, and Imperial datasets, respectively (FIG. 1B-2).

Figure 3A:
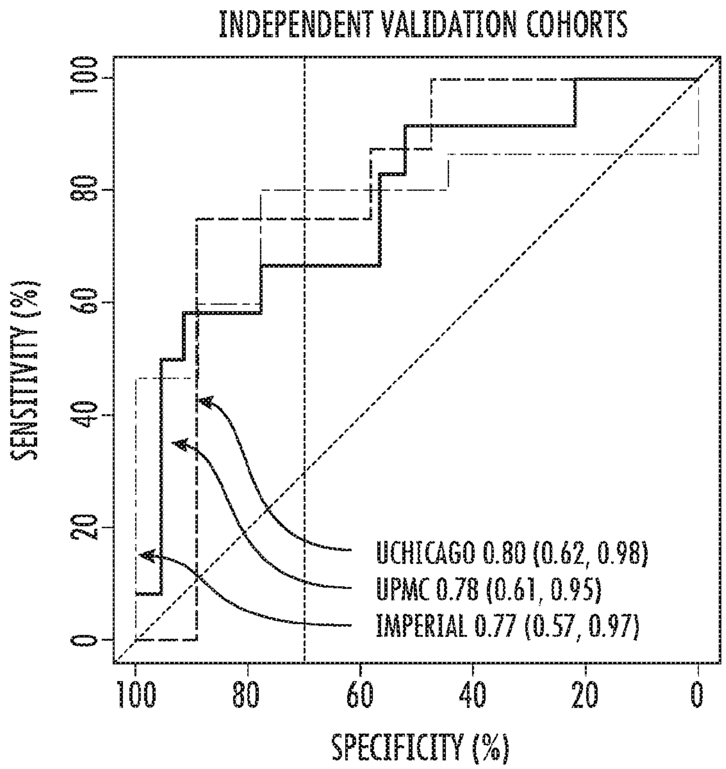
FIGS. 3A-3C. Receiver-Operating-Characteristic (ROC) and Area Under the Curve (AUC) analysis of FVC-gene predictor. AUC values with 95% confidence intervals are displayed in right bottom of each graph. Dotted red line denotes specificity at 75%.
Figure 4A:
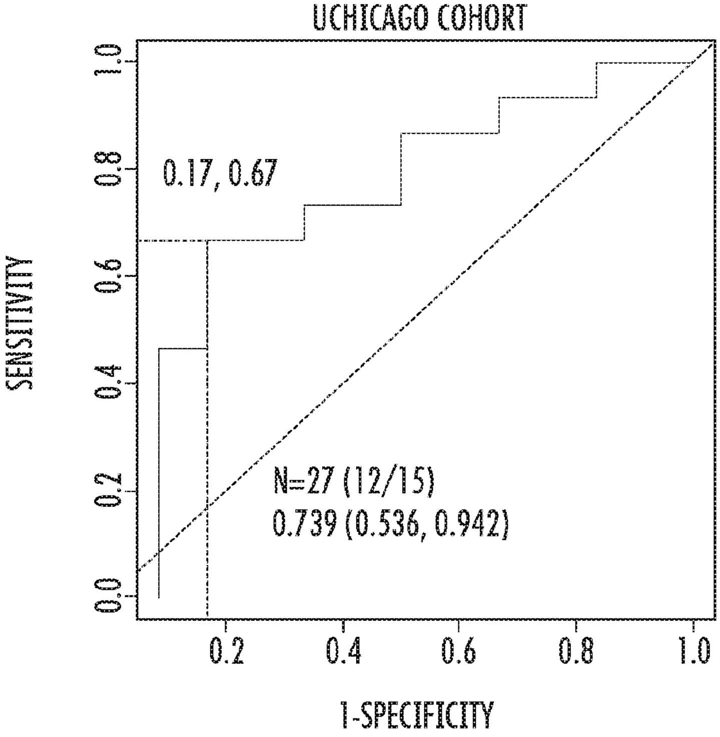
FIGS. 4A-4C. Receiver-Operating-Characteristic (ROC) analysis and area under curve (AUC) of FVC-gene predictor in three independent validation cohorts when FVC decline event was defined as ≥5% relative decline in FVC % of predicted.
Figure 4B:
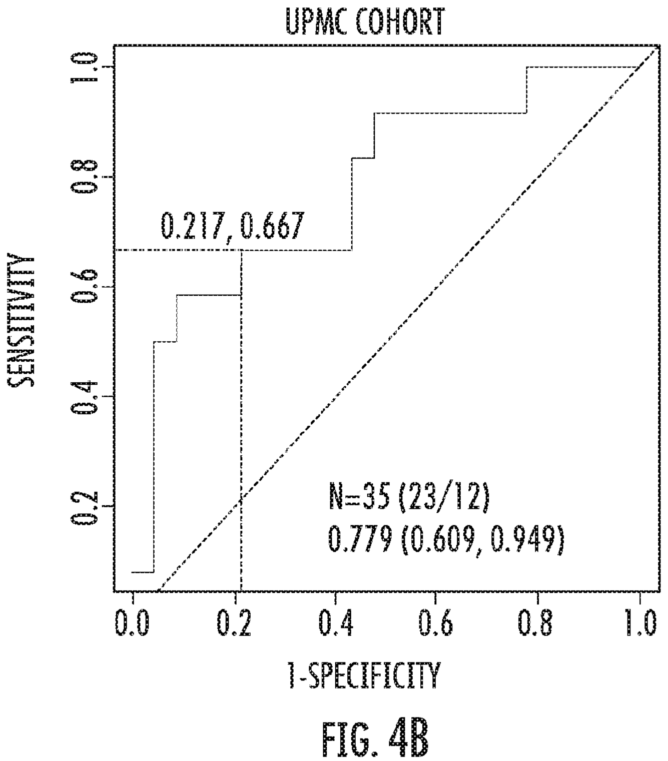
Figure 4C:
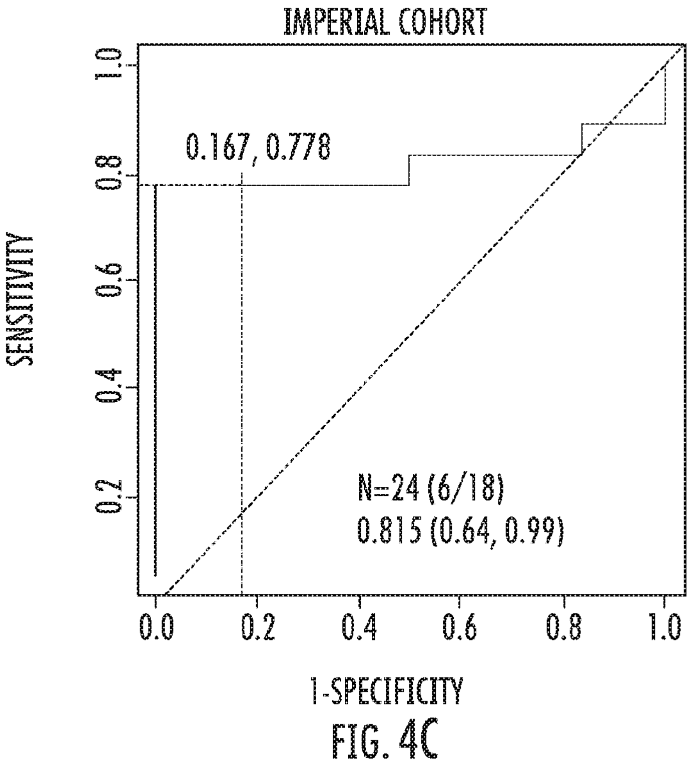

FVC-gene predictor test performance across validation cohorts is shown in Table 5. Sensitivity and specificity were 1.0 in the training cohort and 0.67-0.8 and 0.78-0.89, respectively in the validation cohorts. Positive predictive values (PPV) ranged from 0.62 to 0.86 and negative predictive values (NPV) ranged from 0.7 to 0.89. ROC analysis revealed AUCs of 0.80, 0.78 and 0.77 in UChicago, UPMC, and Imperial cohort, respectively (FIG. 3A). At an anchored specificity of −75%, the sensitivities are 75.0%, 66.7%, and 80.0%, for UChicago, UPMC and Imperial cohorts, respectively. Aggregation of validation cohorts provided a sensitivity/specificity of 74.3%/82.4% with PPV/NPV of 0.74/0.82 (Table 5). AUCs for 5% FVC decline in validation cohorts were 0.74, 0.78, and 0.82 in UChicago, UPMC, and Imperial, respectively (FIGS. 4A-4C).

Example 4

Sensitivity Analysis of Transcriptomic Sampling Timepoints

Figure 3B:
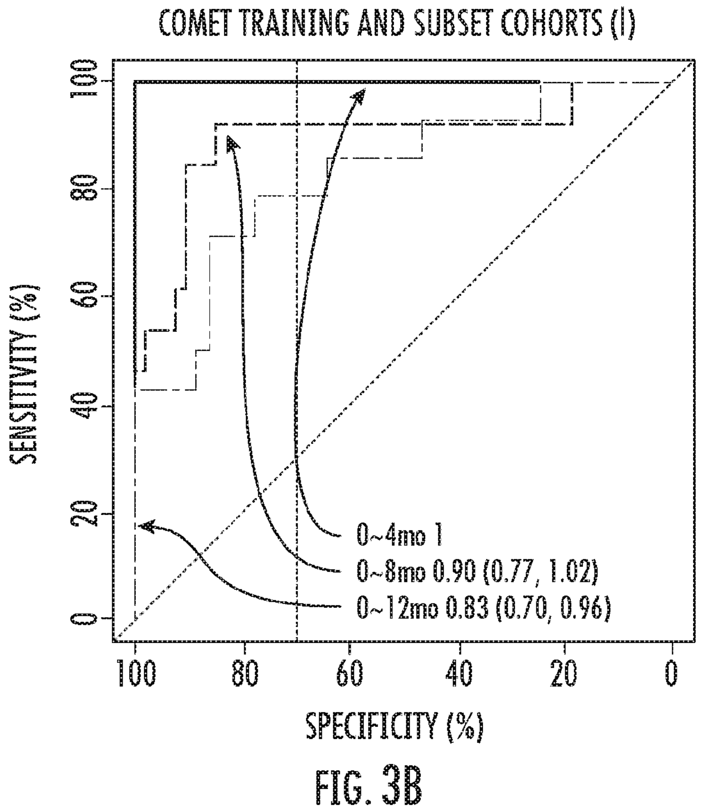
Figure 3C:
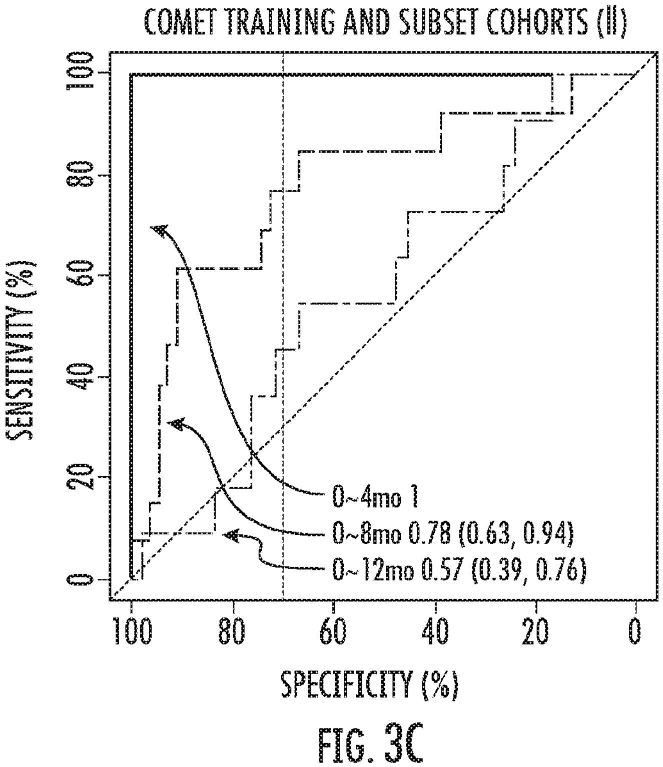
Figure 5A:
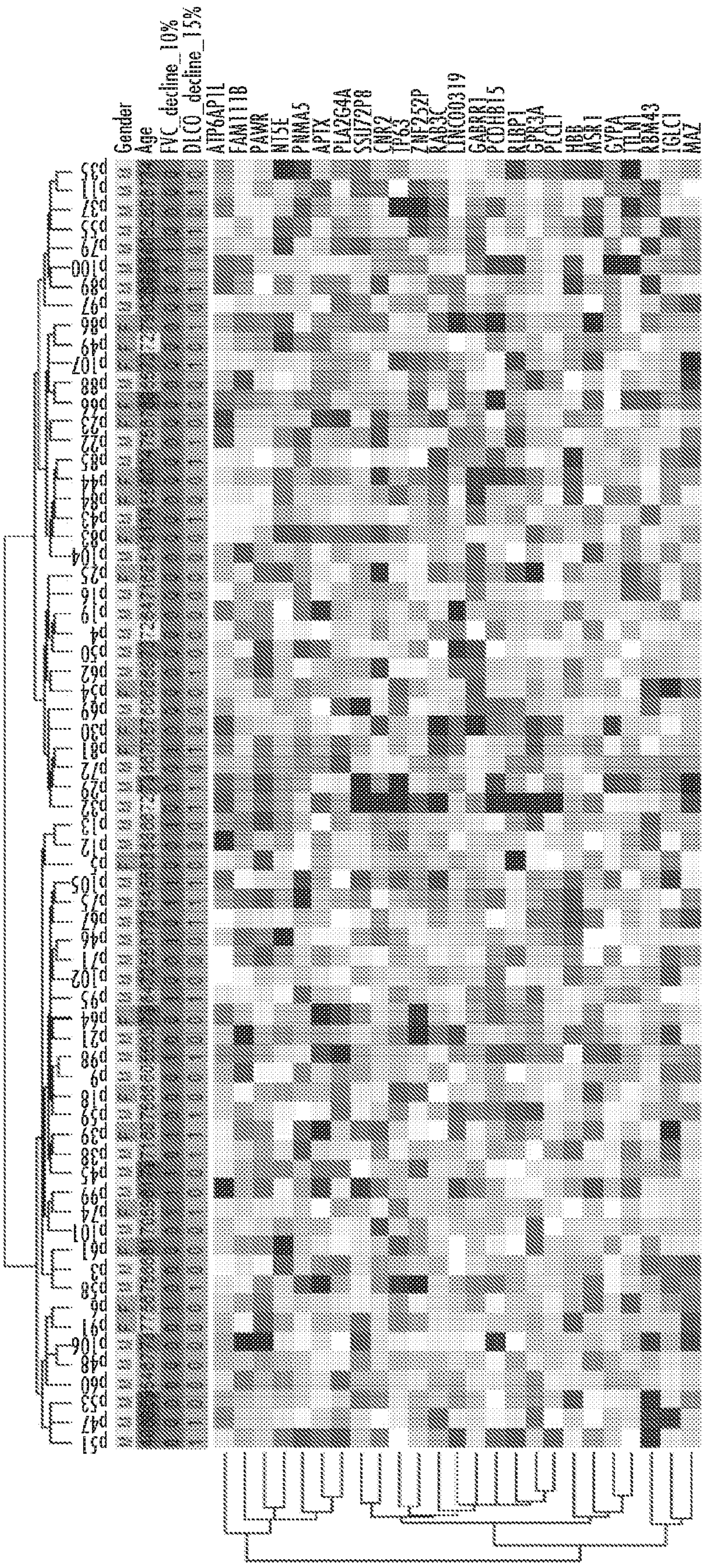
FIGS. 5A-5C. Hierarchical clustering of subsets of COMET cohort based on FVC-gene predictor. Hierarchical clustering of the IPF patients in three COMET subsets with GE sampling duration (in months) of 0-8 month (FIG. 5A), 4-8 month (FIG. 5B), and 0-12 month (FIG. 5C), respectively. Red, white, and blue color in the color version of FIG. 5A indicate ΔGE values above, at, or below the average ΔGE of the corresponding gene. 85%-92% of FVC decline (FVC=1) were enriched in the left cluster, while the FVC stable (FVC=0) patients were classified mainly in the right cluster. The FVC event duration (in months) is defined at < or ≥10% relative decline of FVC % of prediction over 12 months for all three groups.
Figure 5B:
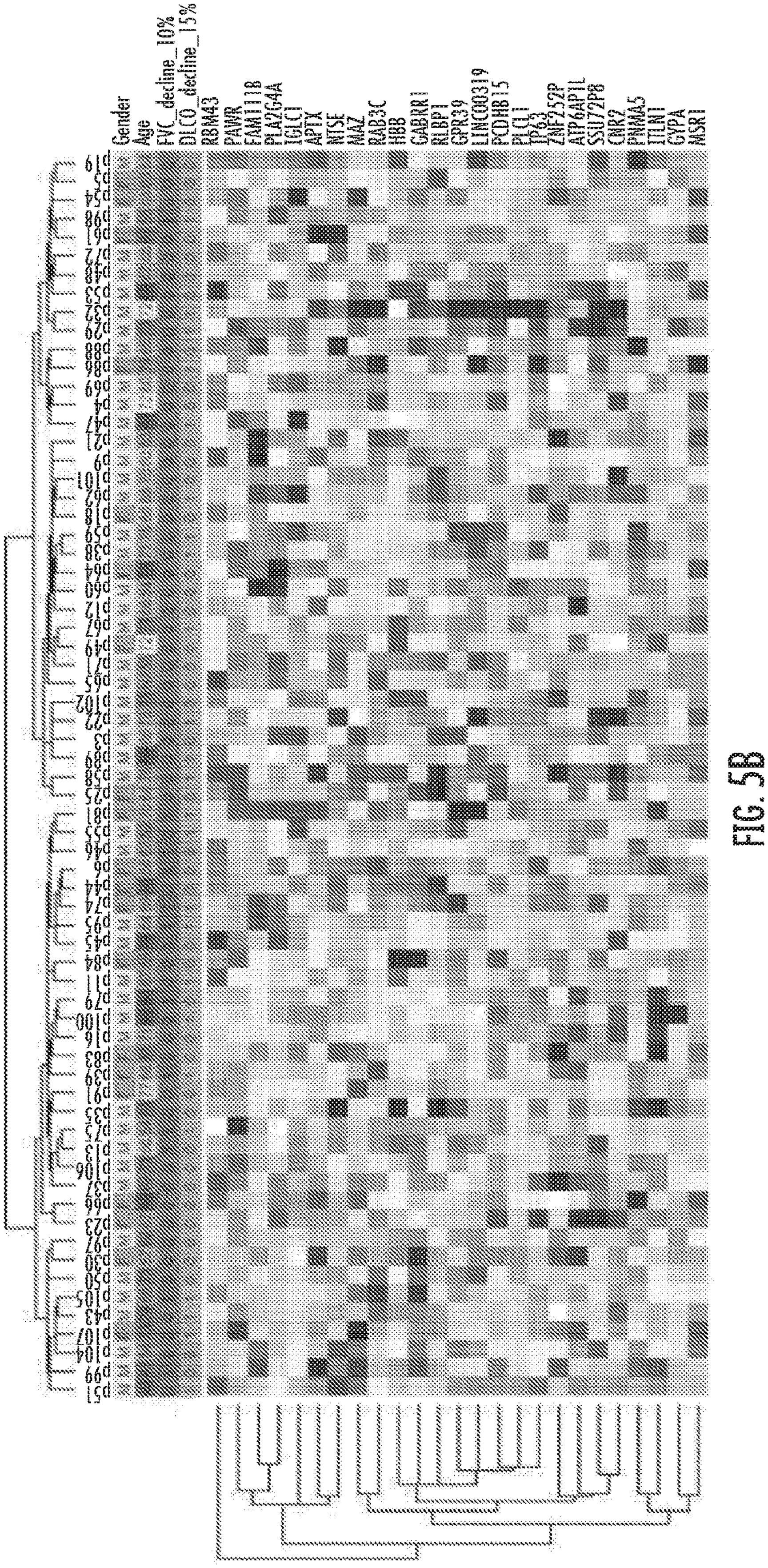
Figure 5C:
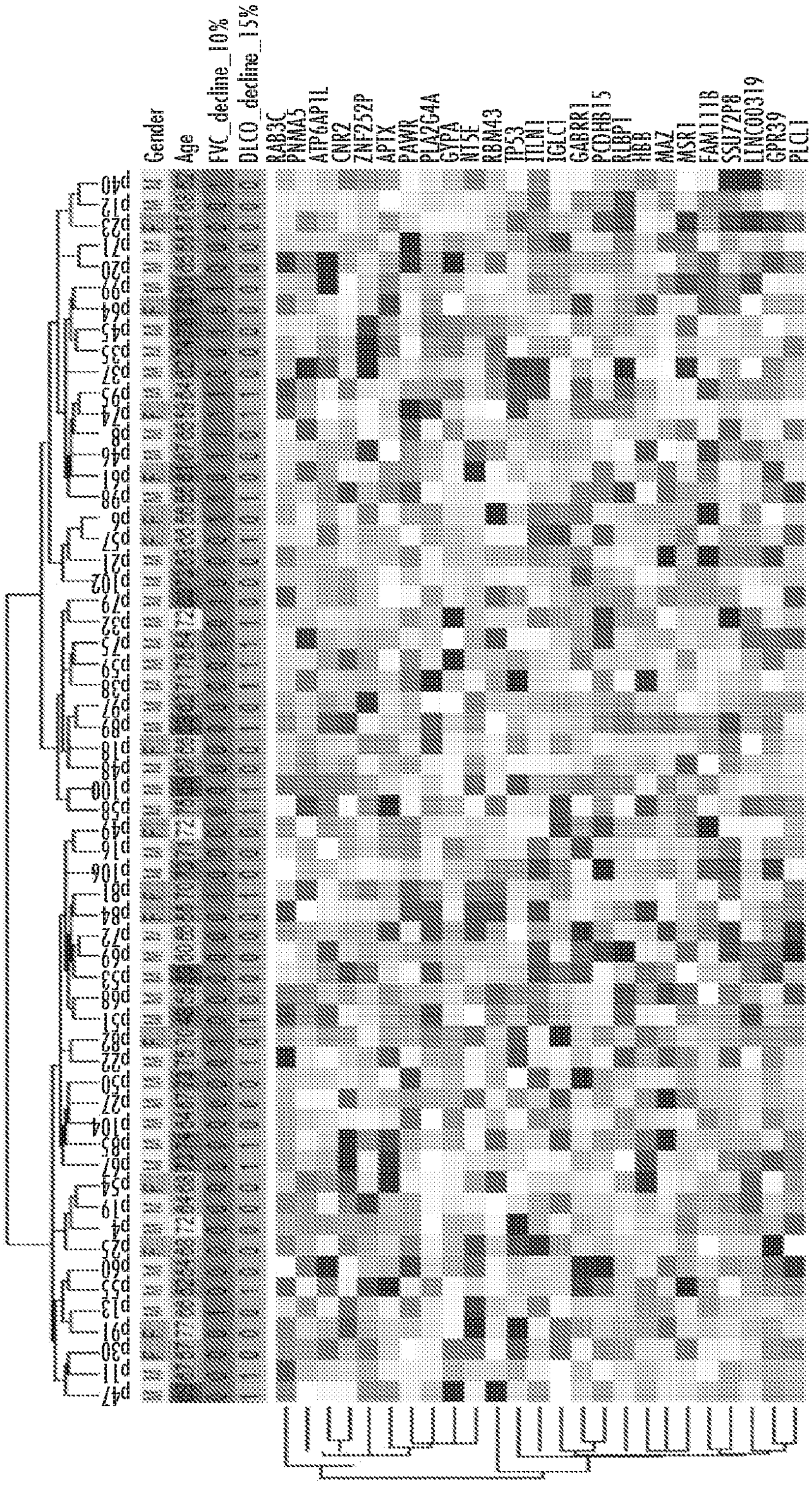
Figure 6A:
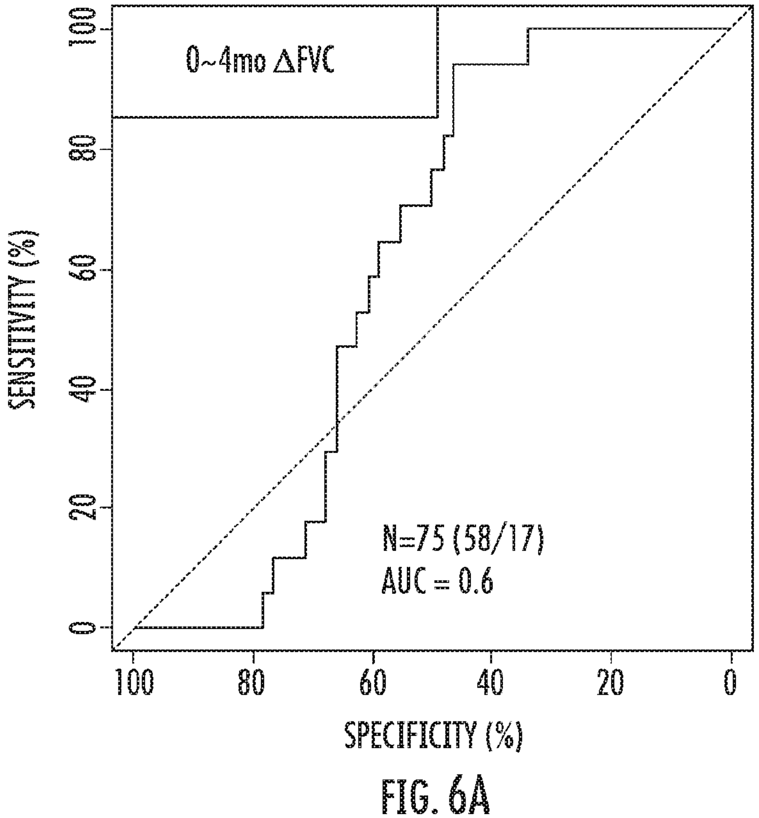
FIGS. 6A-6D. ROC analysis and AUC curve of early (0-4 month) FVC change and peripheral plasma biomarkers in prediction of FVC decline at 12 month.
Figure 6B:
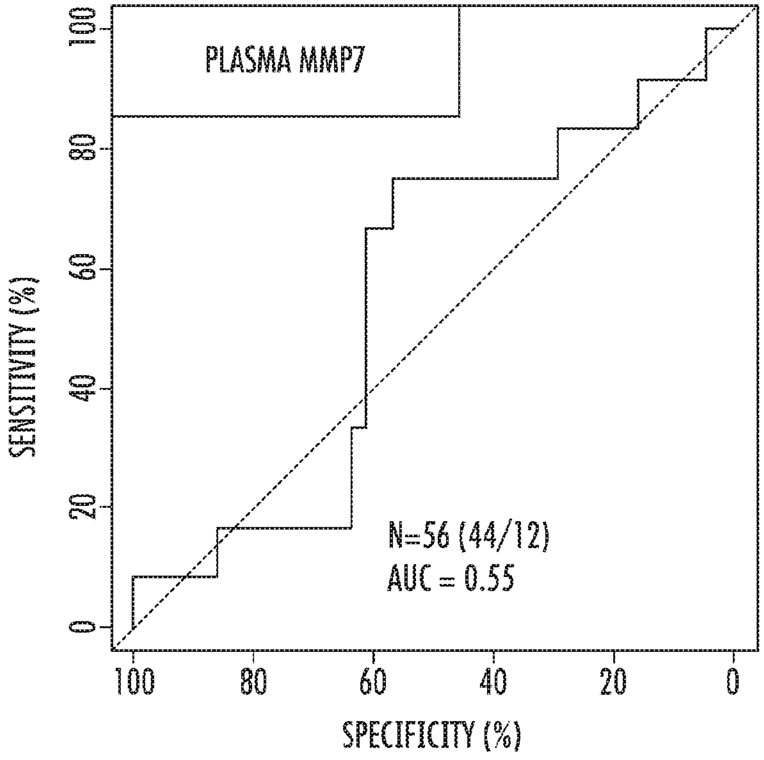
Figure 6C:
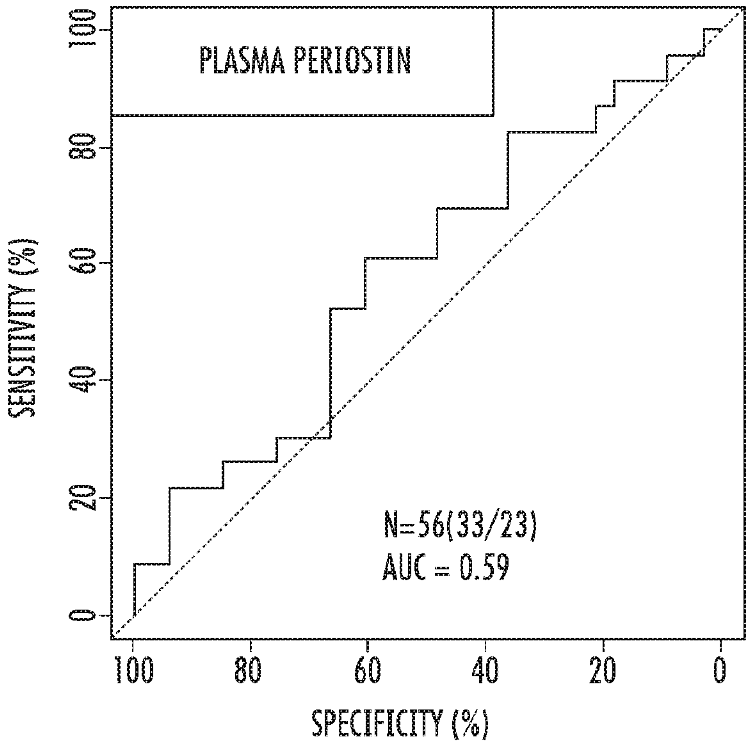
Figure 6D:
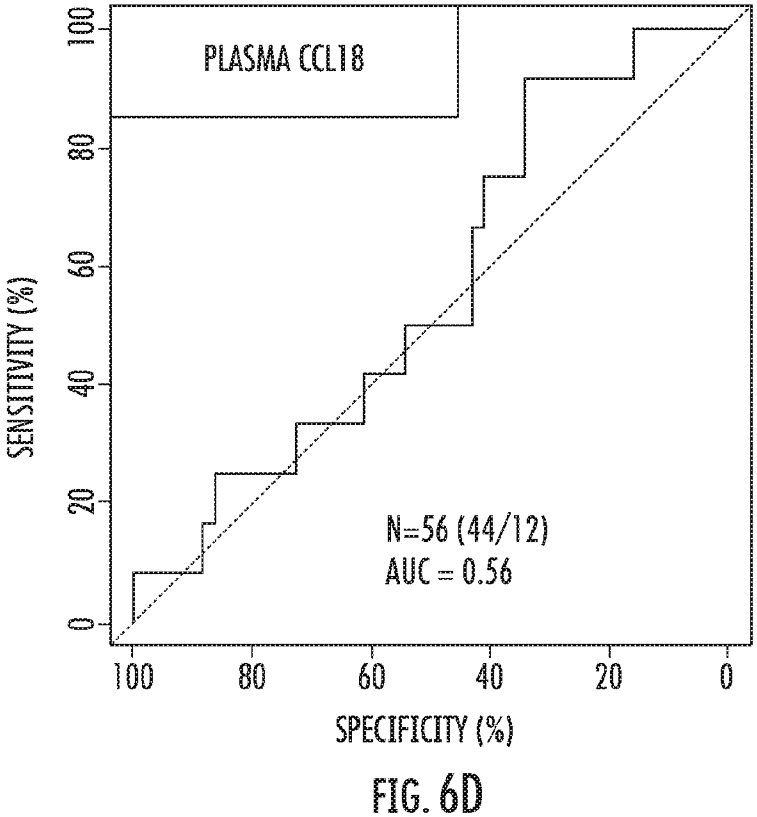

FVC-gene predictor hierarchical clustering (FIG. 5A-5C) and test performance was assessed at other available transcriptomic sampling timepoints in the COMET training cohort (Table 5). Like the 0-4 month timepoint, patients with FVC decline clustered, while those with DLCO decline did not. ROC analysis of the FVC-gene predictor varied with transcriptome sampling timepoints and demonstrated performance decay with increasing time (FIG. 3B). The optimal prediction sensitivity ranged from 0.79 to 0.92, while optimal specificity ranged from 0.67 to 0.85 in the COMET subsets (Table 6). Varying the baseline resulted in worsening test performance as the time from blood draw to FVC measurement decreased (FIG. 3C).

TABLE 5

| FVC-gene Predictor Test Performance | | | | | | | | | | |
|---|---|---|---|---|---|---|---|---|---|---|
| | Training Cohort | | Validation Cohorts | | | | | | | |
| | COMET | | UChicago | | UPMC | | Imperial | | Combined | |
| ROC Test | Observed ≥10% FV Decline | | | | | | | | | |
| Results | (+) | (−) | (+) | (−) | (+) | (−) | (+) | (−) | (+) | (−) |
| Predicted (+) | 16 | 0 | 6 | 2 | 8 | 5 | 12 | 2 | 26 | 9 |
| Predicted (−) | 0 | 58 | 2 | 17 | 4 | 18 | 3 | 7 | 9 | 42 |
| Sensitivity | 1 | | 0.75 | | 0.67 | | 0.80 | | 0.74 | |
| Specificity | 1 | | 0.89 | | 0.78 | | 0.78 | | 0.82 | |
| PPV | 1 | | 0.75 | | 0.62 | | 0.86 | | 0.74 | |
| NPV | 1 | | 0.89 | | 0.82 | | 0.70 | | 0.82 | |
| LR (+) | — | | 6.82 | | 3.05 | | 3.64 | | 4.11 | |
| LR (−) | — | | 0.28 | | 0.42 | | 0.26 | | 0.32 | |

ROC = Receiver-Operating-Characteristics;
PPV = Positive Predictive Value,
NPV = Negative Predictive Value;
LR = Likelihood Ratio

TABLE 6

Receiver-Operating-Characteristic and Area-under-the-Curve Analyses of FVC-gene Predictor for COMET Tand Each COMET Subset Cohort

| Cohort (GE sampling duration) | Sample size (Stable/ progressive) | *AUC (95% CI) | Optimal Sensitivity/ Specificity | Sensitivity of anchored specificity at ~75% |
|---|---|---|---|---|
| COMET (0-4 mo) | 74 (58/16) | 1.00 | 100/100 | 100 |
| COMET (0-8 mo) | 67 (54/13) | 0.90 (0.77, 1.02) | 92.3/85.2 | 92.3 |
| COMET (0-12 mo) | 59 (45/14) | 0.83 (0.7, 0.96) | 78.6/77.8 | 78.6 |
| COMET (4-8 mo) | 67 (55/12) | 0.78 (0.63, 0.94) | 84.6/66.7 | 69.2 |
| COMET (8-12 mo) | 59 (45/14) | 0.57 (0.39 0.76) | NA | 36.4 |

*Area-Under-Curve and 95% confidence intervals in ROC analysis of FVC-gene predictor score for ≥10% relative decline in FVC percent of predicted.

Example 5

Comparative Analysis Between FVC-Gene Predictor and Cross-Sectional Biomarkers Test performance in predicting FVC decline was compared between the FVC-gene predictor, 4 month change in FVC, and circulating plasma MMP7, POSTN, and CCL18. The FVC-gene predictor outperformed each of these clinical and cross-sectional biomarkers (FIG. 6A-6D).

Example 6

Pathway and Functional Analyses

Figure 7A:
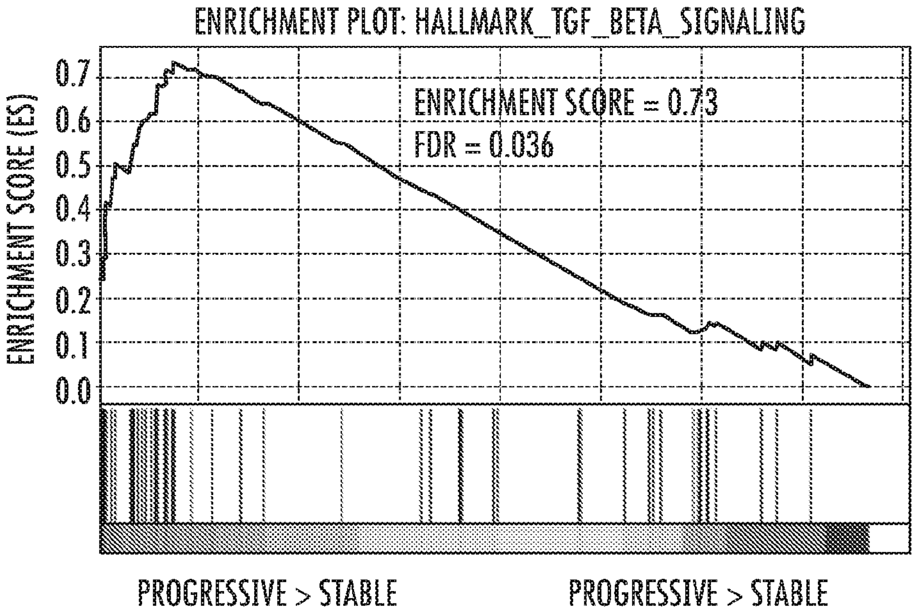
FIGS. 7A and 7B. Gene Set Enrichment Analysis (GSEA) of COMET longitudinal 0-4 month gene expression changes between progressive and stable IPF patients. Enrichment plots of significant functional gene sets expression changes of 19394 annotated genes from baseline to 4 month were analyzed for their differential functional profiles between progressive FVC and stable FVC patients.

Gene Set Enrichment Analysis (GSEA) of 19394 annotated genes in the ΔGE data of COMET training cohort identified several functional pathways. ΔGE of 27 hallmark genes in TGF-beta signaling were higher in progressive patients than in patients with stable disease course (FIG. 7A; FDR=0.036). The gene list, their description, and features related to GSEA score enrichment are shown in Table 7 and included transforming growth factor, beta 1 and its receptor (TGF-β1 & TGFBR1), and SMAD, mothers against DPP homolog 6 & 7 (SMAD6, SMAD7).

TABLE 7

List of Hallmark Genes in TGF-beta Signaling Enriched in GSEA Analysis

| Gene symbol | Gene description | Rank in gene list | Rank metric score | Running enrichment score* |
|---|---|---|---|---|
| SERPINE1 | serpin peptidase inhibitor, clade E (nexin, plasminogen activator inhibitor type 1), member 1 | 16 | 1.581 | 0.064 |
| SKIL | SKI-like | 24 | 1.534 | 0.127 |
| PMEPA1 | prostate transmembrane protein, androgen induced 1 | 25 | 1.533 | 0.190 |
| SMAD7 | SMAD, mothers against DPP homolog 7 | 36 | 1.406 | 0.248 |
| SMAD6 | SMAD, mothers against DPP homolog 6 | 84 | 1.136 | 0.292 |
| THBS1 | thrombospondin 1 | 117 | 1.057 | 0.334 |
| SKI | v-ski sarcoma viral oncogene homolog (avian) | 131 | 1.029 | 0.376 |
| SMURF1 | SMAD specific E3 ubiquitin protein ligase 1 | 152 | 0.997 | 0.416 |
| CTNNB1 | catenin (cadherin-associated protein), beta 1, 88 kDa | 298 | 0.809 | 0.442 |
| ENG | endoglin (Osler-Rendu-Weber syndrome 1) | 316 | 0.796 | 0.474 |
| TGIF1 | TGFB induced factor homeobox 1 | 365 | 0.764 | 0.503 |
| TGFBR1 | transforming growth factor, beta receptor 1 (activin A receptor type II-like kinase, 53 kDa) | 756 | 0.578 | 0.506 |
| SMURF2 | SMAD specific E3 ubiquitin protein ligase 2 | 803 | 0.564 | 0.527 |
| TRIM33 | tripartite motif-containing 33 | 844 | 0.551 | 0.547 |
| BCAR3 | breast cancer anti-estrogen resistance 3 | 969 | 0.511 | 0.562 |
| TGFB1 | transforming growth factor, beta 1 (Camurati-Engelmann disease) | 978 | 0.509 | 0.583 |
| ID3 | inhibitor of DNA binding 3, dominant negative helix-loop-helix protein | 1061 | 0.490 | 0.599 |
| BMP2 | bone morphogenetic protein 2 | 1178 | 0.460 | 0.611 |
| IFNGR2 | interferon gamma receptor 2 (interferon gamma transducer 1) | 1322 | 0.428 | 0.622 |
| CDK9 | cyclin-dependent kinase 9 (CDC2-related kinase) | 1377 | 0.416 | 0.636 |
| FURIN | furin (paired basic amino acid cleaving enzyme) | 1409 | 0.407 | 0.651 |
| SMAD3 | SMAD, mothers against DPP homolog 3 (Drosophila) | 1436 | 0.400 | 0.666 |
| SPTBN1 | spectrin, beta, non-erythrocytic 1 | 1453 | 0.397 | 0.682 |
| ID1 | inhibitor of DNA binding 1, dominant negative helix-loop-helix protein | 1642 | 0.363 | 0.687 |
| PPM1A | protein phosphatase 1A (formerly 2C), magnesium-dependent, alpha isoform | 1662 | 0.358 | 0.701 |
| UBE2D3 | ubiquitin-conjugating enzyme E2D 3 (UBC4/5 homolog, yeast) | 1663 | 0.358 | 0.715 |
| NCOR2 | nuclear receptor co-repressor 2 | 1821 | 0.331 | 0.721 |

Figure 7B:
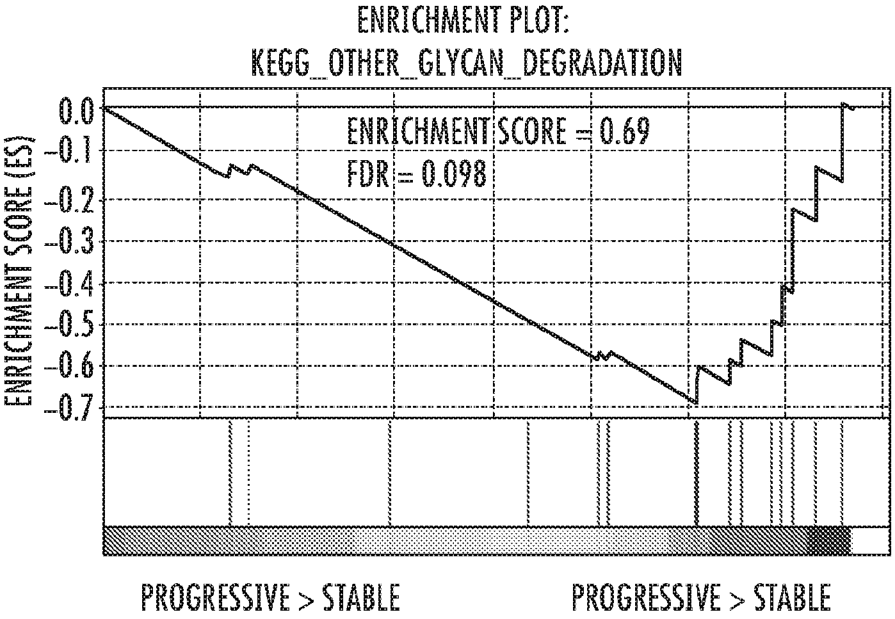

In contrast, ΔGE values of genes involved in Glycan degradation activity were expressed higher in those in the stable group than progressive group (FIG. 7B; Table 8).

TABLE 8

List of Hallmark Genes in TGF-beta Signaling Enriched in GSEA Analysis

| Gene symbol | Gene description | Rank in gene list | Rank metric score | Running enrichment score* |
|---|---|---|---|---|
| ENGASE | endo-beta-N-acetylglucosaminidase | 15208 | −0.234 | −0.603 |
| NEU1 | sialidase 1 (lysosomal sialidase) | 16048 | −0.315 | −0.588 |

TABLE 8-continued

List of Hallmark Genes in TGF-beta Signaling Enriched in GSEA Analysis

| Gene symbol | Gene description | Rank in gene list | Rank metric score | Running enrichment score* |
|---|---|---|---|---|
| HEXB | hexosaminidase B (beta polypeptide) | 16379 | −0.348 | −0.540 |
| MAN2B2 | mannosidase, alpha, class 2B, member 2 | 17153 | −0.448 | −0.496 |
| FUCA2 | fucosidase, alpha-L-2, plasma | 17376 | −0.482 | −0.417 |
| FUCA1 | fucosidase, alpha-L-1, tissue | 17657 | −0.529 | −0.333 |
| AGA | aspartylglucosaminidase | 17683 | −0.532 | −0.234 |
| GBA | glucosidase, beta; acid (includes glucosylceramidase) | 18292 | −0.681 | −0.139 |
| GLB1 | galactosidase, beta 1 | 18945 | −0.986 | 0.012 |

Functional analysis by TopGene and GOsim of the 25 genes prioritized for the predictor revealed enrichment in "Response to hydrogen peroxide", "Pulmonary fibrosis" (Table 9), and "receptor-mediated endocytosis", "positive regulation of fibroblast apoptotic process" (Table 10), respectively.

TABLE 9

TopGene Functional Enrichment of FVC-Classifier

| Function | ID | Name | FDR |
|---|---|---|---|
| GO | GO:0042542 | Response to hydrogen peroxide | $1.56 \times 10^{-2}$ |
| GO | GO:0010035 | Response to inorganic substance | $1.56 \times 10^{-2}$ |
| DisGeNET Curated | C0003504 | Aortic Valve Insufficiency | $2.31 \times 10^{-2}$ |
| DisGeNET Curated | C4025735 | Nonspherocytic hemolytic anemia | $2.31 \times 10^{-2}$ |
| Clinical Variations | cv:C1970028 | Susceptibility to malaria | $2.31 \times 10^{-2}$ |
| OMIM | OMIM:611162 | Malaria, susceptibility to | $2.31 \times 10^{-2}$ |
| DisGeNET Curated | C0034069 | Pulmonary Fibrosis | $2.31 \times 10^{-2}$ |

TABLE 10

TopGene Functional Enrichment of FVC-Classifier

| Gene Ontology Slim | Adj. p-value | Symbol |
|---|---|---|
| Gamma-aminobutyric acid signaling pathway | 0.0005 | GABRR1; PLCL1 |
| Phagocytosis, engulfment | 0.0022 | IGLC1; MSR1 |
| AMP catabolic process | 0.0026 | NT5E |
| Termination of RNA polymerase II transcription | 0.0031 | SSU72; MAZ |
| Nitric oxide transport | 0.0039 | HBB |
| Response to nematode | 0.0039 | ITLN1 |
| Receptor-mediated endocytosis | 0.0048 | HBB; IGLC1; MSR1 |
| Positive regulation of hydrogen peroxide-mediated programmed cell death | 0.0051 | PAWR |
| Platelet activating factor biosynthetic process | 0.0051 | PLA2G4A |
| Negative regulation of nitric-oxide synthase activity | 0.0090 | CNR2 |
| Positive regulation of cholesterol storage | 0.0090 | MSR1 |

TABLE 10-continued

TopGene Functional Enrichment of FVC-Classifier

| Gene Ontology Slim | Adj. p-value | Symbol |
|---|---|---|
| Positive regulation of fibroblast apoptotic process | 0.0090 | TP63 |
| Negative regulation of inflammatory response | 0.0097 | CNR2; NT5E |
| Response to hydrogen peroxide | 0.0097 | HBB; PAWR; APTX |

Example 7

Figure 8A:
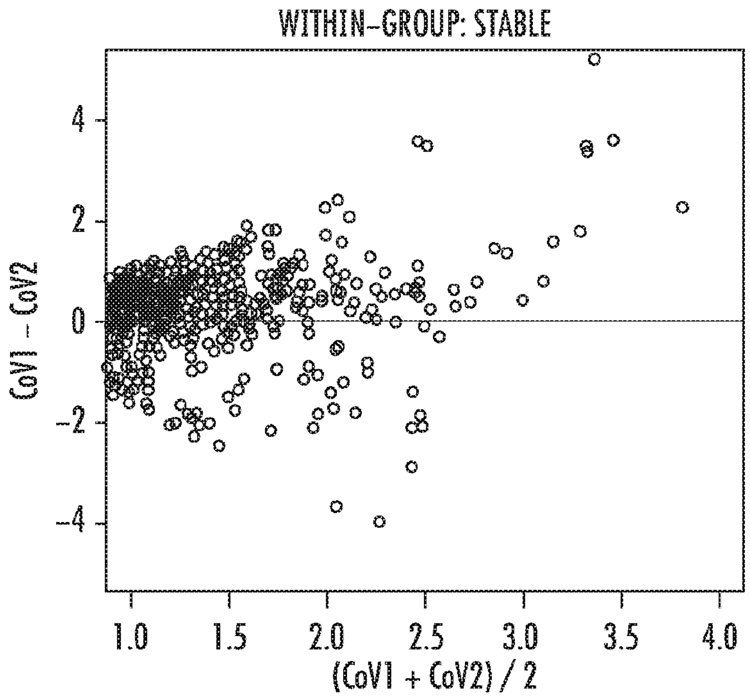
FIGS. 8A-8D. Coefficient of Variation (CoV) analysis and power estimation of COMET cohort data. Training data represents gene expression difference (ΔGE) between baseline and 4 month follow-up, whereas baseline data represents cross-sectional gene expressions (GE).
Figure 8B:
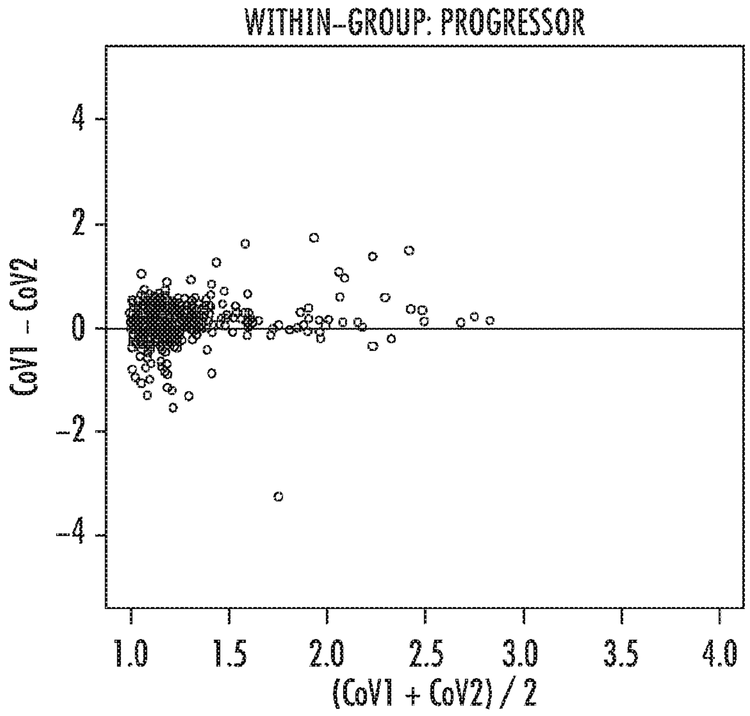
Figure 8C:
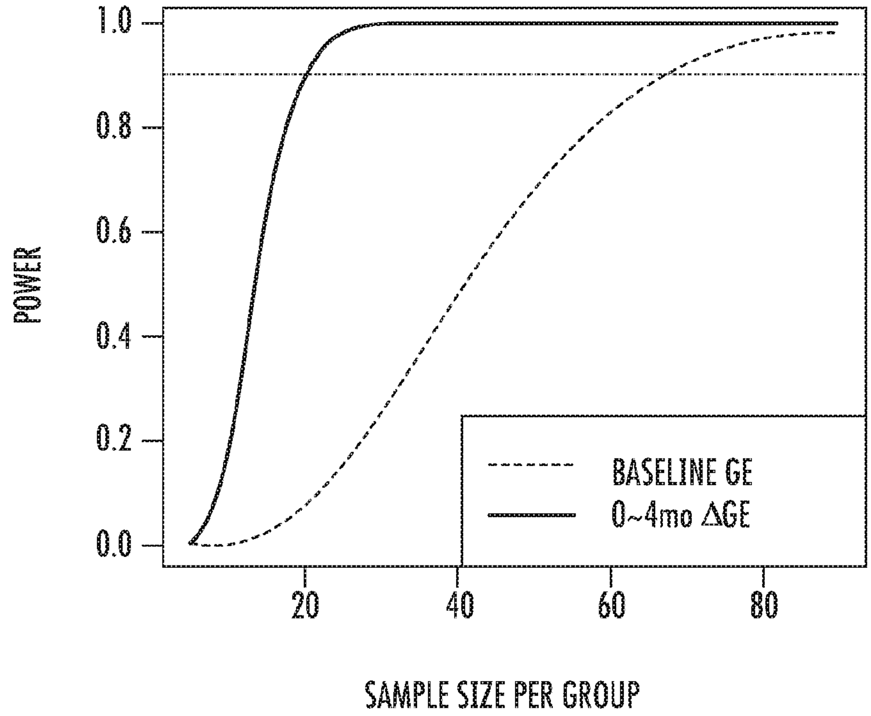

Comparative Analysis Between Longitudinal Gene Expression Change and Cross-Sectional Gene Express in FVC-Gene Predictor Modeling The Coefficient of Variation (CoV) analysis confirmed that longitudinal within-patient ΔGE was more homogenous, and with less within-group variation, than cross-sectional baseline GE data. The majority of the ΔCoV values (difference of CoV between GE and ΔGE) in the MvA (Minus vs Average) plots reside above the CoV1-CoV2=0 line in both groups stratified by FVC decline (FIGS. 8A and 8B; 82.9% and 67.5%, respectively). Using the ΔGE, only requires 16 progressor subjects to achieve a power of 0.9 (1-beta) with an alpha of 0.05 for significance, in contrast to the increase to 63 subjects per group in the cross-sectional baseline GE data (FIG. 8C). Only the within-patient ΔGE approach would succeed as in COMET cohort (n=16 progressors).

Figure 8D:
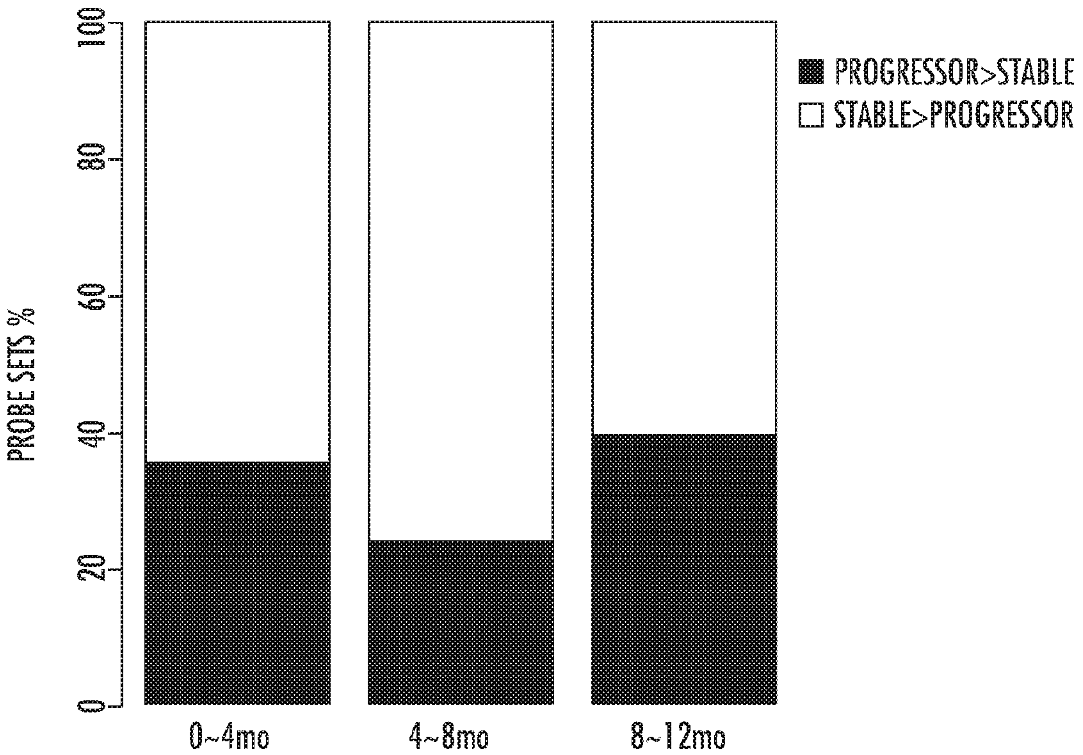

Intra-subject CoV was compared between FVC progressor and stable patients in three consecutive transcriptome sampling time points of COMET cohort. Consistently, 60-76% genes demonstrated larger intra-subject CoV in FVC stable than in progressor patients (FIG. 8D, grey and black bar, respectively).

Discussion of EXAMPLES

As disclosed herein, a novel, longitudinal gene expression-based predictor of FVC decline was developed. This prediction tool demonstrated good test performance for discriminating progressive and stable patients with IPF across multiple independent cohorts. The performance characteristics support generalizability across varied transcriptome sampling time and durations, and independence of transcriptome assay platform. The positive and negative predictive values for this tool support its potential use for clinical trial enrichment.

Most IPF clinical trials are designed to detect a clinically meaningful difference in FVC change over time between treatment arms. However, the percentage of patients experiencing FVC decline is highly variable between clinical trial cohorts (Noth et al., 2012; Idiopathic Pulmonary Fibrosis Clinical Research Network et al., 2010; Idiopathic Pulmonary Fibrosis Clinical Research Network et al., 2012; King et al., 2014; Richeldi et al., 2014), requiring relatively large sample sizes to avoid underpowered studies. As such, biomarker-driven enrichment of clinical trial cohorts remains a goal of precision medicine. The ideal biomarker for this purpose should be easily acquired, generalizable across studies and diverse IPF cohorts and reflect underlying pathologic processes. The present data suggest that this tool could potentially serve this role after further refinement in larger cohorts. With a NPV of roughly 80%, this tool could effectively increase the proportion of patients that will experience FVC decline, thereby reducing the number of patients needed for clinical trial enrollment.

While a cross-sectional biomarker would be preferred over one that requires two or more data acquisitions, but as the present data demonstrate, the longitudinal change in a biomarker may better reflect disease activity. The use of short-term ΔGE established a more homogenous transcriptomic predictor of FVC decline than a cross-sectional approach. Additionally, even though the peripheral blood transcriptome was employed for this study, the genes comprising the FVC-gene predictor largely involved known fibrotic pathways, further supporting a reflection of disease activity with this tool. Similar findings have been demonstrated with longitudinal change in circulating plasma biomarkers (Maher et al., 2017).

The ideal timeframe for blood sample acquisition remains unknown. It was shown that this could be done across multiple time points in the COMET cohort and that a year or more delay in sample acquisition still predicted future FVC decline in the UChicago and UPMC registry cohorts, supporting resiliency for variable sampling timepoints. Shorter timeframes were unable to be assessed with these data; however, the shortest possible timeframe for detection of gene expression changes would be ideal for clinical utility. At present, in some embodiments a 4 month sampling duration is a representative duration, but shorter timeframes also fall within the presently disclosed subject matter.

The test performance of FVC-gene predictor disclosed herein against relevant predictors of IPF mortality was explored, including plasma biomarkers and prior FVC decline. MMP7 is a reliable predictor of IPF mortality (Rosas et al., 2008), has been shown to correlate with FVC decline and predicts outcomes in multiple studies (Richards et al., 2012; Hamai et al., 2016) including interstitial lung abnormalities (Armstrong et al., 2017). CCL18, is predictive of outcomes in IPF (Prasse et al., 2009), and has shown prognostic value for absolute change in FVC in two large clinical trial cohorts (Neighbors et al., 2018). COMET investigators previously demonstrated that periostin (POSTN) levels predicted composite progression outcomes (Naik et al., 2012), while others have shown correlation with FVC decline (Tajiri et al., 2015; Ohta et al., 2017). The FVC gene predictor outperformed each of these in detecting future FVC decline.

Results of pathway analyses of all annotated genes associated with FVC decline, and the subset of 25 genes constituting the FVC-predictor confirm pathologic processes involved in IPF, supporting that short-term transcriptomic changes reflect disease activity. The top two pathways identified by GSEA included TGF-β1 signaling and glycan degradation pathways. Both are directly involved in the fibrotic events of pulmonary fibrosis (Kang et al., 2007) and its pathogenesis (Pardo et al., 2016). Many of the individual genes in the FVC-predictor including TP63, NT5E, FAM1111B, HBB, PLA2G4A, MSR1, CNR2, and ITLN1 are also linked to lung fibrosis. TP63 has been reported in the abnormal re-epithelialization and lung remodeling in IPF (Chilosi et al., 2002) while CD73 (NTE5) enhances radiation-induced lung fibrosis in mice, as examples (Wirsdorfer & Jendrossek, 2016). While the PBMCs are predominantly immune cells, the present findings support that peripheral blood reflect fibrotic signaling in the lungs.

"Loss of transcriptomic robustness" may be explained by the decrease in intra-subject gene expression variation in the FVC progression patients. "Robustness" of a biologic system involves persistence of expression in the face of perturbation (Masel & Siegal, 2009). In essence, alternate pathways other than the perturbed system may be biologically necessary to maintain a healthy response. The CoV analyses disclosed herein showed greater intra-subject gene expression homogeneity in FVC progressor over FVC stable patients. The heterogeneity of ΔGE maintained in patients not experiencing an FVC decline may reflect this preservation of transcriptomic robustness, whereas those with FVC decline may lose this robustness. One cannot infer whether this loss of "robustness" is a cause or a consequence of disease activity, however, this phenomenon establishes a molecular foundation for application of longitudinal blood transcriptomics in prediction of disease progression.

A strength of the presently disclosed subject matter resides in consistent test performance of the FVC-gene predictor in three independent, international IPF cohorts. While the transcriptome sampling and PFT timepoints were fixed in COMET, such timepoints varied substantially across the IPF registry cohorts (Chicago, UPMC), which more closely approximates clinical practice and illustrates flexibility for clinical application. Equally important, was the diverse transcriptome assay platforms used in these cohorts (RNAseq, Agilent, Affymetrix), which supports generalizability. Another strength of the presently disclosed subject matter was the robustness across FVC decline events. A relative FVC decline of 10% or more is strongly associated with future mortality. However, a relative decline of 5% has also been shown to predict future mortality, so the FVC-gene predictor was also tested for this categorical event and showed similar test performance.

The variability in transcriptome assay platforms led to some data loss across platforms, especially the UPMC platform. Accordingly, absolute FVC-gene predictor score thresholds might not be universally applicable, but rather a modified threshold based on ROCs using the available data has been generated. Gene expression requires normalization prior to downstream data analysis. Batch effects associated with RNA isolation and cDNA library preparation also prohibit uniform scoring and cut-off. Although the predictor has been validated in subsets of the COMET cohort and in external cohorts, the size of each cohort is still relatively small. However, none of the subjects were on FDA approved therapies preventing assessment of responses to drugs.

In conclusion, the FVC-gene predictor included genes with increased or decreased expression over baseline sampling and follow-up suggesting a changing/active disease process. Developing such a blood-derived biomarker for disease activity rather than disease severity could carry implications for clinical trial enrichment and assist clinical decision-making for instituting and maintaining pharmacotherapy. Clinical trial enrichment using such a biomarker could assist with accelerated drug development for this devastating disease. Further refinement of the presently disclosed predictor in larger cohorts on a uniform transcriptome assay platform in conjunction with therapeutic intervention might improve test performance characteristics and facilitate a precision medicine approach in IPF.

Summarily, a training cohort (n=74) of IPF patients was stratified according to the presence of progressive disease, defined as ≥10% relative decline in FVC over 12 months. Baseline to 4 month within-patient changes in gene expression were correlated with categorical FVC decline. Genes predictive of FVC decline were identified by two-group comparison with false discovery rate <5%, and further prioritized by logistic LASSO regression with $p<0.05$ and 10-Fold Cross-Validation ≥50% support. An FVC-gene score was derived using regression coefficients and assessed using area under the curve (AUC) analysis. The categorical FVC-gene predictor was then applied to three independent validation cohorts with differing transcriptome assay platforms and blood transcriptome sampling times to assess test performance characteristics.

A longitudinally-derived FVC-gene predictor accurately discriminated most patients with stable and progressive IPF across four independent IPF cohorts and demonstrated sensitivity and specificity of 74% and 82% in the combined validation cohort. TGF-beta was the highest-ranking canonical pathway by Gene Set Enrichment Analysis. The use of longitudinal change in gene expression markedly reduced within-group variation compared to a cross-sectional approach. Therefore, a novel predictor of FVC decline developed from longitudinal gene expression accurately discriminated most patients with progressive versus stable IPF. Disease activity may be better reflected in longitudinal over cross-sectional approaches. The resulting FVC-gene predictor may allow enrichment for progressive disease in clinical trials.

REFERENCES

All references listed below, as well as all references cited in the instant disclosure, including but not limited to all patents, patent applications and publications thereof, scientific journal articles, and database entries (e.g., GENBANK® and UniProt biosequence database entries and all annotations available therein) are incorporated herein by reference in their entireties to the extent that they supplement, explain, provide a background for, or teach methodology, techniques, and/or compositions employed herein.

Alexa et al. (2006) Improved scoring of functional groups from gene expression data by decorrelating GO graph structure. Bioinformatics 22:1600-1607.

Altschul et al. (1990a) Basic local alignment search tool. J Mol Biol 215:403-410.

Altschul et al. (1990b) Protein database searches for multiple alignments. Proc Natl Acad Sci USA 87:14:5509-5513.

Altschul et al. (1997) Gapped BLAST and PSI-BLAST: a new generation of protein database search programs. Nucleic Acids Res 25:3389-3402.

American Thoracic Society & European Respiratory Society (2002) American Thoracic Society/European Respiratory Society International Multidisciplinary Consensus Classification of the Idiopathic Interstitial Pneumonias. This joint statement of the American Thoracic Society (ATS), and the European Respiratory Society (ERS) was adopted by the ATS board of directors, June 2001 and by the ERS Executive Committee, June 2001. Am J Respir Crit Care Med 165:277-304.

Anders et al. (2014) HTSeq-a Python framework to work with high-throughput sequencing data. Bioinformatics 31:166-169.

Armstrong et al. (2017) Serum Matrix Metalloproteinase-7, Respiratory Symptoms, and Mortality in Community-Dwelling Adults. MESA (Multi-Ethnic Study of Atherosclerosis). Am J Respir Crit Care Med 196:1311-1317.

Ausubel et al. (1995) Current Protocols in Molecular Biology, Greene Publishing.

Ballman et al. (2004) Faster cyclic loess: normalizing RNA arrays via linear models. Bioinformatics 20:2778-2786.

Benjamini & Hochberg (1995) Controlling the false discovery rate: a practical and powerful approach to multiple testing. J R Stat Soc 57:289-300.

Chilosi et al. (2002) Abnormal re-epithelialization and lung remodeling in idiopathic pulmonary fibrosis: the role of deltaN-p63. Lab Invest 82:1335-1345.

Dobin et al. (2013) STAR: ultrafast universal RNA-seq aligner. Bioinformatics 29:15-21.

Devereux et al. (1984) A comprehensive set of sequence analysis programs for the VAX. Nucl Acids Res 12:387-395.

du Bois et al. (2011) Forced vital capacity in patients with idiopathic pulmonary fibrosis: test properties and minimal clinically important difference. Am J Respir Crit Care Med 184:1382-1389.

Flaherty et al. (2004) Idiopathic interstitial pneumonia: what is the effect of a multidisciplinary approach to diagnosis? Am J Respir Crit Care Med 170:904-910.

Flaherty et al. (2007) Idiopathic interstitial pneumonia: do community and academic physicians agree on diagnosis? Am J Respir Crit Care Med 175:1054-1060.

Friedman et al. (2010) Regularization Paths for Generalized Linear Models via Coordinate Descent. J Stat Softw 33:1-22.

Gait (1984) Oligonucleotide Synthesis: A Practical Approach, IRL Press, Oxford, England.

Gautier et al. (2004) affy-analysis of Affymetrix GeneChip data at the probe level. Bioinformatics 20:307-315.

Glover (1985) DNA Cloning: a Practical Approach. Oxford Press, Oxford.

Greene et al. (2002) Serum surfactant proteins-A and -D as biomarkers in idiopathic pulmonary fibrosis. Eur Respir J 19:439-446.

Gross & Mienhofer (eds.) (1981) *The Peptides, Vol.* 3. Academic Press, New York, New York, United States of America, pp. 3-88.

Gu et al. (2016) Complex heatmaps reveal patterns and correlations in multidimensional genomic data. Bioinformatics 32:2847-2849.

Harlow & Lane (1988) *Antibodies, a Laboratory Manual*, Cold Spring Harbor Laboratory Publications, Cold Spring Harbor, New York, United States of America.

Hamai et al. (2016) Comparative Study of Circulating MMP-7, CCL18, KL-6, SP-A, and SP-D as Disease Markers of Idiopathic Pulmonary Fibrosis. Dis Markers 2016; 2016: 4759040.

Herazo-Maya et al. (2013) Peripheral blood mononuclear cell gene expression profiles predict poor outcome in idiopathic pulmonary fibrosis. Sci Transl Med 5:205ra136.

Herazo-Maya et al. (2017) Validation of a 52-gene risk profile for outcome prediction in patients with idiopathic pulmonary fibrosis: an international, multicentre, cohort study. Lancet Respir Med 5:857-868.

Hoffmann-Vold et al. (2016) High Level of Chemokine CCL18 Is Associated With Pulmonary Function Deterioration, Lung Fibrosis Progression, and Reduced Survival in Systemic Sclerosis. Chest 150:299-306.

Huang et al. (2017) Microbes Are Associated with Host Innate Immune Response in Idiopathic Pulmonary Fibrosis. Am J Respir Crit Care Med 196:208-219.

Husson et al. (2010) *Exploratory Multivariate Analysis by Example Using R*. CRC Press, Taylor & Francis Group, Boca Raton, Florida, United States of America.

Hyslop & White (2009) Estimating precision using duplicate measurements. J Air Waste Manag Assoc 59:1032-1039.

Idiopathic Pulmonary Fibrosis Clinical Research Network et al. (2010) A controlled trial of sildenafil in advanced idiopathic pulmonary fibrosis. N Engl J Med 363:620-628.

Idiopathic Pulmonary Fibrosis Clinical Research Network et al. (2012) Prednisone, azathioprine, and N-acetylcysteine for pulmonary fibrosis. N Engl J Med 366:1968-1977.

Irizarry et al. (2003) Exploration, normalization, and summaries of high density oligonucleotide array probe level data. Biostatistics 4:249-264.

Jegal et al. (2005) Physiology is a stronger predictor of survival than pathology in fibrotic interstitial pneumonia. Am J Respir Crit Care Med 171:639-644.

Kaimal et al. (2010) ToppCluster: a multiple gene list feature analyzer for comparative enrichment clustering and network-based dissection of biological systems. Nucleic Acids Res 38:W96-102.

Kaner et al. (2019) Design of IPF Clinical Trials in the Era of Approved Therapies. Am J Respir Crit Care Med 200:133-139.

Kang et al. (2007) Transforming growth factor (TGF)-beta1 stimulates pulmonary fibrosis and inflammation via a Bax-dependent, bid-activated pathway that involves matrix metalloproteinase-12. J Biol Chem 282:7723-7732.

Karimi-Shah & Chowdhury (2015) Forced vital capacity in idiopathic pulmonary fibrosis—FDA review of pirfenidone and nintedanib. N Engl J Med 372:1189-1191.

Karlin & Altschul (1990) Methods for assessing the statistical significance of molecular sequence features by using general scoring schemes. Proc Natl Acad Sci USA 87:2264-2268.

Karlin & Altschul (1993) Applications and statistics for multiple high-scoring segments in molecular sequences. Proc Natl Acad Sci USA 90:5873-5877.

King et al. (2014) A phase 3 trial of pirfenidone in patients with idiopathic pulmonary fibrosis. N Engl J Med 370: 2083-2092.

Law et al. (2014) voom: Precision weights unlock linear model analysis tools for RNA-seq read counts. Genome Biol 15:R29.

Ley et al. (2014) Molecular biomarkers in idiopathic pulmonary fibrosis. Am J Physiol Lung Cell Mol Physiol 307:L681-691.

Ley et al. (2016) Predictors of Mortality Poorly Predict Common Measures of Disease Progression in Idiopathic Pulmonary Fibrosis. Am J Respir Crit Care Med 194:711-718.

Li (2008) Automating dChip: toward reproducible sharing of microarray data analysis. BMC Bioinformatics 9:231.

López-Ratón et al. (2014) OptimalCutpoints: An R Package for Selecting Optimal Cutpoints in Diagnostic Tests. Journal of Statistical Software 61:1-36.

Love et al. (2014) Moderated estimation of fold change and dispersion for RNA-Seq data with DESeq2. Genome Biol 15:550.

Macintyre et al. (2005) Standardisation of the single-breath determination of carbon monoxide uptake in the lung. Eur Respir J 26:720-735.

Maher et al. (2017) An epithelial biomarker signature for idiopathic pulmonary fibrosis: an analysis from the multicentre PROFILE cohort study. Lancet Respir Med 5:946-955.

Masel & Siegal (2009) Robustness: mechanisms and consequences. Trends Genet 25:395-403.

Meyer (2014) Support vector machines: the interface to libsvm in package e1071.

Miller et al. (2005a) General considerations for lung function testing. Eur Respir J 26:153-161.

Miller et al. (2005b) Standardisation of spirometry. Eur Respir J 26:319-338.

Mortazavi et al. (2008) Mapping and quantifying mammalian transcriptomes by RNA-Seq. Nat Methods 5:621-628.

Naik et al. (2012) Periostin promotes fibrosis and predicts progression in patients with idiopathic pulmonary fibrosis. Am J Physiol Lung Cell Mol Physiol 303:L1046-1056.

Neighbors et al. (2018) Prognostic and predictive biomarkers for patients with idiopathic pulmonary fibrosis treated with pirfenidone: post-hoc assessment of the CAPACITY and ASCEND trials. Lancet Respir Med 6:615-626.

Noth et al. (2012) Idiopathic Pulmonary Fibrosis Clinical Research N. A placebo-controlled randomized trial of warfarin in idiopathic pulmonary fibrosis. Am J Respir Crit Care Med 186:88-95.

O'Dwyer et al. (2017) The peripheral blood proteome signature of idiopathic pulmonary fibrosis is distinct from normal and is associated with novel immunological processes. Sci Rep 7:46560.

Ohta et al. (2017) The usefulness of monomeric periostin as a biomarker for idiopathic pulmonary fibrosis. PLoS One 12:e0174547.

Pardo et al. (2016) Role of matrix metalloproteinases in the pathogenesis of idiopathic pulmonary fibrosis. Respir Res 17:23.

Peljto et al. (2013) Association between the MUC5B promoter polymorphism and survival in patients with idiopathic pulmonary fibrosis. JAMA 309:2232-2239.

Prasse et al. (2009) Serum CC-chemokine ligand 18 concentration predicts outcome in idiopathic pulmonary fibrosis. Am J Respir Crit Care Med 179: 717-723.

Raghu et al. (2011) An official ATS/ERS/JRS/ALAT statement: idiopathic pulmonary fibrosis: evidence-based guidelines for diagnosis and management. Am J Respir Crit Care Med 183:788-824.

Richards et al. (2012) Plasma proteins for risk prediction in idiopathic pulmonary fibrosis. Am J Respir Crit Care Med 185:1329-1330.

Richeldi et al. (2014) Efficacy and safety of nintedanib in idiopathic pulmonary fibrosis. N Engl J Med 370:2071-2082.

Robin et al. (2011) pROC: an open-source package for R and S+ to analyze and compare ROC curves. BMC Bioinformatics 12:77.

Robinson & Oshlack (2010) A scaling normalization method for differential expression analysis of RNA-seq data. Genome Biol 11:R25.

Robinson et al. (2010) edgeR: a Bioconductor package for differential expression analysis of digital gene expression data. Bioinformatics 26:139-140.

Roe et al. (1996) *DNA Isolation and Sequencing: Essential Techniques*, John Wiley, New York, New York, United States of America.

Rosas et al. (2008) MMP1 and MMP7 as potential peripheral blood biomarkers in idiopathic pulmonary fibrosis. PLoS Med 5:e93.

Sambrook et al. (1989) Molecular Cloning: A Laboratory Manual, Cold Spring Harbor Laboratory Publications, Cold Spring Harbor, New York, United States of America.

Schmidt et al. (2014) Predicting pulmonary fibrosis disease course from past trends in pulmonary function. Chest 145:579-585.

Simon et al. (2011) Regularization Paths for Cox's Proportional Hazards Model via Coordinate Descent. J Stat Softw 39:1-13.

Smyth (2004) Linear models and empirical Bayes methods for assessing differential expression in microarray experiments. Stat Appl Genet Mol Biol 3:Article3.

Subramanian et al. (2005) Gene set enrichment analysis: a knowledge-based approach for interpreting genome-wide expression profiles. Proc Natl Acad Sci USA 102:15545-15550.

Suykens & Vandewalle (1999) Least Squares Support Vector Machine Classifiers. Neural Processing Letters 9:293-300.

Tajiri et al. (2015) Serum level of periostin can predict long-term outcome of idiopathic pulmonary fibrosis. Respir Investig 53:73-81.

Tibshirani et al. (2012) Strong rules for discarding predictors in lasso-type problems. J R Stat Soc Series B Stat Methodol 74:245-266.

Trapnell et al. (2009) TopHat: discovering splice junctions with RNA-Seq. Bioinformatics 25:1105-1111.

U.S. Patent Application Publication Nos. 2010/0120097; 2011/0189679; 2014/0113333; 2015/0307874; 2018/0064695; 2018/0169084; 2019/0030012; 2019/0282565.

U.S. Pat. Nos. 3,974,281; 5,800,992; 6,004,755; 6,013,449; 6,020,135; 6,033,860; 6,040,138; 6,177,248; 6,251,601; 6,309,822; 6,762,180; 7,824,856; 8,592,462; 9,884,802; 9,920,367; 10,028,966; 10,105,365; 10,227,584; each of which is incorporated by reference in its entirety.

Wirsdorfer & Jendrossek (2016) The Role of Lymphocytes in Radiotherapy-Induced Adverse Late Effects in the Lung. Front Immunol 7:591.

While the presently disclosed subject matter has been disclosed with reference to specific embodiments, it is apparent that other embodiments and variations of the presently disclosed subject matter may be devised by others skilled in the art without departing from the true spirit and scope of the presently disclosed subject matter.

What is claimed is:

1. A method for identifying and treating a subject diagnosed with Idiopathic Pulmonary Fibrosis (IPF) at risk for a decline in lung Forced Vital Capacity (FVC), the method comprising:

(a) determining first expression levels for a set of genes in a first biological sample obtained from the subject diagnosed with IPF to establish baseline expression levels for the set of genes, wherein the set of genes is selected from the group consisting of:
  (i) APTX, CNR2, GYPA, ITLN1, MAZ, MSR1, NT5E, PAWR, PLA2G4A, and PNMA5;
  (ii) APTX, ATP6AP1L, ITLN1, LINC00319, MAZ, MSR1, NT5E, PCDHB15, RAB3C, SSU72P8, and TP62;
  (iii) APTX, CNR2, GABRR1, GPR39, GYPA, HBB, ITLN1, MAZ, MSR1, NT5E, PAWR, PCDHB15, PLA2G4A, PNMA5, RLBP1, and SSU72P8; and
  (iv) APTX, ATP6AP1L, CNR2, FAM111B, GABRR1, GPR39, GYPA, HBB, IGLC1, ITLN1, LINC00319, MAZ, MSR1, NT5E, PAWR, PCDHB15, PLA2G4A, PLCL1, PNMA5, RAB3C, RBM43, RLBP1, SSU72P8, TP63, and ZNF252P;

(b) determining second expression levels for the set of genes in a second biological sample obtained from the subject, wherein the first and second biological samples comprise peripheral blood mononuclear cells (PBMCs) and/or nucleic acids extracted from PBMCs;

(c) comparing the first and second expression levels for the set of genes to create an FVC-gene predictor score; and (d) treating the subject based on the FVC-gene predictor score with a treatment selected from the group consisting of lung transplantation and a drug therapy, wherein the drug therapy comprises administering to the subject a pharmaceutical composition in an amount and via a route of administration effective to delay or prevent the development of FVC decline in the subject.

2. The method of claim 1, wherein the pharmaceutical composition comprises pirfenidone, nintedanib, or a combination thereof.

3. The method of claim 1, wherein the subject is a human.

4. The method of claim 1, comprising determining the first and second expression levels for each gene in the set of APTX, ATP6AP1L, CNR2, FAM111B, GABRR1, GPR39, GYPA, HBB, IGLC1, ITLN1, LINC00319, MAZ, MSR1, NT5E, PAWR, PCDHB15, PLA2G4A, PLCL1, PNMA5, RAB3C, RBM43, RLBP1, SSU72P8, TP63, and ZNF252P.

5. The method of claim 1, wherein the second biological sample is obtained from the subject at a time from about 4 to about 12 months subsequent to when the first biological sample was obtained from the subject.

6. The method of claim 1, wherein one or both of the determining steps comprise a technique selected from the group consisting of RNA-seq analysis, quantitative polymerase chain reaction (PCR), quantitative reverse transcription PCR (qRT-PCR), a nucleic acid or protein array, or any combination thereof.

7. The method of claim 1, wherein the comparing of the first and second expression levels for the set of genes comprises comparing normalized expression levels for each gene in the first and second biological samples to generate a fold-increase and/or a fold-decrease of the expression level in the second biological sample relative to the first biological sample for each gene.

8. The method of claim 7, wherein the comparing further comprises summing each fold-increase and/or fold-decrease of the expression level to produce an FVC-gene predictor score for the subject.

9. The method of claim 8, wherein the summing is performed after multiplying each fold-increase and/or fold-decrease of the expression level by a weighting value to produce a weighted FVC-gene predictor score for the subject.

* * * * *

SEQUENCE LISTING

```
<160> NUMBER OF SEQ ID NOS: 66

<210> SEQ ID NO 1
<211> LENGTH: 3139
<212> TYPE: DNA
<213> ORGANISM: Homo sapiens
<220> FEATURE:
<221> NAME/KEY: CDS
<222> LOCATION: (33)..(1724)

<400> SEQUENCE: 1

gatccagcga acagccccgc ttctaacccg ag atg ctg ctg ccg gcg ccc gcg       53
                                    Met Leu Leu Pro Ala Pro Ala
                                    1               5

ctc cgc cgc gcc ctg ctg tcc cgc ccc tgg acc ggg gcc ggc ctg cgg      101
Leu Arg Arg Ala Leu Leu Ser Arg Pro Trp Thr Gly Ala Gly Leu Arg
        10                  15                  20

tgg aag cac acc tcc tcc ctg aag gtg gcc aac gag ccc gtc tta gcc      149
Trp Lys His Thr Ser Ser Leu Lys Val Ala Asn Glu Pro Val Leu Ala
    25                  30                  35

ttc acg cag ggc agc cct gag cga gat gcc ctg caa aag gcc ttg aag      197
Phe Thr Gln Gly Ser Pro Glu Arg Asp Ala Leu Gln Lys Ala Leu Lys
40                  45                  50                  55

gac ctg aag ggc cgg atg gaa gcc atc cca tgc gtg gtg ggg gat gag      245
Asp Leu Lys Gly Arg Met Glu Ala Ile Pro Cys Val Val Gly Asp Glu
                60                  65                  70

gag gtg tgg acg tcg gac gtg cag tac caa gtg tcg cct ttt aac cat      293
Glu Val Trp Thr Ser Asp Val Gln Tyr Gln Val Ser Pro Phe Asn His
            75                  80                  85

gga cat aag gtg gcc aag ttc tgt tat gca gac aag agc ctg ctc aac      341
Gly His Lys Val Ala Lys Phe Cys Tyr Ala Asp Lys Ser Leu Leu Asn
        90                  95                  100

aaa gcc att gag gct gcc ctg gct gcc cgg aaa gag tgg gac ctg aag      389
Lys Ala Ile Glu Ala Ala Leu Ala Ala Arg Lys Glu Trp Asp Leu Lys
    105                 110                 115

cct att gca gac cgg gcc cag atc ttc ctg aag gcg gca gac atg ctg      437
Pro Ile Ala Asp Arg Ala Gln Ile Phe Leu Lys Ala Ala Asp Met Leu
120                 125                 130                 135

agt ggg ccg cgc agg gct gag atc ctc gcc aag acc atg gtg gga cag      485
Ser Gly Pro Arg Arg Ala Glu Ile Leu Ala Lys Thr Met Val Gly Gln
                140                 145                 150

ggt aag acc gtg atc caa gcg gag att gac gct gca gcg gaa ctc atc      533
Gly Lys Thr Val Ile Gln Ala Glu Ile Asp Ala Ala Ala Glu Leu Ile
            155                 160                 165
```

```
gac ttc ttc cgg ttc aat gcc aag tat gcg gtg gag ctg gag ggg cag       581
Asp Phe Phe Arg Phe Asn Ala Lys Tyr Ala Val Glu Leu Glu Gly Gln
        170                 175                 180

cag ccc atc agc gtg ccc ccg agc acc aac agc acg gtg tac cgg ggt       629
Gln Pro Ile Ser Val Pro Pro Ser Thr Asn Ser Thr Val Tyr Arg Gly
    185                 190                 195

ctg gag ggc ttc gtg gcg gcc atc tcg ccc ttt aac ttc act gca atc       677
Leu Glu Gly Phe Val Ala Ala Ile Ser Pro Phe Asn Phe Thr Ala Ile
200                 205                 210                 215

ggc ggc aac ctg gcg ggg gca ccg gcc ctg atg ggc aac gtg gtc cta       725
Gly Gly Asn Leu Ala Gly Ala Pro Ala Leu Met Gly Asn Val Val Leu
                220                 225                 230

tgg aag ccc agt gac act gcc atg ctg gcc agc tat gct gtc tac cgc       773
Trp Lys Pro Ser Asp Thr Ala Met Leu Ala Ser Tyr Ala Val Tyr Arg
            235                 240                 245

atc ctt cgg gag gct ggc ctg ccc ccc aac atc atc cag ttt gtg cca       821
Ile Leu Arg Glu Ala Gly Leu Pro Pro Asn Ile Ile Gln Phe Val Pro
        250                 255                 260

gct gat ggg ccc cta ttt ggg gac act gtc acc agc tca gag cac ctc       869
Ala Asp Gly Pro Leu Phe Gly Asp Thr Val Thr Ser Ser Glu His Leu
    265                 270                 275

tgt ggc atc aac ttc aca ggc agt gtg ccc acc ttc aaa cac ctg tgg       917
Cys Gly Ile Asn Phe Thr Gly Ser Val Pro Thr Phe Lys His Leu Trp
280                 285                 290                 295

aag cag gtg gcc cag aac ctg gac cgg ttc cac acc ttc cca cgc ctg       965
Lys Gln Val Ala Gln Asn Leu Asp Arg Phe His Thr Phe Pro Arg Leu
                300                 305                 310

gct gga gag tgc ggc gga aag aac ttc cac ttc gtg cac cgc tcg gcc      1013
Ala Gly Glu Cys Gly Gly Lys Asn Phe His Phe Val His Arg Ser Ala
            315                 320                 325

gac gtg gag agc gtg gtg agc ggg acc ctc cgc tca gcc ttc gag tac      1061
Asp Val Glu Ser Val Val Ser Gly Thr Leu Arg Ser Ala Phe Glu Tyr
        330                 335                 340

ggt ggc cag aag tgt tcc gcg tgc tcg cgt ctc tac gtg ccg cac tcg      1109
Gly Gly Gln Lys Cys Ser Ala Cys Ser Arg Leu Tyr Val Pro His Ser
    345                 350                 355

ctg tgg ccg cag atc aaa ggg cgg ctg ctg gag gag cac agt cgg atc      1157
Leu Trp Pro Gln Ile Lys Gly Arg Leu Leu Glu Glu His Ser Arg Ile
360                 365                 370                 375

aaa gtg ggc gac cct gca gag gat ttt ggg acc ttc ttc tct gca gtg      1205
Lys Val Gly Asp Pro Ala Glu Asp Phe Gly Thr Phe Phe Ser Ala Val
                380                 385                 390

att gat gcc aag tcc ttt gcc cgt atc aag aag tgg ctg gag cac gca      1253
Ile Asp Ala Lys Ser Phe Ala Arg Ile Lys Lys Trp Leu Glu His Ala
            395                 400                 405

cgc tcc tca ccc agc ctc acc atc ctg gcc ggg ggc aag tgt gat gac      1301
Arg Ser Ser Pro Ser Leu Thr Ile Leu Ala Gly Gly Lys Cys Asp Asp
        410                 415                 420

tcc gtg ggc tac ttt gtg gag ccc tgc atc gtg gag agc aag gac cct      1349
Ser Val Gly Tyr Phe Val Glu Pro Cys Ile Val Glu Ser Lys Asp Pro
    425                 430                 435

cag gag ccc atc atg aag gag gag atc ttc ggg cct gta ctg tct gtg      1397
Gln Glu Pro Ile Met Lys Glu Glu Ile Phe Gly Pro Val Leu Ser Val
440                 445                 450                 455

tac gtc tac ccg gat gac aag tac aag gag acg ctg cag ctg gtt gac      1445
Tyr Val Tyr Pro Asp Asp Lys Tyr Lys Glu Thr Leu Gln Leu Val Asp
                460                 465                 470

agc acc acc agc tat ggc ctc acg ggg gca gtg ttc tcc cag gat aag      1493
Ser Thr Thr Ser Tyr Gly Leu Thr Gly Ala Val Phe Ser Gln Asp Lys
```

```
            475                 480                 485

gac gtc gtg cag gag gcc aca aag gtg ctg agg aat gct gcc ggc aac     1541
Asp Val Val Gln Glu Ala Thr Lys Val Leu Arg Asn Ala Ala Gly Asn
        490                 495                 500

ttc tac atc aac gac aag tcc act ggc tcg ata gtg ggc cag cag ccc     1589
Phe Tyr Ile Asn Asp Lys Ser Thr Gly Ser Ile Val Gly Gln Gln Pro
    505                 510                 515

ttt ggg ggg gcc cga gcc tct gga acc aat gac aag cca ggg ggc cca     1637
Phe Gly Gly Ala Arg Ala Ser Gly Thr Asn Asp Lys Pro Gly Gly Pro
520                 525                 530                 535

cac tac atc ctg cgc tgg acg tcg ccg cag gtc atc aag gag aca cat     1685
His Tyr Ile Leu Arg Trp Thr Ser Pro Gln Val Ile Lys Glu Thr His
                540                 545                 550

aag ccc ctg ggg gac tgg agc tac gcg tac atg cag tga gcccctctcg      1734
Lys Pro Leu Gly Asp Trp Ser Tyr Ala Tyr Met Gln
            555                 560

ggctccaccg tccagctgtc tgtccgtcca ggtggccgac ctcactgcac agaccccact   1794

ccagcccctc caccccttct tcatgcacag ctgcctttct ataatccggg cttgactccc   1854

ttcttaccac tgtattctgg cctctcccat gcctcaggct ctggtttgag atcgtgctgg   1914

ggaggaacat ggccactacc ccttatccca tcggccatgt gggaggtatg accctggtgc   1974

ctggcaggtt ctccctctgc cctccactgg gcccagtggc tcagggacct ggggaaagga   2034

gatggagcag ctcttgggat cctttgggga aaaggaggcc attctgggcc ccttggcaaa   2094

cctcaccact cacagaggct cctggccttg atccctgccc ctccaggtgt ccagggtaaa   2154

gtgtaactca gactgacctg tggggcacag gggcaccag ctggccttgc cctctctggt    2214

ctgggctgtc taccttcctc actgtatctt tgcccagacc cacctgggcc agtaggcccc   2274

tgtccccagc cacacacctt agatgctggc atgccttact ccaggtgcct gtgtttggcc   2334

gaggcctgtg tgattcccgg tctgcaccac atggcggggt tgggggccg ctggaggcca    2394

cctgccaagg cgtgggatgg gatggtcctg ccggtttagg ccgtgattct ggaaaacctt   2454

ggatgggcct tcgtcctatg tcagccttcc ctttgatcct caggccctac ctgtagagac   2514

ctccactcct agagccagtc tcagggtctg ggatttccct gcaggagctc agccaccact   2574

gtgccatggt gacacaggcc aaggcagaca ttggccctcc cttctcccag cccccagagg   2634

cctggccttg ggttcgtcag catgggccga ggacgttgcc tgtagaatcc tcctctgcct   2694

gggagtggct ctgtgtggac cagtccctca ctggcccatt cttttttga cgcagccaat    2754

ctgtgaccac gattcctccc acagatgcct cctgcttgga ttctgagtgg tcagagatct   2814

gtaaagcatg actttcaagg atggttctta ggggactgtg aaagtgttgg gtcttcctcc   2874

aggatgcctg catgggaccc cacccggagc tggtgtggcc attccccaag tgccactggc   2934

ccatggatgg gggtgggtgc tggtgccagc tgggctgggt gtgggttctg tgtccttcca   2994

ggatatgtgt catttcccat gaggggccgg ggcaggtggc tgggtggggg cacaggctgg   3054

agtattctta gttctactgg ttctacactg tgaggtggca atgggatttg ctcagatgcc   3114

acccaataaa atgcctgtta cttaa                                         3139
```

<210> SEQ ID NO 2
<211> LENGTH: 563
<212> TYPE: PRT
<213> ORGANISM: Homo sapiens

<400> SEQUENCE: 2

```
Met Leu Leu Pro Ala Pro Ala Leu Arg Arg Ala Leu Leu Ser Arg Pro
```

-continued

```
1               5                   10                  15

Trp Thr Gly Ala Gly Leu Arg Trp Lys His Thr Ser Ser Leu Lys Val
            20                  25                  30

Ala Asn Glu Pro Val Leu Ala Phe Thr Gln Gly Ser Pro Glu Arg Asp
        35                  40                  45

Ala Leu Gln Lys Ala Leu Lys Asp Leu Lys Gly Arg Met Glu Ala Ile
    50                  55                  60

Pro Cys Val Val Gly Asp Glu Glu Val Trp Thr Ser Asp Val Gln Tyr
65                  70                  75                  80

Gln Val Ser Pro Phe Asn His Gly His Lys Val Ala Lys Phe Cys Tyr
                85                  90                  95

Ala Asp Lys Ser Leu Leu Asn Lys Ala Ile Glu Ala Ala Leu Ala Ala
            100                 105                 110

Arg Lys Glu Trp Asp Leu Lys Pro Ile Ala Asp Arg Ala Gln Ile Phe
        115                 120                 125

Leu Lys Ala Ala Asp Met Leu Ser Gly Pro Arg Arg Ala Glu Ile Leu
    130                 135                 140

Ala Lys Thr Met Val Gly Gln Gly Lys Thr Val Ile Gln Ala Glu Ile
145                 150                 155                 160

Asp Ala Ala Ala Glu Leu Ile Asp Phe Phe Arg Phe Asn Ala Lys Tyr
                165                 170                 175

Ala Val Glu Leu Glu Gly Gln Gln Pro Ile Ser Val Pro Pro Ser Thr
            180                 185                 190

Asn Ser Thr Val Tyr Arg Gly Leu Glu Gly Phe Val Ala Ala Ile Ser
        195                 200                 205

Pro Phe Asn Phe Thr Ala Ile Gly Gly Asn Leu Ala Gly Ala Pro Ala
    210                 215                 220

Leu Met Gly Asn Val Val Leu Trp Lys Pro Ser Asp Thr Ala Met Leu
225                 230                 235                 240

Ala Ser Tyr Ala Val Tyr Arg Ile Leu Arg Glu Ala Gly Leu Pro Pro
                245                 250                 255

Asn Ile Ile Gln Phe Val Pro Ala Asp Gly Pro Leu Phe Gly Asp Thr
            260                 265                 270

Val Thr Ser Ser Glu His Leu Cys Gly Ile Asn Phe Thr Gly Ser Val
        275                 280                 285

Pro Thr Phe Lys His Leu Trp Lys Gln Val Ala Gln Asn Leu Asp Arg
    290                 295                 300

Phe His Thr Phe Pro Arg Leu Ala Gly Glu Cys Gly Gly Lys Asn Phe
305                 310                 315                 320

His Phe Val His Arg Ser Ala Asp Val Glu Ser Val Val Ser Gly Thr
                325                 330                 335

Leu Arg Ser Ala Phe Glu Tyr Gly Gly Gln Lys Cys Ser Ala Cys Ser
            340                 345                 350

Arg Leu Tyr Val Pro His Ser Leu Trp Pro Gln Ile Lys Gly Arg Leu
        355                 360                 365

Leu Glu Glu His Ser Arg Ile Lys Val Gly Asp Pro Ala Glu Asp Phe
    370                 375                 380

Gly Thr Phe Phe Ser Ala Val Ile Asp Ala Lys Ser Phe Ala Arg Ile
385                 390                 395                 400

Lys Lys Trp Leu Glu His Ala Arg Ser Ser Pro Ser Leu Thr Ile Leu
                405                 410                 415

Ala Gly Gly Lys Cys Asp Asp Ser Val Gly Tyr Phe Val Glu Pro Cys
            420                 425                 430
```

Ile Val Glu Ser Lys Asp Pro Gln Glu Pro Ile Met Lys Glu Glu Ile
435 440 445

Phe Gly Pro Val Leu Ser Val Tyr Val Tyr Pro Asp Asp Lys Tyr Lys
450 455 460

Glu Thr Leu Gln Leu Val Asp Ser Thr Thr Ser Tyr Gly Leu Thr Gly
465 470 475 480

Ala Val Phe Ser Gln Asp Lys Asp Val Val Gln Glu Ala Thr Lys Val
485 490 495

Leu Arg Asn Ala Ala Gly Asn Phe Tyr Ile Asn Asp Lys Ser Thr Gly
500 505 510

Ser Ile Val Gly Gln Gln Pro Phe Gly Gly Ala Arg Ala Ser Gly Thr
515 520 525

Asn Asp Lys Pro Gly Gly Pro His Tyr Ile Leu Arg Trp Thr Ser Pro
530 535 540

Gln Val Ile Lys Glu Thr His Lys Pro Leu Gly Asp Trp Ser Tyr Ala
545 550 555 560

Tyr Met Gln

<210> SEQ ID NO 3
<211> LENGTH: 2116
<212> TYPE: DNA
<213> ORGANISM: Homo sapiens
<220> FEATURE:
<221> NAME/KEY: CDS
<222> LOCATION: (186)..(1214)

<400> SEQUENCE: 3
gacgtcatcc cgcagcgccg gaagcggtga ggcacagatg agtaacgtga atttgtccgt 60
ctccgacttc tggagattta tttttttag atgaggtgtt gctgtgttgc ccaagctgga 120
cttgaacccc taggctcaag caatccttcc acctcagtct cccaagtagc agggactaca 180 gagtg atg atg cgg gtg tgc tgg ttg gtg aga cag gac agc cgg cac cag 230
Met Met Arg Val Cys Trp Leu Val Arg Gln Asp Ser Arg His Gln
1 5 10 15 cga atc aga ctt cca cat ttg gaa gca gtt gtg att ggg cgt ggc cca 278
Arg Ile Arg Leu Pro His Leu Glu Ala Val Val Ile Gly Arg Gly Pro
20 25 30 gag acc aag atc act gat aag aaa tgt tct cga cag caa gta cag ttg 326
Glu Thr Lys Ile Thr Asp Lys Lys Cys Ser Arg Gln Gln Val Gln Leu
35 40 45 aaa gca gag tgt aac aag gga tat gtc aag gta aag cag gta gga gtc 374
Lys Ala Glu Cys Asn Lys Gly Tyr Val Lys Val Lys Gln Val Gly Val
50 55 60 aat ccc acc agc att gac tca gtc gta att ggg aag gac caa gag gtg 422
Asn Pro Thr Ser Ile Asp Ser Val Val Ile Gly Lys Asp Gln Glu Val
65 70 75 aag ctg cag cct ggc cag gtt ctc cac atg gtg aat gaa ctt tat cca 470
Lys Leu Gln Pro Gly Gln Val Leu His Met Val Asn Glu Leu Tyr Pro
80 85 90 95 tat att gta gag ttt gag gaa gag gca aag aac cct ggc ctg gaa aca 518
Tyr Ile Val Glu Phe Glu Glu Glu Ala Lys Asn Pro Gly Leu Glu Thr
100 105 110 cac agg aag aga aag aga tca ggc aac agt gat tct ata gaa agg gat 566
His Arg Lys Arg Lys Arg Ser Gly Asn Ser Asp Ser Ile Glu Arg Asp
115 120 125 gct gct cag gaa gct gag gct ggg aca ggg ctg gaa cct ggg agc aac 614
Ala Ala Gln Glu Ala Glu Ala Gly Thr Gly Leu Glu Pro Gly Ser Asn
130 135 140

-continued tct ggc caa tgc tct gtg ccc cta aag aag gga aaa gat gca cct atc 662
Ser Gly Gln Cys Ser Val Pro Leu Lys Lys Gly Lys Asp Ala Pro Ile
145 150 155 aaa aag gaa tcc ctg ggc cac tgg agt caa ggc ttg aag att tct atg 710
Lys Lys Glu Ser Leu Gly His Trp Ser Gln Gly Leu Lys Ile Ser Met
160 165 170 175 cag gac ccc aaa atg cag gtt tac aaa gat gag cag gtg gtg gtg ata 758
Gln Asp Pro Lys Met Gln Val Tyr Lys Asp Glu Gln Val Val Val Ile
180 185 190 aag gat aaa tac cca aag gcc cgt tac cat tgg ctg gtc tta ccg tgg 806
Lys Asp Lys Tyr Pro Lys Ala Arg Tyr His Trp Leu Val Leu Pro Trp
195 200 205 acc tcc att tcc agt ctg aag gct gtg gcc agg gaa cac ctt gaa ctc 854
Thr Ser Ile Ser Ser Leu Lys Ala Val Ala Arg Glu His Leu Glu Leu
210 215 220 ctt aag cat atg cac act gtg ggg gaa aag gtg att gta gat ttt gct 902
Leu Lys His Met His Thr Val Gly Glu Lys Val Ile Val Asp Phe Ala
225 230 235 ggg tcc agc aaa ctc cgc ttc cga ttg ggc tac cac gcc att ccg agt 950
Gly Ser Ser Lys Leu Arg Phe Arg Leu Gly Tyr His Ala Ile Pro Ser
240 245 250 255 atg agc cat gta cat ctt cat gtg atc agc cag gat ttt gat tct cct 998
Met Ser His Val His Leu His Val Ile Ser Gln Asp Phe Asp Ser Pro
260 265 270 tgc ctt aaa aac aaa aaa cat tgg aat tct ttc aat aca gaa tac ttc 1046
Cys Leu Lys Asn Lys Lys His Trp Asn Ser Phe Asn Thr Glu Tyr Phe
275 280 285 cta gaa tca caa gct gtg atc gag atg gta caa gag gct ggt aga gta 1094
Leu Glu Ser Gln Ala Val Ile Glu Met Val Gln Glu Ala Gly Arg Val
290 295 300 act gtc cga gat ggg atg cct gag ctc ttg aag ctg ccc ctt cgt tgt 1142
Thr Val Arg Asp Gly Met Pro Glu Leu Leu Lys Leu Pro Leu Arg Cys
305 310 315 cat gag tgc cag cag ctg ctg cct tcc att cct cag ctg aaa gaa cat 1190
His Glu Cys Gln Gln Leu Leu Pro Ser Ile Pro Gln Leu Lys Glu His
320 325 330 335 ctc agg aag cac tgg aca cag tga ttctgcagag cctgagctgc tgctgtggtg 1244
Leu Arg Lys His Trp Thr Gln
340 tggcccactg gagcaaactg ctggcaccta ttctgggttg cttgtgaact tctactcatt 1304 tcctaaatta aaacatgcag ctttttcaca aatttattct attattgagt ggccacaatg 1364 tagagtggct caaagtactt caggattagg aatttgggtt tgtcatagat gtattctctg 1424 gtgagggtgg ctgggatata cctgacccac catcttcaga aggacccatg tcaggtctga 1484 ccattgggag caaagccatg ttcacactga cctaatgcag agtatggaag cattgggctg 1544 gttatacatt tctgtttctt agatttatcc tccgcctctg taggcatgga caacctttaa 1604 tcagagcatc tagagtggcc tcttgtttat cctgaagata ctgatgggtc ttgttttctg 1664 ttagtctgtt ttgtaatatt cttttccctt ccttcatggg gaggcttagt ttgtccagtc 1724 cttccatgcc cttctatccc agattaccta aatgttccct tctcaggaat tctgtctcat 1784 cagttcttca cagtgagaaa agaggctaga tgatggtgtg gggggttgga gttttcttct 1844 aataccgagg gttcctggct gtgaggaaac agccacatgt tcgtcatgat tgagctgtga 1904 agtcttcttg gacctgttgt ctgaaaataa agttaatttg tttgaggcat ctctcttaag 1964 taggtggaaa ctattgaagt tcagctaaca atcacagcat aggttctgat gcatggaaag 2024

```
gtggttggtg aatgaaaaag ttgcgtagag ccactacttt ctttttccct gagaataaat   2084

ttggataaaa cagttgtatt caaaaaaaaa aa                                 2116


<210> SEQ ID NO 4
<211> LENGTH: 342
<212> TYPE: PRT
<213> ORGANISM: Homo sapiens

<400> SEQUENCE: 4

Met Met Arg Val Cys Trp Leu Val Arg Gln Asp Ser Arg His Gln Arg
1               5                   10                  15

Ile Arg Leu Pro His Leu Glu Ala Val Val Ile Gly Arg Gly Pro Glu
            20                  25                  30

Thr Lys Ile Thr Asp Lys Lys Cys Ser Arg Gln Gln Val Gln Leu Lys
        35                  40                  45

Ala Glu Cys Asn Lys Gly Tyr Val Lys Val Lys Gln Val Gly Val Asn
    50                  55                  60

Pro Thr Ser Ile Asp Ser Val Val Ile Gly Lys Asp Gln Glu Val Lys
65                  70                  75                  80

Leu Gln Pro Gly Gln Val Leu His Met Val Asn Glu Leu Tyr Pro Tyr
                85                  90                  95

Ile Val Glu Phe Glu Glu Glu Ala Lys Asn Pro Gly Leu Glu Thr His
            100                 105                 110

Arg Lys Arg Lys Arg Ser Gly Asn Ser Asp Ser Ile Glu Arg Asp Ala
        115                 120                 125

Ala Gln Glu Ala Glu Ala Gly Thr Gly Leu Glu Pro Gly Ser Asn Ser
    130                 135                 140

Gly Gln Cys Ser Val Pro Leu Lys Lys Gly Lys Asp Ala Pro Ile Lys
145                 150                 155                 160

Lys Glu Ser Leu Gly His Trp Ser Gln Gly Leu Lys Ile Ser Met Gln
                165                 170                 175

Asp Pro Lys Met Gln Val Tyr Lys Asp Glu Gln Val Val Val Ile Lys
            180                 185                 190

Asp Lys Tyr Pro Lys Ala Arg Tyr His Trp Leu Val Leu Pro Trp Thr
        195                 200                 205

Ser Ile Ser Ser Leu Lys Ala Val Ala Arg Glu His Leu Glu Leu Leu
    210                 215                 220

Lys His Met His Thr Val Gly Glu Lys Val Ile Val Asp Phe Ala Gly
225                 230                 235                 240

Ser Ser Lys Leu Arg Phe Arg Leu Gly Tyr His Ala Ile Pro Ser Met
                245                 250                 255

Ser His Val His Leu His Val Ile Ser Gln Asp Phe Asp Ser Pro Cys
            260                 265                 270

Leu Lys Asn Lys Lys His Trp Asn Ser Phe Asn Thr Glu Tyr Phe Leu
        275                 280                 285

Glu Ser Gln Ala Val Ile Glu Met Val Gln Glu Ala Gly Arg Val Thr
    290                 295                 300

Val Arg Asp Gly Met Pro Glu Leu Leu Lys Leu Pro Leu Arg Cys His
305                 310                 315                 320

Glu Cys Gln Gln Leu Leu Pro Ser Ile Pro Gln Leu Lys Glu His Leu
                325                 330                 335

Arg Lys His Trp Thr Gln
            340
```

<210> SEQ ID NO 5
<211> LENGTH: 4371
<212> TYPE: DNA
<213> ORGANISM: Homo sapiens
<220> FEATURE:
<221> NAME/KEY: CDS
<222> LOCATION: (2065)..(2739)

<400> SEQUENCE: 5
gctcttgccc aagccactga gagcgggacg cggggctagg tcagagtagg aaggagtcgc 60
tgagctgaat ctttgtggag tggagtgggg cgagagtcct ccgagtagtc tggaaaatta 120
gacttctgag ccttaattca tacttataag cagctagtaa attgtaaaat atagtgaagc 180
aatgtagtgt agtaactaaa accccaagct ttggagccag attgggcctt taaccctaaa 240
gttgccgttt attttgactg gcgagtcatt tacttataga tttatttatt tttattttta 300
tttttttctg agacagggtc tcactctgtc ttctaggctg ttgtgcagtg gtgcgatctt 360
ggctcactac aacctccgcc tcccgggttc aagcgattgt cccacctcag cctcctgagt 420
agctgggatt acaggcttcc accatcacgc ctggctgatg tttgtatttt cagtagagag 480
ggggtttcac catgttggcc aggctggtgt cgatctcctg acctcgagtg atccgcccgc 540
ctcggcctcc caatgtgctg ggattacagg cgtgagccac cgcgcctggc catttaatta 600
actctttaat actgtttctc ctgtaagatg aactagctgt gagaggtttc tgggatattg 660
gttcactcag caaggatgtt taaaaatgcc ttctatgtgc cagacgctgt tgtaggtacc 720
gggaatatgg cggttaaatt aagagggtga aggtttctgc tctgatacag tttatattct 780
aaatgtgaga ggacagacca gttagataga tgtaaattaa ataattaaat agatgatttt 840
tacatactgt agagctatag agaaaatata gctggatggg tgatagtgac ttggggatgg 900
gggtggctac tctggatagg gtagtttaag gtgacatctc tgtgcagatg tagaatgggc 960
tagtgctttc taagaactga aagatcagtg aagaagggga gcatagtgac tgaggagtag 1020
tgtggcatta gatggggtct gagagttaca caggaacatg tggagcctgt aggccatgca 1080
aggccatcag tgaagagaaa gagtgggaga aaaaggtttg aggagagaag gtataggact 1140
ttcactaacc ttggaccata tatttgccag gaagaatgta agttctccaa catcttcaaa 1200
taaagaagtg gttatgagga atgatcagaa taatggagat atgaaaccat tccagaattt 1260
cacaacaata ccaatcacac agagggtcca tgtgcagatt tgttacgtga gaatagtgca 1320
taatgctgga gtttgcggta tgaatcccat caccctgata gctctcaact acaatctgag 1380
caaagaaggg catttagaaa aagaaccttg gaatgcattc agccatcatg gcccagttaa 1440
tgtctccatc aatggaattc cttgcattct cttctgggcc aaaagaataa tgattaaatt 1500
taagaatcaa acctggctgg accttacaga cgagccattt ggtcagaagg taactgtgga 1560
ccctgacaac tcaaattgca gtgaagaaag tgctagaaaa aaaaagtagg ctcctttgta 1620
taggaccctg acacacatct ttgaggaagt atttactgtc taaaataaag gaacaagtca 1680
gaagttaact tcaaaaattg ttggctgggc atggtggctc acgcctgtaa tcccagcact 1740
tcgggaggcc aagggagtgg atcacctgag gtcaggagtt ggagacaagc ctggccaaca 1800
tggtgaaacc tcgtctctac taaaatacaa aaattagccg ggcgtggtgg caggtgcctg 1860
taatcccagc tactcaggag gctgagacag gagaattgct tgaacctggg aggtggaggt 1920
tgtggtgagc tgagatcgcg ccattgctct ccagcttggg tgacagagtg agtgagactc 1980
catctcaaaa aaaaaaaatt gttatatttt cccggcagtt ttcttctgaa ccttttttgct 2040 aattgtcgga ataacttgta gaaa atg aga ctt tgg aaa gca agg gtt ctc 2091

```
                           Met Arg Leu Trp Lys Ala Arg Val Leu
                           1               5

aaa ctc gtt ttg aaa aca gca aag gat tcc agg ctt ggt ctc aac tcc     2139
Lys Leu Val Leu Lys Thr Ala Lys Asp Ser Arg Leu Gly Leu Asn Ser
10                  15                  20                  25

aaa tgg ttg tct ttg aag ctt ggt gat gct gga aac ccc aga agt ctt     2187
Lys Trp Leu Ser Leu Lys Leu Gly Asp Ala Gly Asn Pro Arg Ser Leu
                30                  35                  40

gct ata aga ttc atc ctt acc aat tac aac aag ttg tcc atc cag agt     2235
Ala Ile Arg Phe Ile Leu Thr Asn Tyr Asn Lys Leu Ser Ile Gln Ser
            45                  50                  55

tgg ttt agt ttg cgc cga gtc gag atc att tcc aac aat tca atc caa     2283
Trp Phe Ser Leu Arg Arg Val Glu Ile Ile Ser Asn Asn Ser Ile Gln
        60                  65                  70

gca gtc ttt aac cca act ggc gta tat gct ccc tct ggt tac tcc tac     2331
Ala Val Phe Asn Pro Thr Gly Val Tyr Ala Pro Ser Gly Tyr Ser Tyr
    75                  80                  85

cgc tgc caa cgc gtg ggc agc ctg cag cag gac cag gcc ctc ttg ctg     2379
Arg Cys Gln Arg Val Gly Ser Leu Gln Gln Asp Gln Ala Leu Leu Leu
90                  95                  100                 105

ccc agc gac acg gat gat ggg tcg agc ctg tgg gag gtc act ttt att     2427
Pro Ser Asp Thr Asp Asp Gly Ser Ser Leu Trp Glu Val Thr Phe Ile
                110                 115                 120

gat ttc cag atc caa ggt ttt gcc atc aag ggg gga cga ttt acc aaa     2475
Asp Phe Gln Ile Gln Gly Phe Ala Ile Lys Gly Gly Arg Phe Thr Lys
            125                 130                 135

gcc caa gac tgc gcc tcc tcc ttc tcg cca gct ttt ctg atc ggc ctg     2523
Ala Gln Asp Cys Ala Ser Ser Phe Ser Pro Ala Phe Leu Ile Gly Leu
        140                 145                 150

gca atg tcc ctg atc ctg ctg ctg gtg ttg gcc tat gcc ctg cac atg     2571
Ala Met Ser Leu Ile Leu Leu Leu Val Leu Ala Tyr Ala Leu His Met
    155                 160                 165

ctc atc tac ctg cgg tat ctg gac caa caa tat gat ctc atc gcc tct     2619
Leu Ile Tyr Leu Arg Tyr Leu Asp Gln Gln Tyr Asp Leu Ile Ala Ser
170                 175                 180                 185

cct gcc cac ttc tcg cag ctg aaa gct cga gac aca gcc gaa gag aag     2667
Pro Ala His Phe Ser Gln Leu Lys Ala Arg Asp Thr Ala Glu Glu Lys
                190                 195                 200

gag ctg ctg agg agc cag ggg gct gaa tgc tat aaa ctg aga agc caa     2715
Glu Leu Leu Arg Ser Gln Gly Ala Glu Cys Tyr Lys Leu Arg Ser Gln
            205                 210                 215

cag atc agc aaa atc tat gtt tag cagcacaggc tggcccccac catgtccaca    2769
Gln Ile Ser Lys Ile Tyr Val
        220

gtgggctccg aaagttgtct ctgttctgtg ctatttgact tgtgaattac agattttcac   2829

caaatggctt gattacaaaa aaaaagaaaa aacacaaaaa ggaaatagat aatgaattct   2889

ttttgaacca tccactggcc tacttaggta gacttggggc aatcaaaaaa ggcatctcag   2949

ggatcccaca gagacaaata tgactgttag ttgcctcaaa gtaccctgaa agcaaagggg   3009

tatttcaagt acggaaaaag agagagagag aagaagaagg aggaggagga ggaggaggag   3069

aaggagaagg aggagcagga ggaagaggag gaggaggagg aaagggaggg agggagggag   3129

agggagagag agagaaagat tggcaacaca gagaagggaa aacacacttg gtcctccttg   3189

cctgtgccag tttggatgtg acaattatag aaataataaa ccaagattat ctggaagttc   3249

ataatttaaa ctattttgta acataatttg catttctaga tattatgtcc caattttgtt   3309

ttaaaaacag tctttttctc tttcatagaa atgttgaggg aggactcaac atgtggcaga   3369
```

```
gcactttatt taaggacctt cttgtccttt actgtgctgt tcagaagcag tacagctcca   3429

tctgtgaagt aggggtaata gtcatggcca tattttacct ttccatttgg gaaggggcca   3489

gggttgtctc acttgtctga tttagacctc catgagctct cataggtcca cttggaataa   3549

acagtagagc taagcaataa cagtgtgctt gctatgcaaa cacagctttg agacattccc   3609

ctgatcttcc ttccaatgag atagtgccct ctaaatgctt cctgaataga aattctggag   3669

ccaccactga tgttcttacc attgctgtct ttcatatgca ttcctcatca tccttttcag   3729

ctcttggcag atactgaaga ttgattcaac cttcatcctc accaaagcgt ctctaataat   3789

ataccttctg tcttaaagag atcttaaaca taaagatgac attgcatttt cccaggtagg   3849

gtttggtaca ggacctaggt tctactaaga agatactcct acacaaaact tagaatgcag   3909

acaggaaaca tgtgcagtgg agggtcacac acagagcaag aaaatcttct gggcagctgt   3969

cacgatgagt ctgctgtcta gtcccatcct aggtggtaag cagtagatga taatgacagt   4029

tttctgatgg gacagtctca tgttgagcat ttattttggc tgcaattttc ttggttatga   4089

atgtaggttt ggttctggcc ctctcagaat tctgtaagat cccatacttt atagtaaatt   4149

tctttctgtt ttaataacag agttgattct gtagtctgca gtgaagaatc ctgatttatg   4209

tagttgttag taccaagagg attgcaggga acagactctc aagaaaatgc aaatctatga   4269

ttgattatcc aactccattt ggctttaaac cagtggaaac tgtcagcctt agagaatggt   4329

attcaataat aaaacagatt tttattgtgg ttcccttgag ca                      4371
```

<210> SEQ ID NO 6
<211> LENGTH: 224
<212> TYPE: PRT
<213> ORGANISM: Homo sapiens

<400> SEQUENCE: 6

```
Met Arg Leu Trp Lys Ala Arg Val Leu Lys Leu Val Leu Lys Thr Ala
1               5                   10                  15

Lys Asp Ser Arg Leu Gly Leu Asn Ser Lys Trp Leu Ser Leu Lys Leu
            20                  25                  30

Gly Asp Ala Gly Asn Pro Arg Ser Leu Ala Ile Arg Phe Ile Leu Thr
        35                  40                  45

Asn Tyr Asn Lys Leu Ser Ile Gln Ser Trp Phe Ser Leu Arg Arg Val
    50                  55                  60

Glu Ile Ile Ser Asn Asn Ser Ile Gln Ala Val Phe Asn Pro Thr Gly
65                  70                  75                  80

Val Tyr Ala Pro Ser Gly Tyr Ser Tyr Arg Cys Gln Arg Val Gly Ser
                85                  90                  95

Leu Gln Gln Asp Gln Ala Leu Leu Leu Pro Ser Asp Thr Asp Asp Gly
            100                 105                 110

Ser Ser Leu Trp Glu Val Thr Phe Ile Asp Phe Gln Ile Gln Gly Phe
        115                 120                 125

Ala Ile Lys Gly Gly Arg Phe Thr Lys Ala Gln Asp Cys Ala Ser Ser
    130                 135                 140

Phe Ser Pro Ala Phe Leu Ile Gly Leu Ala Met Ser Leu Ile Leu Leu
145                 150                 155                 160

Leu Val Leu Ala Tyr Ala Leu His Met Leu Ile Tyr Leu Arg Tyr Leu
                165                 170                 175

Asp Gln Gln Tyr Asp Leu Ile Ala Ser Pro Ala His Phe Ser Gln Leu
            180                 185                 190

Lys Ala Arg Asp Thr Ala Glu Glu Lys Glu Leu Leu Arg Ser Gln Gly
```

```
        195                 200                 205

Ala Glu Cys Tyr Lys Leu Arg Ser Gln Gln Ile Ser Lys Ile Tyr Val
    210                 215                 220


<210> SEQ ID NO 7
<211> LENGTH: 2029
<212> TYPE: DNA
<213> ORGANISM: Homo sapiens
<220> FEATURE:
<221> NAME/KEY: CDS
<222> LOCATION: (114)..(1415)

<400> SEQUENCE: 7

ggcgtgctgc ggcggaacgg ctgttggttt ctgctgggtg taggtccttg gctggtcggg      60

cctccggtgt tctgcttctc cccgctgagc tgctgcctgg tgaagaggaa gcc atg        116
                                                           Met
                                                           1

gcg ctc cga gtc acc agg aac tcg aaa att aat gct gaa aat aag gcg        164
Ala Leu Arg Val Thr Arg Asn Ser Lys Ile Asn Ala Glu Asn Lys Ala
            5                   10                  15

aag atc aac atg gca ggc gca aag cgc gtt cct acg gcc cct gct gca        212
Lys Ile Asn Met Ala Gly Ala Lys Arg Val Pro Thr Ala Pro Ala Ala
        20                  25                  30

acc tcc aag ccc gga ctg agg cca aga aca gct ctt ggg gac att ggt        260
Thr Ser Lys Pro Gly Leu Arg Pro Arg Thr Ala Leu Gly Asp Ile Gly
    35                  40                  45

aac aaa gtc agt gaa caa ctg cag gcc aaa atg cct atg aag aag gaa        308
Asn Lys Val Ser Glu Gln Leu Gln Ala Lys Met Pro Met Lys Lys Glu
50                  55                  60                  65

gca aaa cct tca gct act gga aaa gtc att gat aaa aaa cta cca aaa        356
Ala Lys Pro Ser Ala Thr Gly Lys Val Ile Asp Lys Lys Leu Pro Lys
                70                  75                  80

cct ctt gaa aag gta cct atg ctg gtg cca gtg cca gtg tct gag cca        404
Pro Leu Glu Lys Val Pro Met Leu Val Pro Val Pro Val Ser Glu Pro
            85                  90                  95

gtg cca gag cca gaa cct gag cca gaa cct gag cct gtt aaa gaa gaa        452
Val Pro Glu Pro Glu Pro Glu Pro Glu Pro Glu Pro Val Lys Glu Glu
        100                 105                 110

aaa ctt tcg cct gag cct att ttg gtt gat act gcc tct cca agc cca        500
Lys Leu Ser Pro Glu Pro Ile Leu Val Asp Thr Ala Ser Pro Ser Pro
    115                 120                 125

atg gaa aca tct gga tgt gcc cct gca gaa gaa gac ctg tgt cag gct        548
Met Glu Thr Ser Gly Cys Ala Pro Ala Glu Glu Asp Leu Cys Gln Ala
130                 135                 140                 145

ttc tct gat gta att ctt gca gta aat gat gtg gat gca gaa gat gga        596
Phe Ser Asp Val Ile Leu Ala Val Asn Asp Val Asp Ala Glu Asp Gly
                150                 155                 160

gct gat cca aac ctt tgt agt gaa tat gtg aaa gat att tat gct tat        644
Ala Asp Pro Asn Leu Cys Ser Glu Tyr Val Lys Asp Ile Tyr Ala Tyr
            165                 170                 175

ctg aga caa ctt gag gaa gag caa gca gtc aga cca aaa tac cta ctg        692
Leu Arg Gln Leu Glu Glu Glu Gln Ala Val Arg Pro Lys Tyr Leu Leu
        180                 185                 190

ggt cgg gaa gtc act gga aac atg aga gcc atc cta att gac tgg cta        740
Gly Arg Glu Val Thr Gly Asn Met Arg Ala Ile Leu Ile Asp Trp Leu
    195                 200                 205

gta cag gtt caa atg aaa ttc agg ttg ttg cag gag acc atg tac atg        788
Val Gln Val Gln Met Lys Phe Arg Leu Leu Gln Glu Thr Met Tyr Met
210                 215                 220                 225

act gtc tcc att att gat cgg ttc atg cag aat aat tgt gtg ccc aag        836
```

```
Thr Val Ser Ile Ile Asp Arg Phe Met Gln Asn Asn Cys Val Pro Lys
                230                 235                 240

aag atg ctg cag ctg gtt ggt gtc act gcc atg ttt att gca agc aaa      884
Lys Met Leu Gln Leu Val Gly Val Thr Ala Met Phe Ile Ala Ser Lys
            245                 250                 255

tat gaa gaa atg tac cct cca gaa att ggt gac ttt gct ttt gtg act      932
Tyr Glu Glu Met Tyr Pro Pro Glu Ile Gly Asp Phe Ala Phe Val Thr
        260                 265                 270

gac aac act tat act aag cac caa atc aga cag atg gaa atg aag att      980
Asp Asn Thr Tyr Thr Lys His Gln Ile Arg Gln Met Glu Met Lys Ile
    275                 280                 285

cta aga gct tta aac ttt ggt ctg ggt cgg cct cta cct ttg cac ttc     1028
Leu Arg Ala Leu Asn Phe Gly Leu Gly Arg Pro Leu Pro Leu His Phe
290                 295                 300                 305

ctt cgg aga gca tct aag att gga gag gtt gat gtc gag caa cat act     1076
Leu Arg Arg Ala Ser Lys Ile Gly Glu Val Asp Val Glu Gln His Thr
                310                 315                 320

ttg gcc aaa tac ctg atg gaa cta act atg ttg gac tat gac atg gtg     1124
Leu Ala Lys Tyr Leu Met Glu Leu Thr Met Leu Asp Tyr Asp Met Val
            325                 330                 335

cac ttt cct cct tct caa att gca gca gga gct ttt tgc tta gca ctg     1172
His Phe Pro Pro Ser Gln Ile Ala Ala Gly Ala Phe Cys Leu Ala Leu
        340                 345                 350

aaa att ctg gat aat ggt gaa tgg aca cca act cta caa cat tac ctg     1220
Lys Ile Leu Asp Asn Gly Glu Trp Thr Pro Thr Leu Gln His Tyr Leu
    355                 360                 365

tca tat act gaa gaa tct ctt ctt cca gtt atg cag cac ctg gct aag     1268
Ser Tyr Thr Glu Glu Ser Leu Leu Pro Val Met Gln His Leu Ala Lys
370                 375                 380                 385

aat gta gtc atg gta aat caa gga ctt aca aag cac atg act gtc aag     1316
Asn Val Val Met Val Asn Gln Gly Leu Thr Lys His Met Thr Val Lys
                390                 395                 400

aac aag tat gcc aca tcg aag cat gct aag atc agc act cta cca cag     1364
Asn Lys Tyr Ala Thr Ser Lys His Ala Lys Ile Ser Thr Leu Pro Gln
            405                 410                 415

ctg aat tct gca cta gtt caa gat tta gcc aag gct gtg gca aag gtg     1412
Leu Asn Ser Ala Leu Val Gln Asp Leu Ala Lys Ala Val Ala Lys Val
        420                 425                 430

taa cttgtaaact tgagttggag tactatattt acaaataaaa ttggcaccat          1465

gtgccatctg tacatattac tgttgcattt acttttaata aagcttgtgg cccctttttac  1525

tttttatag cttaactaat ttgaatgtgg ttacttccta ctgtagggta gcggaaaagt    1585

tgtcttaaaa ggtatggtgg ggatattttt aaaaactcct tttggtttac ctggggatcc   1645

aattgatgta tatgtttata tactgggttc ttgttttata tacctggctt ttactttatt   1705

aatatgagtt actgaaggtg atggaggtat ttgaaaattt tacttccata ggacatactg   1765

catgtaagcc aagtcatgga gaatctgctg catagctcta ttttaaagta aaagtctacc   1825

accgaatccc tagtcccccct gttttctgtt tcttcttgtg attgctgcca taattctaag  1885

ttatttactt ttaccactat ttaagttatc aactttagct agtatcttca aactttcact   1945

ttgaaaaatg agaattttat attctaagcc agttttcatt ttggttttgt gttttggtta   2005

ataaaacaat actcaaatac aaaa                                          2029
```

```
<210> SEQ ID NO 8
<211> LENGTH: 433
<212> TYPE: PRT
<213> ORGANISM: Homo sapiens
```

<400> SEQUENCE: 8

Met Ala Leu Arg Val Thr Arg Asn Ser Lys Ile Asn Ala Glu Asn Lys
1 5 10 15

Ala Lys Ile Asn Met Ala Gly Ala Lys Arg Val Pro Thr Ala Pro Ala
20 25 30

Ala Thr Ser Lys Pro Gly Leu Arg Pro Arg Thr Ala Leu Gly Asp Ile
35 40 45

Gly Asn Lys Val Ser Glu Gln Leu Gln Ala Lys Met Pro Met Lys Lys
50 55 60

Glu Ala Lys Pro Ser Ala Thr Gly Lys Val Ile Asp Lys Lys Leu Pro
65 70 75 80

Lys Pro Leu Glu Lys Val Pro Met Leu Val Pro Val Pro Val Ser Glu
85 90 95

Pro Val Pro Glu Pro Glu Pro Glu Pro Glu Pro Glu Pro Val Lys Glu
100 105 110

Glu Lys Leu Ser Pro Glu Pro Ile Leu Val Asp Thr Ala Ser Pro Ser
115 120 125

Pro Met Glu Thr Ser Gly Cys Ala Pro Ala Glu Glu Asp Leu Cys Gln
130 135 140

Ala Phe Ser Asp Val Ile Leu Ala Val Asn Asp Val Asp Ala Glu Asp
145 150 155 160

Gly Ala Asp Pro Asn Leu Cys Ser Glu Tyr Val Lys Asp Ile Tyr Ala
165 170 175

Tyr Leu Arg Gln Leu Glu Glu Glu Gln Ala Val Arg Pro Lys Tyr Leu
180 185 190

Leu Gly Arg Glu Val Thr Gly Asn Met Arg Ala Ile Leu Ile Asp Trp
195 200 205

Leu Val Gln Val Gln Met Lys Phe Arg Leu Leu Gln Glu Thr Met Tyr
210 215 220

Met Thr Val Ser Ile Ile Asp Arg Phe Met Gln Asn Asn Cys Val Pro
225 230 235 240

Lys Lys Met Leu Gln Leu Val Gly Val Thr Ala Met Phe Ile Ala Ser
245 250 255

Lys Tyr Glu Glu Met Tyr Pro Pro Glu Ile Gly Asp Phe Ala Phe Val
260 265 270

Thr Asp Asn Thr Tyr Thr Lys His Gln Ile Arg Gln Met Glu Met Lys
275 280 285

Ile Leu Arg Ala Leu Asn Phe Gly Leu Gly Arg Pro Leu Pro Leu His
290 295 300

Phe Leu Arg Arg Ala Ser Lys Ile Gly Glu Val Asp Val Glu Gln His
305 310 315 320

Thr Leu Ala Lys Tyr Leu Met Glu Leu Thr Met Leu Asp Tyr Asp Met
325 330 335

Val His Phe Pro Pro Ser Gln Ile Ala Ala Gly Ala Phe Cys Leu Ala
340 345 350

Leu Lys Ile Leu Asp Asn Gly Glu Trp Thr Pro Thr Leu Gln His Tyr
355 360 365

Leu Ser Tyr Thr Glu Glu Ser Leu Leu Pro Val Met Gln His Leu Ala
370 375 380

Lys Asn Val Val Met Val Asn Gln Gly Leu Thr Lys His Met Thr Val
385 390 395 400

Lys Asn Lys Tyr Ala Thr Ser Lys His Ala Lys Ile Ser Thr Leu Pro
405 410 415

```
Gln Leu Asn Ser Ala Leu Val Gln Asp Leu Ala Lys Ala Val Ala Lys
            420                 425                 430

Val


<210> SEQ ID NO 9
<211> LENGTH: 5265
<212> TYPE: DNA
<213> ORGANISM: Homo sapiens
<220> FEATURE:
<221> NAME/KEY: CDS
<222> LOCATION: (163)..(1245)

<400> SEQUENCE: 9

ggcactcaac aggtgctctg agtggcaccc acggccaggt cctgggagag gacagaaaac      60

aactgggact cctcagcccc cggcagctcc cagtgcccag ccacccacaa cacaacccaa     120

agccttctag acaagctcag tggaatctga agggcccacc cc atg gag gaa tgc        174
                                               Met Glu Glu Cys
                                               1

tgg gtg aca gag ata gcc aat ggc tcc aag gat ggc ttg gat tcc aac       222
Trp Val Thr Glu Ile Ala Asn Gly Ser Lys Asp Gly Leu Asp Ser Asn
5                   10                  15                  20

cct atg aag gat tac atg atc ctg agt ggt ccc cag aag aca gct gtt       270
Pro Met Lys Asp Tyr Met Ile Leu Ser Gly Pro Gln Lys Thr Ala Val
                25                  30                  35

gct gtg ttg tgc act ctt ctg ggc ctg cta agt gcc ctg gag aac gtg       318
Ala Val Leu Cys Thr Leu Leu Gly Leu Leu Ser Ala Leu Glu Asn Val
            40                  45                  50

gct gtg ctc tat ctg atc ctg tcc tcc cac caa ctc cgc cgg aag ccc       366
Ala Val Leu Tyr Leu Ile Leu Ser Ser His Gln Leu Arg Arg Lys Pro
        55                  60                  65

tca tac ctg ttc att ggc agc ttg gct ggg gct gac ttc ctg gcc agt       414
Ser Tyr Leu Phe Ile Gly Ser Leu Ala Gly Ala Asp Phe Leu Ala Ser
    70                  75                  80

gtg gtc ttt gca tgc agc ttt gtg aat ttc cat gtt ttc cat ggt gtg       462
Val Val Phe Ala Cys Ser Phe Val Asn Phe His Val Phe His Gly Val
85                  90                  95                  100

gat tcc aag gct gtc ttc ctg ctg aag att ggc agc gtg act atg acc       510
Asp Ser Lys Ala Val Phe Leu Leu Lys Ile Gly Ser Val Thr Met Thr
                105                 110                 115

ttc aca gcc tct gtg ggt agc ctc ctg ctg acc gcc att gac cga tac       558
Phe Thr Ala Ser Val Gly Ser Leu Leu Leu Thr Ala Ile Asp Arg Tyr
            120                 125                 130

ctc tgc ctg cgc tat cca cct tcc tac aaa gct ctg ctc acc cgt gga       606
Leu Cys Leu Arg Tyr Pro Pro Ser Tyr Lys Ala Leu Leu Thr Arg Gly
        135                 140                 145

agg gca ctg gtg acc ctg ggc atc atg tgg gtc ctc tca gca cta gtc       654
Arg Ala Leu Val Thr Leu Gly Ile Met Trp Val Leu Ser Ala Leu Val
    150                 155                 160

tcc tac ctg ccc ctc atg gga tgg act tgc tgt ccc agg ccc tgc tct       702
Ser Tyr Leu Pro Leu Met Gly Trp Thr Cys Cys Pro Arg Pro Cys Ser
165                 170                 175                 180

gag ctt ttc cca ctg atc ccc aat gac tac ctg ctg agc tgg ctc ctg       750
Glu Leu Phe Pro Leu Ile Pro Asn Asp Tyr Leu Leu Ser Trp Leu Leu
                185                 190                 195

ttc atc gcc ttc ctc ttt tcc gga atc atc tac acc tat ggg cat gtt       798
Phe Ile Ala Phe Leu Phe Ser Gly Ile Ile Tyr Thr Tyr Gly His Val
            200                 205                 210

ctc tgg aag gcc cat cag cat gtg gcc agc ttg tct ggc cac cag gac       846
Leu Trp Lys Ala His Gln His Val Ala Ser Leu Ser Gly His Gln Asp
```

```
        215                 220                 225

agg cag gtg cca gga atg gcc cga atg agg ctg gat gtg agg ttg gcc      894
Arg Gln Val Pro Gly Met Ala Arg Met Arg Leu Asp Val Arg Leu Ala
    230                 235                 240

aag acc cta ggg cta gtg ttg gct gtg ctc ctc atc tgt tgg ttc cca      942
Lys Thr Leu Gly Leu Val Leu Ala Val Leu Leu Ile Cys Trp Phe Pro
245                 250                 255                 260

gtg ctg gcc ctc atg gcc cac agc ctg gcc act acg ctc agt gac cag      990
Val Leu Ala Leu Met Ala His Ser Leu Ala Thr Thr Leu Ser Asp Gln
                265                 270                 275

gtc aag aag gcc ttt gct ttc tgc tcc atg ctg tgc ctc atc aac tcc     1038
Val Lys Lys Ala Phe Ala Phe Cys Ser Met Leu Cys Leu Ile Asn Ser
            280                 285                 290

atg gtc aac cct gtc atc tat gct cta cgg agt gga gag atc cgc tcc     1086
Met Val Asn Pro Val Ile Tyr Ala Leu Arg Ser Gly Glu Ile Arg Ser
        295                 300                 305

tct gcc cat cac tgc ctg gct cac tgg aag aag tgt gtg agg ggc ctt     1134
Ser Ala His His Cys Leu Ala His Trp Lys Lys Cys Val Arg Gly Leu
    310                 315                 320

ggg tca gag gca aaa gaa gaa gcc ccg aga tcc tca gtc acc gag aca     1182
Gly Ser Glu Ala Lys Glu Glu Ala Pro Arg Ser Ser Val Thr Glu Thr
325                 330                 335                 340

gag gct gat ggg aaa atc act ccg tgg cca gat tcc aga gat cta gac     1230
Glu Ala Asp Gly Lys Ile Thr Pro Trp Pro Asp Ser Arg Asp Leu Asp
                345                 350                 355

ctc tct gat tgc tga tgaggcctct tcccaattta aacaactcaa gtcagaaatc     1285
Leu Ser Asp Cys
            360

agttcactcc ctggaagaga gagaggggtc ttggcactct cttcttactt aaaccagtcc   1345

cagacaccta gacacggacc ccttttgct gatgagtgtt gggactgact cctggaagac   1405

agcctggcct tgcccacctg cacacagtct gttggatagg tagggccacg aggagtagcc   1465

aggtaggcga gacacaaaag gcctgggaca gggtcagtac aagtcaggtc aggcttcatg   1525

cctgcatcct ccagagacca caggagccaa agcgagcctc caggcccagc aatgagggac   1585

ttgggagaaa tctgagaaga atgggttgtt ctcttgggaa gtcagggtat cagatgggat   1645

ggacatccag gtcttctctc tgcctaattg tcaaggcctc cttggctctg gagctatgaa   1705

aggccccact ttcaagtcac ccttgccact gaggaccgag gactatgcta tgatgaggat   1765

taaggtgttg acttgcctct ttcagagata aatgacaagc cttcagtttg gggcatcctg   1825

ttgtttgggc gaggaccctc tctgatattc tgataatccc cacctgtaac ctcaggtccc   1885

tggaaataca gaggaggctg ggatcgcctg agacacaaaa atctttggag aattttcttg   1945

accctctgaa gtccttccag cagcagtcct ggtggtgctg ctggaagcag gcaatgtcct   2005

agtctaacct aactcgaaga aaaaaaggaa gatattcaca aagattgtat aaatctccaa   2065

actgttcccc tatctgcccc caattcagct cccttgcctc ctccacaccc ctattacata   2125

taataagcag agcaagtggg aggaggggaa atgtccttcc tatatgccag gtatggggct   2185

gacatttcag tctattgacc ccagctagaa tatagctcca tgattttaaa gatctcaggg   2245

gccaggcatg gtagctcatg cctgtaatcc cagcactttg ggaggccaag gcaggtggat   2305

cacctgaggt caggagtttg agaccagcct gaccaatatg gtgaaaccct gtctctacta   2365

aaaatacaaa aattagcagg gcatggtggc aggcacctgt agtcccagct actcgggagg   2425

ctgagacagg agaattgctt gaaccctgga ggcagaggtt gcagtgagcc gagattgcac   2485

cactgcactc cagcctgggt gacagagcaa gactgtctca aaaaaataaa ataaaataga   2545
```

tcccagggta ctcatttttc atatgaggga ggctgggttc ctcccagagg agcctaaaac 2605
agccaacaag agaaattgtt ggcggcagga agattgcaga ggaattctaa tgcaattatt 2665
tgggacctca aatggaataa aatgaaagat attggttaaa catgtcttcg tttaatactt 2725
tcaagacaaa atatccacta gctattcact tattcattca tctcataaac atgagccagg 2785
ctctgtgcag ggtcctgagt acccagccat aaatgagact gtgcccctgt ctcatggggc 2845
ttacagtcta tatcctgctt gcaagacagc caataagtca ataaagaaga taattacagg 2905
cagtacaaca aaggaaatat gcaggttcat gtcatgtaat agggattaat tgagttaact 2965
caataaacgg taggatagac ctaccatgtg ccggctcact tttattgagc ctttactatg 3025
tgccaggcag gggctaagt gtttttaaat gccttatttc acttcatgtt tcccaacaac 3085
ctaataagaa ggtcttagtt atcttcattt tacagatgtg gcaacctcaa agatgcaaag 3145
tcacttgtct aaggtcaccc tgctaagtac cagagctgag gtctccaacc tagttctgtt 3205
tgacttcaaa gcctgccctc ttaaccacta accttttgtc ctagttcagt caaattctgc 3265
ttgattattg ctcattaggg ataatattag ctatctgtag catcagattg ctgcaaagtt 3325
aactcatcgt agattctcaa tatactccat tttattaaat ggccccgtat taatctcctg 3385
taataaattt cacaaatcca gtggcttatc aacagaaatt tactgtctca taattctgga 3445
ggccagaagt caaaatcaag atgtggtagg gccctgctcc ctccaaaagt ttaaggggag 3505
aattattcct tgactctttc aacttctggc agtccctgtc attccttggc ttgtggaaac 3565
atcactccta cctctgactc tgtcttcata tggcatttcc tctgtgtctc ttggtgtctt 3625
ttttttttt ttttttttt ttgagacgga atctcattct gttgtccagg caggagtgca 3685
gtgacatgat cttggctcac tgcaacctcc acctctcagg ttcaagtgat tctcctgcct 3745
cagcctccca aatagctggg actacaggca cccgccacca cactcagcta atttttgtat 3805
ttttagtaga gatggggttt caccatcttg cccaggctgg tcttgaactc ctgacctcaa 3865
gtgatccgcc caccttggcc tcctaaattg ctgggattac agacgtgagc caccataccc 3925
ggcctggtgt ctttttttaaa gaatatcagt cactggattt gggcccaccc taatcctaat 3985
agtatgactt catcttaatt taaccaatta tatctgtaga gaccctgttt ccaaataagg 4045
tcacattcac agattccagg tggacaagaa gtttaggcgg acactattca actcagtaca 4105
gacccaggaa caaagtccac ccactgggct gtgttgagtg gcagtcacta gtttatcctc 4165
cctcaacaag atgagctcca ggttgacctc tgcatcccca gtgctcagtc aggacccagc 4225
agagcatctg aagggatctg gtcaatatgt gtggaactga actgtttctg aaaagctctg 4285
acgtatgttt tggaaaatca aatcttgttt taatccagac accaatcttt ttgtaaggca 4345
aacaagtagc ataaatgttt aaaagtgaat ttgcatgttt atatactgtc attccttaaa 4405
gttgaagcat gcctttcttt attcatcggt ggaatccttt ctcattttgg caaagaaaat 4465
gcccaagtgc ctggcacaaa caagcactga gtaaatactt cttgaatgaa taaaactaga 4525
ttctaaaaat catttgatca aacgcaactc cacactttct acttctcttc ttttagaacc 4585
acactgtatt tctgcttttt tttttttttt tttttttttt gacatagaat ctcactctgt 4645
cacccaggtt ggagtgcagt ggcatgcaat cttggctcac tgcaacctct gcctcctggg 4705
ttcaagcagt tctcctgcct tagcctccca tgtagctggg attacaggta cccgccacca 4765
tgcccagcta atttttgtat tgttagtaga gatggaattt caccatattg gccaggctgg 4825
tcttgaactc ctgacttcaa gtgatccacc caccttagcc tcccaaagtg ctaggattac 4885

```
aggtgtgagc caccactccc agcccctatg tctgctttaa gtggagaagc agagcttatg   4945

agggaggaga acaagggtgc aaaagggacc tagatatcac tgagaactgc ccttgttgtt   5005

tggttgagga aatgggccca gacagtggac aagacttgct cagggagaca aacgagatgg   5065

tgtccagtgc aacaaaccta ggtttcctaa cttccagttc tgtccactct acatcagtgc   5125

ctctcacctg tccctgcagg ttcacatttt ggttatgtgg ataaggagaa ataaattgaa   5185

gatcacaatg tcccatttta tcttccccaa gacaagctct gtaacattaa agaccactat   5245

gcaaaccgat tactagaaaa                                               5265
```

<210> SEQ ID NO 10
<211> LENGTH: 360
<212> TYPE: PRT
<213> ORGANISM: Homo sapiens

<400> SEQUENCE: 10

```
Met Glu Glu Cys Trp Val Thr Glu Ile Ala Asn Gly Ser Lys Asp Gly
1               5                   10                  15

Leu Asp Ser Asn Pro Met Lys Asp Tyr Met Ile Leu Ser Gly Pro Gln
            20                  25                  30

Lys Thr Ala Val Ala Val Leu Cys Thr Leu Leu Gly Leu Leu Ser Ala
        35                  40                  45

Leu Glu Asn Val Ala Val Leu Tyr Leu Ile Leu Ser Ser His Gln Leu
    50                  55                  60

Arg Arg Lys Pro Ser Tyr Leu Phe Ile Gly Ser Leu Ala Gly Ala Asp
65                  70                  75                  80

Phe Leu Ala Ser Val Val Phe Ala Cys Ser Phe Val Asn Phe His Val
                85                  90                  95

Phe His Gly Val Asp Ser Lys Ala Val Phe Leu Leu Lys Ile Gly Ser
            100                 105                 110

Val Thr Met Thr Phe Thr Ala Ser Val Gly Ser Leu Leu Leu Thr Ala
        115                 120                 125

Ile Asp Arg Tyr Leu Cys Leu Arg Tyr Pro Pro Ser Tyr Lys Ala Leu
    130                 135                 140

Leu Thr Arg Gly Arg Ala Leu Val Thr Leu Gly Ile Met Trp Val Leu
145                 150                 155                 160

Ser Ala Leu Val Ser Tyr Leu Pro Leu Met Gly Trp Thr Cys Cys Pro
                165                 170                 175

Arg Pro Cys Ser Glu Leu Phe Pro Leu Ile Pro Asn Asp Tyr Leu Leu
            180                 185                 190

Ser Trp Leu Leu Phe Ile Ala Phe Leu Phe Ser Gly Ile Ile Tyr Thr
        195                 200                 205

Tyr Gly His Val Leu Trp Lys Ala His Gln His Val Ala Ser Leu Ser
    210                 215                 220

Gly His Gln Asp Arg Gln Val Pro Gly Met Ala Arg Met Arg Leu Asp
225                 230                 235                 240

Val Arg Leu Ala Lys Thr Leu Gly Leu Val Leu Ala Val Leu Leu Ile
                245                 250                 255

Cys Trp Phe Pro Val Leu Ala Leu Met Ala His Ser Leu Ala Thr Thr
            260                 265                 270

Leu Ser Asp Gln Val Lys Lys Ala Phe Ala Phe Cys Ser Met Leu Cys
        275                 280                 285

Leu Ile Asn Ser Met Val Asn Pro Val Ile Tyr Ala Leu Arg Ser Gly
    290                 295                 300
```

```
Glu Ile Arg Ser Ser Ala His His Cys Leu Ala His Trp Lys Lys Cys
305                 310                 315                 320

Val Arg Gly Leu Gly Ser Glu Ala Lys Glu Glu Ala Pro Arg Ser Ser
                325                 330                 335

Val Thr Glu Thr Glu Ala Asp Gly Lys Ile Thr Pro Trp Pro Asp Ser
            340                 345                 350

Arg Asp Leu Asp Leu Ser Asp Cys
        355                 360


<210> SEQ ID NO 11
<211> LENGTH: 3721
<212> TYPE: DNA
<213> ORGANISM: Homo sapiens
<220> FEATURE:
<221> NAME/KEY: CDS
<222> LOCATION: (28)..(942)

<400> SEQUENCE: 11

gtagtacgaa tccgtcaggc cggaacc atg gca gtg acc aag gag ctc tta cag      54
                              Met Ala Val Thr Lys Glu Leu Leu Gln
                              1               5

atg gac ctg tac gcg ctg cta ggc att gag gag aag gca gcg gac aaa       102
Met Asp Leu Tyr Ala Leu Leu Gly Ile Glu Glu Lys Ala Ala Asp Lys
10                  15                  20                  25

gag gta aag aag gcg tat agg cag aag gcc ctc tcc tgc cac cca gac       150
Glu Val Lys Lys Ala Tyr Arg Gln Lys Ala Leu Ser Cys His Pro Asp
                30                  35                  40

aaa aat cca gat aat ccc aga gca gct gaa ctc ttc cac cag ctt tct       198
Lys Asn Pro Asp Asn Pro Arg Ala Ala Glu Leu Phe His Gln Leu Ser
            45                  50                  55

cag gcc ttg gag gtg ctg acc gat gct gca gcc agg gct gca tat gac       246
Gln Ala Leu Glu Val Leu Thr Asp Ala Ala Ala Arg Ala Ala Tyr Asp
        60                  65                  70

aag gtc agg aaa gcc aag aag caa gca gca gag agg acc cag aaa ctt       294
Lys Val Arg Lys Ala Lys Lys Gln Ala Ala Glu Arg Thr Gln Lys Leu
    75                  80                  85

gat gag aaa agg aag aaa gtg aag ctt gac ctg gag gcc cgg gag cgg       342
Asp Glu Lys Arg Lys Lys Val Lys Leu Asp Leu Glu Ala Arg Glu Arg
90                  95                  100                 105

cag gcc cag gcc cag gag agt gag gag gaa gag gag agc cgg agc acc       390
Gln Ala Gln Ala Gln Glu Ser Glu Glu Glu Glu Glu Ser Arg Ser Thr
                110                 115                 120

agg aca cta gag caa gag atc gaa cgc ctg aga gaa gag ggt tcc cgg       438
Arg Thr Leu Glu Gln Glu Ile Glu Arg Leu Arg Glu Glu Gly Ser Arg
            125                 130                 135

cag ctg gag gaa cag cag agg ctc atc cgg gag cag ata cgc cag gag       486
Gln Leu Glu Glu Gln Gln Arg Leu Ile Arg Glu Gln Ile Arg Gln Glu
        140                 145                 150

cgt gac cag agg ttg aga gga aag gca gaa aat act gaa ggc caa gga       534
Arg Asp Gln Arg Leu Arg Gly Lys Ala Glu Asn Thr Glu Gly Gln Gly
    155                 160                 165

acc ccc aaa cta aag cta aaa tgg aag tgc aag aag gag gat gag tca       582
Thr Pro Lys Leu Lys Leu Lys Trp Lys Cys Lys Lys Glu Asp Glu Ser
170                 175                 180                 185

aaa ggt ggc tac tcc aaa gac gtc ctc cta cgg ctt ttg cag aag tat       630
Lys Gly Gly Tyr Ser Lys Asp Val Leu Leu Arg Leu Leu Gln Lys Tyr
                190                 195                 200

ggt gag gtt ctc aac ctg gtg ctt tcc agt aag aag cca ggc act gct       678
Gly Glu Val Leu Asn Leu Val Leu Ser Ser Lys Lys Pro Gly Thr Ala
            205                 210                 215
```

```
gtg gtg gag ttt gca acc gtc aag gca gcg gag ctg gct gtc cag aat      726
Val Val Glu Phe Ala Thr Val Lys Ala Ala Glu Leu Ala Val Gln Asn
        220                 225                 230

gaa gtt ggc ctg gtg gat aac cct ctg aag att tcc tgg ttg gag gga      774
Glu Val Gly Leu Val Asp Asn Pro Leu Lys Ile Ser Trp Leu Glu Gly
    235                 240                 245

cag ccc cag gat gcc gtg ggc cgc agc cac tca gga ctg tca aag ggc      822
Gln Pro Gln Asp Ala Val Gly Arg Ser His Ser Gly Leu Ser Lys Gly
250                 255                 260                 265

tca gtg ctg tca gag agg gac tac gag agc ctc gtc atg atg cgc atg      870
Ser Val Leu Ser Glu Arg Asp Tyr Glu Ser Leu Val Met Met Arg Met
                270                 275                 280

cgc cag gcg gcc gag cgg caa cag ctg atc gca cgg atg cag cag gaa      918
Arg Gln Ala Ala Glu Arg Gln Gln Leu Ile Ala Arg Met Gln Gln Glu
            285                 290                 295

gac cag gag ggg ccg cct acg tag ccccagctcc agccatccac ccctcagccc     972
Asp Gln Glu Gly Pro Pro Thr
        300

ttttcttcaa cgtcaccaat aaattttttt tttttttaag attttacctc tatcccatac   1032

ataggtataa ggtgctgggc tctgccgcag agcgctccac ccaggcctgg cgcccctccc   1092

aggaagtggg cagaccccca gggaaacgct ccgcagggtg agagtcccag agtccgtgca   1152

caagcagagc acaggcgcag ccactcatca cagccccttta ttggcttggg ctagctatgc  1212

aggagccacg cgccagggcc gctggagtgc ccagctccgg cccggggcag ctgcccgagg   1272

aacatggcct acacaaggcc ctcggcccag gcccgaagca ggagggcagc tgggagcacc   1332

agggcaccgg gcactgccct ctcccactgc ttgacgcagg gtttcagaga aggccattca   1392

ctgccctttg gggctgggcc catggcggtg atgatttggg aagagaggag caaggcagac   1452

ggtgaggcag gagcttggag gtcagggccc acagcagccc ctccacaggg gtgccccgtc   1512

tgcaaatcag catgagaagg tcactccttg tgcagacacc acaccagcgt ctggcccacc   1572

cccgtcatgc tcagcacacg gaagcccctg cgttccagct tgtccaggac tatgcgggga   1632

gggtcatcga cgtagtattc ataactgcaa agagacagga tgggggggt gaggaggggc    1692

acacagcaag ctcctggtac aaagctagtg tctgcagcag gcagcctggc cactcttgta   1752

gtgactcaca cttgctggct gcttgctggg cgctggggta agtgcacgcc ccctgcctcc   1812

tccccttcta ggtacttcac gagctatctc atttattctt cccaacaagc tagtgaaggt   1872

gccactgttg tggccattga tagatgagaa aacagagggg ttaatcaggt tccccagcgt   1932

cccagatggt agaccatgtt agtctgacca cagccctgct gccgccctcc ctgggcttgc   1992

tccccaccca ggcttccagg taggaggagg ctgaggctgc agtgagccat gattgcacca   2052

ccgcactcca gcctgggcga cagagactcc atttcaaaaa aaaataagcc tccaggcccc   2112

tcactgccct ggctgtcctg cagttctgta gcaacaaggc tgagccccag tagctcctgg   2172

ctctgtgcgc cactccctag catggagagt gctggtagtc cttctgtcag gtttaattga   2232

tgctgaaaga ccatgaagca gacaaagggc tcaagcccca agctgggcat ggagaggcaa   2292

gtgcctcatg gcaaagggag ggggctggct tctgtccccg agccttgacc caggggctgg   2352

gatcagccct cctctttccc cgatttgaac tggcactcac tctgacaact cttttcagag   2412

agcctgtgta gcttgggttc tccctgcctc caggggtgag aggaggaatg gaagcagtag   2472

tcacagttta gacatggagg cattaggaag aatgccaagg gaaatggcta ggtccccagg   2532

cagcagccac cctggaggta ggacgcaggc tccctgctcc ctgcttctag ggcttagctt   2592

tgcgactcat gcagatcctc acgacaaaaa cctttctctc tgtgcctgtc tgtccttgat   2652
```

```
gggggtccagc ttaggagagg gcagggcaag gaacagtctg ctagtggagt cctagaccca   2712

gggaacggac tctgtttctg cggttccagt aaggatgtgg aaagctttca gagcaagcct   2772

cgtgggggag agggggggatg ttggagaggc tacagatggg accaactcct ccggagaaca   2832

gagccccagg atgcaggcag gggctctga tgctgggccc tgtccctggg cttggaggtt   2892

gtataaaggg agcagaggca ggtctagggg ctggcaggga gaggatactg agggaggctg   2952

ctacttacaa gttgtttccc aaggctcttc tctttgaagc ccccagatgc tgcatcagct   3012

ctggatccga ctgttcatcg cccaccatag tggggcccac ctcctgcaag gtaagccaca   3072

gtggctgctt ggctggctgc caggaggagg tggaaggtct tgcctgtcct tcctcccctg   3132

cctgctagcc ctgagtaagg ttcaggtaaa ggctacagag agtagcaagg attcttaggg   3192

gctgagcaca agctgtgaag gggtggagcc catcaatgat caggaggagc aatgtaggcg   3252

ccctccctag tgccttaaag ctcagcttta gccaggcaaa gtatcacgag cctatagttc   3312

cagctactga ggctgaggtg ggaggatcgc ttgaggtggg aggagtttga ggctgcagtg   3372

agccatgatt gcaccactgc actccagcct gggtgacaga gtgagactcc atttcaaaaa   3432

aacaaaacaa aataaacatg taaatgaaag aagccagact cagatcacat taccacagaa   3492

aggtaattag tggttatcta gggctgaggg acttggggga aatcaagagt gtctgccagt   3552

gggtacaggg tttccttttg ggtattaga aatgttctaa aactgattat ggtgatggtt   3612

gcacaactct gagtacacta aagaaacaac aacactgaat tgtacacttt aaatcaaaga   3672

atttatggta tgcacattac atatcaataa agccatatct tttaagaaa              3721
```

```
<210> SEQ ID NO 12
<211> LENGTH: 304
<212> TYPE: PRT
<213> ORGANISM: Homo sapiens

<400> SEQUENCE: 12

Met Ala Val Thr Lys Glu Leu Leu Gln Met Asp Leu Tyr Ala Leu Leu
1               5                   10                  15

Gly Ile Glu Glu Lys Ala Ala Asp Lys Glu Val Lys Lys Ala Tyr Arg
            20                  25                  30

Gln Lys Ala Leu Ser Cys His Pro Asp Lys Asn Pro Asp Asn Pro Arg
        35                  40                  45

Ala Ala Glu Leu Phe His Gln Leu Ser Gln Ala Leu Glu Val Leu Thr
    50                  55                  60

Asp Ala Ala Ala Arg Ala Ala Tyr Asp Lys Val Arg Lys Ala Lys Lys
65                  70                  75                  80

Gln Ala Ala Glu Arg Thr Gln Lys Leu Asp Glu Lys Arg Lys Lys Val
                85                  90                  95

Lys Leu Asp Leu Glu Ala Arg Glu Arg Gln Ala Gln Ala Gln Glu Ser
            100                 105                 110

Glu Glu Glu Glu Glu Ser Arg Ser Thr Arg Thr Leu Glu Gln Glu Ile
        115                 120                 125

Glu Arg Leu Arg Glu Glu Gly Ser Arg Gln Leu Glu Glu Gln Gln Arg
    130                 135                 140

Leu Ile Arg Glu Gln Ile Arg Gln Glu Arg Asp Gln Arg Leu Arg Gly
145                 150                 155                 160

Lys Ala Glu Asn Thr Glu Gly Gln Gly Thr Pro Lys Leu Lys Leu Lys
                165                 170                 175

Trp Lys Cys Lys Lys Glu Asp Glu Ser Lys Gly Gly Tyr Ser Lys Asp
```

```
            180                 185                 190

Val Leu Leu Arg Leu Leu Gln Lys Tyr Gly Glu Val Leu Asn Leu Val
        195                 200                 205

Leu Ser Ser Lys Lys Pro Gly Thr Ala Val Val Glu Phe Ala Thr Val
    210                 215                 220

Lys Ala Ala Glu Leu Ala Val Gln Asn Glu Val Gly Leu Val Asp Asn
225                 230                 235                 240

Pro Leu Lys Ile Ser Trp Leu Glu Gly Gln Pro Gln Asp Ala Val Gly
                245                 250                 255

Arg Ser His Ser Gly Leu Ser Lys Gly Ser Val Leu Ser Glu Arg Asp
            260                 265                 270

Tyr Glu Ser Leu Val Met Met Arg Met Arg Gln Ala Ala Glu Arg Gln
        275                 280                 285

Gln Leu Ile Ala Arg Met Gln Gln Glu Asp Gln Glu Gly Pro Pro Thr
    290                 295                 300


<210> SEQ ID NO 13
<211> LENGTH: 13827
<212> TYPE: DNA
<213> ORGANISM: Homo sapiens
<220> FEATURE:
<221> NAME/KEY: CDS
<222> LOCATION: (259)..(1173)

<400> SEQUENCE: 13

acggcccggc gcgtggctcg ggctcgggcg gagctggaga cgtgtggagc tgttcgagga      60

ctcgcgggtg tgcagggatg cggtttaata ttttcatgtg attcctaaaa gaatctgagg     120

ctcaagaaaa gagggcatct taatatcctg cactttcagt cattgagggc atgatcacaa     180

agatcaaagc catttttagg cagtgcacct atgatatgtg ttttagaaat agccgttaaa     240

ctttggtttg aatgaaga atg tct ctc aat cca cct ata ttt ctc aaa cga       291
                    Met Ser Leu Asn Pro Pro Ile Phe Leu Lys Arg
                    1               5                   10

agt gaa gaa aat agt tca aaa ttt gtg gaa aca aaa cag tca caa act       339
Ser Glu Glu Asn Ser Ser Lys Phe Val Glu Thr Lys Gln Ser Gln Thr
            15                  20                  25

act tcc ata gct tca gaa gat ccc ctt caa aac tta tgt tta gca tct       387
Thr Ser Ile Ala Ser Glu Asp Pro Leu Gln Asn Leu Cys Leu Ala Ser
        30                  35                  40

caa gaa gtt ctt caa aaa gct cag caa agt ggg aga tca aaa tgt ctc       435
Gln Glu Val Leu Gln Lys Ala Gln Gln Ser Gly Arg Ser Lys Cys Leu
    45                  50                  55

aaa tgt ggt ggt tcc aga atg ttc tac tgc tat aca tgt tat gtt cca       483
Lys Cys Gly Gly Ser Arg Met Phe Tyr Cys Tyr Thr Cys Tyr Val Pro
60                  65                  70                  75

gtt gaa aat gta cct att gaa cag att cca ctt gtg aag ctt cca ttg       531
Val Glu Asn Val Pro Ile Glu Gln Ile Pro Leu Val Lys Leu Pro Leu
                80                  85                  90

aag att gac atc att aaa cat cca aat gaa aca gat ggc aaa agt act       579
Lys Ile Asp Ile Ile Lys His Pro Asn Glu Thr Asp Gly Lys Ser Thr
            95                  100                 105

gct ata cat gca aaa ctc tta gca cct gaa ttt gta aac att tac acg       627
Ala Ile His Ala Lys Leu Leu Ala Pro Glu Phe Val Asn Ile Tyr Thr
        110                 115                 120

tat ccg tgt att cca gaa tat gaa gaa aag gac cat gaa gtt gca ctc       675
Tyr Pro Cys Ile Pro Glu Tyr Glu Glu Lys Asp His Glu Val Ala Leu
    125                 130                 135

att ttt cct gga cct cag tct atc tca ata aaa gat att tct ttt cat       723
```

```
Ile Phe Pro Gly Pro Gln Ser Ile Ser Ile Lys Asp Ile Ser Phe His
140                 145                 150                 155

ctg caa aaa agg att caa aat aat gtt aga ggc aaa aat gat gac cct      771
Leu Gln Lys Arg Ile Gln Asn Asn Val Arg Gly Lys Asn Asp Asp Pro
                160                 165                 170

gac aag cca tct ttt aaa cgc aaa aga act gaa gaa caa gag ttc tgt      819
Asp Lys Pro Ser Phe Lys Arg Lys Arg Thr Glu Glu Gln Glu Phe Cys
            175                 180                 185

gat ttg aat gac agc aag tgc aaa ggc aca aca ctg aaa aaa att ata      867
Asp Leu Asn Asp Ser Lys Cys Lys Gly Thr Thr Leu Lys Lys Ile Ile
        190                 195                 200

ttt ata gat agc acc tgg aac caa aca aac aaa ata ttc act gat gag      915
Phe Ile Asp Ser Thr Trp Asn Gln Thr Asn Lys Ile Phe Thr Asp Glu
    205                 210                 215

cga ctt caa ggg ttg tta caa gtt gag ttg aaa aca aga aaa act tgc      963
Arg Leu Gln Gly Leu Leu Gln Val Glu Leu Lys Thr Arg Lys Thr Cys
220                 225                 230                 235

ttt tgg cgc cat caa aaa gga aag cca gat act ttc ctt tct aca att     1011
Phe Trp Arg His Gln Lys Gly Lys Pro Asp Thr Phe Leu Ser Thr Ile
                240                 245                 250

gaa gcc att tac tac ttt ctg gta gac tac cat act gat ata tta aaa     1059
Glu Ala Ile Tyr Tyr Phe Leu Val Asp Tyr His Thr Asp Ile Leu Lys
            255                 260                 265

gag aaa tac aga ggg caa tat gac aat ctt tta ttt ttc tat tct ttt     1107
Glu Lys Tyr Arg Gly Gln Tyr Asp Asn Leu Leu Phe Phe Tyr Ser Phe
        270                 275                 280

atg tac cag ttg ata aag aat gcc aaa tgc tct gga gat aag gaa aca     1155
Met Tyr Gln Leu Ile Lys Asn Ala Lys Cys Ser Gly Asp Lys Glu Thr
    285                 290                 295

gga aaa ctt aca cat tag tttttaacaa gccacttatg tctttttatt            1203
Gly Lys Leu Thr His
300

ttgctaacat taataaactt atatttgtgc tttgtttttt cttaagaaat aatcatatat   1263

aatgcctgta agaccatttg aaaaaattcc agtttcatat atatcacttc atatttcttg   1323

aaggaaattg tatctggggg aatttttcag agatactgtt gattgaaaaa cttacttcag   1383

aagttatttg ctcagtgaaa cctcagtttc attactacat tttaatatag tgtgttatgt   1443

ctctgtgatt agatataaca tattccatta gatctaatta gctatttatt tcaacatctt   1503

tatatctttt cacctgtact catgaccacc tttagaagta aatggggtta caatctgctg   1563

gctgaaaaat aggtcataag tgatttttct tgaggttagt agcaaacata ggcagaacta   1623

gaattagaat tctggtatct agggctgttt ctttaagtcc taaggttgtt aaaagcagag   1683

actctggagc tagactacct gaatctaaat ctcagccttt ctgcttatca gccatgtcat   1743

tttcttccat ttgtacaaag caggcaatac tgagcaacta ccttatagga ataactgagt   1803

taatatctaa ggggctttca gcagtacctg aaatatagta agtgttacat atatgtttac   1863

tctttttatt ttatttggaa ttgtgaactg ataataattg aagcctacct gctagtggcc   1923

atctctgctg ccaggtgaaa agagcctgac ttagaatgaa gtcagcgaag gaaagcagag   1983

tggagagaaa aagagagact gagtcctgat gacatcattt atttacctag acctagctgc   2043

ttgtgaatag agccctactg tgctgaatag cttctgtctg ctcttttcta ttctgctccc   2103

tgctctgtga ggtaggttcc tttgctctct tgcttttggt tgggttcaac aaatgggaag   2163

caccagtggg agattagaag ttgagaggaa aatgaaatga tgttatttat ttccctggct   2223

cctttcctgc catgtcatca tcagttggct gtgttcctct actaaatagt accttatcag   2283
```

gaatcctatc tcttctgttc ccaagcagtt accccagtta cctcactagg tttagttcct 2343 gctccctccc tttacccctt ttcacttagg gttggtaata gcttacagtt attactagcc 2403 ccagtatagt tcactacaac ttgttgcttt acctaaaccc tgctcataca tttgtaaata 2463 ctgtagttgt tttattacac tcttctcaaa tgtccccact tgaaatagcc ttctatttct 2523 tttggggact ctgataaatt cacctgtttg ggtgaaataa tagcacattt cctgaagtat 2583 atacagtggg acacatgatg ttttatgggg gaaagagttc ttggtgaaat tagtttgctg 2643 tacattacgt tgtttccctc ccagggattc agaaggcaaa acatattaaa ggttctgaaa 2703 agtcctgaaa taaacatttt gaactttatt taagctgata tatcttaaac ttacttgaat 2763 atgtagcacc tattaacatg ccatggaaat aggacgtttg gagtattgta attaagaaca 2823 attcctatta atatacatgg ggcaactgag aattaaagag gtaagtaaat tattgataga 2883 tcatacacct agttagtagc agagcctgtt ctagaatctg gaacttctga tttggtttgg 2943 ttcagtaagg tcaccattat attatgctat tcataaaaag gaatgtggat tatataaggc 3003 ttgaacatta ttagtcttac agtcttagcc aaataaacta actggcttgc ttattttagc 3063 agttattcta caagaatgga attaaaatag attttttttt tcatgtttag aacttggccc 3123 tgggaataga ggaaggcttg aattgattta agcagggcca aagttggatt tctctaggct 3183 aaatttggac ttccctgagc caaaatctat tgcatttaac tggctttaca aaccaactaa 3243 acataacagt tcagagggaa aagaaaaaaa aaagcgagag acagagaaca attctatcac 3303 tcatttgcct ccatctctca gctggcataa gaaagatgac ccacgtactt cataagagcc 3363 taatttacag ctaaggccag ataaaatctc aggttctttt caaaagaagt tagtaatacc 3423 tattagaaca atgaattgac tatacttgtc ttagtttttt ttgtttgttt tttgtttttt 3483 gtttttttgg tgtgatagat gtaacagtgg ccctaattct ttatccttgc ttgtattcat 3543 ggtcattttt caggttcctt tgaagtactc cccccactgt gattctgggt catctgcatt 3603 cagagattta gtgcattttt acttacactt gtgcttctgc tgttgacata agaatatgca 3663 tggctgagtt agcctgctgg agcatgagac tccatggaac agagccaggt tgccctggtc 3723 accctcactg aatcttgtct agattggctg atggccagcc aaacccaaga tatgtgaatg 3783 attccagcca agatcagcag agtcatctaa ctgacaccta cctgattcca aacatgtgag 3843 caaggaatgt ctattatgcc accaatgtct tatagctatt tattgtggct atagatatct 3903 catctttgga tgcattatca gatcatcttc ttcaagtacc ttagaagatt ctcagtctca 3963 tgtttcttgg gctcttgacc acttgctttg ccttagctac cacctcatat agtaacagat 4023 taccagcagg tttgtatgat tcctctgctt gagatcaatt agccatatgt tcagaatccc 4083 tggcctataa caacacttct gtgctttaaa aaccccatgc cacaatgact gttaaaaggg 4143 ctaggcgatg tagtctggta ggtttgtgaa gttaactgtc tgaaaaactt ggatcaatgg 4203 actagaaaaa gctgctgggt aaattgctct tcttctgatg gactgtatag agacactgtt 4263 tttcatcttg cctgtccaga agcgtactct gtggccaagc aagtgtactt gccacatgat 4323 tggcagtgtc tcttcatggc ttttcatgaa acagcagcaa gtgctacaca gtaatttatc 4383 agtttgcatt tgcctcccat tattgccagc ctcacttcct ttcttcctcg ctcttaccag 4443 cctggattgt acctttaata aagtagtgga tatatttcct ttagggtctc tttttctagg 4503 gaagtcaggt gttttagtct ggatttagtt agaaaagcag catcgttaca agtattacat 4563 gaataaagaa gtttagtaaa gaaattaagg tttaccccaa tgtgagaatt actggggtaa 4623 taaaggtctg gaaggctgca gcagaagaga tttagagaag cagtgactaa ctaggtcagc 4683

```
cggagattct caaagtactc atgacttcat ttgtagaaac atgtatatct taagcatatc   4743
aagtgtctca ttcctctaat ctttctagga gccctttggt tcatcctgaa ggtcccccta   4803
aatcccttca gaagtcttaa aaaggagtaa atggccacac cttttatttg ttcttttctt   4863
tgaggccatg ttaatggcag tcccttgatt tggtctttgt actaggctgt ttttaatgat   4923
cacattttat ttgatgagaa acaattttat tttctagttc tgcatatcct aggttatgta   4983
tttcatttca gttccatttc catacccatt gccttaattt tgagcttgtc tgtttcttac   5043
atttctcatt ttgacagaat aagctgactg ttattaagta caatagataa ggtacctaag   5103
agcctcgaaa catcaccaaa taccatgaat gcattaggta tatttttttgt cttccatgtt   5163
actggaagca ttaattatag caacttttta tctccaaata ctgacaatta aaagacccta   5223
gtgaaaactt taaccaaaca cttactgacc ctacattgaa ggccaccagc caaaaatcac   5283
cacccataca taagagccaa acatcactag acacttggtg aaatccttca aatataaaag   5343
gggaaaagga ggggagaaaa tccaaaggaa atagacaaac ggagaataat ggcaacaaaa   5403
aaaaaactgt cttcaaaata agagtatatt atattcacaa aacaagaata ggagagtgtg   5463
aaaaagaaca agcaataaaa aagatctcag aaatttaaaa agtgattgct gaaataaaaa   5523
ttaaatataa gagttgaaga taaaatatag cataagaata gaaaattctg aattccaaat   5583
acctaaggcc aatcttagtt aaaagttgta aatgcaacca taggctacat gttacattgt   5643
atttaattaa aaaccttaag aggaaaggca atagagcttg taacagctat taccttggt    5703
tgtaaaggag aaggttggag attatttgta taccaactac ttaagtttac aaaaaataat   5763
gagcattagg tagatggaat gaaagtctat tcatacactg tatattaagc tctatataca   5823
ctgcatatca tcatcatgac attgagtttc tagctggatt gcagagatga gccaaagcgc   5883
ttctccccaa attattattt attcattttt gagacagagt ctcactcttg tctcccaggc   5943
tgcagtgcag tggtgcgatc tcagctcact acaacctcca cctcccaagt tcaagcaatt   6003
atcatgcctt agccccccga gtagctggga tcacaggcat gtgccaccac accccgctaa   6063
tttttgtatt tttagtagag atggagtttt gtcatgtttg gccagcctta tctgaaactc   6123
ctgacctcaa gtgatcctgc ctttgcttcc caaagtgctg ggattaacag gcctgagcca   6183
caacacccag cctaaattat ttttaattat gacatttttt gtattccctt gaggcactga   6243
caactatagt cttattttat atgttatagt gaatcatatt tatctcatta tatattacag   6303
aatattttgt ttgatggaga aaattcactg acctgtgctg taatgtttat accagcaatt   6363
agctgattga tttactatga cctcactctt tattcagcag ttctgccact attactagct   6423
aatccaacaa cgaggcctta ttttggcttt ctttcgaaag gtcatttctg accccagctt   6483
gaagtttgtt tattttcact tgaagagatc tctcagaaag tcaaagaaaa taggaggaaa   6543
aaaacttaag attaagggcc aatctaagag gtccttcatt tgaataatag gagtaacaga   6603
atgggaaagg cgtggaaaaa aatttgtgat ttctaaaatt gaggacatta agtcattaga   6663
gtaaaaaaaa gatgtacatt aaggcttatc atcaaggaat ttcagaacac tgtggataga   6723
aaatactaaa agatttcaaa cagaagaaat aggtcgtata tcgaccaata atcaggatat   6783
taaaggactt cttaacaaca ttggaaacta gaagacatgg ggtgatgcct ttagaacttt   6843
aagtgaaaat agttttctat ttggattcta tttttagtca tgcaattaat caagtatgaa   6903
tatagtataa agacacagaa ggtctcaaag gtattacctc ccatatattc ttgagataaa   6963
gatgcttagg agaatactga agatgttttc cagtaaaacg gagaaggaaa ccaaaaacca   7023
```

aaaaagagag cattaagaag tcagcaggcc aggcgcggtg gctcacgcct ctaatcccag 7083
cactttagga ggccaaggca ggtggatcgc ctgaggtctg gagtttaaga ccagcctggc 7143
taacatggcg aaactctgtc tctactaaaa atacaaaaat tagtcgggtg tgatggcatg 7203
tgtctgtaat cccagctact cgggaggctg aagcaggaga atcacttaga acctgggagg 7263
cagaagttgt agtgagccga gatggtgcca ttgcactcca gcctgggtga cagagtgaga 7323
ctccgtctca aaaaaaataa ataaaaaaat aaaaagtcag caaagggaag tttcagggtt 7383
tcaggattca ttcatccatt ctaaaaaatt ttgagtgcat actatgtgtc aaattattgt 7443
ctaggtgatg gctatagcat gccgaggtag taagtgctaa gaagaaaata aagcagagta 7503
aggaactgat agtgactggt gcaggaaagg ggtgccagtt taaatagcat ggtcagatgg 7563
aaaagcctgt gataaggtaa aattgagcag agacctaaat gagagagagt gaaccatgcg 7623
aataattaag tgaataatgt tttaattata gggaacaata tgtgtgtgtc tatatatata 7683
tatacacaca aaggtactga ggcagcagta tacttggcat gtttgaggaa taacaaggac 7743
actagtttgg aacagtgtgt gggagggaaa aaatgataga agatgacatc atagggagta 7803
atggtgtgga gccatggtaa gatgttaaga ttttactctg agtgatgaga taggaagcca 7863
tcagagaatt taagcaaatg agtgacagga tctgacttat atttttaaag gattatttgg 7923
cttctttatg aaaaatagac tgcaagagag taagaaataa aataggaaga tcaattagaa 7983
tgctatttca gtagtccatt tgagagatga tatttgcctg gacaagggtt gtgatcatgg 8043
gcgagtggta cagaatgaca agatcctgca tgtattttta aggtagagcc agtatttgca 8103
gatagtttag acattgtggt agatatgaaa atgtgctgcc tatatccccc ttctaggaag 8163
gacttgctaa ttagctgcag ggagtgtgaa gaacagaaat ccaccagtat cagcacttca 8223
tctgcaacag ctatagaaaa agcttcacct gaggttaccc tcgtcttaga tctcagggca 8283
gccctcagtg gagatgtaag gccttgctac ttcagcctca tttattacac tgtcaggcaa 8343
aaccttcctc agagctccct ctattacaac ttaatttctt cttctgccca atcctgcttc 8403
ctccccttcc cctgaaaggt gacactttct aataaacatc ttacacccca aactccatct 8463
cagcattcct ctttagagga ctcgacctgt ggtaattgtt agtaggagtg atctgagctg 8523
ccaatgagaa tcccatcaca tgtggcacat ggaacaaaag cccatggctc aaggtggtaa 8583
cttttattag tggtaaaatg agaagattta cccacggaag agaatgtgcc agcaagtgca 8643
gtatatcagg tatttgagac tcatgaagga aatagtaaat ttaagaataa cagaattgaa 8703
tggccaagtg ccactaatgc tctgtagaaa gagggcttct ttggttgcat acaaatctca 8763
tctagaattt aatagtccaa gtagccaaac tggtatttgt ccttaagaat aaatactgga 8823
agatcaagca cagaaagtct agaatagagg catgtgaatg gacatacttg tgtcaagtat 8883
gtacatgaac tgtgaaggtc tctgtattac gtgcagtgcc caccagagag cattcagtac 8943
tgaagagtct ctaaacaata aagcaaacta aacacattgc ctagttgacg tcatccttcc 9003
tgcttcagtt attcgccacc cagtgctagc acagtgggca catgaatgga atgtccactg 9063
tggaaaggat gaagactaag catagggttc agtagcttga gtttcaactt accaaggctg 9123
ccttagctgc tgctgctgtt gaatgtccaa cctacaagca acacagacaa tactgcaccc 9183
ctgatataat accattcttc aatatcaagt tggttacatt gggccccttc cacactggaa 9243
ggaccagcat ttccttgtca tagaaataga cacaatttcc agataggagt ttgcttttcc 9303
tctttgcaga gcctcagtca gtatcaccat ttgagtttac ttagtattgt attgaccagc 9363
atgcgatctc acattatatc atatcagatc cggaaaccta ttttatggaa aaccaagcgc 9423 aggagtggac ccatatccac aggatccact aataatatca ctttttttcac cacttggaat 9483
ttgtcagctt gatagaacat tggaacaacc tgctgaaggt acagctgaac accagctcat 9543
aggcaaattc tacaaggata ggatgccata ctccaagata cagagtatgt actggatcaa 9603
ttatccttat atagcatgtg ccccaatatg aagaataaat gggtcttgga acccatttat 9663
tcctaggggt agatgcaaag agagtagaag aagaggtgcc tcccctccgt gccatcactt 9723
ttaatgaccc atatggtact ttgcacctct tcataactct gaactctgca gtgagaggtc 9783
ttggtcccac aaggggacac agttttgctg agagatatat aaaaaatctc actgaaaaac 9843
ataagctgca gcagctacct ggatactttc ggttccttgt gtctgtctag ggagcagcag 9903
ccaataaaag gagtcaagat cagttgaccc taatcaagag gagattggaa tcctggttac 9963
acaatctggg cagaagtaat aaatgtggtg cccaagtgat aaacctacca aattgagact 10023
aatgtgtagg tgtggcaacc catcctcaaa agggcatgat ggcctggaac tcaggcctct 10083
caaggaatgt gggtctgaat tataccagat aaaccaccag gagcagcaga ggtggtagca 10143
gaggctgagg gaaatctaga attgatagtg gaggatgagg ggatgtgaca agtattgatg 10203
gcattcccaa gccccactgc agcagcaagc actgtaattt gtcccactaa tctcccatct 10263
tctaaatttc tgagaggtca agaaaagagg tctcttgatt cctttaggaa ctgctcccta 10323
agcatacagg gagacataga tctatgtgga gcaaagggtg gattgtaata agcaaagaga 10383
tacactgcct gattcacttt aagaaaggac tgacctccca gttgcaagga atgaggtcag 10443
cagcctccaa ctgtcagctc cttcagagtc tgcttcaact gcagaaggac actgtgcttg 10503
aggtcatacc cttcccatgt ctggtgactg aagtccagct gaatgtagct gccaaagtta 10563
ccttaatgcc catgggaagc aaaaaatcaa agagtttaaa cagaattttg agaaatccca 10623
aatcagtttt ttttcagcat atgacatttt ggagtagttt gttattcagc aatagataac 10683
agaaattggt atcaggagtg gggtgttacc ataacaaaag gttaaacctt acatggtaaa 10743
aaggactttg cctctgtcat taagttaagc actttgaaat gtagagatta tcctgaatta 10803
tctaggtagg ctcaatataa gcatgagtcc ttaaaagtgg aagacggata catgagagga 10863
tgtcagaatg atgtgaaatg agaagaactc aacctgctat tgttggcttt acaggtgagt 10923
gataggaacc acaagcccca agcagcctct ggaagctgga aaaagcaaag aaacagattc 10983
tttccagagt gtccagaaag gaatgcagtt cagctaacat cttgatttta gatcagtgag 11043
atttttgtgt tggacttcta cagaactata taagaataaa ttgtgttgct taagcacact 11103
ataatacatg tggcaagaag ctgccagcta agccttgaag aatagtgaac aaactcttac 11163
tggaggatgg gaaggcagta aataaattat tgaattattg aaataaatgg aggattgagt 11223
tatgcattga cagaatgctt agcaataatt ttgcttgtct taatgtggaa cagaaaatga 11283
aacttaatag cttgtagatg tcttaaggag atttccaggt gaatgttgaa agtactgatg 11343
aacttattat ggctgcatct cataatgtac aggaagacat ttactgagtg aactaaagaa 11403
ggaactgttc aatttgaaag cagaatttag aggaaatttt tcaacctagt acttgtcatt 11463
tttttataga aaaggaaaaa tagatggaag atggagccaa aatcccagag ggaggagcca 11523
agaagcaagg agagcaatgg attaggaaac cactaccaga gggatgaact gaaccacaat 11583
caaggaatag cctcttcctt tggtgtaggg ggaccctgaa aacaatttaa ttttatgctt 11643
cctgtttcct tgtctccttt tttgaatgat agtctctgtg tggtgttcct atcctagaaa 11703
accttaactg ggacaagcta ctctcaagca tcttcacttg agaaacagta actgaggaag 11763 tttattgtat ctggacatgg tttagatgat aagattctga acttaaactt atgccataat 11823 ggagtgagac tcttagggta cagagtaagt acatttttgc atgttagtga gacaagaact 11883 gtggccgggg gcagactgtg atagtttttg aagatgtccc tcaaacaatt ccttcccttc 11943 cttggactcc tctcttcaga gggtagagtc catttccttt tccttttaat ctggattggc 12003 cttctaactc actttgacca ataaaatgtg gtaaaagtaa ggtctggcag ttttcacttt 12063 cactctcctg aaccttcata ttagaattcc aggatatcct tctagagata tccatatctc 12123 tagggacatg gtgagtccct agagacacca catggaaagg ccacctaggg aagaactgag 12183 atgccccagt caatagcact gccttagtca gtttgggcta gtataacaga aatatcatag 12243 attgagtgac ttttttcttt taaaaaaatg agattgtgga acctgaaaat acagtgtagt 12303 aagagtggag agaaaggcca cctaaggaag aactgagacg tcccagtcaa tagcactgcc 12363 ttagtcagtt ggagctactg taacaaaaaa tatcatagat tgagtgactt aaacaacaga 12423 aatttatatc ttacatttct ggagactgaa aatatggaaa tccaagatca gagtttcagc 12483 atggttaggt gtttagtggg cgctcccttc ctggtttgca gacagccatc ttcctgctat 12543 atcctcacat gatgcagaga gagagaactc tggtatcttt gtccccttat aagggcacca 12603 atctcatcat ggagggtctt caacctcatg gcttcttgga accaaattac ttcccaaagt 12663 cctcacctcc aaatctagca cattgaggtt tagggcttca acatatgaat ttcagtgcat 12723 agaaagcacc aagtcctcag acaaagagaa cttgaacctt ctaactcagc ttagccatta 12783 tctgcatgca accacataag tgaccctggg taacaccatc tggagctgaa gaaccaccag 12843 ccagtacaca gaaatgagaa attttaaaat ggttgattta ggtaattaag ttttggggtg 12903 gtttattaca tagcaattga taactgatac aacagtcttt tcgttagtag aagagggggt 12963 aagaaagaaa gacttatgaa gaaaagacct gtagaaaatc gggcctacgt acctctattt 13023 tttttcata ctcccgtgtt ttttttagtc catgctggtg gtatcctcat caatgcaatt 13083 ttctttaaaa ctctgtgagc ctttatatca gattagtcca ccccattaga acaaaagcaa 13143 cttctataaa tattgagaca ttccctttct acctttggct aagaattggg gtgctataga 13203 taattcccaa aagattatct agcctacagg gccgatgagg tatagcttga agtcattcta 13263 aagtcttcac aaaggatctt acagcctttg attttattat cactctggga ccacgtttta 13323 ctgttggcac gttcggcttt tctcatcttt tccctgagat catttatgat gtggaaatta 13383 ctttgctggc tgaagttggg aatagaaaac agtagagaat acttcaagag tattctaggt 13443 atgcactaag tttatgggaa gatatgccat ctacataatt taccttcctc tctaggccca 13503 tcataaaaat ctttgaaaaa ttaatactac attttagtat gaatataagt taaacttaga 13563 ggtgatatct attttgtggt taaatgtgtt ataaacattt atttagtgaa atacagtaca 13623 attacaacaa gcatcaatga atatttaatg agcagctgtt aatttctgaa gcagaaagaa 13683 agatgaataa aagttctggt tttactttta aaagtgaagg ctaactgtta gctcaagaaa 13743 tactttatgt ttgtcctata tgaaagtgtt gattgcacct ggttctttgc tgtaaattaa 13803 ataaaaattc aaatatttgt aaaa 13827

<210> SEQ ID NO 14
<211> LENGTH: 304
<212> TYPE: PRT
<213> ORGANISM: Homo sapiens

<400> SEQUENCE: 14

Met Ser Leu Asn Pro Pro Ile Phe Leu Lys Arg Ser Glu Glu Asn Ser

```
1               5                   10                  15

Ser Lys Phe Val Glu Thr Lys Gln Ser Gln Thr Thr Ser Ile Ala Ser
            20                  25                  30

Glu Asp Pro Leu Gln Asn Leu Cys Leu Ala Ser Gln Glu Val Leu Gln
        35                  40                  45

Lys Ala Gln Gln Ser Gly Arg Ser Lys Cys Leu Lys Cys Gly Gly Ser
    50                  55                  60

Arg Met Phe Tyr Cys Tyr Thr Cys Tyr Val Pro Val Glu Asn Val Pro
65                  70                  75                  80

Ile Glu Gln Ile Pro Leu Val Lys Leu Pro Leu Lys Ile Asp Ile Ile
                85                  90                  95

Lys His Pro Asn Glu Thr Asp Gly Lys Ser Thr Ala Ile His Ala Lys
            100                 105                 110

Leu Leu Ala Pro Glu Phe Val Asn Ile Tyr Thr Tyr Pro Cys Ile Pro
        115                 120                 125

Glu Tyr Glu Glu Lys Asp His Glu Val Ala Leu Ile Phe Pro Gly Pro
    130                 135                 140

Gln Ser Ile Ser Ile Lys Asp Ile Ser Phe His Leu Gln Lys Arg Ile
145                 150                 155                 160

Gln Asn Asn Val Arg Gly Lys Asn Asp Asp Pro Asp Lys Pro Ser Phe
                165                 170                 175

Lys Arg Lys Arg Thr Glu Glu Gln Glu Phe Cys Asp Leu Asn Asp Ser
            180                 185                 190

Lys Cys Lys Gly Thr Thr Leu Lys Lys Ile Ile Phe Ile Asp Ser Thr
        195                 200                 205

Trp Asn Gln Thr Asn Lys Ile Phe Thr Asp Glu Arg Leu Gln Gly Leu
    210                 215                 220

Leu Gln Val Glu Leu Lys Thr Arg Lys Thr Cys Phe Trp Arg His Gln
225                 230                 235                 240

Lys Gly Lys Pro Asp Thr Phe Leu Ser Thr Ile Glu Ala Ile Tyr Tyr
                245                 250                 255

Phe Leu Val Asp Tyr His Thr Asp Ile Leu Lys Glu Lys Tyr Arg Gly
            260                 265                 270

Gln Tyr Asp Asn Leu Leu Phe Phe Tyr Ser Phe Met Tyr Gln Leu Ile
        275                 280                 285

Lys Asn Ala Lys Cys Ser Gly Asp Lys Glu Thr Gly Lys Leu Thr His
    290                 295                 300


<210> SEQ ID NO 15
<211> LENGTH: 3506
<212> TYPE: DNA
<213> ORGANISM: Homo sapiens
<220> FEATURE:
<221> NAME/KEY: CDS
<222> LOCATION: (192)..(2396)

<400> SEQUENCE: 15

aaatccagag cggcgggcac tgacgggcac ttgcaccgtg tggacagact ctccggttct      60

ggggaaatcc agtccctgtt actccatttt ggccagaaat tcaagacatt tcaggtggca     120

gaataaattc aatccttgtt tctccatctt atcgagtagt agaagttagt tacattctct     180

ttgaactcat c atg aat tcc atg aag act gaa gaa aac aag tca ttt agc      230
             Met Asn Ser Met Lys Thr Glu Glu Asn Lys Ser Phe Ser
             1               5                   10

gct atg gaa gat gac cag agg act aga cct gaa gtt tca aag gat act      278
Ala Met Glu Asp Asp Gln Arg Thr Arg Pro Glu Val Ser Lys Asp Thr
```

```
    15                  20                  25

gtc atg aag cag aca cat gct gac aca cct gtt gat cat tgt cta tct      326
Val Met Lys Gln Thr His Ala Asp Thr Pro Val Asp His Cys Leu Ser
30                  35                  40                  45

ggc ata aga aag tgt agc agc acc ttt aag ctt aaa agt gaa gtc aac      374
Gly Ile Arg Lys Cys Ser Ser Thr Phe Lys Leu Lys Ser Glu Val Asn
                50                  55                  60

aag cat gaa aca gcc ctt gaa atg cag aat cca aat ttg aac aat aaa      422
Lys His Glu Thr Ala Leu Glu Met Gln Asn Pro Asn Leu Asn Asn Lys
            65                  70                  75

gaa tgt tgt ttc acc ttt acg ttg aat gga aac tcc aga aaa tta gac      470
Glu Cys Cys Phe Thr Phe Thr Leu Asn Gly Asn Ser Arg Lys Leu Asp
        80                  85                  90

cgt agt gtg ttt aca gca tat ggt aaa ccc agc gag agt atc tac tca      518
Arg Ser Val Phe Thr Ala Tyr Gly Lys Pro Ser Glu Ser Ile Tyr Ser
    95                  100                 105

gcc ctg agt gct aat gac tat ttc agt gaa agg ata aag aat cag ttt      566
Ala Leu Ser Ala Asn Asp Tyr Phe Ser Glu Arg Ile Lys Asn Gln Phe
110                 115                 120                 125

aat aag aac att att gtt tat gaa gaa aag aca ata gat gga cat ata      614
Asn Lys Asn Ile Ile Val Tyr Glu Glu Lys Thr Ile Asp Gly His Ile
                130                 135                 140

aat tta gga atg cct ctc aag tgc ctg cct agt gat tct cat ttt aaa      662
Asn Leu Gly Met Pro Leu Lys Cys Leu Pro Ser Asp Ser His Phe Lys
            145                 150                 155

att aca ttt ggt caa aga aag agt agc aaa gaa gat gga cac ata tta      710
Ile Thr Phe Gly Gln Arg Lys Ser Ser Lys Glu Asp Gly His Ile Leu
        160                 165                 170

cgc caa tgt gaa aat cca aac atg gaa tgc att ctt ttt cat gtt gtt      758
Arg Gln Cys Glu Asn Pro Asn Met Glu Cys Ile Leu Phe His Val Val
    175                 180                 185

gct ata gga agg aca aga aag aag att gtt aag atc aac gaa ctt cat      806
Ala Ile Gly Arg Thr Arg Lys Lys Ile Val Lys Ile Asn Glu Leu His
190                 195                 200                 205

gaa aaa gga agt aaa ctt tgt att tat gcc ttg aag ggt gag act att      854
Glu Lys Gly Ser Lys Leu Cys Ile Tyr Ala Leu Lys Gly Glu Thr Ile
                210                 215                 220

gaa gga gcc tta tgc aag gat ggc cgt ttt cgg tct gac ata ggt gaa      902
Glu Gly Ala Leu Cys Lys Asp Gly Arg Phe Arg Ser Asp Ile Gly Glu
            225                 230                 235

ttt gaa tgg aaa cta aag gaa ggt cat aag aaa att tat gga aaa cag      950
Phe Glu Trp Lys Leu Lys Glu Gly His Lys Lys Ile Tyr Gly Lys Gln
        240                 245                 250

tcc atg gtg gat gaa gta tct gga aaa gtc tta gaa atg gac att tca      998
Ser Met Val Asp Glu Val Ser Gly Lys Val Leu Glu Met Asp Ile Ser
    255                 260                 265

aaa aaa aaa gca tta caa cag aaa gat atc cat aaa aaa att aaa cag     1046
Lys Lys Lys Ala Leu Gln Gln Lys Asp Ile His Lys Lys Ile Lys Gln
270                 275                 280                 285

aat gaa agt gcc act gat gaa att aat cac cag agt ctg ata cag tct     1094
Asn Glu Ser Ala Thr Asp Glu Ile Asn His Gln Ser Leu Ile Gln Ser
                290                 295                 300

aag aaa aaa gtc cac aaa cca aag aaa gat gga gag acc aaa gat gta     1142
Lys Lys Lys Val His Lys Pro Lys Lys Asp Gly Glu Thr Lys Asp Val
            305                 310                 315

gaa cac agc aga gag caa att ctc cca cct cag gat cta agc cat tat     1190
Glu His Ser Arg Glu Gln Ile Leu Pro Pro Gln Asp Leu Ser His Tyr
        320                 325                 330

att aaa gat aaa act cgc cag aca att ccc agg att aga aat tat tac     1238
```

-continued

```
Ile Lys Asp Lys Thr Arg Gln Thr Ile Pro Arg Ile Arg Asn Tyr Tyr
    335                 340                 345

ttt tgt agt ttg ccc cga aaa tat agg caa ata aac tca caa gtt aga      1286
Phe Cys Ser Leu Pro Arg Lys Tyr Arg Gln Ile Asn Ser Gln Val Arg
350                 355                 360                 365

cgg agg ccg cat ctg ggt agg cgg tat gct att aat ctg gat gtc caa      1334
Arg Arg Pro His Leu Gly Arg Arg Tyr Ala Ile Asn Leu Asp Val Gln
                370                 375                 380

aag gag gca att aat ctc tta aag aat tat caa acg ttg aat gaa gcc      1382
Lys Glu Ala Ile Asn Leu Leu Lys Asn Tyr Gln Thr Leu Asn Glu Ala
            385                 390                 395

ata atg cat cag tat ccg aat ttt aaa gag gag gca cag tgg gta aga      1430
Ile Met His Gln Tyr Pro Asn Phe Lys Glu Glu Ala Gln Trp Val Arg
        400                 405                 410

aaa tat ttt cgg gaa gaa caa aag aga atg aat ctt tca cca gct aag      1478
Lys Tyr Phe Arg Glu Glu Gln Lys Arg Met Asn Leu Ser Pro Ala Lys
    415                 420                 425

caa ttc aac ata tat aaa aag gac ttc gga aaa atg act gca aat tct      1526
Gln Phe Asn Ile Tyr Lys Lys Asp Phe Gly Lys Met Thr Ala Asn Ser
430                 435                 440                 445

gtt tca gtt gca acc tgc gaa cag ctt aca tat tat agc aag tca gtt      1574
Val Ser Val Ala Thr Cys Glu Gln Leu Thr Tyr Tyr Ser Lys Ser Val
                450                 455                 460

ggg ttc atg caa tgg gac aat aat gga aac aca ggt aat gct act tgc      1622
Gly Phe Met Gln Trp Asp Asn Asn Gly Asn Thr Gly Asn Ala Thr Cys
            465                 470                 475

ttt gtc ttc aat ggt ggt tat att ttc acc tgt cga cat gtt gta cat      1670
Phe Val Phe Asn Gly Gly Tyr Ile Phe Thr Cys Arg His Val Val His
        480                 485                 490

ctt atg gtg ggt aaa aac aca cat cca agt ttg tgg cca gat ata att      1718
Leu Met Val Gly Lys Asn Thr His Pro Ser Leu Trp Pro Asp Ile Ile
    495                 500                 505

agc aaa tgt gcg aag gta acc ttc act tat aca gag ttc tgc cct act      1766
Ser Lys Cys Ala Lys Val Thr Phe Thr Tyr Thr Glu Phe Cys Pro Thr
510                 515                 520                 525

cct gac aat tgg ttt tcc att gag cca tgg ctt aaa gtg tcc aat gaa      1814
Pro Asp Asn Trp Phe Ser Ile Glu Pro Trp Leu Lys Val Ser Asn Glu
                530                 535                 540

aat cta gat tat gcc att tta aaa cta aaa gaa aat gga aat gcg ttt      1862
Asn Leu Asp Tyr Ala Ile Leu Lys Leu Lys Glu Asn Gly Asn Ala Phe
            545                 550                 555

cct cca gga cta tgg cga cag att tct cct caa cca tct act ggt ttg      1910
Pro Pro Gly Leu Trp Arg Gln Ile Ser Pro Gln Pro Ser Thr Gly Leu
        560                 565                 570

att tat tta att ggt cat cct gaa ggc cag atc aag aaa ata gat ggt      1958
Ile Tyr Leu Ile Gly His Pro Glu Gly Gln Ile Lys Lys Ile Asp Gly
    575                 580                 585

tgt act gtg att cct cta aac gaa cga ttg aaa aaa tat cca aac gat      2006
Cys Thr Val Ile Pro Leu Asn Glu Arg Leu Lys Lys Tyr Pro Asn Asp
590                 595                 600                 605

tgt caa gat ggg ttg gta gat ctc tat gat acc acc agt aat gta tac      2054
Cys Gln Asp Gly Leu Val Asp Leu Tyr Asp Thr Thr Ser Asn Val Tyr
                610                 615                 620

tgt atg ttt acc caa aga agt ttc cta tca gag gtt tgg aac aca cac      2102
Cys Met Phe Thr Gln Arg Ser Phe Leu Ser Glu Val Trp Asn Thr His
            625                 630                 635

acg ctt agt tat gat act tgt ttc tct gat ggg tcc tca ggc tcc cca      2150
Thr Leu Ser Tyr Asp Thr Cys Phe Ser Asp Gly Ser Ser Gly Ser Pro
        640                 645                 650
```

```
gtg ttt aat gca tct ggc aaa ttg gtt gct ttg cat acc ttt ggg ctt     2198
Val Phe Asn Ala Ser Gly Lys Leu Val Ala Leu His Thr Phe Gly Leu
    655                 660                 665

ttt tat caa cga gga ttt aat gtg cat gcc ctt att gaa ttt ggt tat     2246
Phe Tyr Gln Arg Gly Phe Asn Val His Ala Leu Ile Glu Phe Gly Tyr
670                 675                 680                 685

tct atg gat tct att ctt tgt gat att aaa aag aca aat gag agc ttg     2294
Ser Met Asp Ser Ile Leu Cys Asp Ile Lys Lys Thr Asn Glu Ser Leu
                690                 695                 700

tat aaa tca tta aat gat gag aaa ctt gag acc tac gat gaa gag aaa     2342
Tyr Lys Ser Leu Asn Asp Glu Lys Leu Glu Thr Tyr Asp Glu Glu Lys
            705                 710                 715

ggt aaa caa gag tca tca ctt caa gat cat cag att gaa ccc atg gaa     2390
Gly Lys Gln Glu Ser Ser Leu Gln Asp His Gln Ile Glu Pro Met Glu
        720                 725                 730

tgt tag aaaagagatg ctgtcttcaa gaaaatatgc caataattcc tggcaaagat      2446
Cys

ttcatgacaa agacacttaa agcaattgca acaaaagtga aaattggcaa atgagaccta   2506

attaaatctt ctgcacagca aaagaaacta tcaacagggt aaacacacaa cctacggaat   2566

gggagaaaat atttgcaaac tatgcataca gcaaagatct aatattcaga atccattagg   2626

aacttaaaca gattaacaag caaaaaaaac aagcaacccc attaaaaagt gggcaaagga   2686

catgaacaaa cacttttcaa aagaagatat acacatggcc aacaaggata tgaaaaaata   2746

cctgatatca ctaatcatta gagaaatgca aatcaaaaaa atgccatcac actaatcaga   2806

atggctgtta ttaaaatgcc aaaaaattac agatgctggc gaggttgcag agaaagggga   2866

atgcttatac actgctagtg ggaaaataaa ttagttcagc cattgtggaa agcagttggg   2926

tgatttctaa aagaacttaa aacagctacc attcaagcca gcaatctcat gactgggtat   2986

atgtccaaag gaatataaat tgttctacca taaagacatg cacatatatg ttcactgcag   3046

cactattcac aatagcaaaa catgaaatca acctaaatgc ccatcaatgg tagactggat   3106

aaagaaaatg tgacacatat acaccatagc atactacaca gccataaaaa agtacaagat   3166

catgtgcttt gcagcaacat ggatggaact gaaggtcatt atcctaagcg aactaatgca   3226

ggaacagaaa gccaagtacc acatgttctc tcataagtgg aagctaaata ttgagtacac   3286

atggacacaa agaagaaaac aacagatatg gggcctactt gagggtggag ggtgggagga   3346

gggtgaagac tgaaaaactg cctatggggt actatgctta ttacctgggt gatgaaataa   3406

tctgaacaca aaaccctggt gacatgcagt ttacctatat aacaaaactg cacatggact   3466

cttaaaccta aataaaagtt taaaatatat ataatgccaa                         3506


<210> SEQ ID NO 16
<211> LENGTH: 734
<212> TYPE: PRT
<213> ORGANISM: Homo sapiens

<400> SEQUENCE: 16

Met Asn Ser Met Lys Thr Glu Glu Asn Lys Ser Phe Ser Ala Met Glu
1               5                   10                  15

Asp Asp Gln Arg Thr Arg Pro Glu Val Ser Lys Asp Thr Val Met Lys
            20                  25                  30

Gln Thr His Ala Asp Thr Pro Val Asp His Cys Leu Ser Gly Ile Arg
        35                  40                  45

Lys Cys Ser Ser Thr Phe Lys Leu Lys Ser Glu Val Asn Lys His Glu
    50                  55                  60
```

-continued

```
Thr Ala Leu Glu Met Gln Asn Pro Asn Leu Asn Asn Lys Glu Cys Cys
65                  70                  75                  80

Phe Thr Phe Thr Leu Asn Gly Asn Ser Arg Lys Leu Asp Arg Ser Val
                85                  90                  95

Phe Thr Ala Tyr Gly Lys Pro Ser Glu Ser Ile Tyr Ser Ala Leu Ser
            100                 105                 110

Ala Asn Asp Tyr Phe Ser Glu Arg Ile Lys Asn Gln Phe Asn Lys Asn
        115                 120                 125

Ile Ile Val Tyr Glu Glu Lys Thr Ile Asp Gly His Ile Asn Leu Gly
    130                 135                 140

Met Pro Leu Lys Cys Leu Pro Ser Asp Ser His Phe Lys Ile Thr Phe
145                 150                 155                 160

Gly Gln Arg Lys Ser Ser Lys Glu Asp Gly His Ile Leu Arg Gln Cys
                165                 170                 175

Glu Asn Pro Asn Met Glu Cys Ile Leu Phe His Val Val Ala Ile Gly
            180                 185                 190

Arg Thr Arg Lys Lys Ile Val Lys Ile Asn Glu Leu His Glu Lys Gly
        195                 200                 205

Ser Lys Leu Cys Ile Tyr Ala Leu Lys Gly Glu Thr Ile Glu Gly Ala
    210                 215                 220

Leu Cys Lys Asp Gly Arg Phe Arg Ser Asp Ile Gly Glu Phe Glu Trp
225                 230                 235                 240

Lys Leu Lys Glu Gly His Lys Lys Ile Tyr Gly Lys Gln Ser Met Val
                245                 250                 255

Asp Glu Val Ser Gly Lys Val Leu Glu Met Asp Ile Ser Lys Lys Lys
            260                 265                 270

Ala Leu Gln Gln Lys Asp Ile His Lys Lys Ile Lys Gln Asn Glu Ser
        275                 280                 285

Ala Thr Asp Glu Ile Asn His Gln Ser Leu Ile Gln Ser Lys Lys Lys
    290                 295                 300

Val His Lys Pro Lys Lys Asp Gly Glu Thr Lys Asp Val Glu His Ser
305                 310                 315                 320

Arg Glu Gln Ile Leu Pro Pro Gln Asp Leu Ser His Tyr Ile Lys Asp
                325                 330                 335

Lys Thr Arg Gln Thr Ile Pro Arg Ile Arg Asn Tyr Tyr Phe Cys Ser
            340                 345                 350

Leu Pro Arg Lys Tyr Arg Gln Ile Asn Ser Gln Val Arg Arg Arg Pro
        355                 360                 365

His Leu Gly Arg Arg Tyr Ala Ile Asn Leu Asp Val Gln Lys Glu Ala
    370                 375                 380

Ile Asn Leu Leu Lys Asn Tyr Gln Thr Leu Asn Glu Ala Ile Met His
385                 390                 395                 400

Gln Tyr Pro Asn Phe Lys Glu Glu Ala Gln Trp Val Arg Lys Tyr Phe
                405                 410                 415

Arg Glu Glu Gln Lys Arg Met Asn Leu Ser Pro Ala Lys Gln Phe Asn
            420                 425                 430

Ile Tyr Lys Lys Asp Phe Gly Lys Met Thr Ala Asn Ser Val Ser Val
        435                 440                 445

Ala Thr Cys Glu Gln Leu Thr Tyr Tyr Ser Lys Ser Val Gly Phe Met
    450                 455                 460

Gln Trp Asp Asn Asn Gly Asn Thr Gly Asn Ala Thr Cys Phe Val Phe
465                 470                 475                 480

Asn Gly Gly Tyr Ile Phe Thr Cys Arg His Val Val His Leu Met Val
```

```
                485                 490                 495

Gly Lys Asn Thr His Pro Ser Leu Trp Pro Asp Ile Ile Ser Lys Cys
            500                 505                 510

Ala Lys Val Thr Phe Thr Tyr Thr Glu Phe Cys Pro Thr Pro Asp Asn
        515                 520                 525

Trp Phe Ser Ile Glu Pro Trp Leu Lys Val Ser Asn Glu Asn Leu Asp
    530                 535                 540

Tyr Ala Ile Leu Lys Leu Lys Glu Asn Gly Asn Ala Phe Pro Pro Gly
545                 550                 555                 560

Leu Trp Arg Gln Ile Ser Pro Gln Pro Ser Thr Gly Leu Ile Tyr Leu
                565                 570                 575

Ile Gly His Pro Glu Gly Gln Ile Lys Lys Ile Asp Gly Cys Thr Val
            580                 585                 590

Ile Pro Leu Asn Glu Arg Leu Lys Lys Tyr Pro Asn Asp Cys Gln Asp
        595                 600                 605

Gly Leu Val Asp Leu Tyr Asp Thr Thr Ser Asn Val Tyr Cys Met Phe
    610                 615                 620

Thr Gln Arg Ser Phe Leu Ser Glu Val Trp Asn Thr His Thr Leu Ser
625                 630                 635                 640

Tyr Asp Thr Cys Phe Ser Asp Gly Ser Ser Gly Ser Pro Val Phe Asn
                645                 650                 655

Ala Ser Gly Lys Leu Val Ala Leu His Thr Phe Gly Leu Phe Tyr Gln
            660                 665                 670

Arg Gly Phe Asn Val His Ala Leu Ile Glu Phe Gly Tyr Ser Met Asp
        675                 680                 685

Ser Ile Leu Cys Asp Ile Lys Lys Thr Asn Glu Ser Leu Tyr Lys Ser
    690                 695                 700

Leu Asn Asp Glu Lys Leu Glu Thr Tyr Asp Glu Glu Lys Gly Lys Gln
705                 710                 715                 720

Glu Ser Ser Leu Gln Asp His Gln Ile Glu Pro Met Glu Cys
                725                 730


<210> SEQ ID NO 17
<211> LENGTH: 2742
<212> TYPE: DNA
<213> ORGANISM: Homo sapiens
<220> FEATURE:
<221> NAME/KEY: CDS
<222> LOCATION: (37)..(1476)

<400> SEQUENCE: 17

ctgtttctgg agagagctgt ttgaatttgg aaaccc atg ttg gct gtc cca aat       54
                                        Met Leu Ala Val Pro Asn
                                        1               5

atg aga ttt ggc atc ttt ctt ttg tgg tgg gga tgg gtt ttg gcc act      102
Met Arg Phe Gly Ile Phe Leu Leu Trp Trp Gly Trp Val Leu Ala Thr
            10                  15                  20

gaa agc aga atg cac tgg ccc gga aga gaa gtc cac gag atg tct aag      150
Glu Ser Arg Met His Trp Pro Gly Arg Glu Val His Glu Met Ser Lys
        25                  30                  35

aaa ggc agg ccc caa aga caa aga cga gaa gta cat gaa gat gcc cac      198
Lys Gly Arg Pro Gln Arg Gln Arg Arg Glu Val His Glu Asp Ala His
    40                  45                  50

aag caa gtc agc cca att ctg aga cga agt cct gac atc acc aaa tcg      246
Lys Gln Val Ser Pro Ile Leu Arg Arg Ser Pro Asp Ile Thr Lys Ser
55                  60                  65                  70

cct ctg aca aag tca gaa cag ctt ctg agg ata gat gac cat gat ttc      294
```

```
Pro Leu Thr Lys Ser Glu Gln Leu Leu Arg Ile Asp Asp His Asp Phe
            75                  80                  85

agc atg agg cct ggc ttt gga ggc cct gcc att cct gtt ggt gtg gat      342
Ser Met Arg Pro Gly Phe Gly Gly Pro Ala Ile Pro Val Gly Val Asp
            90                  95                  100

gtg cag gtg gag agt ttg gat agc atc tca gag gtt gac atg gac ttt      390
Val Gln Val Glu Ser Leu Asp Ser Ile Ser Glu Val Asp Met Asp Phe
        105                 110                 115

acg atg acc ctc tac ctg agg cac tac tgg aag gac gag agg ctg tct      438
Thr Met Thr Leu Tyr Leu Arg His Tyr Trp Lys Asp Glu Arg Leu Ser
    120                 125                 130

ttt cca agc acc aac aac ctc agc atg acg ttt gac ggc cgg ctg gtc      486
Phe Pro Ser Thr Asn Asn Leu Ser Met Thr Phe Asp Gly Arg Leu Val
135                 140                 145                 150

aag aag atc tgg gtc cct gac atg ttt ttc gtg cac tcc aaa cgc tcc      534
Lys Lys Ile Trp Val Pro Asp Met Phe Phe Val His Ser Lys Arg Ser
            155                 160                 165

ttc atc cac gac acc acc aca gac aac gtc atg ttg cgg gtc cag cct      582
Phe Ile His Asp Thr Thr Thr Asp Asn Val Met Leu Arg Val Gln Pro
            170                 175                 180

gat ggg aaa gtg ctc tat agt ctc agg gtt aca gta act gca atg tgc      630
Asp Gly Lys Val Leu Tyr Ser Leu Arg Val Thr Val Thr Ala Met Cys
        185                 190                 195

aac atg gac ttc agc cga ttt ccc ttg gac aca caa acg tgc tct ctt      678
Asn Met Asp Phe Ser Arg Phe Pro Leu Asp Thr Gln Thr Cys Ser Leu
    200                 205                 210

gaa att gaa agc tat gcc tat aca gaa gat gac ctc atg ctg tac tgg      726
Glu Ile Glu Ser Tyr Ala Tyr Thr Glu Asp Asp Leu Met Leu Tyr Trp
215                 220                 225                 230

aaa aag ggc aat gac tcc tta aag aca gat gaa cgg atc tca ctc tcc      774
Lys Lys Gly Asn Asp Ser Leu Lys Thr Asp Glu Arg Ile Ser Leu Ser
            235                 240                 245

cag ttc ctc att cag gaa ttc cac acc acc acc aaa ctg gct ttc tac      822
Gln Phe Leu Ile Gln Glu Phe His Thr Thr Thr Lys Leu Ala Phe Tyr
            250                 255                 260

agc agc aca ggc tgg tac aac cgt ctc tac att aat ttc acg ttg cgt      870
Ser Ser Thr Gly Trp Tyr Asn Arg Leu Tyr Ile Asn Phe Thr Leu Arg
        265                 270                 275

cgc cac atc ttc ttc ttc ttg ctc caa act tat ttc ccc gct acc ctg      918
Arg His Ile Phe Phe Phe Leu Leu Gln Thr Tyr Phe Pro Ala Thr Leu
    280                 285                 290

atg gtc atg ctg tcc tgg gtg tcc ttc tgg atc gac cgc aga gcc gtg      966
Met Val Met Leu Ser Trp Val Ser Phe Trp Ile Asp Arg Arg Ala Val
295                 300                 305                 310

cct gcc aga gtc ccc tta ggt atc aca acg gtg ctg acc atg tcc acc     1014
Pro Ala Arg Val Pro Leu Gly Ile Thr Thr Val Leu Thr Met Ser Thr
            315                 320                 325

atc atc acg ggc gtg aat gcc tcc atg ccg cgc gtc tcc tac atc aag     1062
Ile Ile Thr Gly Val Asn Ala Ser Met Pro Arg Val Ser Tyr Ile Lys
            330                 335                 340

gcc gtg gac atc tac ctc tgg gtc agc ttt gtg ttc gtg ttc ctc tcg     1110
Ala Val Asp Ile Tyr Leu Trp Val Ser Phe Val Phe Val Phe Leu Ser
        345                 350                 355

gtg ctg gag tat gcg gcc gtc aac tac ctg acc act gtg cag gag agg     1158
Val Leu Glu Tyr Ala Ala Val Asn Tyr Leu Thr Thr Val Gln Glu Arg
    360                 365                 370

aag gaa cag aag ctg cgg gag aag ctt ccc tgc acc agc gga tta cct     1206
Lys Glu Gln Lys Leu Arg Glu Lys Leu Pro Cys Thr Ser Gly Leu Pro
375                 380                 385                 390
```

```
ccg ccc cgc act gcg atg ctg gac ggc aac tac agt gat ggg gag gtg     1254
Pro Pro Arg Thr Ala Met Leu Asp Gly Asn Tyr Ser Asp Gly Glu Val
                395                 400                 405

aat gac ctg gac aac tac atg cca gag aat gga gag aag ccc gac agg     1302
Asn Asp Leu Asp Asn Tyr Met Pro Glu Asn Gly Glu Lys Pro Asp Arg
            410                 415                 420

atg atg gtg cag ctg acc ctg gcc tca gag agg agc tcc cca cag agg     1350
Met Met Val Gln Leu Thr Leu Ala Ser Glu Arg Ser Ser Pro Gln Arg
        425                 430                 435

aaa agt cag aga agc agc tat gtg agc atg aga atc gac acc cac gcc     1398
Lys Ser Gln Arg Ser Ser Tyr Val Ser Met Arg Ile Asp Thr His Ala
    440                 445                 450

att gat aaa tac tcc agg atc atc ttt cca gca gca tac att tta ttc     1446
Ile Asp Lys Tyr Ser Arg Ile Ile Phe Pro Ala Ala Tyr Ile Leu Phe
455                 460                 465                 470

aat tta ata tac tgg tct att ttc tcc tag atgcttgtaa ttctacaaat       1496
Asn Leu Ile Tyr Trp Ser Ile Phe Ser
                475

ttcacatttc catggcatgc actacagaaa taactgtata atgaaaaagt atttaaggat   1556

atggttaaaa aaaaatccca ggacccaccc atgttttcac tatcccttct gcagctttcc   1616

aaagctacat tgacgagaca cttactggtt taatttgcac ttattaacca tctattgaat   1676

acacagcatt atattaggtg ctgcaggaaa tacgacactg tagcgactga tgttagttgt   1736

tacccagatc ccctggaaaa gcacactacc agtgttgtgg gcacatttag ttccacccgt   1796

tagacccttg atgctattca catgaataat ttattttcct caagtgtcat tacattgttc   1856

aggctacgtg aacttggaag cacctacagg ccatttgcat gaaattcaca tgcacctaaa   1916

tcctcacttt gacagaaact catgcttcag tttataacct attacctatt ttgtatgcga   1976

ctccacctcc gcatgtttat tttaataaaa ggcaatgata acattcacat tatttttctt   2036

tatatgctgt ggttcacagg ctttacccct tcacaagaaa agctctttag attggcgcaa   2096

ttgcttctga ttttggtgaa attttccctg gtagggaaac tttgaagata agagtacaca   2156

catgcatttt gtctgttgtg tcatagaggt aactaggcta gaaaatttgt gtttaaatgt   2216

tccctatttt atataatcac cacttcatgt ttcttcttct tggagcatgt ccttgttcaa   2276

agagaagtgc tttctcagtg atgtgatatc ttcactgagg aacttgggta gagaatgatt   2336

tcttctgcat aaacacttca aggaaataca taatttggga ctacttgtaa ctcattagaa   2396

tgagaaatac tcacatggtt tcttaagaga aaaagaacat cggaaagcaa aataaatggg   2456

aagatatcac tggacatctg catttatact cgaaatacca gcattttcta tggaccagaa   2516

aactgccatc acctagacca cacagcccag ataccaggca gacggatggc ccaatggcaa   2576

ctgatgtcag ggcatggggt aaaggagagg gttctaatct ggtgtatcac ttaaaaacag   2636

ttatttatat tatatatctg ctatatagat caacctccac caaacttacc caaacagcat   2696

ttgttttatt tgaaactcac tttaataaag tgaattatat acacaa                  2742


<210> SEQ ID NO 18
<211> LENGTH: 479
<212> TYPE: PRT
<213> ORGANISM: Homo sapiens

<400> SEQUENCE: 18

Met Leu Ala Val Pro Asn Met Arg Phe Gly Ile Phe Leu Leu Trp Trp
1               5                   10                  15

Gly Trp Val Leu Ala Thr Glu Ser Arg Met His Trp Pro Gly Arg Glu
            20                  25                  30
```

```
Val His Glu Met Ser Lys Lys Gly Arg Pro Gln Arg Gln Arg Arg Glu
        35                  40                  45

Val His Glu Asp Ala His Lys Gln Val Ser Pro Ile Leu Arg Arg Ser
    50                  55                  60

Pro Asp Ile Thr Lys Ser Pro Leu Thr Lys Ser Glu Gln Leu Leu Arg
65                  70                  75                  80

Ile Asp Asp His Asp Phe Ser Met Arg Pro Gly Phe Gly Gly Pro Ala
                85                  90                  95

Ile Pro Val Gly Val Asp Val Gln Val Glu Ser Leu Asp Ser Ile Ser
            100                 105                 110

Glu Val Asp Met Asp Phe Thr Met Thr Leu Tyr Leu Arg His Tyr Trp
        115                 120                 125

Lys Asp Glu Arg Leu Ser Phe Pro Ser Thr Asn Asn Leu Ser Met Thr
    130                 135                 140

Phe Asp Gly Arg Leu Val Lys Lys Ile Trp Val Pro Asp Met Phe Phe
145                 150                 155                 160

Val His Ser Lys Arg Ser Phe Ile His Asp Thr Thr Thr Asp Asn Val
                165                 170                 175

Met Leu Arg Val Gln Pro Asp Gly Lys Val Leu Tyr Ser Leu Arg Val
            180                 185                 190

Thr Val Thr Ala Met Cys Asn Met Asp Phe Ser Arg Phe Pro Leu Asp
        195                 200                 205

Thr Gln Thr Cys Ser Leu Glu Ile Glu Ser Tyr Ala Tyr Thr Glu Asp
    210                 215                 220

Asp Leu Met Leu Tyr Trp Lys Lys Gly Asn Asp Ser Leu Lys Thr Asp
225                 230                 235                 240

Glu Arg Ile Ser Leu Ser Gln Phe Leu Ile Gln Glu Phe His Thr Thr
                245                 250                 255

Thr Lys Leu Ala Phe Tyr Ser Ser Thr Gly Trp Tyr Asn Arg Leu Tyr
            260                 265                 270

Ile Asn Phe Thr Leu Arg Arg His Ile Phe Phe Phe Leu Leu Gln Thr
        275                 280                 285

Tyr Phe Pro Ala Thr Leu Met Val Met Leu Ser Trp Val Ser Phe Trp
    290                 295                 300

Ile Asp Arg Arg Ala Val Pro Ala Arg Val Pro Leu Gly Ile Thr Thr
305                 310                 315                 320

Val Leu Thr Met Ser Thr Ile Ile Thr Gly Val Asn Ala Ser Met Pro
                325                 330                 335

Arg Val Ser Tyr Ile Lys Ala Val Asp Ile Tyr Leu Trp Val Ser Phe
            340                 345                 350

Val Phe Val Phe Leu Ser Val Leu Glu Tyr Ala Ala Val Asn Tyr Leu
        355                 360                 365

Thr Thr Val Gln Glu Arg Lys Glu Gln Lys Leu Arg Glu Lys Leu Pro
    370                 375                 380

Cys Thr Ser Gly Leu Pro Pro Pro Arg Thr Ala Met Leu Asp Gly Asn
385                 390                 395                 400

Tyr Ser Asp Gly Glu Val Asn Asp Leu Asp Asn Tyr Met Pro Glu Asn
                405                 410                 415

Gly Glu Lys Pro Asp Arg Met Met Val Gln Leu Thr Leu Ala Ser Glu
            420                 425                 430

Arg Ser Ser Pro Gln Arg Lys Ser Gln Arg Ser Ser Tyr Val Ser Met
        435                 440                 445
```

```
Arg Ile Asp Thr His Ala Ile Asp Lys Tyr Ser Arg Ile Ile Phe Pro
    450                 455                 460

Ala Ala Tyr Ile Leu Phe Asn Leu Ile Tyr Trp Ser Ile Phe Ser
465                 470                 475


<210> SEQ ID NO 19
<211> LENGTH: 2576
<212> TYPE: DNA
<213> ORGANISM: Homo sapiens
<220> FEATURE:
<221> NAME/KEY: CDS
<222> LOCATION: (239)..(1600)

<400> SEQUENCE: 19

acatacactc ccaaacctca acacccaggc gcctcctggg cctctcctag gttgggctgc      60

tccagcaagt ttccatgaaa gcacctgaaa tactaagtta ccttcgcgag gagaactcga     120

gtgagataaa atcgtgcgcc cacgcaggtg agtttgcagc caagaatttt ggacgctgct     180

gggaggagaa agggaagttg agaaagtctt tggacctggt agcctggtgc tctttctc       238

atg gct tca ccc agc ctc ccg ggc agt gac tgc tcc caa atc att gat       286
Met Ala Ser Pro Ser Leu Pro Gly Ser Asp Cys Ser Gln Ile Ile Asp
1               5                   10                  15

cac agt cat gtc ccc gag ttt gag gtg gcc acc tgg atc aaa atc acc       334
His Ser His Val Pro Glu Phe Glu Val Ala Thr Trp Ile Lys Ile Thr
            20                  25                  30

ctt att ctg gtg tac ctg atc atc ttc gtg atg ggc ctt ctg ggg aac       382
Leu Ile Leu Val Tyr Leu Ile Ile Phe Val Met Gly Leu Leu Gly Asn
        35                  40                  45

agc gcc acc att cgg gtc acc cag gtg ctg cag aag aaa gga tac ttg       430
Ser Ala Thr Ile Arg Val Thr Gln Val Leu Gln Lys Lys Gly Tyr Leu
    50                  55                  60

cag aag gag gtg aca gac cac atg gtg agt ttg gct tgc tcg gac atc       478
Gln Lys Glu Val Thr Asp His Met Val Ser Leu Ala Cys Ser Asp Ile
65                  70                  75                  80

ttg gtg ttc ctc atc ggc atg ccc atg gag ttc tac agc atc atc tgg       526
Leu Val Phe Leu Ile Gly Met Pro Met Glu Phe Tyr Ser Ile Ile Trp
                85                  90                  95

aat ccc ctg acc acg tcc agc tac acc ctg tcc tgc aag ctg cac act       574
Asn Pro Leu Thr Thr Ser Ser Tyr Thr Leu Ser Cys Lys Leu His Thr
            100                 105                 110

ttc ctc ttc gag gcc tgc agc tac gct acg ctg ctg cac gtg ctg aca       622
Phe Leu Phe Glu Ala Cys Ser Tyr Ala Thr Leu Leu His Val Leu Thr
        115                 120                 125

ctc agc ttt gag cgc tac atc gcc atc tgt cac ccc ttc agg tac aag       670
Leu Ser Phe Glu Arg Tyr Ile Ala Ile Cys His Pro Phe Arg Tyr Lys
    130                 135                 140

gct gtg tcg gga cct tgc cag gtg aag ctg ctg att ggc ttc gtc tgg       718
Ala Val Ser Gly Pro Cys Gln Val Lys Leu Leu Ile Gly Phe Val Trp
145                 150                 155                 160

gtc acc tcc gcc ctg gtg gca ctg ccc ttg ctg ttt gcc atg ggt act       766
Val Thr Ser Ala Leu Val Ala Leu Pro Leu Leu Phe Ala Met Gly Thr
                165                 170                 175

gag tac ccc ctg gtg aac gtg ccc agc cac cgg ggt ctc act tgc aac       814
Glu Tyr Pro Leu Val Asn Val Pro Ser His Arg Gly Leu Thr Cys Asn
            180                 185                 190

cgc tcc agc acc cgc cac cac gag cag ccc gag acc tcc aat atg tcc       862
Arg Ser Ser Thr Arg His His Glu Gln Pro Glu Thr Ser Asn Met Ser
        195                 200                 205

atc tgt acc aac ctc tcc agc cgc tgg acc gtg ttc cag tcc agc atc       910
Ile Cys Thr Asn Leu Ser Ser Arg Trp Thr Val Phe Gln Ser Ser Ile
```

```
    210                 215                 220

ttc ggc gcc ttc gtg gtc tac ctc gtg gtc ctg ctc tcc gta gcc ttc      958
Phe Gly Ala Phe Val Val Tyr Leu Val Val Leu Leu Ser Val Ala Phe
225                 230                 235                 240

atg tgc tgg aac atg atg cag gtg ctc atg aaa agc cag aag ggc tcg     1006
Met Cys Trp Asn Met Met Gln Val Leu Met Lys Ser Gln Lys Gly Ser
                245                 250                 255

ctg gcc ggg ggc acg cgg cct ccg cag ctg agg aag tcc gag agc gaa     1054
Leu Ala Gly Gly Thr Arg Pro Pro Gln Leu Arg Lys Ser Glu Ser Glu
            260                 265                 270

gag agc agg acc gcc agg agg cag acc atc atc ttc ctg agg ctg att     1102
Glu Ser Arg Thr Ala Arg Arg Gln Thr Ile Ile Phe Leu Arg Leu Ile
        275                 280                 285

gtt gtg aca ttg gcc gta tgc tgg atg ccc aac cag att cgg agg atc     1150
Val Val Thr Leu Ala Val Cys Trp Met Pro Asn Gln Ile Arg Arg Ile
    290                 295                 300

atg gct gcg gcc aaa ccc aag cac gac tgg acg agg tcc tac ttc cgg     1198
Met Ala Ala Ala Lys Pro Lys His Asp Trp Thr Arg Ser Tyr Phe Arg
305                 310                 315                 320

gcg tac atg atc ctc ctc ccc ttc tcg gag acg ttt ttc tac ctc agc     1246
Ala Tyr Met Ile Leu Leu Pro Phe Ser Glu Thr Phe Phe Tyr Leu Ser
                325                 330                 335

tcg gtc atc aac ccg ctc ctg tac acg gtg tcc tcg cag cag ttt cgg     1294
Ser Val Ile Asn Pro Leu Leu Tyr Thr Val Ser Ser Gln Gln Phe Arg
            340                 345                 350

cgg gtg ttc gtg cag gtg ctg tgc tgc cgc ctg tcg ctg cag cac gcc     1342
Arg Val Phe Val Gln Val Leu Cys Cys Arg Leu Ser Leu Gln His Ala
        355                 360                 365

aac cac gag aag cgc ctg cgc gta cat gcg cac tcc acc acc gac agc     1390
Asn His Glu Lys Arg Leu Arg Val His Ala His Ser Thr Thr Asp Ser
    370                 375                 380

gcc cgc ttt gtg cag cgc ccg ttg ctc ttc gcg tcc cgg cgc cag tcc     1438
Ala Arg Phe Val Gln Arg Pro Leu Leu Phe Ala Ser Arg Arg Gln Ser
385                 390                 395                 400

tct gca agg aga act gag aag att ttc tta agc act ttt cag agc gag     1486
Ser Ala Arg Arg Thr Glu Lys Ile Phe Leu Ser Thr Phe Gln Ser Glu
                405                 410                 415

gcc gag ccc cag tct aag tcc cag tca ttg agt ctc gag tca cta gag     1534
Ala Glu Pro Gln Ser Lys Ser Gln Ser Leu Ser Leu Glu Ser Leu Glu
            420                 425                 430

ccc aac tca ggc gcg aaa cca gcc aat tct gct gca gag aat ggt ttt     1582
Pro Asn Ser Gly Ala Lys Pro Ala Asn Ser Ala Ala Glu Asn Gly Phe
        435                 440                 445

cag gag cat gaa gtt tga atgtcaagcg agggagcctt gagtgggaac            1630
Gln Glu His Glu Val
    450

tggccctcca gccctaagaa aacgtcactc tcactctgca gtctcaaact atgcccccat   1690

cagggatgga atggacactg gaggctttac aaaaggcaga tgcccacctc agtgacttct   1750

aaggactgac tctgccagcc tggccttgac tccggttaca cagacatggg ggtgaacttt   1810

cactccacct ccttccttca agtacatact gaaaattcag tcaggctgaa tttattcaga   1870

atgctttacc gagctctttc attatttgca caggaacaaa agagaacacg gactcccgct   1930

ccctacccag aataaaagga cacccagaag aaactcactc agggaggtgg ggggttgggg   1990

gcgagggctg gaagaacaat gcaggagggg gtggcatctc cttcagcttc agcagtgtgc   2050

cgagaagagg gctaatttga ggaacaggat ggtggtgcgg agccctggcc tgagggccga   2110

ggcagaactt cccctttctt tgggccttgg cccgttacaa agaggggtgt tgcagcagct   2170
```

```
gatgcaaact gagttcagtt tccctgggga gcagaaggac tggtacccgg cagaggcgat   2230

gagacaggcc gctgatgatg cacaggactt gcggtacatg atccctgtaa cacagaccca   2290

aaggagctga gttaacgtgc accggcaaaa gaatagctgt ccctctcagc ccaaatccaa   2350

acggacagct cttccttact cctcccacag cccagagact aggtgaggtc agggaagtgc   2410

ttcggattgt ctcattgata ttcaagatag atggtgaaag agacaggcac tatttcatta   2470

gttttaacaa aactgttcca aaagcgattt gagatgccaa tacctgtgaa tacctgttaa   2530

taaagagctg ttaaatagac ttatttacat tttaagtcag agttca                  2576


<210> SEQ ID NO 20
<211> LENGTH: 453
<212> TYPE: PRT
<213> ORGANISM: Homo sapiens

<400> SEQUENCE: 20

Met Ala Ser Pro Ser Leu Pro Gly Ser Asp Cys Ser Gln Ile Ile Asp
1               5                   10                  15

His Ser His Val Pro Glu Phe Glu Val Ala Thr Trp Ile Lys Ile Thr
            20                  25                  30

Leu Ile Leu Val Tyr Leu Ile Ile Phe Val Met Gly Leu Leu Gly Asn
        35                  40                  45

Ser Ala Thr Ile Arg Val Thr Gln Val Leu Gln Lys Lys Gly Tyr Leu
    50                  55                  60

Gln Lys Glu Val Thr Asp His Met Val Ser Leu Ala Cys Ser Asp Ile
65                  70                  75                  80

Leu Val Phe Leu Ile Gly Met Pro Met Glu Phe Tyr Ser Ile Ile Trp
                85                  90                  95

Asn Pro Leu Thr Thr Ser Ser Tyr Thr Leu Ser Cys Lys Leu His Thr
            100                 105                 110

Phe Leu Phe Glu Ala Cys Ser Tyr Ala Thr Leu Leu His Val Leu Thr
        115                 120                 125

Leu Ser Phe Glu Arg Tyr Ile Ala Ile Cys His Pro Phe Arg Tyr Lys
    130                 135                 140

Ala Val Ser Gly Pro Cys Gln Val Lys Leu Leu Ile Gly Phe Val Trp
145                 150                 155                 160

Val Thr Ser Ala Leu Val Ala Leu Pro Leu Leu Phe Ala Met Gly Thr
                165                 170                 175

Glu Tyr Pro Leu Val Asn Val Pro Ser His Arg Gly Leu Thr Cys Asn
            180                 185                 190

Arg Ser Ser Thr Arg His His Glu Gln Pro Glu Thr Ser Asn Met Ser
        195                 200                 205

Ile Cys Thr Asn Leu Ser Ser Arg Trp Thr Val Phe Gln Ser Ser Ile
    210                 215                 220

Phe Gly Ala Phe Val Val Tyr Leu Val Val Leu Leu Ser Val Ala Phe
225                 230                 235                 240

Met Cys Trp Asn Met Met Gln Val Leu Met Lys Ser Gln Lys Gly Ser
                245                 250                 255

Leu Ala Gly Gly Thr Arg Pro Pro Gln Leu Arg Lys Ser Glu Ser Glu
            260                 265                 270

Glu Ser Arg Thr Ala Arg Arg Gln Thr Ile Ile Phe Leu Arg Leu Ile
        275                 280                 285

Val Val Thr Leu Ala Val Cys Trp Met Pro Asn Gln Ile Arg Arg Ile
    290                 295                 300
```

```
Met Ala Ala Ala Lys Pro Lys His Asp Trp Thr Arg Ser Tyr Phe Arg
305                 310                 315                 320

Ala Tyr Met Ile Leu Leu Pro Phe Ser Glu Thr Phe Phe Tyr Leu Ser
                325                 330                 335

Ser Val Ile Asn Pro Leu Leu Tyr Thr Val Ser Ser Gln Gln Phe Arg
            340                 345                 350

Arg Val Phe Val Gln Val Leu Cys Cys Arg Leu Ser Leu Gln His Ala
        355                 360                 365

Asn His Glu Lys Arg Leu Arg Val His Ala His Ser Thr Thr Asp Ser
    370                 375                 380

Ala Arg Phe Val Gln Arg Pro Leu Leu Phe Ala Ser Arg Arg Gln Ser
385                 390                 395                 400

Ser Ala Arg Arg Thr Glu Lys Ile Phe Leu Ser Thr Phe Gln Ser Glu
                405                 410                 415

Ala Glu Pro Gln Ser Lys Ser Gln Ser Leu Ser Leu Glu Ser Leu Glu
            420                 425                 430

Pro Asn Ser Gly Ala Lys Pro Ala Asn Ser Ala Ala Glu Asn Gly Phe
        435                 440                 445

Gln Glu His Glu Val
    450


<210> SEQ ID NO 21
<211> LENGTH: 2627
<212> TYPE: DNA
<213> ORGANISM: Homo sapiens
<220> FEATURE:
<221> NAME/KEY: CDS
<222> LOCATION: (84)..(536)

<400> SEQUENCE: 21

aggctaaggt cagacactga cacttgcagt tgtctttggt agttttttg cactaacttc      60

aggaaccagc tcatgatctc agg atg tat gga aaa ata atc ttt gta tta cta     113
                          Met Tyr Gly Lys Ile Ile Phe Val Leu Leu
                          1               5                   10

ttg tca gaa att gtg agc ata tca gca tta agt acc act gag gtg gca       161
Leu Ser Glu Ile Val Ser Ile Ser Ala Leu Ser Thr Thr Glu Val Ala
                15                  20                  25

atg cac act tca act tct tct tca gtc aca aag agt tac atc tca tca       209
Met His Thr Ser Thr Ser Ser Ser Val Thr Lys Ser Tyr Ile Ser Ser
            30                  35                  40

cag aca aat gat acg cac aaa cgg gac aca tat gca gcc act cct aga       257
Gln Thr Asn Asp Thr His Lys Arg Asp Thr Tyr Ala Ala Thr Pro Arg
        45                  50                  55

gct cat gaa gtt tca gaa att tct gtt aga act gtt tac cct cca gaa       305
Ala His Glu Val Ser Glu Ile Ser Val Arg Thr Val Tyr Pro Pro Glu
    60                  65                  70

gag gaa acc gga gaa agg gta caa ctt gcc cat cat ttc tct gaa cca       353
Glu Glu Thr Gly Glu Arg Val Gln Leu Ala His His Phe Ser Glu Pro
75                  80                  85                  90

gag ata aca ctc att att ttt ggg gtg atg gct ggt gtt att gga acg       401
Glu Ile Thr Leu Ile Ile Phe Gly Val Met Ala Gly Val Ile Gly Thr
                95                  100                 105

atc ctc tta att tct tac ggt att cgc cga ctg ata aag aaa agc cca       449
Ile Leu Leu Ile Ser Tyr Gly Ile Arg Arg Leu Ile Lys Lys Ser Pro
            110                 115                 120

tct gat gta aaa cct ctc ccc tca cct gac aca gac gtg cct tta agt       497
Ser Asp Val Lys Pro Leu Pro Ser Pro Asp Thr Asp Val Pro Leu Ser
        125                 130                 135
```

```
tct gtt gaa ata gaa aat cca gag aca agt gat caa tga gaatctgttc       546
Ser Val Glu Ile Glu Asn Pro Glu Thr Ser Asp Gln
    140                 145                 150

accaaaccaa atgtggaaag aacacaaaga agacataaga cttcagtcaa gtgaaaaatt    606

aacatgtgga ctggacactc caataaatta tatacctgcc taagttgtac aatttcagaa    666

tgcaattttc attataatga gttccagtga ctcaatgatg gggaaaaaaa tctctgctca    726

ttaatatttc aagataaaga acaaatgttt ccttgaatgc ttgcttttgt gtgttagcat    786

aatttttaga attgtttgag aattctgatc caaaacttta gttgaattca tctacgtttg    846

tttaatatta acttaaccta ttctattgta ttataatgat gattctgtca aatgaaaggc    906

ttgaaatacc tagatgaagt ttagattttc ttcctattgt aaacttttga gtctggtttc    966

attgttttaa ataaattaag ggacactaa agtcctatca ttcatttcct tcattgctga    1026

acaggcaaga tataatatta catgaatgat tactatattt tgttcacact aataaagctt   1086

atgctcagaa atgccataca cacacacaca cacacacaca aacacacaca tttatcattt   1146

aatgcataaa tcaacacaaa aggttttccc attaatatga aatattacat atatataagt   1206

gccatattta aaataatttg tctaacagta gaactgtgtc ggagcactca ctgaagcttg   1266

cattccactg aaagagttat ttgtgtaagt agagtatccg gagaaggaaa agaacttacg   1326

acctttcttt ataacagaaa ctcaactcta aattcaacaa gatgtgcaaa ccggacatgc   1386

aggtgaatat tttaataggt tactataagg ttctcaatta aattctttaa tctgtccagt   1446

cccagtttct cttattaata aaactttgga aattgcttta aaccatttaa aggaaatttc   1506

tagatataga aactaaggac tgtgactata cagctgtcac tcatttgtag taaaacttaa   1566

aaagcaaaaa caaaaaaacaa aaaagacctt cctgtgatac tttatttccg aactaataaa  1626

aatctatatg actttttatt attgtgtgat aaccaagtaa atgttttcta ttttgcatat   1686

tttcaggcat ggtaacagaa atttaccttt taataaatta aaaaatctaa attttaacct   1746

acttgtatgt tcggagagtg tttttgtact atattgacta cttaaaatag agaatgagac   1806

taagaaggga acatttctgt tgatacatgt tttttaaaag taattttaag agcattatta   1866

ggttaattaa tccaattaat gacccaaatg ccaaggtaat tttaaattta catttttaat   1926

aaaagcaaca tgttgaaaca agagagggtg agattaacct ttttgctaaa gtaatttaca   1986

agtcaaagac aggaagagat cagagtgaat gtgccttctt aaccagagct acagaattta   2046

gtgaataatt aaagtacaaa ctgctttgac ctccttgaac ttttccaagc aatttctctg   2106

tacttctata tatgaatgtc ttagccaatt ttctgctact ataacagaat acgacagact   2166

gggtaattta aaaagaaaag aaatttattt tcttcctagt tctggaggct gggaaggcga   2226

agggcatggc actgacatct gccttgtaac tgatgagaac cttcttactg catgataaca   2286

aagcagcaag gcaagcaaaa gcgtaagatg aagagagagg aaatgaagcc aaacacatcc   2346

tttcatcaga agcccattcc ctctataagg cgttattaca tttatgagaa tggagtcctc   2406

atgacctaat cgtgacctta aaggcccctc ccaacactgt tacaatggca attaaatttc   2466

aacaaaggtt ccagaggtga cattcgaatc agcaatgaaa ttttcatagt taaatttggt   2526

attcgtgggg gaagaaatga ccatttccct tgtattttta taattaaatc agcaaaatat   2586

tgtaataaag aaatctttcc tgtgaagata ccatgacccc a                        2627
```

<210> SEQ ID NO 22
<211> LENGTH: 150
<212> TYPE: PRT

```
<213> ORGANISM: Homo sapiens

<400> SEQUENCE: 22

Met Tyr Gly Lys Ile Ile Phe Val Leu Leu Leu Ser Glu Ile Val Ser
1               5                   10                  15

Ile Ser Ala Leu Ser Thr Thr Glu Val Ala Met His Thr Ser Thr Ser
            20                  25                  30

Ser Ser Val Thr Lys Ser Tyr Ile Ser Ser Gln Thr Asn Asp Thr His
        35                  40                  45

Lys Arg Asp Thr Tyr Ala Ala Thr Pro Arg Ala His Glu Val Ser Glu
    50                  55                  60

Ile Ser Val Arg Thr Val Tyr Pro Pro Glu Glu Glu Thr Gly Glu Arg
65                  70                  75                  80

Val Gln Leu Ala His His Phe Ser Glu Pro Glu Ile Thr Leu Ile Ile
                85                  90                  95

Phe Gly Val Met Ala Gly Val Ile Gly Thr Ile Leu Leu Ile Ser Tyr
            100                 105                 110

Gly Ile Arg Arg Leu Ile Lys Lys Ser Pro Ser Asp Val Lys Pro Leu
        115                 120                 125

Pro Ser Pro Asp Thr Asp Val Pro Leu Ser Ser Val Glu Ile Glu Asn
    130                 135                 140

Pro Glu Thr Ser Asp Gln
145                 150


<210> SEQ ID NO 23
<211> LENGTH: 628
<212> TYPE: DNA
<213> ORGANISM: Homo sapiens
<220> FEATURE:
<221> NAME/KEY: CDS
<222> LOCATION: (51)..(494)

<400> SEQUENCE: 23

acatttgctt ctgacacaac tgtgttcact agcaacctca aacagacacc atg gtg         56
                                                       Met Val
                                                       1

cat ctg act cct gag gag aag tct gcc gtt act gcc ctg tgg ggc aag       104
His Leu Thr Pro Glu Glu Lys Ser Ala Val Thr Ala Leu Trp Gly Lys
        5                   10                  15

gtg aac gtg gat gaa gtt ggt ggt gag gcc ctg ggc agg ctg ctg gtg       152
Val Asn Val Asp Glu Val Gly Gly Glu Ala Leu Gly Arg Leu Leu Val
    20                  25                  30

gtc tac cct tgg acc cag agg ttc ttt gag tcc ttt ggg gat ctg tcc       200
Val Tyr Pro Trp Thr Gln Arg Phe Phe Glu Ser Phe Gly Asp Leu Ser
35                  40                  45                  50

act cct gat gct gtt atg ggc aac cct aag gtg aag gct cat ggc aag       248
Thr Pro Asp Ala Val Met Gly Asn Pro Lys Val Lys Ala His Gly Lys
                55                  60                  65

aaa gtg ctc ggt gcc ttt agt gat ggc ctg gct cac ctg gac aac ctc       296
Lys Val Leu Gly Ala Phe Ser Asp Gly Leu Ala His Leu Asp Asn Leu
            70                  75                  80

aag ggc acc ttt gcc aca ctg agt gag ctg cac tgt gac aag ctg cac       344
Lys Gly Thr Phe Ala Thr Leu Ser Glu Leu His Cys Asp Lys Leu His
        85                  90                  95

gtg gat cct gag aac ttc agg ctc ctg ggc aac gtg ctg gtc tgt gtg       392
Val Asp Pro Glu Asn Phe Arg Leu Leu Gly Asn Val Leu Val Cys Val
    100                 105                 110

ctg gcc cat cac ttt ggc aaa gaa ttc acc cca cca gtg cag gct gcc       440
Leu Ala His His Phe Gly Lys Glu Phe Thr Pro Pro Val Gln Ala Ala
```

```
115                 120                 125                 130

tat cag aaa gtg gtg gct ggt gtg gct aat gcc ctg gcc cac aag tat      488
Tyr Gln Lys Val Val Ala Gly Val Ala Asn Ala Leu Ala His Lys Tyr
                135                 140                 145

cac taa gctcgctttc ttgctgtcca atttctatta aaggttcctt tgttccctaa       544
His

gtccaactac taaactgggg gatattatga agggccttga gcatctggat tctgcctaat    604

aaaaaacatt tattttcatt gcaa                                           628


<210> SEQ ID NO 24
<211> LENGTH: 147
<212> TYPE: PRT
<213> ORGANISM: Homo sapiens

<400> SEQUENCE: 24

Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg Leu
            20                  25                  30

Leu Val Val Tyr Pro Trp Thr Gln Arg Phe Phe Glu Ser Phe Gly Asp
        35                  40                  45

Leu Ser Thr Pro Asp Ala Val Met Gly Asn Pro Lys Val Lys Ala His
    50                  55                  60

Gly Lys Lys Val Leu Gly Ala Phe Ser Asp Gly Leu Ala His Leu Asp
65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr His
145


<210> SEQ ID NO 25
<211> LENGTH: 3991
<212> TYPE: DNA
<213> ORGANISM: Homo sapiens
<220> FEATURE:
<221> NAME/KEY: CDS
<222> LOCATION: (53)..(829)

<400> SEQUENCE: 25

ccttcttttc ctgactgcag ctcttttcat tttgccatcc ttttccagct cc atg atg     58
                                                          Met Met
                                                          1

gtt ctg cag gtt tct gcg gcc ccc cgg aca gtg gct ctg acg gcg tta      106
Val Leu Gln Val Ser Ala Ala Pro Arg Thr Val Ala Leu Thr Ala Leu
        5                   10                  15

ctg atg gtg ctg ctc aca tct gtg gtc cag ggc agg gcc act cca gag      154
Leu Met Val Leu Leu Thr Ser Val Val Gln Gly Arg Ala Thr Pro Glu
    20                  25                  30

aat tac ctt ttc cag gga cgg cag gaa tgc tac gcg ttt aat ggg aca      202
Asn Tyr Leu Phe Gln Gly Arg Gln Glu Cys Tyr Ala Phe Asn Gly Thr
35                  40                  45                  50

cag cgc ttc ctg gag aga tac atc tac aac cgg gag gag ttc gcg cgc      250
```

```
Gln Arg Phe Leu Glu Arg Tyr Ile Tyr Asn Arg Glu Glu Phe Ala Arg
                55                  60                  65

ttc gac agc gac gtg ggg gag ttc cgg gcg gtg acg gag ctg ggg cgg      298
Phe Asp Ser Asp Val Gly Glu Phe Arg Ala Val Thr Glu Leu Gly Arg
            70                  75                  80

cct gct gcg gag tac tgg aac agc cag aag gac atc ctg gag gag aag      346
Pro Ala Ala Glu Tyr Trp Asn Ser Gln Lys Asp Ile Leu Glu Glu Lys
        85                  90                  95

cgg gca gtg ccg gac agg atg tgc aga cac aac tac gag ctg ggc ggg      394
Arg Ala Val Pro Asp Arg Met Cys Arg His Asn Tyr Glu Leu Gly Gly
    100                 105                 110

ccc atg acc ctg cag cgc cga gtc cag cct agg gtg aat gtt tcc ccc      442
Pro Met Thr Leu Gln Arg Arg Val Gln Pro Arg Val Asn Val Ser Pro
115                 120                 125                 130

tcc aag aag ggg ccc ttg cag cac cac aac ctg ctt gtc tgc cac gtg      490
Ser Lys Lys Gly Pro Leu Gln His His Asn Leu Leu Val Cys His Val
                135                 140                 145

acg gat ttc tac cca ggc agc att caa gtc cga tgg ttc ctg aat gga      538
Thr Asp Phe Tyr Pro Gly Ser Ile Gln Val Arg Trp Phe Leu Asn Gly
            150                 155                 160

cag gag gaa aca gct ggg gtc gtg tcc acc aac ctg atc cgt aat gga      586
Gln Glu Glu Thr Ala Gly Val Val Ser Thr Asn Leu Ile Arg Asn Gly
        165                 170                 175

gac tgg acc ttc cag atc ctg gtg atg ctg gaa atg acc ccc cag cag      634
Asp Trp Thr Phe Gln Ile Leu Val Met Leu Glu Met Thr Pro Gln Gln
    180                 185                 190

gga gat gtc tac acc tgc caa gtg gag cac acc agc ctg gat agt cct      682
Gly Asp Val Tyr Thr Cys Gln Val Glu His Thr Ser Leu Asp Ser Pro
195                 200                 205                 210

gtc acc gtg gag tgg aag gca cag tct gat tct gcc cgg agt aag aca      730
Val Thr Val Glu Trp Lys Ala Gln Ser Asp Ser Ala Arg Ser Lys Thr
                215                 220                 225

ttg acg gga gct ggg ggc ttc gtg ctg ggg ctc atc atc tgt gga gtg      778
Leu Thr Gly Ala Gly Gly Phe Val Leu Gly Leu Ile Ile Cys Gly Val
            230                 235                 240

ggc atc ttc atg cac agg agg agc aag aaa gtt caa cga gga tct gca      826
Gly Ile Phe Met His Arg Arg Ser Lys Lys Val Gln Arg Gly Ser Ala
        245                 250                 255

taa acagggttcc tgagctcact gaaaagacta ttgtgcctta ggaaaagcat           879

ttgctgtgtt tcgttagcat ctggctccag gacagacctt caacttccaa attggatact    939

gctgccaaga agttgctctg aagtcagttt ctatcattct gctctttgat tcaaagcact    999

gtttctctca ctgggcctcc aaccatgttc ccttcttctt agcaccacaa ataatcaaaa   1059

cccaacatga ctgtttgttt tcctttaaaa atatgcacca aatcatctct catcactttt   1119

ctctgagggt tttagtagac agtaggagtt aataaagaag ttcattttgg tttaaacata   1179

ggaaagaaga gaaccatgaa aatggggata tgttaactat tgtataatgg ggcctgttac   1239

acatgacact cttctgaatt gactgtattt cagtgagctg cccccaaatc aagtttagtg   1299

ccctcatcca tttatgtctc agaccactat tcttaactat tcaatggtga gcagactgca   1359

aatctgcctg ataggaccca tattcccaca gcactaattc aacatatacc ttactgagag   1419

catgttttat cattaccatt aagaagttaa atgaacatca gaatttaaaa tcataaatat   1479

aatctaatac actttaacca ttttctttgt gtgccatcac aaatactcct taaccaaata   1539

cggcttggac ttttgaatgc atccaataga cgtcatttgt cgtctaagtc tgcattcatc   1599

caccagccta ggcctcctgt cttaattttc atacagacag aaatgactcc ccactgggga   1659
```

```
aagagcaaag caatacatgt agcactcttt ttcaaacact ggtctttttt tttttcttaa   1719
caatccaaca ttgttatgtg ttttgcgtct catattgaca ccttttggtc aaggtagagg   1779
acatgtttgt tgtaagcttt ctttttcgtg tagaggatgg attcttcact cctgatacac   1839
acaatcagtg cacagcagct ctcttataca tccagttgat gccttcagtc tccctggctt   1899
cttacaagca tcttctgggc cttgtgtgtc cctgggcacc tgtccctggt caattcccga   1959
aagctactgt gctcctcttg cccatctccc cttgcaaata atatcttcca tcgggggacc   2019
ggcttcctcc aatttcagga gaggtggggc tgaaggcaca gacttgggcg tcactggcac   2079
agatataagt aaatacagct ggagtctgca gagaggctgg actgagtcag ggagtcagga   2139
aagagaagcc acacacaagg acaaccaatc atgtttctca taatcttctt aacctaggga   2199
ataggacaca atcatttttt ctttttaaaa catctttatc cctgatcagc ctcatttcct   2259
caaaaactat aaaggaaaat gctgctgact tgtttttgcg tagtaatttc agctgtcaca   2319
taataagcta aggaagacag tatatagtaa ataaggaccc tttatctgtc ttattttccc   2379
ttttggcttc acaggaaact tgtgagaaac ctatgcagca taaaattaat atgatttcaa   2439
tccagggatt caacgatgga aggaggtcat gagaatagca gaaagtcttc aaatcgagat   2499
cattatgaaa tcctcagacc cagagcacat aaatcctacc ctcagagtca ctgagcagtt   2559
aacattacaa attacaaacc atatccagtc agagtcattc tctttcctgc ttgtctcctg   2619
tactcatgtt acaggttagg gcagtacccc gagtggagtg aacaatctct ggactaacac   2679
ttgtcaggat cagaagctga ggtatctgca cccacattac aggaacagga tatgtgctcc   2739
tagggaactg agggtgtcag gagatgagga atgtccctgg agtcacagaa agaaggtatc   2799
agatgtgtct cactctgaca tatgcaggtg tttatgaaac tctgggattt ctaaggaagg   2859
atgcagtgca gagacaggtc ccagaggaga caagagctga gagaccatcc aaactgggac   2919
caccttgtca ctagacttca aattttcaat attgatagag tgttttctaa gagtcaggcc   2979
ctttgctgag tgctatgtgc agcaggatca aaggcagcca ggaggtagag gagtcttgag   3039
gtacatcagt cattggagtt gaagagcaga gattcaaagg aaagttggaa ctggagcttt   3099
aaaggagatg tgaagtgggt gactcaacct ctgactcaga aaaattgata cctgcagaag   3159
aaaaaacccg gcgggcttag gactcccagc tgagtgttgt atcctccatc cctttccacc   3219
tggtcccttc attttctacc cctcacagtt ccctaacgag aaggtggtcc acccaacaga   3279
caacactgcc tcagatggtt atcaaggggt accctaagaa gaaatcatct caccctctct   3339
ttgtccccat ttgtcaagta gcagtgaggc cgagccaggg gatggtgaaa gtggaaggag   3399
gtgggagttg ggcatcgggt gtgaagatgc tcttgaaagg ggttttaata accacttgct   3459
accaggccag tgaacactta ccatagttga tgccttttga gcatgttgca ttgtaaactg   3519
tccctgaaat tactgtgcac ttggcttatg ggatgaaaca tcctcctagt tcttttgtct   3579
ctcagcttct ctgaagtctc attgagcacc ttctcttcaa tttcttttac acagtaagaa   3639
taggatcagc tgtgctaaac taacaaatac ccagatatcc aggtttggct catgttacac   3699
gtccaaagta agtcatgcag gaagctctgc tcatcatcgt actcaggaag tcaggctgac   3759
agtctttctc ctgcacatct gctcccagaa cctccccagc agaatgaagg gaacctaaga   3819
atttattcac tggcttttaa tgatccctcc tagaaagaac acacttctcg catttcattt   3879
tccaatgtaa atcatatggc tgcaactaac ttcaaataag tgggaatact tgaaggtgga   3939
aaacatttaa gaagtacaca ctaaataaat aataaaatac ttctacaaga ga           3991
```

<210> SEQ ID NO 26
<211> LENGTH: 258
<212> TYPE: PRT
<213> ORGANISM: Homo sapiens

<400> SEQUENCE: 26

```
Met Met Val Leu Gln Val Ser Ala Ala Pro Arg Thr Val Ala Leu Thr
1               5                   10                  15

Ala Leu Leu Met Val Leu Leu Thr Ser Val Val Gln Gly Arg Ala Thr
            20                  25                  30

Pro Glu Asn Tyr Leu Phe Gln Gly Arg Gln Glu Cys Tyr Ala Phe Asn
        35                  40                  45

Gly Thr Gln Arg Phe Leu Glu Arg Tyr Ile Tyr Asn Arg Glu Glu Phe
    50                  55                  60

Ala Arg Phe Asp Ser Asp Val Gly Glu Phe Arg Ala Val Thr Glu Leu
65                  70                  75                  80

Gly Arg Pro Ala Ala Glu Tyr Trp Asn Ser Gln Lys Asp Ile Leu Glu
                85                  90                  95

Glu Lys Arg Ala Val Pro Asp Arg Met Cys Arg His Asn Tyr Glu Leu
            100                 105                 110

Gly Gly Pro Met Thr Leu Gln Arg Arg Val Gln Pro Arg Val Asn Val
        115                 120                 125

Ser Pro Ser Lys Lys Gly Pro Leu Gln His His Asn Leu Leu Val Cys
    130                 135                 140

His Val Thr Asp Phe Tyr Pro Gly Ser Ile Gln Val Arg Trp Phe Leu
145                 150                 155                 160

Asn Gly Gln Glu Glu Thr Ala Gly Val Val Ser Thr Asn Leu Ile Arg
                165                 170                 175

Asn Gly Asp Trp Thr Phe Gln Ile Leu Val Met Leu Glu Met Thr Pro
            180                 185                 190

Gln Gln Gly Asp Val Tyr Thr Cys Gln Val Glu His Thr Ser Leu Asp
        195                 200                 205

Ser Pro Val Thr Val Glu Trp Lys Ala Gln Ser Asp Ser Ala Arg Ser
    210                 215                 220

Lys Thr Leu Thr Gly Ala Gly Gly Phe Val Leu Gly Leu Ile Ile Cys
225                 230                 235                 240

Gly Val Gly Ile Phe Met His Arg Arg Ser Lys Lys Val Gln Arg Gly
                245                 250                 255

Ser Ala
```

<210> SEQ ID NO 27
<211> LENGTH: 899
<212> TYPE: DNA
<213> ORGANISM: Homo sapiens
<220> FEATURE:
<221> NAME/KEY: CDS
<222> LOCATION: (322)..(741)

<400> SEQUENCE: 27

```
agatgcccct ctgggagaga tccccagggg tgacagccat ggaccctgga agggcctggg      60

ctagggacag ggaccagagc cagtccaggg agaggacaga gccaatggac tggggtgtac     120

tgtaacagcc ctgctggcga gagggaccag ggcaccgtcc tccagggagc ccatgctgca     180

agtcgggcca gaggtgcccc tgaacctgaa ggccaatgag acccaagaca ggccaagtgg     240

gttgtgagac ccctgaggag ctgggccctg gtcccaggca gcgctggccc ctgctgctgc     300

tgggtctggc catggtcgcc c atg gcc tgc tgc gcc caa tgg ttg cac cgc      351
```

```
                        Met Ala Cys Cys Ala Gln Trp Leu His Arg
                        1               5                   10

aaa gcg ggg acc cag acc ctg gag cct cag ttg gaa gca gcc gat cca      399
Lys Ala Gly Thr Gln Thr Leu Glu Pro Gln Leu Glu Ala Ala Asp Pro
                15                  20                  25

gcc tgc gga gcc tgt ggg gca ggt cag ccc aag gct gcc ccc tcg gtc      447
Ala Cys Gly Ala Cys Gly Ala Gly Gln Pro Lys Ala Ala Pro Ser Val
            30                  35                  40

act ctg ttc ccg ccc tcc tct gag gag ctt caa gcc aac aag gcc aca      495
Thr Leu Phe Pro Pro Ser Ser Glu Glu Leu Gln Ala Asn Lys Ala Thr
        45                  50                  55

ctg gtg tgt ctc ata agt gac ttc tac ccg gga gcc gtg aca gtg gcc      543
Leu Val Cys Leu Ile Ser Asp Phe Tyr Pro Gly Ala Val Thr Val Ala
    60                  65                  70

tgg aag gca gat agc agc ccc gtc aag gcg gga gtg gag acc acc aca      591
Trp Lys Ala Asp Ser Ser Pro Val Lys Ala Gly Val Glu Thr Thr Thr
75                  80                  85                  90

ccc tcc aaa caa agc aac aac aag tac gcg gcc agc agc tac ctg agc      639
Pro Ser Lys Gln Ser Asn Asn Lys Tyr Ala Ala Ser Ser Tyr Leu Ser
                95                  100                 105

ctg acg cct gag cag tgg aag tcc cac aga agc tac agc tgc cag gtc      687
Leu Thr Pro Glu Gln Trp Lys Ser His Arg Ser Tyr Ser Cys Gln Val
            110                 115                 120

acg cat gaa ggg agc acc gtg gag aag aca gtg gcc cct aca gaa tgt      735
Thr His Glu Gly Ser Thr Val Glu Lys Thr Val Ala Pro Thr Glu Cys
        125                 130                 135

tca tag gttctcaacc ctcacccccca ccacgggaga ctagagctgc aggatcccag      791
Ser

gggaggggtc tctcctccca ccccaaggca tcaagccctt ctccctgcac tcaataaacc    851

ctcaataaat attctcattg tcaatcaaaa aaaaaaaaaa aaaaaaaa                 899


<210> SEQ ID NO 28
<211> LENGTH: 139
<212> TYPE: PRT
<213> ORGANISM: Homo sapiens

<400> SEQUENCE: 28

Met Ala Cys Cys Ala Gln Trp Leu His Arg Lys Ala Gly Thr Gln Thr
1               5                   10                  15

Leu Glu Pro Gln Leu Glu Ala Ala Asp Pro Ala Cys Gly Ala Cys Gly
            20                  25                  30

Ala Gly Gln Pro Lys Ala Ala Pro Ser Val Thr Leu Phe Pro Pro Ser
        35                  40                  45

Ser Glu Glu Leu Gln Ala Asn Lys Ala Thr Leu Val Cys Leu Ile Ser
    50                  55                  60

Asp Phe Tyr Pro Gly Ala Val Thr Val Ala Trp Lys Ala Asp Ser Ser
65                  70                  75                  80

Pro Val Lys Ala Gly Val Glu Thr Thr Thr Pro Ser Lys Gln Ser Asn
                85                  90                  95

Asn Lys Tyr Ala Ala Ser Ser Tyr Leu Ser Leu Thr Pro Glu Gln Trp
            100                 105                 110

Lys Ser His Arg Ser Tyr Ser Cys Gln Val Thr His Glu Gly Ser Thr
        115                 120                 125

Val Glu Lys Thr Val Ala Pro Thr Glu Cys Ser
    130                 135


<210> SEQ ID NO 29
```

```
<211> LENGTH: 1192
<212> TYPE: DNA
<213> ORGANISM: Homo sapiens
<220> FEATURE:
<221> NAME/KEY: CDS
<222> LOCATION: (127)..(1068)

<400> SEQUENCE: 29

attccacatc aggagcgttt ttggagaaag ctgcactctg ttgagctcca gggcgcagtg     60

gagggaggga gtgaaggagc tctctgtacc caaggaaagt gcagctgaga ctcagacaag    120

attaca atg aac caa ctc agc ttc ctg ctg ttt ctc ata gcg acc acc       168
       Met Asn Gln Leu Ser Phe Leu Leu Phe Leu Ile Ala Thr Thr
       1               5                   10

aga gga tgg agt aca gat gag gct aat act tac ttc aag gaa tgg acc      216
Arg Gly Trp Ser Thr Asp Glu Ala Asn Thr Tyr Phe Lys Glu Trp Thr
15                  20                  25                  30

tgt tct tcg tct cca tct ctg ccc aga agc tgc aag gaa atc aaa gac      264
Cys Ser Ser Ser Pro Ser Leu Pro Arg Ser Cys Lys Glu Ile Lys Asp
                35                  40                  45

gaa tgt cct agt gca ttt gat ggc ctg tat ttt ctc cgc act gag aat      312
Glu Cys Pro Ser Ala Phe Asp Gly Leu Tyr Phe Leu Arg Thr Glu Asn
            50                  55                  60

ggt gtt atc tac cag acc ttc tgt gac atg acc tct ggg ggt ggc ggc      360
Gly Val Ile Tyr Gln Thr Phe Cys Asp Met Thr Ser Gly Gly Gly Gly
        65                  70                  75

tgg acc ctg gtg gcc agc gtg cac gag aat gac atg cgt ggg aag tgc      408
Trp Thr Leu Val Ala Ser Val His Glu Asn Asp Met Arg Gly Lys Cys
    80                  85                  90

acg gtg ggc gat cgc tgg tcc agt cag cag ggc agc aaa gca gtc tac      456
Thr Val Gly Asp Arg Trp Ser Ser Gln Gln Gly Ser Lys Ala Val Tyr
95                  100                 105                 110

cca gag ggg gac ggc aac tgg gcc aac tac aac acc ttt gga tct gca      504
Pro Glu Gly Asp Gly Asn Trp Ala Asn Tyr Asn Thr Phe Gly Ser Ala
                115                 120                 125

gag gcg gcc acg agc gat gac tac aag aac cct ggc tac tac gac atc      552
Glu Ala Ala Thr Ser Asp Asp Tyr Lys Asn Pro Gly Tyr Tyr Asp Ile
            130                 135                 140

cag gcc aag gac ctg ggc atc tgg cac gtg ccc aat aag tcc ccc atg      600
Gln Ala Lys Asp Leu Gly Ile Trp His Val Pro Asn Lys Ser Pro Met
        145                 150                 155

cag cac tgg aga aac agc tcc ctg ctg agg tac cgc acg gac act ggc      648
Gln His Trp Arg Asn Ser Ser Leu Leu Arg Tyr Arg Thr Asp Thr Gly
    160                 165                 170

ttc ctc cag aca ctg gga cat aat ctg ttt ggc atc tac cag aaa tat      696
Phe Leu Gln Thr Leu Gly His Asn Leu Phe Gly Ile Tyr Gln Lys Tyr
175                 180                 185                 190

cca gtg aaa tat gga gaa gga aag tgt tgg act gac aac ggc ccg gtg      744
Pro Val Lys Tyr Gly Glu Gly Lys Cys Trp Thr Asp Asn Gly Pro Val
                195                 200                 205

atc cct gtg gtc tat gat ttt ggc gac gcc cag aaa aca gca tct tat      792
Ile Pro Val Val Tyr Asp Phe Gly Asp Ala Gln Lys Thr Ala Ser Tyr
            210                 215                 220

tac tca ccc tat ggc cag cgg gaa ttc act gcg gga ttt gtt cag ttc      840
Tyr Ser Pro Tyr Gly Gln Arg Glu Phe Thr Ala Gly Phe Val Gln Phe
        225                 230                 235

agg gta ttt aat aac gag aga gca gcc aac gcc ttg tgt gct gga atg      888
Arg Val Phe Asn Asn Glu Arg Ala Ala Asn Ala Leu Cys Ala Gly Met
    240                 245                 250

agg gtc acc gga tgt aac act gag cac cac tgc att ggt gga gga gga      936
Arg Val Thr Gly Cys Asn Thr Glu His His Cys Ile Gly Gly Gly Gly
```

```
255                 260                 265                 270

tac ttt cca gag gcc agt ccc cag cag tgt gga gat ttt tct ggt ttt      984
Tyr Phe Pro Glu Ala Ser Pro Gln Gln Cys Gly Asp Phe Ser Gly Phe
                275                 280                 285

gat tgg agt gga tat gga act cat gtt ggt tac agc agc agc cgt gag     1032
Asp Trp Ser Gly Tyr Gly Thr His Val Gly Tyr Ser Ser Ser Arg Glu
            290                 295                 300

ata act gag gca gct gtg ctt cta ttc tat cgt tga gagttttgtg          1078
Ile Thr Glu Ala Ala Val Leu Leu Phe Tyr Arg
        305                 310

ggagggaacc cagacctctc ctcccaacca tgagatccca aggatggaga acaacttacc   1138

cagtagctag aatgttaatg gcagaagaga aaacaataaa tcatattgac tcaa         1192


<210> SEQ ID NO 30
<211> LENGTH: 313
<212> TYPE: PRT
<213> ORGANISM: Homo sapiens

<400> SEQUENCE: 30

Met Asn Gln Leu Ser Phe Leu Leu Phe Leu Ile Ala Thr Thr Arg Gly
1               5                   10                  15

Trp Ser Thr Asp Glu Ala Asn Thr Tyr Phe Lys Glu Trp Thr Cys Ser
            20                  25                  30

Ser Ser Pro Ser Leu Pro Arg Ser Cys Lys Glu Ile Lys Asp Glu Cys
        35                  40                  45

Pro Ser Ala Phe Asp Gly Leu Tyr Phe Leu Arg Thr Glu Asn Gly Val
    50                  55                  60

Ile Tyr Gln Thr Phe Cys Asp Met Thr Ser Gly Gly Gly Gly Trp Thr
65                  70                  75                  80

Leu Val Ala Ser Val His Glu Asn Asp Met Arg Gly Lys Cys Thr Val
                85                  90                  95

Gly Asp Arg Trp Ser Ser Gln Gln Gly Ser Lys Ala Val Tyr Pro Glu
            100                 105                 110

Gly Asp Gly Asn Trp Ala Asn Tyr Asn Thr Phe Gly Ser Ala Glu Ala
        115                 120                 125

Ala Thr Ser Asp Asp Tyr Lys Asn Pro Gly Tyr Tyr Asp Ile Gln Ala
    130                 135                 140

Lys Asp Leu Gly Ile Trp His Val Pro Asn Lys Ser Pro Met Gln His
145                 150                 155                 160

Trp Arg Asn Ser Ser Leu Leu Arg Tyr Arg Thr Asp Thr Gly Phe Leu
                165                 170                 175

Gln Thr Leu Gly His Asn Leu Phe Gly Ile Tyr Gln Lys Tyr Pro Val
            180                 185                 190

Lys Tyr Gly Glu Gly Lys Cys Trp Thr Asp Asn Gly Pro Val Ile Pro
        195                 200                 205

Val Val Tyr Asp Phe Gly Asp Ala Gln Lys Thr Ala Ser Tyr Tyr Ser
    210                 215                 220

Pro Tyr Gly Gln Arg Glu Phe Thr Ala Gly Phe Val Gln Phe Arg Val
225                 230                 235                 240

Phe Asn Asn Glu Arg Ala Ala Asn Ala Leu Cys Ala Gly Met Arg Val
                245                 250                 255

Thr Gly Cys Asn Thr Glu His His Cys Ile Gly Gly Gly Gly Tyr Phe
            260                 265                 270

Pro Glu Ala Ser Pro Gln Gln Cys Gly Asp Phe Ser Gly Phe Asp Trp
        275                 280                 285
```

```
Ser Gly Tyr Gly Thr His Val Gly Tyr Ser Ser Ser Arg Glu Ile Thr
    290                 295                 300

Glu Ala Ala Val Leu Leu Phe Tyr Arg
305                 310


<210> SEQ ID NO 31
<211> LENGTH: 2901
<212> TYPE: DNA
<213> ORGANISM: Homo sapiens

<400> SEQUENCE: 31

gtttagatta ggttggaagt cacctgggct gagctgatgg ctgattccgt cagcaaaaag     60

aactgtggaa catactggca cttgggccgg tgtgaagcca ccccccctgcc atgaaaaatg    120

gctcttccct gccacagccg gcccagcggg agccaggtca gggcctggag acacagcgcc    180

ccccaccgga gccactgccc ggcccagcag cacctgcgga gaatcccacc agctcccacg    240

cctcccgccg cgccaccgcc ccggctttct gcaaatccac cttatggaag ccggataagc    300

acctcctcct ctgatgcgtc acagtcacag gtcctggtga ggagggagcc acgccaagca    360

cagcggctgg aacaggggca agtgggtgcc caccccgaag tgcaggcaat gaacttgtgc    420

tgtagcccat ggtgagctgt ggggctgttt gtgactgcag cgtagccaag cccatcccgc    480

ctgatgcggc ctcttcatcc agagtggggg tgacgtgcca gcccccacct caccggaatg    540

ctgggaggag cgtctccacg gaaggagctc actttgtcag ctgtaatgtg ctgtgactat    600

cgtaaagttc cttccgggtg cagagtgata catgaaccct ggggactcac tccaacttgg    660

tattgatttt ctccacggag gacccagcag tcacggcccg tgtctgcaca gcccccttgga    720

tcctgcggag gaattcagcc ggcccctccc cctgtgccga aaaccacgga ggcaaagcca    780

ggccagggta cagtgagaac acgggagagg actgagagac cgctggctgc cgagggagga    840

agagcaggat tcgcaccccc gtcatcgctg ggcccacacg ccgccgacag cttccgcgtg    900

tggccatctg tctttcagaa accctctggc agagggaccc agcagatgac acgggggccg    960

ttcacactct gaaacctgcc tggagtcaaa acactgctgg cgagcctcca ccgcaaaccc   1020

aatccagatg gtcttccctg gtggccctcg ggtggcggg caccctgccc actccctgcc   1080

agcccctgcc cgctggactc caggcccggc cgagcccccg accggtctcc tgacccagca   1140

tgctgctctc ccctgggccc ggctttctcg cccgctggga ctcccaggcc cctccagccc   1200

agccccgaga gcaggagccc caagggaggc ttggcggctg tggaggcgag tgggccacgt   1260

gtagctggga ggccggcagg accaggagcc cctcacagcg cagcacccac agcatcacga   1320

gccacttcca ctcctgggtg gcctgggggc ccccaccctg ctctgagctg ccccttgttg   1380

tgacctgggg tcccccgtgg tgggcccgcc ccttgagcct gggatccagc ctcagcgagg   1440

ctccagaagt gtcgtctccg ccggccaggc gtcagcgcct ccacccagga tcacacactc   1500

ctatctctgc acttctgccc tccatcctgc tccacgccgc ctctgcttgt tattccagca   1560

cattccaggg tgatgcctgc tgaagccacg cagccagtgc ctccacccta ccccccatct   1620

gacccaccgg ccccttccgc acgctggaag cctgcccggc ctgaagtgtc ctcacctgtc   1680

gccctatcct cccctccact ccagcccacc ggtgactcag ccctcacagc tctctcctcc   1740

ccgagggagc cggtgacttg gctctgatgg tgccgggacc cagccccggc atgttcagaa   1800

tccttgtcct ttaacctgcg tccacatgta gtcgcctcca cctccctgcc tgaacctcca   1860

ggccctgcag agcaaacact gctgcctgca ggagacccct ggggccttct ccgtcccctc   1920
```

```
atcctcctaa ggagcctccc ctgccaccgt gccagaatgt gccggaggaa cagaggcccg   1980

agcctcccgt ggccccagcg aggcttcctc tggggaagac agtgagccca acgccctggc   2040

tctcgagggg tggacggagt ccagctggca tcgaccgggt gcccctcttc accggtgtcc   2100

acagtccttg agagcaaagg gttcccagag gcgacctccc tcctgcacag gcatttgtca   2160

tccttaccct ctaggacagc tttgccatgt gcagtgaacc cctggacagt gttgcgtgcc   2220

actttgccgg atttggactg tatacagacc gaagcatgtg gcatgaagcc ttctgctgtc   2280

agcaagttcc ttgtccctcg acagtatgtg cccaggctgc ccttcaaggt ggcagtgatg   2340

gcagttgtct cttgcacgct gcgtacagtt ctgtcactga ctcttacaca cagccctgga   2400

gacgggagag tgccgggagc attctatgca agtgtcctgg cctttgcggg cgtctccaca   2460

gcacaaacac gagtcaggga ccacccctct tctgcttcca tgattccacc aactgggtgg   2520

ggcagagcag tgccagggcc ggaggcacgc cccaggtgag ggcaggtggc catgccagtg   2580

agtgcactgc gttctcagtt aattcatccg aaatatttct aagtttcttg attattgcag   2640

ttgcatcccc aagataatgc cgccctcacc aagtagaagg cacatgtgct ctgatggccc   2700

ctcccacact ggggtcaggg cacagcaact tagcgaggcg acgtgggggc tcagaggacc   2760

tcggaccagg ctcggcacat ggggcttctc cagccagcca gggggaagca ccctgcagac   2820

tgctaacttt tgcaaaatag agtaaaaaag atcagctaga aaataaaac aaaaaaggaa    2880

agatatacaa aatacaaggc c                                             2901


<210> SEQ ID NO 32
<211> LENGTH: 2540
<212> TYPE: DNA
<213> ORGANISM: Homo sapiens
<220> FEATURE:
<221> NAME/KEY: CDS
<222> LOCATION: (174)..(1607)

<400> SEQUENCE: 32

ctcttttcct ccctcccgcc ggccggggtg cgcgggcggc ggggcggccc gcgggccatg     60

cgttcggcgc ggcccagccc ggccggccgg gggcggcgcc ccgagcccgg gccccgcgcg    120

gcccgcgccc ccggcccccg ctgagccccg ggggccccgc tgcggccgag gcc atg       176
                                                           Met
                                                           1

ttc ccg gtg ttt cct tgc acg ctg ctg gcc ccc ccc ttc ccc gtg ctg      224
Phe Pro Val Phe Pro Cys Thr Leu Leu Ala Pro Pro Phe Pro Val Leu
            5                   10                  15

ggc ctg gac tcc cgg ggg gtg ggc ggc ctc atg aac tcc ttc ccg cca      272
Gly Leu Asp Ser Arg Gly Val Gly Gly Leu Met Asn Ser Phe Pro Pro
        20                  25                  30

cct cag ggt cac gcc cag aac ccc ctg cag gtc ggg gct gag ctc cag      320
Pro Gln Gly His Ala Gln Asn Pro Leu Gln Val Gly Ala Glu Leu Gln
    35                  40                  45

tcc cgc ttc ttt gcc tcc cag ggc tgc gcc cag agt cca ttc cag gcc      368
Ser Arg Phe Phe Ala Ser Gln Gly Cys Ala Gln Ser Pro Phe Gln Ala
50                  55                  60                  65

gcg ccg gcg ccc ccg ccc acg ccc cag gcc ccg gcg gcc gag ccc ctc      416
Ala Pro Ala Pro Pro Pro Thr Pro Gln Ala Pro Ala Ala Glu Pro Leu
                70                  75                  80

cag gtg gac ttg ctc ccg gtg ctc gcc gcc gcc cag gag tcc gcc gcg      464
Gln Val Asp Leu Leu Pro Val Leu Ala Ala Ala Gln Glu Ser Ala Ala
            85                  90                  95

gct gct gcg gcc gct gcc gcc gct gct gcc gcc gtc gct gcc gcg ccc      512
Ala Ala Ala Ala Ala Ala Ala Ala Ala Ala Ala Val Ala Ala Ala Pro
```

```
        100                 105                 110

ccg gcc cct gcc gcc gcc tct acg gtg gac aca gcg gcc ctg aag cag      560
Pro Ala Pro Ala Ala Ala Ser Thr Val Asp Thr Ala Ala Leu Lys Gln
    115                 120                 125

cct ccg gcg ccc cct ccg cca ccc ccg cca gtg tcg gcg ccc gcg gcc      608
Pro Pro Ala Pro Pro Pro Pro Pro Pro Pro Val Ser Ala Pro Ala Ala
130                 135                 140                 145

gag gcc gcg ccc ccc gcc tcc gcc gcc act atc gcc gcg gcg gcg gcc      656
Glu Ala Ala Pro Pro Ala Ser Ala Ala Thr Ile Ala Ala Ala Ala Ala
                150                 155                 160

acc gcc gtc gta gcc cca acc tcg acg gtc gcc gtg gcc ccg gtc gcg      704
Thr Ala Val Val Ala Pro Thr Ser Thr Val Ala Val Ala Pro Val Ala
            165                 170                 175

tct gcc ttg gag aag aag aca aag agc aag ggg ccc tac atc tgc gct      752
Ser Ala Leu Glu Lys Lys Thr Lys Ser Lys Gly Pro Tyr Ile Cys Ala
        180                 185                 190

ctg tgc gcc aag gag ttc aag aac ggc tac aat ctc cgg agg cac gaa      800
Leu Cys Ala Lys Glu Phe Lys Asn Gly Tyr Asn Leu Arg Arg His Glu
    195                 200                 205

gcc atc cac acg gga gcc aag gcc ggc cgg gtc ccc tcg ggt gct atg      848
Ala Ile His Thr Gly Ala Lys Ala Gly Arg Val Pro Ser Gly Ala Met
210                 215                 220                 225

aag atg ccg acc atg gtg ccc ctg agc ctc ctg agc gtg ccc cag ctg      896
Lys Met Pro Thr Met Val Pro Leu Ser Leu Leu Ser Val Pro Gln Leu
                230                 235                 240

agc gga gcc ggc ggg gga ggg gga gag gcg ggt gcc ggc ggc ggc gct      944
Ser Gly Ala Gly Gly Gly Gly Gly Glu Ala Gly Ala Gly Gly Gly Ala
            245                 250                 255

gcc gca gtg gcc gcc ggt ggc gtg gtg acc acg acc gcc tcg ggg aag      992
Ala Ala Val Ala Ala Gly Gly Val Val Thr Thr Thr Ala Ser Gly Lys
        260                 265                 270

cgc atc cgg aag aac cat gcc tgc gag atg tgt ggc aag gcc ttc cgc     1040
Arg Ile Arg Lys Asn His Ala Cys Glu Met Cys Gly Lys Ala Phe Arg
    275                 280                 285

gac gtc tac cac ctg aac cga cac aag ctg tcg cac tcg gac gag aag     1088
Asp Val Tyr His Leu Asn Arg His Lys Leu Ser His Ser Asp Glu Lys
290                 295                 300                 305

ccc tac cag tgc ccg gtg tgc cag cag cgc ttc aag cgc aag gac cgc     1136
Pro Tyr Gln Cys Pro Val Cys Gln Gln Arg Phe Lys Arg Lys Asp Arg
                310                 315                 320

atg agc tac cac gtg cgc tca cat gac ggc gct gtg cac aag ccc tac     1184
Met Ser Tyr His Val Arg Ser His Asp Gly Ala Val His Lys Pro Tyr
            325                 330                 335

aac tgc tcc cac tgt ggc aag agc ttc tcc cgg ccg gat cac ctc aac     1232
Asn Cys Ser His Cys Gly Lys Ser Phe Ser Arg Pro Asp His Leu Asn
        340                 345                 350

agt cac gtc aga caa gtg cac tca aca gaa cgg ccc ttc aaa tgt gag     1280
Ser His Val Arg Gln Val His Ser Thr Glu Arg Pro Phe Lys Cys Glu
    355                 360                 365

aaa tgt gag gca gct ttc gcc acg aag gat cgg ctg cgg gcg cac aca     1328
Lys Cys Glu Ala Ala Phe Ala Thr Lys Asp Arg Leu Arg Ala His Thr
370                 375                 380                 385

gta cga cac gag gag aaa gtg cca tgt cac gtg tgt ggc aag atg ctg     1376
Val Arg His Glu Glu Lys Val Pro Cys His Val Cys Gly Lys Met Leu
                390                 395                 400

agc tcg gct tat att tcg gac cac atg aag gtg cac agc cag ggt cct     1424
Ser Ser Ala Tyr Ile Ser Asp His Met Lys Val His Ser Gln Gly Pro
            405                 410                 415

cac cat gtc tgt gag ctc tgc aac aaa ggt act ggt gag gtt tgt cca     1472
```

```
His His Val Cys Glu Leu Cys Asn Lys Gly Thr Gly Glu Val Cys Pro
        420                 425                 430

atg gcg gcg gca gcg gca gcg gcg gca gcg gca gca gcg gca gca gta      1520
Met Ala Ala Ala Ala Ala Ala Ala Ala Ala Ala Ala Ala Ala Ala Val
    435                 440                 445

gca gcc cct ccc aca gct gtg ggc tcc ctc tcg ggg gcg gag ggg gtg      1568
Ala Ala Pro Pro Thr Ala Val Gly Ser Leu Ser Gly Ala Glu Gly Val
450                 455                 460                 465

cct gtg agc tct cag cca ctt ccc tcc caa ccc tgg tga gctccaagtt       1617
Pro Val Ser Ser Gln Pro Leu Pro Ser Gln Pro Trp
                470                 475

ggttgcgggg gagaggggag aatggagtag agtcccttgg tacaagctcc tctccccct     1677

cttttcccac caactcctat ttccctacca accaaggagc ctccagaagg aaaggaggaa    1737

gaaatgtttt cttaggggaa ttcgctaggt tttaacgatt tgtttctcct gctcctcttc    1797

tgtcagacct gaccccacac aaacctgtcc cctcggttgt gttgaagtcc cctggacagt    1857

gggcaggggt ggcagaggac acgagcagcc actgcccgta ccccctctcc tctctgtaag    1917

cccatgccct gtcttcccag ggacttgtga gcctcttccc tcgacggtcc tcttctctcc    1977

ttccagtcct ctcccctgc tgtctgcagc ccctccccgg ggagttggtg ctttcttttc     2037

cttttttttt tttttccagg gggagggagg agaggaagga gggggatcag agctgtccca    2097

aagagggaaa gcggtgaggt ttgaggaggg gcagaagcag ggccggcaaa ggttgtacct    2157

tcataaggtg gtatgggggg ttggggtcag gccctgaaca tcgtcctact tgagaatctg    2217

tcaggggaaa aagtcaaggg gagcaggagg aagagccagg agggccagag gcagagaaga    2277

gatggagtct taggggccag ggtgagcgag gggtccaggg cctagaggtg cttcctgggg    2337

gcgggggaat gcagccagtg tccccctccc ctcttccacc ccagctccag ccctggtctt    2397

gtcttttcat ccctcttccc cacgacagaa gaagttgtgg ccctggccat gtcatcgtgt    2457

tcctgtgtcc cctgcatgta ccccaccctc caccccttcc ttttgcgcgg accccattac    2517

aataaatttt aaataaaatc ctg                                            2540


<210> SEQ ID NO 33
<211> LENGTH: 477
<212> TYPE: PRT
<213> ORGANISM: Homo sapiens

<400> SEQUENCE: 33

Met Phe Pro Val Phe Pro Cys Thr Leu Leu Ala Pro Pro Phe Pro Val
1               5                   10                  15

Leu Gly Leu Asp Ser Arg Gly Val Gly Gly Leu Met Asn Ser Phe Pro
            20                  25                  30

Pro Pro Gln Gly His Ala Gln Asn Pro Leu Gln Val Gly Ala Glu Leu
        35                  40                  45

Gln Ser Arg Phe Phe Ala Ser Gln Gly Cys Ala Gln Ser Pro Phe Gln
    50                  55                  60

Ala Ala Pro Ala Pro Pro Pro Thr Pro Gln Ala Pro Ala Ala Glu Pro
65                  70                  75                  80

Leu Gln Val Asp Leu Leu Pro Val Leu Ala Ala Ala Gln Glu Ser Ala
                85                  90                  95

Ala Ala Ala Ala Ala Ala Ala Ala Ala Ala Ala Ala Val Ala Ala Ala
            100                 105                 110

Pro Pro Ala Pro Ala Ala Ala Ser Thr Val Asp Thr Ala Ala Leu Lys
        115                 120                 125
```

```
Gln Pro Pro Ala Pro Pro Pro Pro Pro Pro Pro Val Ser Ala Pro Ala
    130                 135                 140

Ala Glu Ala Ala Pro Pro Ala Ser Ala Ala Thr Ile Ala Ala Ala Ala
145                 150                 155                 160

Ala Thr Ala Val Val Ala Pro Thr Ser Thr Val Ala Val Ala Pro Val
                165                 170                 175

Ala Ser Ala Leu Glu Lys Lys Thr Lys Ser Lys Gly Pro Tyr Ile Cys
            180                 185                 190

Ala Leu Cys Ala Lys Glu Phe Lys Asn Gly Tyr Asn Leu Arg Arg His
        195                 200                 205

Glu Ala Ile His Thr Gly Ala Lys Ala Gly Arg Val Pro Ser Gly Ala
    210                 215                 220

Met Lys Met Pro Thr Met Val Pro Leu Ser Leu Leu Ser Val Pro Gln
225                 230                 235                 240

Leu Ser Gly Ala Gly Gly Gly Gly Gly Glu Ala Gly Ala Gly Gly Gly
                245                 250                 255

Ala Ala Ala Val Ala Ala Gly Gly Val Val Thr Thr Thr Ala Ser Gly
            260                 265                 270

Lys Arg Ile Arg Lys Asn His Ala Cys Glu Met Cys Gly Lys Ala Phe
        275                 280                 285

Arg Asp Val Tyr His Leu Asn Arg His Lys Leu Ser His Ser Asp Glu
    290                 295                 300

Lys Pro Tyr Gln Cys Pro Val Cys Gln Gln Arg Phe Lys Arg Lys Asp
305                 310                 315                 320

Arg Met Ser Tyr His Val Arg Ser His Asp Gly Ala Val His Lys Pro
                325                 330                 335

Tyr Asn Cys Ser His Cys Gly Lys Ser Phe Ser Arg Pro Asp His Leu
            340                 345                 350

Asn Ser His Val Arg Gln Val His Ser Thr Glu Arg Pro Phe Lys Cys
        355                 360                 365

Glu Lys Cys Glu Ala Ala Phe Ala Thr Lys Asp Arg Leu Arg Ala His
    370                 375                 380

Thr Val Arg His Glu Glu Lys Val Pro Cys His Val Cys Gly Lys Met
385                 390                 395                 400

Leu Ser Ser Ala Tyr Ile Ser Asp His Met Lys Val His Ser Gln Gly
                405                 410                 415

Pro His His Val Cys Glu Leu Cys Asn Lys Gly Thr Gly Glu Val Cys
            420                 425                 430

Pro Met Ala Ala Ala Ala Ala Ala Ala Ala Ala Ala Ala Ala Ala Ala
        435                 440                 445

Val Ala Ala Pro Pro Thr Ala Val Gly Ser Leu Ser Gly Ala Glu Gly
    450                 455                 460

Val Pro Val Ser Ser Gln Pro Leu Pro Ser Gln Pro Trp
465                 470                 475
```

<210> SEQ ID NO 34
<211> LENGTH: 3723
<212> TYPE: DNA
<213> ORGANISM: Homo sapiens
<220> FEATURE:
<221> NAME/KEY: CDS
<222> LOCATION: (35)..(601)

<400> SEQUENCE: 34

```
aaacccaaag cggccgccgt aggcgaaggt gaag atg gct gcc tct gcc ttt gct      55
                                      Met Ala Ala Ser Ala Phe Ala
```

-continued

```
                                        1               5

ggt gca gtg aga gca gct tca gga atc cta cgg ccc ctg aat att ttg      103
Gly Ala Val Arg Ala Ala Ser Gly Ile Leu Arg Pro Leu Asn Ile Leu
        10                  15                  20

gca tct tca acc tac cgc aac tgt gtc aag aat gcc tct ctt att tct      151
Ala Ser Ser Thr Tyr Arg Asn Cys Val Lys Asn Ala Ser Leu Ile Ser
    25                  30                  35

gca ttg tcc act gga cgt ttt agt cat att cag aca cca gtt gtt tcc      199
Ala Leu Ser Thr Gly Arg Phe Ser His Ile Gln Thr Pro Val Val Ser
40                  45                  50                  55

tcc act ccc aga ctt acc aca tct gag aga aac ctg aca tgt ggg cat      247
Ser Thr Pro Arg Leu Thr Thr Ser Glu Arg Asn Leu Thr Cys Gly His
                60                  65                  70

acc tca gtg atc ctt aat aga atg gcc ccc gtg ctt cca agt gtc ctg      295
Thr Ser Val Ile Leu Asn Arg Met Ala Pro Val Leu Pro Ser Val Leu
            75                  80                  85

aag ctg cca gtc aga tct cta aca tac ttc agt gca aga aaa ggc aag      343
Lys Leu Pro Val Arg Ser Leu Thr Tyr Phe Ser Ala Arg Lys Gly Lys
        90                  95                  100

aga aag acc gtg aaa gct gtc atc gat agg ttt ctt cga ctt cat tgt      391
Arg Lys Thr Val Lys Ala Val Ile Asp Arg Phe Leu Arg Leu His Cys
    105                 110                 115

ggc ctt tgg gtg agg aga aag gct ggc tat aag aaa aaa tta tgg aaa      439
Gly Leu Trp Val Arg Arg Lys Ala Gly Tyr Lys Lys Lys Leu Trp Lys
120                 125                 130                 135

aag aca cct gca agg aag aag cga ttg agg gaa ttt gta ttc tgc aat      487
Lys Thr Pro Ala Arg Lys Lys Arg Leu Arg Glu Phe Val Phe Cys Asn
                140                 145                 150

aaa acc cag agt aaa ctc tta gat aaa atg acg acg tcc ttc tgg aag      535
Lys Thr Gln Ser Lys Leu Leu Asp Lys Met Thr Thr Ser Phe Trp Lys
            155                 160                 165

agg cga aac tgg tac gtt gat gat cct tat cag aag tat cat gat cga      583
Arg Arg Asn Trp Tyr Val Asp Asp Pro Tyr Gln Lys Tyr His Asp Arg
        170                 175                 180

aca aac ctg aaa gta tag atcagaagtt tcacttgttt ctcagttatt             631
Thr Asn Leu Lys Val
    185

ggatatgtat ctttgtgtac atatctttgc aaaaatggat aagtacaaaa cttgatgtaa    691

attgtaccaa tgaatacgta aacatacagt gacaacatta aacttagaaa agttttaaaa    751

cttaatggat cagactttgc cagatttggt tagggaaaca gaaatttaga atggtgcatt    811

atttttaaca aatggtattg gcttaactag ttgtttcagt tatgctcttt tagttgcaag    871

gaatctcaag tgggacaaac ataaaaagac tcaaaagcta caagttagct caagcaatgt    931

gacattattt caaggatatg tgccagggaa ttcaggaacc acctcaccaa ccccatctcc    991

cactcagaaa tcacctccca gcctcaggaa gagtagaaat tgggtggtgc tcctcagcag   1051

gggaaggtgg atgtttaggc ttgggctctg catgcatgtg acttgcttct ttttgcattg   1111

ttaactccat tctctctatt caccaacttc tctacacagc ttttgcatac ttacagtttc   1171

tgttcctttg taataacttt aacttgcacc tttgaggttc ttttctacat gatgaccttc   1231

agctcctgct gctagtctcc aattgccaag ggaatttaac tgggccagac taccttttta   1291

tactaggtct ggttgggtca ttgtctagag tagggattgg ctgtccttaa gtcaggagcc   1351

cgctttgtat tagcaggttt gcatgcagca aaaaaacagt tatgtgagca gtttcacttg   1411

gaggttcaca tggggtggca gcacacttaa catctaacac accaggttca ttgtgttcat   1471

aacacttgtc atttactgta acaacatttt ttcataggag agtaaatagc ccttcagcat   1531
```

gctcattcat gaaacagaag aggctgtaca agtgaagaca agggcttttt atgcaagttt 1591 tgaaagatag gtatttattt tttctagaga caggagtttt gctctgttgc ccaggctgga 1651 gtgcagtggt gcaatcatag ctcattgaag cctcgcactc ctgggctcaa gtggtcctcc 1711 tgcctcagct tactgagtaa ggatatgtat ttcttaaaag ttagtttatc cacttcagat 1771 ttcatgtttt catttgtaag gataaacttt tcccacaaat tttcaacaat cattgtagaa 1831 actaaggggg agaaagtaat ctcagttgtt ttagaaacga aaaagttaag cattgtttac 1891 ttgaagtggg cagggaagca gcactgagta aagttcaatt gagtggttac agtctagggc 1951 agtggttccc aactctccga tcagaatcat ctgggaagca ttttcaaaca gcaaagtact 2011 ttgaaaacca ttattaaata gaattatgca tgaattactg tttcagatcc tttaatgtgg 2071 tagttggtaa taataagatg aaattcctct gttgttagta aaattatgaa attgaagttc 2131 tgcagcatgt caggccagga ttattaggga gattcctcga aactagtgtg tgtttattaa 2191 aaggagaaag gataacaata gaatgttcta aaaccagaag tccaagtgcg tgtctactta 2251 tgggaccaat aaataaagaa cagacatttg atttgaggtg aggtaaaagc ctgaaacatg 2311 gaatggcatt ctgttttgat ggattttcat ttcttcgcac ttctgagacg gcaaagccaa 2371 ccacttagaa gccttccaca tctttgtcac ctgcctggct cctgctctct gatgtacctc 2431 tgggtagtga gatggaaatg gtgcctgcag aagttgggga gaaggatact tttgcacagc 2491 ctccatgatg tctttattgc aaatatggat gacaagggtc tctgttacag gggcctcaga 2551 gcaccttcgt ttctcctcta gaccagggac aggtgtagag ataaggactg gcaaccagag 2611 cctcagcatc caaagatgga ctgaagtggg atggctgaca ggcacataac ttacgggaaa 2671 gggaatttca tacatacgat ttttgttttg tgggtaggag ggcttatcat caacactgat 2731 tttataatct gacaataaat gtctttcatt aaagagttta cctaaatgat gttcgattat 2791 atgtataatt tataaaatat ttatgtatag tttgtttatt caggtatatg tataatttat 2851 tgaacaccta ctatgtccca gcatatctac aaaactgggt acatacatac tgtctaactg 2911 ctaatccaca tttccagtct tacaaaggac ataatgatta gttaagccct aatttagatt 2971 tgaggaaact gaagctgaga gagggttaag taaattaccc aaagtacagc taataagacc 3031 cagaatctca gtctcactcc ttgggatcct gtgtatttcc ctgagtcttc taacatatga 3091 aaattcatat ctaaatcaac aagtgactgt aatctggtac tataaatact aaataaacac 3151 ttcttcataa cactgtacca attcagcttt taaattttat tactttgctt tcctgtcctt 3211 tgccaactct taacctagtt aatcctagtt ctgttgacat tggaccaggc tcagtaaata 3271 aacgaatgga tttccagcct ttttttccca tctgttcctg cttttagtcc tctgaatctg 3331 cttcttttct tactgctgct ttattttaca gtgattttgt caaacataga atacaggact 3391 aaaaatgcaa agaaattggg tctgtgttta attttgatgt ttcaaatttt gagcttccaa 3451 gtctttgtgg ccacccaatg aagtttgagt ctgcctgttc agatgtgaaa ggtaagggct 3511 gcagcaggtt taagggtggc ccttcaccac cctgttgtca cctgcacagg cactccccca 3571 tttgcagatg aagaaatgtt cagagaagaa aaatgatgga ccaaacgtct gtttgcacaa 3631 ttgaaactct accagtggac tattctattt tcacagctac ctagtttctg ccgatgattt 3691 ttttaaatgt gaaataaaca gtgatacttt ca 3723

<210> SEQ ID NO 35
<211> LENGTH: 188
<212> TYPE: PRT

<213> ORGANISM: Homo sapiens

<400> SEQUENCE: 35

```
Met Ala Ala Ser Ala Phe Ala Gly Ala Val Arg Ala Ala Ser Gly Ile
1               5                   10                  15

Leu Arg Pro Leu Asn Ile Leu Ala Ser Ser Thr Tyr Arg Asn Cys Val
            20                  25                  30

Lys Asn Ala Ser Leu Ile Ser Ala Leu Ser Thr Gly Arg Phe Ser His
        35                  40                  45

Ile Gln Thr Pro Val Val Ser Ser Thr Pro Arg Leu Thr Thr Ser Glu
    50                  55                  60

Arg Asn Leu Thr Cys Gly His Thr Ser Val Ile Leu Asn Arg Met Ala
65                  70                  75                  80

Pro Val Leu Pro Ser Val Leu Lys Leu Pro Val Arg Ser Leu Thr Tyr
                85                  90                  95

Phe Ser Ala Arg Lys Gly Lys Arg Lys Thr Val Lys Ala Val Ile Asp
            100                 105                 110

Arg Phe Leu Arg Leu His Cys Gly Leu Trp Val Arg Arg Lys Ala Gly
        115                 120                 125

Tyr Lys Lys Lys Leu Trp Lys Lys Thr Pro Ala Arg Lys Lys Arg Leu
    130                 135                 140

Arg Glu Phe Val Phe Cys Asn Lys Thr Gln Ser Lys Leu Leu Asp Lys
145                 150                 155                 160

Met Thr Thr Ser Phe Trp Lys Arg Arg Asn Trp Tyr Val Asp Asp Pro
                165                 170                 175

Tyr Gln Lys Tyr His Asp Arg Thr Asn Leu Lys Val
            180                 185
```

<210> SEQ ID NO 36
<211> LENGTH: 3618
<212> TYPE: DNA
<213> ORGANISM: Homo sapiens
<220> FEATURE:
<221> NAME/KEY: CDS
<222> LOCATION: (59)..(1414)

<400> SEQUENCE: 36

```
aattgtaaag agagagaagt ggataaatca gtgctgcttt ctttaggacg aaagaagt       58

atg gag cag tgg gat cac ttt cac aat caa cag gag gac act gat agc      106
Met Glu Gln Trp Asp His Phe His Asn Gln Gln Glu Asp Thr Asp Ser
1               5                   10                  15

tgc tcc gaa tct gtg aaa ttt gat gct cgc tca atg aca gct ttg ctt      154
Cys Ser Glu Ser Val Lys Phe Asp Ala Arg Ser Met Thr Ala Leu Leu
            20                  25                  30

cct ccg aat cct aaa aac agc cct tcc ctt caa gag aaa ctg aag tcc      202
Pro Pro Asn Pro Lys Asn Ser Pro Ser Leu Gln Glu Lys Leu Lys Ser
        35                  40                  45

ttc aaa gct gca ctg att gcc ctt tac ctc ctc gtg ttt gca gtt ctc      250
Phe Lys Ala Ala Leu Ile Ala Leu Tyr Leu Leu Val Phe Ala Val Leu
    50                  55                  60

atc cct ctc att gga ata gtg gca gct caa ctc ctg aag tgg gaa acg      298
Ile Pro Leu Ile Gly Ile Val Ala Ala Gln Leu Leu Lys Trp Glu Thr
65                  70                  75                  80

aag aat tgc tca gtt agt tca act aat gca aat gat ata act caa agt      346
Lys Asn Cys Ser Val Ser Ser Thr Asn Ala Asn Asp Ile Thr Gln Ser
                85                  90                  95

ctc acg gga aaa gga aat gac agc gaa gag gaa atg aga ttt caa gaa      394
Leu Thr Gly Lys Gly Asn Asp Ser Glu Glu Glu Met Arg Phe Gln Glu
```

```
            100                 105                 110

gtc ttt atg gaa cac atg agc aac atg gag aag aga atc cag cat att      442
Val Phe Met Glu His Met Ser Asn Met Glu Lys Arg Ile Gln His Ile
        115                 120                 125

tta gac atg gaa gcc aac ctc atg gac aca gag cat ttc caa aat ttc      490
Leu Asp Met Glu Ala Asn Leu Met Asp Thr Glu His Phe Gln Asn Phe
    130                 135                 140

agc atg aca act gat caa aga ttt aat gac att ctt ctg cag cta agt      538
Ser Met Thr Thr Asp Gln Arg Phe Asn Asp Ile Leu Leu Gln Leu Ser
145                 150                 155                 160

acc ttg ttt tcc tca gtc cag gga cat ggg aat gca ata gat gaa atc      586
Thr Leu Phe Ser Ser Val Gln Gly His Gly Asn Ala Ile Asp Glu Ile
                165                 170                 175

tcc aag tcc tta ata agt ttg aat acc aca ttg ctt gat ttg cag ctc      634
Ser Lys Ser Leu Ile Ser Leu Asn Thr Thr Leu Leu Asp Leu Gln Leu
            180                 185                 190

aac ata gaa aat ctg aat ggc aaa atc caa gag aat acc ttc aaa caa      682
Asn Ile Glu Asn Leu Asn Gly Lys Ile Gln Glu Asn Thr Phe Lys Gln
        195                 200                 205

caa gag gaa atc agt aaa tta gag gag cgt gtt tac aat gta tca gca      730
Gln Glu Glu Ile Ser Lys Leu Glu Glu Arg Val Tyr Asn Val Ser Ala
    210                 215                 220

gaa att atg gct atg aaa gaa gaa caa gtg cat ttg gaa cag gaa ata      778
Glu Ile Met Ala Met Lys Glu Glu Gln Val His Leu Glu Gln Glu Ile
225                 230                 235                 240

aaa gga gaa gtg aaa gta ctg aat aac atc act aat gat ctc aga ctg      826
Lys Gly Glu Val Lys Val Leu Asn Asn Ile Thr Asn Asp Leu Arg Leu
                245                 250                 255

aaa gat tgg gaa cat tct cag acc ttg aga aat atc act tta att caa      874
Lys Asp Trp Glu His Ser Gln Thr Leu Arg Asn Ile Thr Leu Ile Gln
            260                 265                 270

ggt cct cct gga ccc ccg ggt gaa aaa gga gat cga ggt ccc act gga      922
Gly Pro Pro Gly Pro Pro Gly Glu Lys Gly Asp Arg Gly Pro Thr Gly
        275                 280                 285

gaa agt ggt cca cga gga ttt cca ggt cca ata ggt cct ccg ggt ctt      970
Glu Ser Gly Pro Arg Gly Phe Pro Gly Pro Ile Gly Pro Pro Gly Leu
    290                 295                 300

aaa ggt gat cgg gga gca att ggc ttt cct gga agt cga gga ctc cca     1018
Lys Gly Asp Arg Gly Ala Ile Gly Phe Pro Gly Ser Arg Gly Leu Pro
305                 310                 315                 320

gga tat gcc gga agg cca gga aat tct gga cca aaa ggc cag aaa ggg     1066
Gly Tyr Ala Gly Arg Pro Gly Asn Ser Gly Pro Lys Gly Gln Lys Gly
                325                 330                 335

gaa aag ggg agt gga aac aca tta act cca ttt acg aaa gtt cga ctg     1114
Glu Lys Gly Ser Gly Asn Thr Leu Thr Pro Phe Thr Lys Val Arg Leu
            340                 345                 350

gtc ggt ggg agc ggc cct cac gag ggg agg gtg gag ata ctc cac agc     1162
Val Gly Gly Ser Gly Pro His Glu Gly Arg Val Glu Ile Leu His Ser
        355                 360                 365

ggc cag tgg ggt aca att tgt gac gat cgc tgg gaa gtg cgc gtt gga     1210
Gly Gln Trp Gly Thr Ile Cys Asp Asp Arg Trp Glu Val Arg Val Gly
    370                 375                 380

cag gtc gtc tgt agg agc ttg gga tac cca ggt gtt caa gcc gtg cac     1258
Gln Val Val Cys Arg Ser Leu Gly Tyr Pro Gly Val Gln Ala Val His
385                 390                 395                 400

aag gca gct cac ttt gga caa ggt act ggt cca ata tgg ctg aat gaa     1306
Lys Ala Ala His Phe Gly Gln Gly Thr Gly Pro Ile Trp Leu Asn Glu
                405                 410                 415

gtg ttt tgt ttt ggg aga gaa tca tct att gaa gaa tgt aaa att cgg     1354
```

```
Val Phe Cys Phe Gly Arg Glu Ser Ser Ile Glu Glu Cys Lys Ile Arg
            420                 425                 430

caa tgg ggg aca aga gcc tgt tca cat tct gaa gat gct gga gtc act     1402
Gln Trp Gly Thr Arg Ala Cys Ser His Ser Glu Asp Ala Gly Val Thr
        435                 440                 445

tgc act tta taa tgcatcatat tttcattcac aactatgaaa tcgctgctca         1454
Cys Thr Leu
    450

aaaatgattt tattaccttg ttcctgtaaa atccatttaa tcaatattta agagattaag   1514

aatattgccc aaataatatt ttagattaca ggattaatat attgaacacc ttcatgctta   1574

ctattttatg tctatattta aatcatttta acttctatag gtttttaaat ggaattttct   1634

aatataatga cttatatgct gaattgaaca ttttgaagtt tatagcttcc agattacaaa   1694

ggccaagggt aatagaaatg cataccagta attggctcca attcataata tgttcaccag   1754

gagattacaa ttttttgctc ttcttgtctt tgtaatctat ttagttgatt ttaattactt   1814

tctgaataac ggaagggatc agaagatatc ttttgtgcct agattgcaaa atctccaatc   1874

cacacatatt gttttaaaat aagaatgtta tccaactatt aagatatctc aatgtgcaat   1934

aacttgtgta ttagatatca atgttaatga tatgtcttgg ccactatgga ccagggagct   1994

tatttttctt gtcatgtact gacaactgtt taattgaatc atgaagtaaa ttgaaagcag   2054

gacatatgag aaaactgacc atcagtatat ttgtccagat aattggtgga tcaaaaatgc   2114

cacttaacag gaagtttagt ttgttatgca ctttaaatgg aataattagc ttgttacaat   2174

tctaggacat ggtgtttaaa atttaaatct gattaatcca ttttaacaaa caatgcaaac   2234

atcttcagtg cagaaggaag agtggtttca actgtttgga gtcttttatg aagtcagtca   2294

acatttacaa ccaaagggcg gggggggggg tggggggtgc gtctttagtc ctaaagggac   2354

aataactctg agcatgcccc aaaaaagtag tttagcaacc ttttgttggt agtcaaccca   2414

tccccagggc catagtgtag agtgtgaaaa gctaccctga aacccagtaa ttctaccctg   2474

aaagtgactg cctgcagaaa gaccagcagt tgatattaaa gcgcaaatga attcaacctc   2534

agccctgaaa ataacagaat tctgaagttt cctatgacta attcacaaaa aaagtaattg   2594

taaactagta ctattatgga attactctac tgttctttct ttaatagtgg caaatgaaag   2654

cataagctta agcatttttt catattctga agtctcacca cacataataa ccaagtggta   2714

gactcacagc cgtccaactt aaaaaggcaa aaccttacct tggaattgga attactgtaa   2774

acagcctact gaaaatgcat ttttatcatg taacattctt ctacttgttt aacattgctg   2834

attttctctg gcagcataat tttgtggtta agagaatgaa ttctgaatgt acactttctg   2894

tctcaaaccc tggctgtaat ttcagctagt taataattct ttgtgttcag ttccactatc   2954

taggtatttt cttcaaaagg taaatacaat ggtttctgaa agaatcattt gcattatcag   3014

cctgtttggg atgtctgaga tcagtgcctc tgggttgtta atactgtatt gctgtatggt   3074

atatgtatgc tgatttacta cttatgcgta agtggtatgc atgggatgtc tgaaatcagt   3134

gcctatgggt tgtcaatagt attaactatt agtgttaact gttagtatta actattagta   3194

ttattaacac taataatagt actattacta ttactatttt tattttaaaa taaaatttac   3254

ctttaaaata ataatagtac tattgctagt actagtacta ttgctattac tagtactatt   3314

actagtacta gtactatgac actgttaata gtactattaa caacccatag gcacttggga   3374

tgtctgagat cagtgcctat gggttgttaa tactatattg ctgtatggta tatgcatgct   3434

gatttaccac ttatgcatag atatatcttt aataagtaat ctaaaaatcc tttttgtatt   3494
```

```
tgagagaatc tactaagttc agtccagtca agaaaagaac ctaatagcac caatacaaat   3554

tgaggactta atttactttg gaatgttgaa ttgcatttgt tccattaaaa aaaacagaaa   3614

tttg                                                                3618


<210> SEQ ID NO 37
<211> LENGTH: 451
<212> TYPE: PRT
<213> ORGANISM: Homo sapiens

<400> SEQUENCE: 37

Met Glu Gln Trp Asp His Phe His Asn Gln Gln Glu Asp Thr Asp Ser
1               5                   10                  15

Cys Ser Glu Ser Val Lys Phe Asp Ala Arg Ser Met Thr Ala Leu Leu
            20                  25                  30

Pro Pro Asn Pro Lys Asn Ser Pro Ser Leu Gln Glu Lys Leu Lys Ser
        35                  40                  45

Phe Lys Ala Ala Leu Ile Ala Leu Tyr Leu Leu Val Phe Ala Val Leu
    50                  55                  60

Ile Pro Leu Ile Gly Ile Val Ala Ala Gln Leu Leu Lys Trp Glu Thr
65                  70                  75                  80

Lys Asn Cys Ser Val Ser Ser Thr Asn Ala Asn Asp Ile Thr Gln Ser
                85                  90                  95

Leu Thr Gly Lys Gly Asn Asp Ser Glu Glu Glu Met Arg Phe Gln Glu
            100                 105                 110

Val Phe Met Glu His Met Ser Asn Met Glu Lys Arg Ile Gln His Ile
        115                 120                 125

Leu Asp Met Glu Ala Asn Leu Met Asp Thr Glu His Phe Gln Asn Phe
    130                 135                 140

Ser Met Thr Thr Asp Gln Arg Phe Asn Asp Ile Leu Leu Gln Leu Ser
145                 150                 155                 160

Thr Leu Phe Ser Ser Val Gln Gly His Gly Asn Ala Ile Asp Glu Ile
                165                 170                 175

Ser Lys Ser Leu Ile Ser Leu Asn Thr Thr Leu Leu Asp Leu Gln Leu
            180                 185                 190

Asn Ile Glu Asn Leu Asn Gly Lys Ile Gln Glu Asn Thr Phe Lys Gln
        195                 200                 205

Gln Glu Glu Ile Ser Lys Leu Glu Glu Arg Val Tyr Asn Val Ser Ala
    210                 215                 220

Glu Ile Met Ala Met Lys Glu Glu Gln Val His Leu Glu Gln Glu Ile
225                 230                 235                 240

Lys Gly Glu Val Lys Val Leu Asn Asn Ile Thr Asn Asp Leu Arg Leu
                245                 250                 255

Lys Asp Trp Glu His Ser Gln Thr Leu Arg Asn Ile Thr Leu Ile Gln
            260                 265                 270

Gly Pro Pro Gly Pro Pro Gly Glu Lys Gly Asp Arg Gly Pro Thr Gly
        275                 280                 285

Glu Ser Gly Pro Arg Gly Phe Pro Gly Pro Ile Gly Pro Pro Gly Leu
    290                 295                 300

Lys Gly Asp Arg Gly Ala Ile Gly Phe Pro Gly Ser Arg Gly Leu Pro
305                 310                 315                 320

Gly Tyr Ala Gly Arg Pro Gly Asn Ser Gly Pro Lys Gly Gln Lys Gly
                325                 330                 335

Glu Lys Gly Ser Gly Asn Thr Leu Thr Pro Phe Thr Lys Val Arg Leu
            340                 345                 350
```

```
Val Gly Gly Ser Gly Pro His Glu Gly Arg Val Glu Ile Leu His Ser
        355                 360                 365

Gly Gln Trp Gly Thr Ile Cys Asp Asp Arg Trp Glu Val Arg Val Gly
    370                 375                 380

Gln Val Val Cys Arg Ser Leu Gly Tyr Pro Gly Val Gln Ala Val His
385                 390                 395                 400

Lys Ala Ala His Phe Gly Gln Gly Thr Gly Pro Ile Trp Leu Asn Glu
                405                 410                 415

Val Phe Cys Phe Gly Arg Glu Ser Ser Ile Glu Glu Cys Lys Ile Arg
            420                 425                 430

Gln Trp Gly Thr Arg Ala Cys Ser His Ser Glu Asp Ala Gly Val Thr
        435                 440                 445

Cys Thr Leu
    450


<210> SEQ ID NO 38
<211> LENGTH: 3562
<212> TYPE: DNA
<213> ORGANISM: Homo sapiens
<220> FEATURE:
<221> NAME/KEY: CDS
<222> LOCATION: (58)..(1782)

<400> SEQUENCE: 38

actcgccggc actcgcccgg ctcgcccgct ttcgcaccca gttcacgcgc cacagct        57

atg tgt ccc cga gcc gcg cgg gcg ccc gcg acg cta ctc ctc gcc ctg      105
Met Cys Pro Arg Ala Ala Arg Ala Pro Ala Thr Leu Leu Leu Ala Leu
1               5                   10                  15

ggc gcg gtg ctg tgg cct gcg gct ggc gcc tgg gag ctt acg att ttg      153
Gly Ala Val Leu Trp Pro Ala Ala Gly Ala Trp Glu Leu Thr Ile Leu
            20                  25                  30

cac acc aac gac gtg cac agc cgg ctg gag cag acc agc gag gac tcc      201
His Thr Asn Asp Val His Ser Arg Leu Glu Gln Thr Ser Glu Asp Ser
        35                  40                  45

agc aag tgc gtc aac gcc agc cgc tgc atg ggt ggc gtg gct cgg ctc      249
Ser Lys Cys Val Asn Ala Ser Arg Cys Met Gly Gly Val Ala Arg Leu
    50                  55                  60

ttc acc aag gtt cag cag atc cgc cgc gcc gaa ccc aac gtg ctg ctg      297
Phe Thr Lys Val Gln Gln Ile Arg Arg Ala Glu Pro Asn Val Leu Leu
65                  70                  75                  80

ctg gac gcc ggc gac cag tac cag ggc act atc tgg ttc acc gtg tac      345
Leu Asp Ala Gly Asp Gln Tyr Gln Gly Thr Ile Trp Phe Thr Val Tyr
                85                  90                  95

aag ggc gcc gag gtg gcg cac ttc atg aac gcc ctg cgc tac gat gcc      393
Lys Gly Ala Glu Val Ala His Phe Met Asn Ala Leu Arg Tyr Asp Ala
            100                 105                 110

atg gca ctg gga aat cat gaa ttt gat aat ggt gtg gaa gga ctg atc      441
Met Ala Leu Gly Asn His Glu Phe Asp Asn Gly Val Glu Gly Leu Ile
        115                 120                 125

gag cca ctc ctc aaa gag gcc aaa ttt cca att ctg agt gca aac att      489
Glu Pro Leu Leu Lys Glu Ala Lys Phe Pro Ile Leu Ser Ala Asn Ile
    130                 135                 140

aaa gca aag ggg cca cta gca tct caa ata tca gga ctt tat ttg cca      537
Lys Ala Lys Gly Pro Leu Ala Ser Gln Ile Ser Gly Leu Tyr Leu Pro
145                 150                 155                 160

tat aaa gtt ctt cct gtt ggt gat gaa gtt gtg gga atc gtt gga tac      585
Tyr Lys Val Leu Pro Val Gly Asp Glu Val Val Gly Ile Val Gly Tyr
                165                 170                 175
```

```
act tcc aaa gaa acc cct ttt ctc tca aat cca ggg aca aat tta gtg      633
Thr Ser Lys Glu Thr Pro Phe Leu Ser Asn Pro Gly Thr Asn Leu Val
            180                 185                 190

ttt gaa gat gaa atc act gca tta caa cct gaa gta gat aag tta aaa      681
Phe Glu Asp Glu Ile Thr Ala Leu Gln Pro Glu Val Asp Lys Leu Lys
        195                 200                 205

act cta aat gtg aac aaa att att gca ctg gga cat tcg ggt ttt gaa      729
Thr Leu Asn Val Asn Lys Ile Ile Ala Leu Gly His Ser Gly Phe Glu
    210                 215                 220

atg gat aaa ctc atc gct cag aaa gtg agg ggt gtg gac gtc gtg gtg      777
Met Asp Lys Leu Ile Ala Gln Lys Val Arg Gly Val Asp Val Val Val
225                 230                 235                 240

gga gga cac tcc aac aca ttt ctt tac aca ggc aat cca cct tcc aaa      825
Gly Gly His Ser Asn Thr Phe Leu Tyr Thr Gly Asn Pro Pro Ser Lys
                245                 250                 255

gag gtg cct gct ggg aag tac cca ttc ata gtc act tct gat gat ggg      873
Glu Val Pro Ala Gly Lys Tyr Pro Phe Ile Val Thr Ser Asp Asp Gly
            260                 265                 270

cgg aag gtt cct gta gtc cag gcc tat gct ttt ggc aaa tac cta ggc      921
Arg Lys Val Pro Val Val Gln Ala Tyr Ala Phe Gly Lys Tyr Leu Gly
        275                 280                 285

tat ctg aag atc gag ttt gat gaa aga gga aac gtc atc tct tcc cat      969
Tyr Leu Lys Ile Glu Phe Asp Glu Arg Gly Asn Val Ile Ser Ser His
    290                 295                 300

gga aat ccc att ctt cta aac agc agc att cct gaa gat cca agc ata     1017
Gly Asn Pro Ile Leu Leu Asn Ser Ser Ile Pro Glu Asp Pro Ser Ile
305                 310                 315                 320

aaa gca gac att aac aaa tgg agg ata aaa ttg gat aat tat tct acc     1065
Lys Ala Asp Ile Asn Lys Trp Arg Ile Lys Leu Asp Asn Tyr Ser Thr
                325                 330                 335

cag gaa tta ggg aaa aca att gtc tat ctg gat ggc tcc tct caa tca     1113
Gln Glu Leu Gly Lys Thr Ile Val Tyr Leu Asp Gly Ser Ser Gln Ser
            340                 345                 350

tgc cgc ttt aga gaa tgc aac atg ggc aac ctg att tgt gat gca atg     1161
Cys Arg Phe Arg Glu Cys Asn Met Gly Asn Leu Ile Cys Asp Ala Met
        355                 360                 365

att aac aac aac ctg aga cac acg gat gaa atg ttc tgg aac cac gta     1209
Ile Asn Asn Asn Leu Arg His Thr Asp Glu Met Phe Trp Asn His Val
    370                 375                 380

tcc atg tgc att tta aat gga ggt ggt atc cgg tcg ccc att gat gaa     1257
Ser Met Cys Ile Leu Asn Gly Gly Gly Ile Arg Ser Pro Ile Asp Glu
385                 390                 395                 400

cgc aac aat ggc aca att acc tgg gag aac ctg gct gct gta ttg ccc     1305
Arg Asn Asn Gly Thr Ile Thr Trp Glu Asn Leu Ala Ala Val Leu Pro
                405                 410                 415

ttt gga ggc aca ttt gac cta gtc cag tta aaa ggt tcc acc ctg aag     1353
Phe Gly Gly Thr Phe Asp Leu Val Gln Leu Lys Gly Ser Thr Leu Lys
            420                 425                 430

aag gcc ttt gag cat agc gtg cac cgc tac ggc cag tcc act gga gag     1401
Lys Ala Phe Glu His Ser Val His Arg Tyr Gly Gln Ser Thr Gly Glu
        435                 440                 445

ttc ctg cag gtg ggc gga atc cat gtg gtg tat gat ctt tcc cga aaa     1449
Phe Leu Gln Val Gly Gly Ile His Val Val Tyr Asp Leu Ser Arg Lys
    450                 455                 460

cct gga gac aga gta gtc aaa tta gat gtt ctt tgc acc aag tgt cga     1497
Pro Gly Asp Arg Val Val Lys Leu Asp Val Leu Cys Thr Lys Cys Arg
465                 470                 475                 480

gtg ccc agt tat gac cct ctc aaa atg gac gag gta tat aag gtg atc     1545
Val Pro Ser Tyr Asp Pro Leu Lys Met Asp Glu Val Tyr Lys Val Ile
                485                 490                 495
```

```
ctc cca aac ttc ctg gcc aat ggt gga gat ggg ttc cag atg ata aaa     1593
Leu Pro Asn Phe Leu Ala Asn Gly Gly Asp Gly Phe Gln Met Ile Lys
            500                 505                 510

gat gaa tta tta aga cat gac tct ggt gac caa gat atc aac gtg gtt     1641
Asp Glu Leu Leu Arg His Asp Ser Gly Asp Gln Asp Ile Asn Val Val
        515                 520                 525

tct aca tat atc tcc aaa atg aaa gta att tat cca gca gtt gaa ggt     1689
Ser Thr Tyr Ile Ser Lys Met Lys Val Ile Tyr Pro Ala Val Glu Gly
    530                 535                 540

cgg atc aag ttt tcc aca gga agt cac tgc cat gga agc ttt tct tta     1737
Arg Ile Lys Phe Ser Thr Gly Ser His Cys His Gly Ser Phe Ser Leu
545                 550                 555                 560

ata ttt ctt tca ctt tgg gca gtg atc ttt gtt tta tac caa tag         1782
Ile Phe Leu Ser Leu Trp Ala Val Ile Phe Val Leu Tyr Gln
                565                 570

ccaaaaattc tccttgcctt taatgtgtga aactgcattt tttcaagtga gattcaaatc   1842

tgccttttag gacctggctt tgtgacagca aaaaccatct ttacaggctc ctagaagctg   1902

aaggttagag cattataaaa tgaagagaca gacatgatta ctcagggtca gcaacctagt   1962

gagttagaaa aaaaattaac atagggccct ataaggagaa agccaactat gttaagttta   2022

cgtgtccaaa ttttaatgaa attttactaa caattttaaa ccatattttt cttcttcata   2082

tccatttcta atccatcaaa cagcttatgt ttacataaaa ttttatcatt cacaaggaag   2142

ttttaagcac actgtctcat ttgatatcca caacttattt ttggtaggaa agagagatgt   2202

ttttcccacc tgtcagatga aaaaactgaa gctcaaaaag ggttgacttg accatacagc   2262

taatgctgac agatccaaga cctagaccta ggtcttttga actcaagtcc agcattctca   2322

actatatcaa gttactgttc agaatactta atatctcctc tcttcataat tatcaatagc   2382

cccaagctca tggatgacaa atctctgctt tatttcttgt ctctattttt tcactttata   2442

gctcctgtta taatagcaag tttaatggta taaacacagg ataccatcct ctcttgcaac   2502

acccatgtgc ctttgatgag tcaggtagca agctgtagta gataatgaga aaggccagag   2562

gctgcaaaag acagtcaaag gacacgagag aaaggaaggg gaagaacagg actccaggac   2622

tgttttatat tatagaaaag caagagctaa agagcattta cacatgttaa acagatactt   2682

gttaagcata gtgcctgaca cacggcatta gctgttattt tatgagattc catcagctct   2742

gcctctgtcc tctttcttct aacatgaagg tatcatgaga agagaacctt ctaacataag   2802

ctgtaattct aaacctgcac ttgtccctct ccagcaagag gctagcactg aattcattct   2862

actcatacta cacacccagt tatggaatgt ccagagttct cgaagaaaat aaatgacttt   2922

aggaagaggt atacattttt taagtcgctc tgcctccaaa tctgaacagt cactgtaaat   2982

cattcttaag cccagatatg agaacttctg ctggaaagtg ggaccctctg agtgggtggt   3042

cagaaaatac ccatgctgat gaaatgacct atgcccaaag aacaaatact taacgtggga   3102

gtggaaccac atgagcctgc tcagctctgc ataagtaatt caagaaatgg gaggcttcac   3162

cttaaaaaca gtgtgcaaat ggcagctaga ggttttgata ggaagtatgt ttgtttctta   3222

gtgtttacaa atattaagta ctcttgatac aaaatatact tttaaacttc ataacctttt   3282

tataaaagtt gttgcagcaa aataatagcc tcggttctat gcatatatgg attagctata   3342

aaaaatgtca ataagattgt acaaggaaaa ttagagaaag tcacatttag ggtttatttt   3402

ttacacttgg ccagtaaaat agggtaaatc ctattagaat tttttaaaga acttttttta   3462

agtttcctaa atctgtgtgt gtattgtgaa gtggtataag aaatgacttt gaaccacttt   3522
```

gcaattgtag attcccaaca ataaaattga agataagctc 3562

<210> SEQ ID NO 39
<211> LENGTH: 574
<212> TYPE: PRT
<213> ORGANISM: Homo sapiens

<400> SEQUENCE: 39

```
Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365
```

```
Ile Asn Asn Asn Leu Arg His Thr Asp Glu Met Phe Trp Asn His Val
    370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
        435                 440                 445

Phe Leu Gln Val Gly Gly Ile His Val Val Tyr Asp Leu Ser Arg Lys
    450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
        515                 520                 525

Ser Thr Tyr Ile Ser Lys Met Lys Val Ile Tyr Pro Ala Val Glu Gly
    530                 535                 540

Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
                565                 570


<210> SEQ ID NO 40
<211> LENGTH: 8991
<212> TYPE: DNA
<213> ORGANISM: Homo sapiens
<220> FEATURE:
<221> NAME/KEY: CDS
<222> LOCATION: (241)..(1263)

<400> SEQUENCE: 40

actttccgcg cggcggaaga gcgcgcgcca gcttcggcac acctgggagc cggatcccag      60

ccctacgcct cgtcccctac aagctcctcc aagccccgcc ggctgctgtg ggagcggcgg     120

ccgtccctct cctggaggtc gtctcctggc atcctcgggg ccgcaggaag gaagaggagg     180

cagcggccgg agccctggtg ggcggcctga ggtgagagcc cgaccggccc ctttgggaat     240

atg gcg acc ggt ggc tac cgg acc agc agc ggc ctc ggc ggc agc acc      288
Met Ala Thr Gly Gly Tyr Arg Thr Ser Ser Gly Leu Gly Gly Ser Thr
1               5                   10                  15

aca gac ttc ctg gag gag tgg aag gcg aaa cgc gag aag atg cgc gcc      336
Thr Asp Phe Leu Glu Glu Trp Lys Ala Lys Arg Glu Lys Met Arg Ala
            20                  25                  30

aag cag aac ccc ccg ggc ccg gcc ccc ccg gga ggg ggc agc agc gac      384
Lys Gln Asn Pro Pro Gly Pro Ala Pro Pro Gly Gly Gly Ser Ser Asp
        35                  40                  45

gcc gct ggg aag ccc ccc gcg ggg gct ctg ggc acc ccg gcg gcc gcc      432
Ala Ala Gly Lys Pro Pro Ala Gly Ala Leu Gly Thr Pro Ala Ala Ala
    50                  55                  60

gct gcc aac gag ctc aac aac aac ctc ccg ggc ggc gcg ccg gcc gca      480
Ala Ala Asn Glu Leu Asn Asn Asn Leu Pro Gly Gly Ala Pro Ala Ala
65                  70                  75                  80

cct gcc gtc ccc ggt ccc ggg ggc gtg aac tgc gcg gtc ggc tcc gcc      528
```

```
Pro Ala Val Pro Gly Pro Gly Gly Val Asn Cys Ala Val Gly Ser Ala
                85                  90                  95

atg ctg acg cgg gcg gcc ccc ggc ccg cgg cgg tcg gag gac gag ccc      576
Met Leu Thr Arg Ala Ala Pro Gly Pro Arg Arg Ser Glu Asp Glu Pro
            100                 105                 110

cca gcc gcc tct gcc tcg gct gca ccg ccg ccc cag cgt gac gag gag      624
Pro Ala Ala Ser Ala Ser Ala Ala Pro Pro Pro Gln Arg Asp Glu Glu
        115                 120                 125

gag ccg gac ggc gtc cca gag aag ggc aag agc tcg ggc ccc agt gcc      672
Glu Pro Asp Gly Val Pro Glu Lys Gly Lys Ser Ser Gly Pro Ser Ala
    130                 135                 140

agg aaa ggc aag ggg cag atc gag aag agg aag ctg cgg gag aag cgg      720
Arg Lys Gly Lys Gly Gln Ile Glu Lys Arg Lys Leu Arg Glu Lys Arg
145                 150                 155                 160

cgc tcc acc ggc gtg gtc aac atc cct gcc gca gag tgc tta gat gag      768
Arg Ser Thr Gly Val Val Asn Ile Pro Ala Ala Glu Cys Leu Asp Glu
                165                 170                 175

tac gaa gat gat gaa gca ggg cag aaa gag cgg aaa cga gaa gat gca      816
Tyr Glu Asp Asp Glu Ala Gly Gln Lys Glu Arg Lys Arg Glu Asp Ala
            180                 185                 190

att aca caa cag aac act att cag aat gaa gct gta aac tta cta gat      864
Ile Thr Gln Gln Asn Thr Ile Gln Asn Glu Ala Val Asn Leu Leu Asp
        195                 200                 205

cca ggc agt tcc tat ctg cta cag gag cca cct aga aca gtt tca ggc      912
Pro Gly Ser Ser Tyr Leu Leu Gln Glu Pro Pro Arg Thr Val Ser Gly
    210                 215                 220

aga tat aaa agc aca acc agt gtc tct gaa gaa gat gtc tca agt aga      960
Arg Tyr Lys Ser Thr Thr Ser Val Ser Glu Glu Asp Val Ser Ser Arg
225                 230                 235                 240

tat tct cga aca gat aga agt ggg ttc cct aga tat aac agg gat gca     1008
Tyr Ser Arg Thr Asp Arg Ser Gly Phe Pro Arg Tyr Asn Arg Asp Ala
                245                 250                 255

aat gtt tca ggt act ctg gtt tca agt agc aca ctg gaa aag aaa att     1056
Asn Val Ser Gly Thr Leu Val Ser Ser Ser Thr Leu Glu Lys Lys Ile
            260                 265                 270

gaa gat ctt gaa aag gaa gta gta aga gaa aga caa gaa aac cta aga     1104
Glu Asp Leu Glu Lys Glu Val Val Arg Glu Arg Gln Glu Asn Leu Arg
        275                 280                 285

ctt gtg aga ctg atg caa gat aaa gag gaa atg att gga aaa ctc aaa     1152
Leu Val Arg Leu Met Gln Asp Lys Glu Glu Met Ile Gly Lys Leu Lys
    290                 295                 300

gaa gaa att gat tta tta aat aga gac cta gat gac ata gaa gat gaa     1200
Glu Glu Ile Asp Leu Leu Asn Arg Asp Leu Asp Asp Ile Glu Asp Glu
305                 310                 315                 320

aat gaa cag cta aag cag gaa aat aaa act ctt ttg aaa gtt gtg ggt     1248
Asn Glu Gln Leu Lys Gln Glu Asn Lys Thr Leu Leu Lys Val Val Gly
                325                 330                 335

cag ctg acc agg tag aggattcaag actcaatgtg gaaaaaatat tttaaactac     1303
Gln Leu Thr Arg
            340

tgattgaatg ttaatggtca atgctagcac aatattccta tgctgcaata cattaaaata   1363

actaagcaag tatatttatt tctagcaaac agatgtttgt tttcaaaata cttctttttc   1423

attattggtt ttaaaaaagc attatccttt tatctcacaa ataagtaata tctttcagtt   1483

attaaatgat agataatgcc tttttggttt tgtgtggtat tcaactaata catggtttaa   1543

agtcacagcc gtttgaatat attttatctt ggtagtacat tttctccctt aggaatatac   1603

atagtctttg tttacatgag ttcaaatact tttgggatgt taccttcaca tgtcctatta   1663
```

ctgatgtgtg caacctttta tgtgttgatg actcactcat aaaggttttt gtctactgtc 1723
atttgttctt tccacttatt ctaagcattt agagtaatag agtcatactt ttttataaca 1783
gcaacctttt aaaaggaaag ctcttataaa gtcactgtca tgttttagtt gactaaatat 1843
aaatttaaga gaatacttga attgtgctat agtaaataaa aatttactat tttgtgtttg 1903
aatattgaaa aattgaatca ctttaactcc tgaaaaacat acaattgtaa tttcaatgta 1963
aaatttctta tgtaggtact accttttttt atcgttccaa ggtttgctag tgaacacagg 2023
atattttaaa agtttttat tcttcgggcc tggaaagtgt acaaagtcag tgtaggagaa 2083
aaaaatccat attttatat tagcatgcac actaaaaacc aaaatattat tcatacttaa 2143
aacattcata caaaacaata tgtaagcaga aatagtacta aaatactttg cctaatttct 2203
aagttgaaga ataacactgg gacacagttt tttcatatga gagaatattc cgctatttca 2263
aatttaaggg attttcttcc taacattgaa attttaaaaa cagagttact tctaaataat 2323
tatacagatt ttttcttcta ttaaatatta ttatttagaa ttgtttttgt attacatatt 2383
catgttaaga accccgtctt cccttaaaat acattaaaat tatgacattt ttgctttgtg 2443
attgaatttc aaatagcagt atggtatcct tttatctagt taatatatga aagtggcttg 2503
aatatagtca aatccatttt aggtactcta ctgacttttt ccttcacttg ccaagccctt 2563
ttattgttca ctgttagaaa aatagagaag gtgagacagc tgggggaaaa tgtggagtaa 2623
atgataatca aatgttgaat tctaaaagtc tctacattta cctaggttgg ctttctcccc 2683
cagttcagaa gtttccagct tggccaatca tcagaatcac ttgaggaact tagaaagaac 2743
tccctggctg tagctcctat gtaggtttag gttgagactc tggattccac aatttttaaa 2803
ggttaccatc tgaggtttct gatcatagtc tacttttgaa gcagctgctg ctgtttcttt 2863
attccattga acaccctgga attgacataa ttttatctat cagcatttct ccccttttag 2923
tttatttaat aattaacccg gtctccaggg cagttttcat atgaccatgt gtatattcac 2983
tgctcacgaa aaagtttaat gttagattac caaatttaat atagttacag aattactgca 3043
taagggcttc ccttcttgga gactcttacc cagcatggga acagtgatct gcccacatga 3103
cagggtggta tgccaggcat agttaactgc ttttggttgt gaggtactca tcttccttta 3163
gttaccctta gttatgtggc acacatgtcc ttattgccta gttcgtcatc cacactttgg 3223
atcttgtgaa aatgctgtta gtatccaacc ttaaaatata ttagtatatg ggtttttatt 3283
aaaagaatta ctttgaattt tctatttaat tcatatgtaa ataaaggaac atttcatttc 3343
acttaaaaaa attatatcag ttattaggct gggtgcagtg gctcatgcct gtaatcccag 3403
cactttggga ggccaaggcg ggtggattac cagagttcgg gagtttgaga ccagcttgac 3463
caacatggag aaaccccgtc tctactaaaa atacaaaatt agccaggtgt ggtggcgcat 3523
gcctgtaatc ctggctactc aggaggctga ggcaggagaa tcgcttgaaa acccaggaga 3583
cagaggttgc ggtgagctga gattgcgcca ttgtactcca gcctgggcaa gaagagcgaa 3643
actctgtctc caaaaaaaaa aaaaaaaaaa ttattaatac ttttaaagac tgagctgttt 3703
aagaattttt tggggaacat ttctagcagt gattttttttg gcctttaatg atagcgtaaa 3763
gacaggagcc ttacaactta ggcaaagcat ttcacatgca gtccttcttc catctcaaaa 3823
tatgtactta ttttacatac agaattttac actaaccatt gaaaaataaa gtaggatctg 3883
ctacagtttc acctgaaaat ttataaaaag tgttgagatt ggtagaaggt agtttttaag 3943
tacatgtgca ctaccctaaa agacttgtct attgtcaata aagtgttagt atttgtgaaa 4003
ttattattcc tgttcagaaa tactatttct taaatctcct gggaatttgt ggcataataa 4063 agcacattca aagttctaat gtatttatga gctcattttc aaaatagtaa gtttgtcatc 4123
tttaaaatga acatgacttg cctccttgat ttctgaaatg aattaattga agattgctat 4183
agtaatcttt atttcatctt tctagagttg ttgacaattt tattatacaa cagttaccat 4243
tagagaagga gggaagggct tttgggtgtg tatttatagg tactaaggga tttactaaat 4303
atagtagatt agcactgtca cacttgttca agtagtttca aacatagaaa attaagtatc 4363
aggtatgtgg agcaatgtag ttttttttt tcttcagttt aaaaaatttt taattgtggt 4423
agaagcaatg tattcttaag gtgaaaaacc tacctcggtt acatgtggtt tgtgtttttt 4483
ggattaatct ggattttata attagaaata aaaatgtaag attttgaatc cacttaattt 4543
cttgaaaata gtacaagtca gtgtaataga gaagcattca tatattcaac actgtaagac 4603
aaaacagcag agaccttgga tttgataatt gatctgatat cctggacagt attcatatgt 4663
acagtgatag gtatctttct ttggagtttt ttttttgtgc atatgtgtat agttttatgg 4723
gttctgagtt ggtgaccagt aagttgcatg tagtgctggc acttacttaa taactattca 4783
tgatattgtt aataacttgt tataggattg tattcccaat tacagtctct aagattgtaa 4843
ttgatattat ctgagaggta gtgtgacaac tttcttttgt tgttacatta agccgaaaac 4903
ataatactaa tagacaacta acagtttgct tatcaggcac atcaactaag gcacctcccc 4963
ccatgctaag tttctcctgg atatatggaa gttgattgtt tcccagttta aaaacttgaa 5023
ctaatatctc ctaagaaaat ctgagtccat attgttttta ttttacttag ctagaatctc 5083
atagcatgtt aaagtcatat ccttatcccc actaaaaata actatgtcta tgtgagagga 5143
atatagtatg tgggagctgt attaaatact attacaggtg ttacagaatc tttaaataaa 5203
tggacatgga ccaactttcc atctagtagt gtacgatcta tatagtgcat gtcagtagca 5263
caaaatgcag tcttagcatt agcctgtcta atctgaatag tttactcaaa agtacttctt 5323
tgtgttaagt attcagccac tgtttttaga tctagttaat aggttctatt taatttgcta 5383
caacatttac tgaatggtgg agtgaaaaaa ctgatgcata ctgggaaata tctaccattt 5443
tttaaagata atgttaatta ggaaaagaac acttttaagg aatttatagc agtgatgaaa 5503
tgaattcagt tatatcagat acaccaaact gttgatggta tttaaatgtg acttcaagtt 5563
agtatttctg tatatattat tgattactgg tttgttttta gatatgtaag tctgttctaa 5623
tctacagttc acatatcgac agttactctg gtaataatag aatgttagtg atgatcactt 5683
ggtggatgtt gattaagtgc ctgtgttttg tttcctcctc tggataccaa ataggtgtat 5743
gctacttttt tggtgaactt atttcttgga agatttggct atgctattca gggtttttat 5803
tcttatgttt ttcttctaaa tttaagtagc atcctgctgc taccatatta aagctaaaat 5863
ttaacttttg ctgaagaatc agctaattca ggtaatccaa atatttgtgg aaaaacatct 5923
ggataattta ttgaacacat tagtattgtg ttagacagct ttgatcattc ccatttcata 5983
ggtttttatt gtggaatagt caacttaata tagattcact ttcaatttgc atgtataaag 6043
taatactcaa taaaattttt ttcatttatt tttcaacagt ggttattttt tttcttcctg 6103
tactatcagt aaaatcctga ctatgagttt tacttttgaa gctaaaggat aatgctggta 6163
atctaattat gtacctctta cagaaaccat atgcagcact ttaaaaatct ttatttggta 6223
tattatttta ggtggacaat gatttaagac tcaaagccat catattaagg tctaaataca 6283
ttagtggtgg ggtttctcga ataaatgagg aagtgcacaa aagttcagcc tgactgaaaa 6343
ttttaattgt gttttaaaac tacatgaata atttcttgat tcaaaatcag aactcttata 6403 aactaaatct gatggtgtcc aaagaatttc aggtccttca aagtttgtaa aagataagta 6463 ggggcctagg aatataaaaa tttagacttt tttagtaaat ggtttacata accttttgtc 6523 ttaatttgtc attcttcata cacaggcaca agctaatcag tcttctctac ttctagaact 6583 ctaaatcttc tcagtaatgt catacaagtc taacaagagg aaaagcatcc ttaagtcagt 6643 ctatttagat aaactcttca agtccctata taaggacgta ttccactagc aagccagtaa 6703 atttttccaa ggtcacataa tcttacatga aatggaacct ttcatcttag acttcatcaa 6763 actcaatttt ttcccttcta gattcacttt gtgtttatgc atgcatgcac gcgtgcacac 6823 aattctatca gcagctgtaa actacccaca tattttctta atctcatttt ttcagttttt 6883 cttcatcttt aaaagaggtt acatttcatt cctggtcaac tcttaaaaag aattatgtaa 6943 tgttgggcct tcatattaaa gagagagact ggttataaga tcctttacag tccattcatt 7003 ttattctgat gtctaaccag atagacacta gcaagcaaaa cttccctctt aatcctggac 7063 caaatgcata attttactgt cactttcaaa aatctgttat gactgaatca aaatcctttt 7123 aaagaaagga aaaagctcct tttgtgtcaa atagttgaac aacatgaaaa cagtatgagc 7183 cggttaaaga tagattgaat ttttacttta cacatatgaa aaacagtaag ttttgactgc 7243 tgtgtatgtt attcatgtta atatgtgctc agttattcac tattgttaat ccacatataa 7303 tcagttgcta tccctggtta gacacactat ggaacttgaa atgcacaata tttacattgt 7363 tagaggcttc tatccaaata tctgcattcc tttaaaatgt gaactatttg ctgtgattaa 7423 ccaaaggtag attatgtcat cagtggacat tttagcttta tggaaacaaa ttattaagaa 7483 atgaatagaa aggtgtcttt ttctttgtgt agtgcaaaag cctaaagcta tcagtcaaag 7543 gcctaagaaa tccacatttg aaaaacgtaa atcatgattg gtaagaatac attcatctga 7603 tagtattgag aaaagttgaa aaactgttag ccttccataa cacattaaac attttatgta 7663 tggatggctg aaagtattga gaaaagctga aaaactgtta gccttccata acacattaaa 7723 cgttttgtgt atggatggct taggacaata aacaacatca ttaaagtaaa attatgtcag 7783 tctgttcata ttaacttatt taaatcaatg aaaattttga tgagatgact aaatggatgc 7843 tttggaaatg caggattata ggaggcctaa aagtgcatct tgtttcttgt aacccttttta 7903 aaaccaatat gcctggctag gtgcagtggc tcatgcctgt aataccaacg ggtaacaca 7963 gggttatgcc gtctatacaa aaaaataaat gagctgggca agatggcatg cacctgtagt 8023 cccagctgct tggtaggctg agggggaagg attgcttgag cctgggaggt cgagactgca 8083 gtgagccaag atcacaccac tgcactccag cctgggtgac agagcaagac tctacctcaa 8143 aaataaaaat aatcaatata gtttcaatga agcaaagcat ctcaggtaac aatttgagca 8203 taactttaac cataacttat gatagcataa taacattcat tagtaattca gtagccgtat 8263 gtgccaggct gtgttaggtg ctttatatat tgtttaattt ttaaaaactt gtggagtgta 8323 cagattggta aggtgacatt gtatcacaaa gctagtcttt gagtccaaag ttttgtggtt 8383 ttatgttatg atatactttt atcatggaat tgtcttatta aatgttttgc cagtggttct 8443 taaagtgtgt ttctgacacc agtagcattg acttcactta gaaacctgtt agaaatacaa 8503 attatttggc cccacccaac acttgagtca caaactttgc agatggggct caatctgttt 8563 taacaagcgc ttcatgtaat tttgatgcag gcctaagttt ttgagccact gcagtatgca 8623 tttctatttt taagcaaaga tcttggtctt tctttttgga cattgtagaa ataacatgaa 8683 cttgtttttt gtttgttttt gttttgtttt gttttaagct cctgatcttt gttggttatg 8743 ttgcaaaaga ttgtatcagg agaagcctca gcatggacat tggcatcctg acataacccc 8803

```
cattaattta gtattctttc tgaaactcaa atggattctc aagtccaaga gactatggaa   8863

taaaatcatt gtttgtctgt gttaagtttt atctctgtta ttgcctgaag acttttggta   8923

acaataatgc gctttcatca aacttttaag acttgattgg aaaaaataaa tgtatgtttc   8983

atcagtta                                                            8991


<210> SEQ ID NO 41
<211> LENGTH: 340
<212> TYPE: PRT
<213> ORGANISM: Homo sapiens

<400> SEQUENCE: 41

Met Ala Thr Gly Gly Tyr Arg Thr Ser Ser Gly Leu Gly Gly Ser Thr
1               5                   10                  15

Thr Asp Phe Leu Glu Glu Trp Lys Ala Lys Arg Glu Lys Met Arg Ala
            20                  25                  30

Lys Gln Asn Pro Pro Gly Pro Ala Pro Pro Gly Gly Gly Ser Ser Asp
        35                  40                  45

Ala Ala Gly Lys Pro Pro Ala Gly Ala Leu Gly Thr Pro Ala Ala Ala
    50                  55                  60

Ala Ala Asn Glu Leu Asn Asn Asn Leu Pro Gly Gly Ala Pro Ala Ala
65                  70                  75                  80

Pro Ala Val Pro Gly Pro Gly Gly Val Asn Cys Ala Val Gly Ser Ala
                85                  90                  95

Met Leu Thr Arg Ala Ala Pro Gly Pro Arg Arg Ser Glu Asp Glu Pro
            100                 105                 110

Pro Ala Ala Ser Ala Ser Ala Ala Pro Pro Pro Gln Arg Asp Glu Glu
        115                 120                 125

Glu Pro Asp Gly Val Pro Glu Lys Gly Lys Ser Ser Gly Pro Ser Ala
    130                 135                 140

Arg Lys Gly Lys Gly Gln Ile Glu Lys Arg Lys Leu Arg Glu Lys Arg
145                 150                 155                 160

Arg Ser Thr Gly Val Val Asn Ile Pro Ala Ala Glu Cys Leu Asp Glu
                165                 170                 175

Tyr Glu Asp Asp Glu Ala Gly Gln Lys Glu Arg Lys Arg Glu Asp Ala
            180                 185                 190

Ile Thr Gln Gln Asn Thr Ile Gln Asn Glu Ala Val Asn Leu Leu Asp
        195                 200                 205

Pro Gly Ser Ser Tyr Leu Leu Gln Glu Pro Pro Arg Thr Val Ser Gly
    210                 215                 220

Arg Tyr Lys Ser Thr Thr Ser Val Ser Glu Glu Asp Val Ser Ser Arg
225                 230                 235                 240

Tyr Ser Arg Thr Asp Arg Ser Gly Phe Pro Arg Tyr Asn Arg Asp Ala
                245                 250                 255

Asn Val Ser Gly Thr Leu Val Ser Ser Ser Thr Leu Glu Lys Lys Ile
            260                 265                 270

Glu Asp Leu Glu Lys Glu Val Val Arg Glu Arg Gln Glu Asn Leu Arg
        275                 280                 285

Leu Val Arg Leu Met Gln Asp Lys Glu Glu Met Ile Gly Lys Leu Lys
    290                 295                 300

Glu Glu Ile Asp Leu Leu Asn Arg Asp Leu Asp Asp Ile Glu Asp Glu
305                 310                 315                 320

Asn Glu Gln Leu Lys Gln Glu Asn Lys Thr Leu Leu Lys Val Val Gly
                325                 330                 335
```

```
Gln Leu Thr Arg
            340


<210> SEQ ID NO 42
<211> LENGTH: 3971
<212> TYPE: DNA
<213> ORGANISM: Homo sapiens
<220> FEATURE:
<221> NAME/KEY: CDS
<222> LOCATION: (185)..(2548)

<400> SEQUENCE: 42

agacctcttt cagcctaaga ggaaagcctg ttagcagagc acggaccagt gtctccggag      60

aatgctattc tcctacattt ccgaacaggt tatcaacgca cagatcgatc actgcctctg     120

tcccatcgct ccctgaagta gctctgactc cggttccttg aaaggggcgt gtacagaagt     180

aaag atg gag cct gca ggg gag cgc ttt ccc gaa caa agg caa gtc ctg      229
     Met Glu Pro Ala Gly Glu Arg Phe Pro Glu Gln Arg Gln Val Leu
     1               5                   10                  15

att ctc ctt ctt tta ctg gaa gtg act ctg gca ggc tgg gaa ccc cgt      277
Ile Leu Leu Leu Leu Leu Glu Val Thr Leu Ala Gly Trp Glu Pro Arg
                20                  25                  30

cgc tat tct gtg atg gag gaa aca gag aga ggt tct ttt gta gcc aac      325
Arg Tyr Ser Val Met Glu Glu Thr Glu Arg Gly Ser Phe Val Ala Asn
            35                  40                  45

ctg gcc aat gac cta ggg ctg gga gtg ggg gag cta gcc gag cgg gga      373
Leu Ala Asn Asp Leu Gly Leu Gly Val Gly Glu Leu Ala Glu Arg Gly
        50                  55                  60

gcc cgg gta gtt tct gag gat aac gaa caa ggc ttg cag ctt gat ctg      421
Ala Arg Val Val Ser Glu Asp Asn Glu Gln Gly Leu Gln Leu Asp Leu
    65                  70                  75

cag acc ggg cag ttg ata tta aat gag aag ctg gac cgg gag aag ctg      469
Gln Thr Gly Gln Leu Ile Leu Asn Glu Lys Leu Asp Arg Glu Lys Leu
80                  85                  90                  95

tgt ggc cct act gag ccc tgt ata atg cat ttc caa gtg tta ctg aaa      517
Cys Gly Pro Thr Glu Pro Cys Ile Met His Phe Gln Val Leu Leu Lys
                100                 105                 110

aaa cct ttg gaa gta ttt cga gct gaa cta cta gtg aca gac ata aac      565
Lys Pro Leu Glu Val Phe Arg Ala Glu Leu Leu Val Thr Asp Ile Asn
            115                 120                 125

gat cat tct cct gag ttt cct gaa aga gaa atg acc ctg aaa atc cca      613
Asp His Ser Pro Glu Phe Pro Glu Arg Glu Met Thr Leu Lys Ile Pro
        130                 135                 140

gaa act agc tcc ctt ggg act gtg ttt cct ctg aaa aaa gct cgg gac      661
Glu Thr Ser Ser Leu Gly Thr Val Phe Pro Leu Lys Lys Ala Arg Asp
    145                 150                 155

ttg gac gtg ggc agc aat aat gtt caa aac tac aat att tct ccc aat      709
Leu Asp Val Gly Ser Asn Asn Val Gln Asn Tyr Asn Ile Ser Pro Asn
160                 165                 170                 175

tct cat ttc cat gtt tcc act cgc acc cga ggg gat ggc agg aaa tac      757
Ser His Phe His Val Ser Thr Arg Thr Arg Gly Asp Gly Arg Lys Tyr
                180                 185                 190

cca gag ctg gtg ctg gac aca gaa ctg gat cgc gag gag cag gcc gag      805
Pro Glu Leu Val Leu Asp Thr Glu Leu Asp Arg Glu Glu Gln Ala Glu
            195                 200                 205

ctc aga tta acc ttg aca gcg gtg gac ggt ggc tct cca ccc cga tct      853
Leu Arg Leu Thr Leu Thr Ala Val Asp Gly Gly Ser Pro Pro Arg Ser
        210                 215                 220

ggc acc gtc cag atc ctc atc ttg gtc ttg gac gcc aat gac aat gcc      901
Gly Thr Val Gln Ile Leu Ile Leu Val Leu Asp Ala Asn Asp Asn Ala
```

```
    225                 230                 235

ccg gag ttt gtg cag gcg ctc tac gag gtg cag gtc cca gag aac agc      949
Pro Glu Phe Val Gln Ala Leu Tyr Glu Val Gln Val Pro Glu Asn Ser
240                 245                 250                 255

cca gta ggc tcc cta gtt gtc aag gtc tct gct agg gat tta gac act      997
Pro Val Gly Ser Leu Val Val Lys Val Ser Ala Arg Asp Leu Asp Thr
                260                 265                 270

ggg aca aat gga gag ata tca tac tcc ctt tat tac agc tct cag gag     1045
Gly Thr Asn Gly Glu Ile Ser Tyr Ser Leu Tyr Tyr Ser Ser Gln Glu
            275                 280                 285

ata gac aaa cct ttt gag cta agc agc ctt tca gga gaa att cga cta     1093
Ile Asp Lys Pro Phe Glu Leu Ser Ser Leu Ser Gly Glu Ile Arg Leu
        290                 295                 300

att aaa aaa cta gat ttt gag aca atg tct tcg tat gat cta gat ata     1141
Ile Lys Lys Leu Asp Phe Glu Thr Met Ser Ser Tyr Asp Leu Asp Ile
    305                 310                 315

gag gca tct gat ggc ggg gga ctt tct gga aaa tgc tct gtc tct gtt     1189
Glu Ala Ser Asp Gly Gly Gly Leu Ser Gly Lys Cys Ser Val Ser Val
320                 325                 330                 335

aag gtg ctg gat gtt aac gat aac ttc ccg gaa cta agt att tca tca     1237
Lys Val Leu Asp Val Asn Asp Asn Phe Pro Glu Leu Ser Ile Ser Ser
                340                 345                 350

ctt acc agc cct att ccc gag aat tct cca gag aca gaa gtg gcc ctg     1285
Leu Thr Ser Pro Ile Pro Glu Asn Ser Pro Glu Thr Glu Val Ala Leu
            355                 360                 365

ttt agg att aga gac cga gac tct ggg gaa aat gga aaa atg att tgc     1333
Phe Arg Ile Arg Asp Arg Asp Ser Gly Glu Asn Gly Lys Met Ile Cys
        370                 375                 380

tca att cag gat gat gtt cct ttt aag cta aaa cct tct gtt gag aat     1381
Ser Ile Gln Asp Asp Val Pro Phe Lys Leu Lys Pro Ser Val Glu Asn
    385                 390                 395

ttc tac agg ctg gta aca gaa ggg gcg ctg gac aga gag acc aga gcc     1429
Phe Tyr Arg Leu Val Thr Glu Gly Ala Leu Asp Arg Glu Thr Arg Ala
400                 405                 410                 415

gag tac aac atc acc atc acc atc aca gac ttg ggg act cca agg ctg     1477
Glu Tyr Asn Ile Thr Ile Thr Ile Thr Asp Leu Gly Thr Pro Arg Leu
                420                 425                 430

aaa acc gag cag agc ata acc gtg ctg gtg tcg gac gtc aat gac aac     1525
Lys Thr Glu Gln Ser Ile Thr Val Leu Val Ser Asp Val Asn Asp Asn
            435                 440                 445

gcc ccc gcc ttc acc caa acc tcc tac acc ctg ttc gtc cgc gag aac     1573
Ala Pro Ala Phe Thr Gln Thr Ser Tyr Thr Leu Phe Val Arg Glu Asn
        450                 455                 460

aac agc ccc gcc ctg cac atc ggc agt gtc agc gcc aca gac aga gac     1621
Asn Ser Pro Ala Leu His Ile Gly Ser Val Ser Ala Thr Asp Arg Asp
    465                 470                 475

tcg ggc acc aac gcc cag gtc acc tac tcg ctg ctg ccg ccc cgg gac     1669
Ser Gly Thr Asn Ala Gln Val Thr Tyr Ser Leu Leu Pro Pro Arg Asp
480                 485                 490                 495

ccg cac ctg ccc ctc acc tcc ctg gtc tcc att aac acg gac aac ggc     1717
Pro His Leu Pro Leu Thr Ser Leu Val Ser Ile Asn Thr Asp Asn Gly
                500                 505                 510

cac ctg ttc gct ctc cag tcg ctg gac tac gag gcc ctg cag gct ttc     1765
His Leu Phe Ala Leu Gln Ser Leu Asp Tyr Glu Ala Leu Gln Ala Phe
            515                 520                 525

gag ttc cgc gtg ggc gcc aca gac cgc ggc ttc ccg gcg ctg agc agc     1813
Glu Phe Arg Val Gly Ala Thr Asp Arg Gly Phe Pro Ala Leu Ser Ser
        530                 535                 540

gag gcg ctg gtg cga gtg ctg gtg ctg gac gcc aac gac aac tcg ccc     1861
```

```
Glu Ala Leu Val Arg Val Leu Val Leu Asp Ala Asn Asp Asn Ser Pro
    545                 550                 555

ttc gtg ctg tac ccg ctg cag aac ggc tcc gcg ccc tgc acc gag ctg     1909
Phe Val Leu Tyr Pro Leu Gln Asn Gly Ser Ala Pro Cys Thr Glu Leu
560                 565                 570                 575

gtg ccc cgg gcg gcc gag ccg ggc tac ctg gtg acc aag gtg gtg gcg     1957
Val Pro Arg Ala Ala Glu Pro Gly Tyr Leu Val Thr Lys Val Val Ala
                580                 585                 590

gtg gac ggc gac tcg ggc cag aac gcc tgg ctg tcg tac cag ctg ctc     2005
Val Asp Gly Asp Ser Gly Gln Asn Ala Trp Leu Ser Tyr Gln Leu Leu
            595                 600                 605

aag gcc acg gag ccc ggg ctg ttc ggc gtg tgg gcg cac aat ggc gag     2053
Lys Ala Thr Glu Pro Gly Leu Phe Gly Val Trp Ala His Asn Gly Glu
        610                 615                 620

gtg cgc acc gcc agg ctg ctg agc gag cgc gac gtg gcc aag cac agg     2101
Val Arg Thr Ala Arg Leu Leu Ser Glu Arg Asp Val Ala Lys His Arg
    625                 630                 635

cta gtg gtg ctg gtc aag gac aat ggc gag cct ccg cgc tcg gcc acc     2149
Leu Val Val Leu Val Lys Asp Asn Gly Glu Pro Pro Arg Ser Ala Thr
640                 645                 650                 655

gcc acg ctg caa gtg ctc ctg gtg gac ggc ttc tct cag ccc tac ctg     2197
Ala Thr Leu Gln Val Leu Leu Val Asp Gly Phe Ser Gln Pro Tyr Leu
                660                 665                 670

ccg ctc cca gag gcg gcc ccg gcc caa gcc cag gcc gac tcg ctt acc     2245
Pro Leu Pro Glu Ala Ala Pro Ala Gln Ala Gln Ala Asp Ser Leu Thr
            675                 680                 685

gtc tac ctg gtg gtg gca ttg gcc tcg gtg tct tcg ctc ttc ctc ttc     2293
Val Tyr Leu Val Val Ala Leu Ala Ser Val Ser Ser Leu Phe Leu Phe
        690                 695                 700

tcg gtg ttc ctg ttc gtg gca gtg cgg ctg tgc agg agg agc agg gcg     2341
Ser Val Phe Leu Phe Val Ala Val Arg Leu Cys Arg Arg Ser Arg Ala
    705                 710                 715

gcc tca gtg ggt cgc tgc tcg gtg ccc gag ggc ccc ttt cca ggg cat     2389
Ala Ser Val Gly Arg Cys Ser Val Pro Glu Gly Pro Phe Pro Gly His
720                 725                 730                 735

ctg gtg gac gtg agc ggc acc ggg acc ctt tcc cag agc tac cag tac     2437
Leu Val Asp Val Ser Gly Thr Gly Thr Leu Ser Gln Ser Tyr Gln Tyr
                740                 745                 750

gag gtg tgt ctg acg gga ggc tct gaa agt aat gat ttc aag ttc ttg     2485
Glu Val Cys Leu Thr Gly Gly Ser Glu Ser Asn Asp Phe Lys Phe Leu
            755                 760                 765

aag cct ata ttc cca aat att gta agc cag gac tct agg agg aaa tca     2533
Lys Pro Ile Phe Pro Asn Ile Val Ser Gln Asp Ser Arg Arg Lys Ser
        770                 775                 780

gaa ttt cta gaa taa tgtaggtatc tgtagctttc cgaccgtctg ttaattttgt     2588
Glu Phe Leu Glu
    785

cttcctcact tttcacctta gttttttta accctttagt aatcttgaat tctacttttt   2648

tttaaatttc tactgttgtc tttagtaatg ttactcattt cctttgtctg attgttagtt   2708

ttcaaattat tgtattatta taaatatttt atatcaggaa agttcatatt tctgaataaa   2768

ttaatagtat tcattcctga agggtgatat gaaagttaac cccacctaat aaacataact   2828

ctaattctga aattaccttt cacactatat gacactacat aagaatgtat gatttttgaa   2888

gtcatatttt aagtttttt tatagttttt cttattcaca cagcttgact ttttgacaaa   2948

agtttggggt gtaatcattt catatttatc catgtgtaat ttcttccaag cttcatattt   3008

ggagttttgt tttttccaat aaggagcaac atggataagt ttaagctact cttttcaagg   3068
```

```
tcacacttgt aagcattaga ttttcattct aaaacacata tgtcatctca taaaaatata   3128

tctgcgtaat gtattctgtc tcatgtaaat taacatagaa aagactaatg ggttcttcct   3188

tatctctatc taatgttatg atcctattgg ggggactgga caggctttct aatacccaga   3248

tttactgtgt ttaaggtgtt cgtataaggc caatagacac taggaccaag taatgcatct   3308

cctgcaattt cctcttttca cagcaggaaa atcttaacga gttccaaatt ctgggcttag   3368

aggagcttct gatggtacag tatgccaaca tctacttgtt ttggatggca acattgttct   3428

gattcataag gaatttgaaa gaaaatacat tgtagaatta atattagtta accaaacaaa   3488

atttattaaa ggatatgttg gtgaaggagt tgaattattt gaggaaaaaa catctgctct   3548

cttgtcagga cttttctgtc tccaggagct tctcaacttt gcagatactc tagaatggta   3608

ttgcatgcaa aataatgacc gccaagatgt tcctgcccta atccccagaa cctatgaata   3668

tgttatattg caaagaaatt aaggttcaaa cagaattaag gttgccaatc agctaaactt   3728

aaaataggga gactctccta gataatctgg gtgggtctat ttcaatcagt ggaaaggcca   3788

taaaagcaga gttgagtctt ccgtgagatg aaaataaatt ttgtttaagg acagcagctt   3848

cagcttatgc cccagaattc cagcctgccc ctcctaactg cctgctgtac agattttgga   3908

cttgtccagc cacgtttcaa aactgagtaa gtcacttcct tgcaataaat tgattactac   3968

aca                                                                 3971
```

<210> SEQ ID NO 43
<211> LENGTH: 787
<212> TYPE: PRT
<213> ORGANISM: Homo sapiens

<400> SEQUENCE: 43

```
Met Glu Pro Ala Gly Glu Arg Phe Pro Glu Gln Arg Gln Val Leu Ile
1               5                   10                  15

Leu Leu Leu Leu Leu Glu Val Thr Leu Ala Gly Trp Glu Pro Arg Arg
            20                  25                  30

Tyr Ser Val Met Glu Glu Thr Glu Arg Gly Ser Phe Val Ala Asn Leu
        35                  40                  45

Ala Asn Asp Leu Gly Leu Gly Val Gly Glu Leu Ala Glu Arg Gly Ala
    50                  55                  60

Arg Val Val Ser Glu Asp Asn Glu Gln Gly Leu Gln Leu Asp Leu Gln
65                  70                  75                  80

Thr Gly Gln Leu Ile Leu Asn Glu Lys Leu Asp Arg Glu Lys Leu Cys
                85                  90                  95

Gly Pro Thr Glu Pro Cys Ile Met His Phe Gln Val Leu Leu Lys Lys
            100                 105                 110

Pro Leu Glu Val Phe Arg Ala Glu Leu Leu Val Thr Asp Ile Asn Asp
        115                 120                 125

His Ser Pro Glu Phe Pro Glu Arg Glu Met Thr Leu Lys Ile Pro Glu
    130                 135                 140

Thr Ser Ser Leu Gly Thr Val Phe Pro Leu Lys Lys Ala Arg Asp Leu
145                 150                 155                 160

Asp Val Gly Ser Asn Asn Val Gln Asn Tyr Asn Ile Ser Pro Asn Ser
                165                 170                 175

His Phe His Val Ser Thr Arg Thr Arg Gly Asp Gly Arg Lys Tyr Pro
            180                 185                 190

Glu Leu Val Leu Asp Thr Glu Leu Asp Arg Glu Glu Gln Ala Glu Leu
        195                 200                 205
```

```
Arg Leu Thr Leu Thr Ala Val Asp Gly Gly Ser Pro Pro Arg Ser Gly
    210                 215                 220

Thr Val Gln Ile Leu Ile Leu Val Leu Asp Ala Asn Asp Asn Ala Pro
225                 230                 235                 240

Glu Phe Val Gln Ala Leu Tyr Glu Val Gln Val Pro Glu Asn Ser Pro
                245                 250                 255

Val Gly Ser Leu Val Val Lys Val Ser Ala Arg Asp Leu Asp Thr Gly
            260                 265                 270

Thr Asn Gly Glu Ile Ser Tyr Ser Leu Tyr Tyr Ser Ser Gln Glu Ile
        275                 280                 285

Asp Lys Pro Phe Glu Leu Ser Ser Leu Ser Gly Glu Ile Arg Leu Ile
    290                 295                 300

Lys Lys Leu Asp Phe Glu Thr Met Ser Ser Tyr Asp Leu Asp Ile Glu
305                 310                 315                 320

Ala Ser Asp Gly Gly Gly Leu Ser Gly Lys Cys Ser Val Ser Val Lys
                325                 330                 335

Val Leu Asp Val Asn Asp Asn Phe Pro Glu Leu Ser Ile Ser Ser Leu
            340                 345                 350

Thr Ser Pro Ile Pro Glu Asn Ser Pro Glu Thr Glu Val Ala Leu Phe
        355                 360                 365

Arg Ile Arg Asp Arg Asp Ser Gly Glu Asn Gly Lys Met Ile Cys Ser
    370                 375                 380

Ile Gln Asp Asp Val Pro Phe Lys Leu Lys Pro Ser Val Glu Asn Phe
385                 390                 395                 400

Tyr Arg Leu Val Thr Glu Gly Ala Leu Asp Arg Glu Thr Arg Ala Glu
                405                 410                 415

Tyr Asn Ile Thr Ile Thr Ile Thr Asp Leu Gly Thr Pro Arg Leu Lys
            420                 425                 430

Thr Glu Gln Ser Ile Thr Val Leu Val Ser Asp Val Asn Asp Asn Ala
        435                 440                 445

Pro Ala Phe Thr Gln Thr Ser Tyr Thr Leu Phe Val Arg Glu Asn Asn
    450                 455                 460

Ser Pro Ala Leu His Ile Gly Ser Val Ser Ala Thr Asp Arg Asp Ser
465                 470                 475                 480

Gly Thr Asn Ala Gln Val Thr Tyr Ser Leu Leu Pro Pro Arg Asp Pro
                485                 490                 495

His Leu Pro Leu Thr Ser Leu Val Ser Ile Asn Thr Asp Asn Gly His
            500                 505                 510

Leu Phe Ala Leu Gln Ser Leu Asp Tyr Glu Ala Leu Gln Ala Phe Glu
        515                 520                 525

Phe Arg Val Gly Ala Thr Asp Arg Gly Phe Pro Ala Leu Ser Ser Glu
    530                 535                 540

Ala Leu Val Arg Val Leu Val Leu Asp Ala Asn Asp Asn Ser Pro Phe
545                 550                 555                 560

Val Leu Tyr Pro Leu Gln Asn Gly Ser Ala Pro Cys Thr Glu Leu Val
                565                 570                 575

Pro Arg Ala Ala Glu Pro Gly Tyr Leu Val Thr Lys Val Val Ala Val
            580                 585                 590

Asp Gly Asp Ser Gly Gln Asn Ala Trp Leu Ser Tyr Gln Leu Leu Lys
        595                 600                 605

Ala Thr Glu Pro Gly Leu Phe Gly Val Trp Ala His Asn Gly Glu Val
    610                 615                 620

Arg Thr Ala Arg Leu Leu Ser Glu Arg Asp Val Ala Lys His Arg Leu
```

```
625                 630                 635                 640

Val Val Leu Val Lys Asp Asn Gly Glu Pro Pro Arg Ser Ala Thr Ala
                645                 650                 655

Thr Leu Gln Val Leu Leu Val Asp Gly Phe Ser Gln Pro Tyr Leu Pro
            660                 665                 670

Leu Pro Glu Ala Ala Pro Ala Gln Ala Gln Ala Asp Ser Leu Thr Val
        675                 680                 685

Tyr Leu Val Val Ala Leu Ala Ser Val Ser Ser Leu Phe Leu Phe Ser
    690                 695                 700

Val Phe Leu Phe Val Ala Val Arg Leu Cys Arg Arg Ser Arg Ala Ala
705                 710                 715                 720

Ser Val Gly Arg Cys Ser Val Pro Glu Gly Pro Phe Pro Gly His Leu
                725                 730                 735

Val Asp Val Ser Gly Thr Gly Thr Leu Ser Gln Ser Tyr Gln Tyr Glu
            740                 745                 750

Val Cys Leu Thr Gly Gly Ser Glu Ser Asn Asp Phe Lys Phe Leu Lys
        755                 760                 765

Pro Ile Phe Pro Asn Ile Val Ser Gln Asp Ser Arg Arg Lys Ser Glu
    770                 775                 780

Phe Leu Glu
785


<210> SEQ ID NO 44
<211> LENGTH: 2940
<212> TYPE: DNA
<213> ORGANISM: Homo sapiens
<220> FEATURE:
<221> NAME/KEY: CDS
<222> LOCATION: (206)..(2455)

<400> SEQUENCE: 44

aaacatctgc aaaagcgcaa ggagaccagc ccacatttta gcccctccta ctcaggataa      60

gactttctct aagtccggag ctgaaaaagg atcctgactg aaagctagag gcattgagga     120

gcctgaagat tctcaggttt taaagacgct agagtgccaa agaagacttt gaagtgtgaa     180

aacatttcct gtaattgaaa ccaaa atg tca ttt ata gat cct tac cag cac       232
                            Met Ser Phe Ile Asp Pro Tyr Gln His
                            1               5

att ata gtg gag cac cag tat tcc cac aag ttt acg gta gtg gtg tta       280
Ile Ile Val Glu His Gln Tyr Ser His Lys Phe Thr Val Val Val Leu
10                  15                  20                  25

cgt gcc acc aaa gtg aca aag ggg gcc ttt ggt gac atg ctt gat act       328
Arg Ala Thr Lys Val Thr Lys Gly Ala Phe Gly Asp Met Leu Asp Thr
                30                  35                  40

cca gat ccc tat gtg gaa ctt ttt atc tct aca acc cct gac agc agg       376
Pro Asp Pro Tyr Val Glu Leu Phe Ile Ser Thr Thr Pro Asp Ser Arg
            45                  50                  55

aag aga aca aga cat ttc aat aat gac ata aac cct gtg tgg aat gag       424
Lys Arg Thr Arg His Phe Asn Asn Asp Ile Asn Pro Val Trp Asn Glu
        60                  65                  70

acc ttt gaa ttt att ttg gat cct aat cag gaa aat gtt ttg gag att       472
Thr Phe Glu Phe Ile Leu Asp Pro Asn Gln Glu Asn Val Leu Glu Ile
    75                  80                  85

acg tta atg gat gcc aat tat gtc atg gat gaa act cta ggg aca gca       520
Thr Leu Met Asp Ala Asn Tyr Val Met Asp Glu Thr Leu Gly Thr Ala
90                  95                  100                 105

aca ttt act gta tct tct atg aag gtg gga gaa aag aaa gaa gtt cct       568
Thr Phe Thr Val Ser Ser Met Lys Val Gly Glu Lys Lys Glu Val Pro
```

```
                110                 115                 120

ttt att ttc aac caa gtc act gaa atg gtt cta gaa atg tct ctt gaa      616
Phe Ile Phe Asn Gln Val Thr Glu Met Val Leu Glu Met Ser Leu Glu
            125                 130                 135

gtt tgc tca tgc cca gac cta cga ttt agt atg gct ctg tgt gat cag      664
Val Cys Ser Cys Pro Asp Leu Arg Phe Ser Met Ala Leu Cys Asp Gln
        140                 145                 150

gag aag act ttc aga caa cag aga aaa gaa cac ata agg gag agc atg      712
Glu Lys Thr Phe Arg Gln Gln Arg Lys Glu His Ile Arg Glu Ser Met
    155                 160                 165

aag aaa ctc ttg ggt cca aag aat agt gaa gga ttg cat tct gca cgt      760
Lys Lys Leu Leu Gly Pro Lys Asn Ser Glu Gly Leu His Ser Ala Arg
170                 175                 180                 185

gat gtg cct gtg gta gcc ata ttg ggt tca ggt ggg ggt ttc cga gcc      808
Asp Val Pro Val Val Ala Ile Leu Gly Ser Gly Gly Gly Phe Arg Ala
                190                 195                 200

atg gtg gga ttc tct ggt gtg atg aag gca tta tac gaa tca gga att      856
Met Val Gly Phe Ser Gly Val Met Lys Ala Leu Tyr Glu Ser Gly Ile
            205                 210                 215

ctg gat tgt gct acc tac gtt gct ggt ctt tct ggc tcc acc tgg tat      904
Leu Asp Cys Ala Thr Tyr Val Ala Gly Leu Ser Gly Ser Thr Trp Tyr
        220                 225                 230

atg tca acc ttg tat tct cac cct gat ttt cca gag aaa ggg cca gag      952
Met Ser Thr Leu Tyr Ser His Pro Asp Phe Pro Glu Lys Gly Pro Glu
    235                 240                 245

gag att aat gaa gaa cta atg aaa aat gtt agc cac aat ccc ctt tta     1000
Glu Ile Asn Glu Glu Leu Met Lys Asn Val Ser His Asn Pro Leu Leu
250                 255                 260                 265

ctt ctc aca cca cag aaa gtt aaa aga tat gtt gag tct tta tgg aag     1048
Leu Leu Thr Pro Gln Lys Val Lys Arg Tyr Val Glu Ser Leu Trp Lys
                270                 275                 280

aag aaa agc tct gga caa cct gtc acc ttt act gat atc ttt ggg atg     1096
Lys Lys Ser Ser Gly Gln Pro Val Thr Phe Thr Asp Ile Phe Gly Met
            285                 290                 295

tta ata gga gaa aca cta att cat aat aga atg aat act act ctg agc     1144
Leu Ile Gly Glu Thr Leu Ile His Asn Arg Met Asn Thr Thr Leu Ser
        300                 305                 310

agt ttg aag gaa aaa gtt aat act gca caa tgc cct tta cct ctt ttc     1192
Ser Leu Lys Glu Lys Val Asn Thr Ala Gln Cys Pro Leu Pro Leu Phe
    315                 320                 325

acc tgt ctt cat gtc aaa cct gac gtt tca gag ctg atg ttt gca gat     1240
Thr Cys Leu His Val Lys Pro Asp Val Ser Glu Leu Met Phe Ala Asp
330                 335                 340                 345

tgg gtt gaa ttt agt cca tac gaa att ggc atg gct aaa tat ggt act     1288
Trp Val Glu Phe Ser Pro Tyr Glu Ile Gly Met Ala Lys Tyr Gly Thr
                350                 355                 360

ttt atg gct ccc gac tta ttt gga agc aaa ttt ttt atg gga aca gtc     1336
Phe Met Ala Pro Asp Leu Phe Gly Ser Lys Phe Phe Met Gly Thr Val
            365                 370                 375

gtt aag aag tat gaa gaa aac ccc ttg cat ttc tta atg ggt gtc tgg     1384
Val Lys Lys Tyr Glu Glu Asn Pro Leu His Phe Leu Met Gly Val Trp
        380                 385                 390

ggc agt gcc ttt tcc ata ttg ttc aac aga gtt ttg ggc gtt tct ggt     1432
Gly Ser Ala Phe Ser Ile Leu Phe Asn Arg Val Leu Gly Val Ser Gly
    395                 400                 405

tca caa agc aga ggc tcc aca atg gag gaa gaa tta gaa aat att acc     1480
Ser Gln Ser Arg Gly Ser Thr Met Glu Glu Glu Leu Glu Asn Ile Thr
410                 415                 420                 425

aca aag cat att gtg agt aat gat agc tcg gac agt gat gat gaa tca     1528
```

```
Thr Lys His Ile Val Ser Asn Asp Ser Ser Asp Ser Asp Asp Glu Ser
                430                 435                 440

cac gaa ccc aaa ggc act gaa aat gaa gat gct gga agt gac tat caa      1576
His Glu Pro Lys Gly Thr Glu Asn Glu Asp Ala Gly Ser Asp Tyr Gln
            445                 450                 455

agt gat aat caa gca agt tgg att cat cgt atg ata atg gcc ttg gtg      1624
Ser Asp Asn Gln Ala Ser Trp Ile His Arg Met Ile Met Ala Leu Val
        460                 465                 470

agt gat tca gct tta ttc aat acc aga gaa gga cgt gct ggg aag gta      1672
Ser Asp Ser Ala Leu Phe Asn Thr Arg Glu Gly Arg Ala Gly Lys Val
    475                 480                 485

cac aac ttc atg ctg ggc ttg aat ctc aat aca tct tat cca ctg tct      1720
His Asn Phe Met Leu Gly Leu Asn Leu Asn Thr Ser Tyr Pro Leu Ser
490                 495                 500                 505

cct ttg agt gac ttt gcc aca cag gac tcc ttt gat gat gat gaa ctg      1768
Pro Leu Ser Asp Phe Ala Thr Gln Asp Ser Phe Asp Asp Asp Glu Leu
                510                 515                 520

gat gca gct gta gca gat cct gat gaa ttt gag cga ata tat gag cct      1816
Asp Ala Ala Val Ala Asp Pro Asp Glu Phe Glu Arg Ile Tyr Glu Pro
            525                 530                 535

ctg gat gtc aaa agt aaa aag att cat gta gtg gac agt ggg ctc aca      1864
Leu Asp Val Lys Ser Lys Lys Ile His Val Val Asp Ser Gly Leu Thr
        540                 545                 550

ttt aac ctg ccg tat ccc ttg ata ctg aga cct cag aga ggg gtt gat      1912
Phe Asn Leu Pro Tyr Pro Leu Ile Leu Arg Pro Gln Arg Gly Val Asp
    555                 560                 565

ctc ata atc tcc ttt gac ttt tct gca agg cca agt gac tct agt cct      1960
Leu Ile Ile Ser Phe Asp Phe Ser Ala Arg Pro Ser Asp Ser Ser Pro
570                 575                 580                 585

ccg ttc aag gaa ctt cta ctt gca gaa aag tgg gct aaa atg aac aag      2008
Pro Phe Lys Glu Leu Leu Leu Ala Glu Lys Trp Ala Lys Met Asn Lys
                590                 595                 600

ctc ccc ttt cca aag att gat cct tat gtg ttt gat cgg gaa ggg ctg      2056
Leu Pro Phe Pro Lys Ile Asp Pro Tyr Val Phe Asp Arg Glu Gly Leu
            605                 610                 615

aag gag tgc tat gtc ttt aaa ccc aag aat cct gat atg gag aaa gat      2104
Lys Glu Cys Tyr Val Phe Lys Pro Lys Asn Pro Asp Met Glu Lys Asp
        620                 625                 630

tgc cca acc atc atc cac ttt gtt ctg gcc aac atc aac ttc aga aag      2152
Cys Pro Thr Ile Ile His Phe Val Leu Ala Asn Ile Asn Phe Arg Lys
    635                 640                 645

tac aag gct cca ggt gtt cca agg gaa act gag gaa gag aaa gaa atc      2200
Tyr Lys Ala Pro Gly Val Pro Arg Glu Thr Glu Glu Glu Lys Glu Ile
650                 655                 660                 665

gct gac ttt gat att ttt gat gac cca gaa tca cca ttt tca acc ttc      2248
Ala Asp Phe Asp Ile Phe Asp Asp Pro Glu Ser Pro Phe Ser Thr Phe
                670                 675                 680

aat ttt caa tat cca aat caa gca ttc aaa aga cta cat gat ctt atg      2296
Asn Phe Gln Tyr Pro Asn Gln Ala Phe Lys Arg Leu His Asp Leu Met
            685                 690                 695

cac ttc aat act ctg aac aac att gat gtg ata aaa gaa gcc atg gtt      2344
His Phe Asn Thr Leu Asn Asn Ile Asp Val Ile Lys Glu Ala Met Val
        700                 705                 710

gaa agc att gaa tat aga aga cag aat cca tct cgt tgc tct gtt tcc      2392
Glu Ser Ile Glu Tyr Arg Arg Gln Asn Pro Ser Arg Cys Ser Val Ser
    715                 720                 725

ctt agt aat gtt gag gca aga aga ttt ttc aac aag gag ttt cta agt      2440
Leu Ser Asn Val Glu Ala Arg Arg Phe Phe Asn Lys Glu Phe Leu Ser
730                 735                 740                 745
```

```
aaa ccc aaa gca tag ttcatgtact ggaaatggca gcagtttctg atgctgaggc     2495
Lys Pro Lys Ala

agtttgcaat cccatgacaa ctggatttaa aagtacagta cagatagtcg tactgatcat   2555

gagagactgg ctgatactca aagttgcagt tacttagctg catgagaata atactattat   2615

aagttaggtt gacaaatgat gttgattatg taaggatata cttagctaca ttttcagtca   2675

gtatgaactt cctgatacaa atgtagggat atatactgta tttttaaaca tttctcacca   2735

actttcttat gtgtgttctt tttaaaaatt ttttttcttt taaaatattt aacagttcaa   2795

tctcaataag acctcgcatt atgtatgaat gttattcact gactagattt attcatacca   2855

tgagacaaca ctatttttat ttatatatgc atatatatac atacatgaaa taaatacatc   2915

aatataaaaa taaaaaaaaa aaaaa                                          2940
```

<210> SEQ ID NO 45
<211> LENGTH: 749
<212> TYPE: PRT
<213> ORGANISM: Homo sapiens

<400> SEQUENCE: 45

```
Met Ser Phe Ile Asp Pro Tyr Gln His Ile Ile Val Glu His Gln Tyr
1               5                   10                  15

Ser His Lys Phe Thr Val Val Val Leu Arg Ala Thr Lys Val Thr Lys
            20                  25                  30

Gly Ala Phe Gly Asp Met Leu Asp Thr Pro Asp Pro Tyr Val Glu Leu
        35                  40                  45

Phe Ile Ser Thr Thr Pro Asp Ser Arg Lys Arg Thr Arg His Phe Asn
    50                  55                  60

Asn Asp Ile Asn Pro Val Trp Asn Glu Thr Phe Glu Phe Ile Leu Asp
65                  70                  75                  80

Pro Asn Gln Glu Asn Val Leu Glu Ile Thr Leu Met Asp Ala Asn Tyr
                85                  90                  95

Val Met Asp Glu Thr Leu Gly Thr Ala Thr Phe Thr Val Ser Ser Met
            100                 105                 110

Lys Val Gly Glu Lys Lys Glu Val Pro Phe Ile Phe Asn Gln Val Thr
        115                 120                 125

Glu Met Val Leu Glu Met Ser Leu Glu Val Cys Ser Cys Pro Asp Leu
    130                 135                 140

Arg Phe Ser Met Ala Leu Cys Asp Gln Glu Lys Thr Phe Arg Gln Gln
145                 150                 155                 160

Arg Lys Glu His Ile Arg Glu Ser Met Lys Lys Leu Leu Gly Pro Lys
                165                 170                 175

Asn Ser Glu Gly Leu His Ser Ala Arg Asp Val Pro Val Val Ala Ile
            180                 185                 190

Leu Gly Ser Gly Gly Gly Phe Arg Ala Met Val Gly Phe Ser Gly Val
        195                 200                 205

Met Lys Ala Leu Tyr Glu Ser Gly Ile Leu Asp Cys Ala Thr Tyr Val
    210                 215                 220

Ala Gly Leu Ser Gly Ser Thr Trp Tyr Met Ser Thr Leu Tyr Ser His
225                 230                 235                 240

Pro Asp Phe Pro Glu Lys Gly Pro Glu Glu Ile Asn Glu Glu Leu Met
                245                 250                 255

Lys Asn Val Ser His Asn Pro Leu Leu Leu Leu Thr Pro Gln Lys Val
            260                 265                 270

Lys Arg Tyr Val Glu Ser Leu Trp Lys Lys Lys Ser Ser Gly Gln Pro
```

```
        275                 280                 285

Val Thr Phe Thr Asp Ile Phe Gly Met Leu Ile Gly Glu Thr Leu Ile
    290                 295                 300

His Asn Arg Met Asn Thr Thr Leu Ser Ser Leu Lys Glu Lys Val Asn
305                 310                 315                 320

Thr Ala Gln Cys Pro Leu Pro Leu Phe Thr Cys Leu His Val Lys Pro
                325                 330                 335

Asp Val Ser Glu Leu Met Phe Ala Asp Trp Val Glu Phe Ser Pro Tyr
            340                 345                 350

Glu Ile Gly Met Ala Lys Tyr Gly Thr Phe Met Ala Pro Asp Leu Phe
        355                 360                 365

Gly Ser Lys Phe Phe Met Gly Thr Val Val Lys Lys Tyr Glu Glu Asn
    370                 375                 380

Pro Leu His Phe Leu Met Gly Val Trp Gly Ser Ala Phe Ser Ile Leu
385                 390                 395                 400

Phe Asn Arg Val Leu Gly Val Ser Gly Ser Gln Ser Arg Gly Ser Thr
                405                 410                 415

Met Glu Glu Glu Leu Glu Asn Ile Thr Thr Lys His Ile Val Ser Asn
            420                 425                 430

Asp Ser Ser Asp Ser Asp Asp Glu Ser His Glu Pro Lys Gly Thr Glu
        435                 440                 445

Asn Glu Asp Ala Gly Ser Asp Tyr Gln Ser Asp Asn Gln Ala Ser Trp
    450                 455                 460

Ile His Arg Met Ile Met Ala Leu Val Ser Asp Ser Ala Leu Phe Asn
465                 470                 475                 480

Thr Arg Glu Gly Arg Ala Gly Lys Val His Asn Phe Met Leu Gly Leu
                485                 490                 495

Asn Leu Asn Thr Ser Tyr Pro Leu Ser Pro Leu Ser Asp Phe Ala Thr
            500                 505                 510

Gln Asp Ser Phe Asp Asp Asp Glu Leu Asp Ala Ala Val Ala Asp Pro
        515                 520                 525

Asp Glu Phe Glu Arg Ile Tyr Glu Pro Leu Asp Val Lys Ser Lys Lys
    530                 535                 540

Ile His Val Val Asp Ser Gly Leu Thr Phe Asn Leu Pro Tyr Pro Leu
545                 550                 555                 560

Ile Leu Arg Pro Gln Arg Gly Val Asp Leu Ile Ile Ser Phe Asp Phe
                565                 570                 575

Ser Ala Arg Pro Ser Asp Ser Ser Pro Pro Phe Lys Glu Leu Leu Leu
            580                 585                 590

Ala Glu Lys Trp Ala Lys Met Asn Lys Leu Pro Phe Pro Lys Ile Asp
        595                 600                 605

Pro Tyr Val Phe Asp Arg Glu Gly Leu Lys Glu Cys Tyr Val Phe Lys
    610                 615                 620

Pro Lys Asn Pro Asp Met Glu Lys Asp Cys Pro Thr Ile Ile His Phe
625                 630                 635                 640

Val Leu Ala Asn Ile Asn Phe Arg Lys Tyr Lys Ala Pro Gly Val Pro
                645                 650                 655

Arg Glu Thr Glu Glu Glu Lys Glu Ile Ala Asp Phe Asp Ile Phe Asp
            660                 665                 670

Asp Pro Glu Ser Pro Phe Ser Thr Phe Asn Phe Gln Tyr Pro Asn Gln
        675                 680                 685

Ala Phe Lys Arg Leu His Asp Leu Met His Phe Asn Thr Leu Asn Asn
    690                 695                 700
```

```
Ile Asp Val Ile Lys Glu Ala Met Val Glu Ser Ile Glu Tyr Arg Arg
705                 710                 715                 720

Gln Asn Pro Ser Arg Cys Ser Val Ser Leu Ser Asn Val Glu Ala Arg
                725                 730                 735

Arg Phe Phe Asn Lys Glu Phe Leu Ser Lys Pro Lys Ala
            740                 745


<210> SEQ ID NO 46
<211> LENGTH: 6696
<212> TYPE: DNA
<213> ORGANISM: Homo sapiens
<220> FEATURE:
<221> NAME/KEY: CDS
<222> LOCATION: (508)..(3795)

<400> SEQUENCE: 46

agagctgagt ggaggccgcc gccgccgccg cacttcctgg gaccgctgcg ccgcagtccg      60

cgggcaggtg gcgggtgcgc ccggccgcag tcgcccggct ctggccccta tcgggccgcc     120

ggcgtccggg ctccagaggc cgcctggctg ggcgcccggt gccttttgtc tggcgcaggg     180

ccggcgtttg catcacattt cggatacctc cctctctttt tcgcctctcc ttctgcctcc     240

cgctcacatc gcctccccac tcccgccacc gtcccccgcc ggactgctag cctcctagac     300

cgaagcccga ggacgtctct gcccgagcga tgtcccctct ccagaaagtt gccgccgccg     360

ccgccgccgc cgccactgcc gccgctgggc ggtgaaacaa agtctggcgg ggccgcctcc     420

cggtgcagga gcgcaccggt gcctagcggc tggactccgc tgccgggcgt cccgctttcc     480

cccggggagc cctaaacgct ccaggcc atg gcc gag ggc gcg gcc ggc agg gag     534
                              Met Ala Glu Gly Ala Ala Gly Arg Glu
                              1               5

gat ccg gcg ccg ccc gac gcg gcg ggg ggc gaa gac gac ccc cga gtg       582
Asp Pro Ala Pro Pro Asp Ala Ala Gly Gly Glu Asp Asp Pro Arg Val
10                  15                  20                  25

ggc ccg gat gcc gcc ggg gac tgc gtg acg gcg gcc tct ggg ggc cgg       630
Gly Pro Asp Ala Ala Gly Asp Cys Val Thr Ala Ala Ser Gly Gly Arg
                30                  35                  40

atg agg gac cgt cgc agc ggg gtc gca ctg cca ggc gcc gcg ggg acc       678
Met Arg Asp Arg Arg Ser Gly Val Ala Leu Pro Gly Ala Ala Gly Thr
            45                  50                  55

cca gcg gac agc gag gcg ggc ctc ctg gag gca gca cgg gcg acc ccc       726
Pro Ala Asp Ser Glu Ala Gly Leu Leu Glu Ala Ala Arg Ala Thr Pro
        60                  65                  70

cgg cgc agc agc atc atc aag gat cct tca aac caa aaa tgt ggt gga       774
Arg Arg Ser Ser Ile Ile Lys Asp Pro Ser Asn Gln Lys Cys Gly Gly
    75                  80                  85

aga aag aaa acc gtg tct ttc agc agc atg cca tcg gaa aag aaa att       822
Arg Lys Lys Thr Val Ser Phe Ser Ser Met Pro Ser Glu Lys Lys Ile
90                  95                  100                 105

agc agt gca aat gac tgc atc agc ttc atg caa gct ggc tgt gag ttg       870
Ser Ser Ala Asn Asp Cys Ile Ser Phe Met Gln Ala Gly Cys Glu Leu
                110                 115                 120

aag aaa gtc cgg cca aat tct cgc att tac aac cgt ttt ttc act ctg       918
Lys Lys Val Arg Pro Asn Ser Arg Ile Tyr Asn Arg Phe Phe Thr Leu
            125                 130                 135

gac aca gac ctt caa gct ctt cgc tgg gaa cct tca aag aaa gac ctc       966
Asp Thr Asp Leu Gln Ala Leu Arg Trp Glu Pro Ser Lys Lys Asp Leu
        140                 145                 150

gag aaa gcc aag ctt gat att tct gcc ata aaa gag atc aga ctg ggg      1014
Glu Lys Ala Lys Leu Asp Ile Ser Ala Ile Lys Glu Ile Arg Leu Gly
```

-continued

```
    155                 160                 165

aaa aac acg gaa aca ttt aga aac aat ggc ctt gct gac cag atc tgt      1062
Lys Asn Thr Glu Thr Phe Arg Asn Asn Gly Leu Ala Asp Gln Ile Cys
170                 175                 180                 185

gag gac tgt gcc ttt tcc ata ctc cac ggg gaa aac tat gag tct ctg      1110
Glu Asp Cys Ala Phe Ser Ile Leu His Gly Glu Asn Tyr Glu Ser Leu
                190                 195                 200

gac cta gtt gcc aat tca gca gat gtg gca aac atc tgg gtg tct ggg      1158
Asp Leu Val Ala Asn Ser Ala Asp Val Ala Asn Ile Trp Val Ser Gly
            205                 210                 215

tta cgg tac ctg gtt tct cga agt aag cag cct ctt gat ttt atg gag      1206
Leu Arg Tyr Leu Val Ser Arg Ser Lys Gln Pro Leu Asp Phe Met Glu
        220                 225                 230

ggc aac cag aac aca cca cgg ttc atg tgg ttg aaa aca gtg ttt gaa      1254
Gly Asn Gln Asn Thr Pro Arg Phe Met Trp Leu Lys Thr Val Phe Glu
    235                 240                 245

gca gca gat gtt gat ggg aat ggg att atg ttg gaa gac acc tct gta      1302
Ala Ala Asp Val Asp Gly Asn Gly Ile Met Leu Glu Asp Thr Ser Val
250                 255                 260                 265

gag tta ata aaa caa ctc aac cct act ctg aag gaa gcc aag atc agg      1350
Glu Leu Ile Lys Gln Leu Asn Pro Thr Leu Lys Glu Ala Lys Ile Arg
                270                 275                 280

tta aag ttt aaa gaa atc cag aag agc aag gaa aaa cta acc acc cgc      1398
Leu Lys Phe Lys Glu Ile Gln Lys Ser Lys Glu Lys Leu Thr Thr Arg
            285                 290                 295

gtg acc gaa gag gaa ttt tgt gaa gct ttt tgt gaa ctt tgc acc agg      1446
Val Thr Glu Glu Glu Phe Cys Glu Ala Phe Cys Glu Leu Cys Thr Arg
        300                 305                 310

cca gaa gtg tat ttc tta ctt gta cag ata tct aaa aac aaa gaa tat      1494
Pro Glu Val Tyr Phe Leu Leu Val Gln Ile Ser Lys Asn Lys Glu Tyr
    315                 320                 325

ttg gat gcc aat gat ctc atg ctc ttt tta gaa gct gag caa gga gtc      1542
Leu Asp Ala Asn Asp Leu Met Leu Phe Leu Glu Ala Glu Gln Gly Val
330                 335                 340                 345

acc cat atc acc gag gat ata tgc tta gac atc ata agg aga tac gaa      1590
Thr His Ile Thr Glu Asp Ile Cys Leu Asp Ile Ile Arg Arg Tyr Glu
                350                 355                 360

ctt tct gaa gag gga cgt caa aaa ggg ttt ctt gca att gat ggc ttt      1638
Leu Ser Glu Glu Gly Arg Gln Lys Gly Phe Leu Ala Ile Asp Gly Phe
            365                 370                 375

acc cag tat tta ttg tca tca gaa tgt gac att ttt gat cct gag caa      1686
Thr Gln Tyr Leu Leu Ser Ser Glu Cys Asp Ile Phe Asp Pro Glu Gln
        380                 385                 390

aag aag gtt gcc caa gat atg acc cag cca tta tct cac tac tat atc      1734
Lys Lys Val Ala Gln Asp Met Thr Gln Pro Leu Ser His Tyr Tyr Ile
    395                 400                 405

aat gcc tct cat aac acc tat cta ata gaa gac cag ttc agg ggg cca      1782
Asn Ala Ser His Asn Thr Tyr Leu Ile Glu Asp Gln Phe Arg Gly Pro
410                 415                 420                 425

gct gac atc aat ggg tac att aga gct ttg aaa atg ggc tgt cga agc      1830
Ala Asp Ile Asn Gly Tyr Ile Arg Ala Leu Lys Met Gly Cys Arg Ser
                430                 435                 440

gtt gaa ctc gat gta agt gat ggt tca gat aat gaa cca atc ctt tgt      1878
Val Glu Leu Asp Val Ser Asp Gly Ser Asp Asn Glu Pro Ile Leu Cys
            445                 450                 455

aat cga aat aac atg aca acc cat gtt tcc ttt cga agt gtc ata gag      1926
Asn Arg Asn Asn Met Thr Thr His Val Ser Phe Arg Ser Val Ile Glu
        460                 465                 470

gta ata aat aaa ttt gcc ttt gtt gct tct gaa tac cca ctc att ctt      1974
```

-continued

```
Val Ile Asn Lys Phe Ala Phe Val Ala Ser Glu Tyr Pro Leu Ile Leu
    475                 480                 485

tgc ttg gga aat cac tgc tcc ttg ccg cag cag aag gta atg gct caa      2022
Cys Leu Gly Asn His Cys Ser Leu Pro Gln Gln Lys Val Met Ala Gln
490                 495                 500                 505

cag atg aaa aag gtc ttt ggc aat aaa ctc tat act gaa gca cct ttg      2070
Gln Met Lys Lys Val Phe Gly Asn Lys Leu Tyr Thr Glu Ala Pro Leu
                510                 515                 520

ccc tca gaa tcc tac ctc cca tca cca gaa aaa tta aaa aga atg atc      2118
Pro Ser Glu Ser Tyr Leu Pro Ser Pro Glu Lys Leu Lys Arg Met Ile
            525                 530                 535

att gtg aaa gga aag aag ttg cct tct gat cca gat gtg tta gaa gga      2166
Ile Val Lys Gly Lys Lys Leu Pro Ser Asp Pro Asp Val Leu Glu Gly
        540                 545                 550

gaa gta aca gat gaa gat gaa gaa gct gaa atg tct cga agg atg tcg      2214
Glu Val Thr Asp Glu Asp Glu Glu Ala Glu Met Ser Arg Arg Met Ser
    555                 560                 565

gta gat tac aat ggt gag cag aag caa atc cga ctc tgt agg gag ctc      2262
Val Asp Tyr Asn Gly Glu Gln Lys Gln Ile Arg Leu Cys Arg Glu Leu
570                 575                 580                 585

tct gat ttg gtg tct att tgt aaa tct gtt caa tac agg gat ttt gaa      2310
Ser Asp Leu Val Ser Ile Cys Lys Ser Val Gln Tyr Arg Asp Phe Glu
                590                 595                 600

cta tct atg aaa agc caa aac tat tgg gaa atg tgt tca ttt agt gaa      2358
Leu Ser Met Lys Ser Gln Asn Tyr Trp Glu Met Cys Ser Phe Ser Glu
            605                 610                 615

aca gag gcc agc cgc att gca aat gag tac cca gag gat ttt gtt aat      2406
Thr Glu Ala Ser Arg Ile Ala Asn Glu Tyr Pro Glu Asp Phe Val Asn
        620                 625                 630

tat aat aag aag ttc tta tca aga atc tat cca agt gcc atg agg atc      2454
Tyr Asn Lys Lys Phe Leu Ser Arg Ile Tyr Pro Ser Ala Met Arg Ile
    635                 640                 645

gat tcc agt aac ttg aat cca cag gac ttt tgg aat tgt ggc tgt cag      2502
Asp Ser Ser Asn Leu Asn Pro Gln Asp Phe Trp Asn Cys Gly Cys Gln
650                 655                 660                 665

att gta gca atg aat ttt cag act ccg ggt cca atg atg gac ctt cac      2550
Ile Val Ala Met Asn Phe Gln Thr Pro Gly Pro Met Met Asp Leu His
                670                 675                 680

acg ggc tgg ttt ctt caa aac ggg gga tgt ggt tat gtt cta agg ccg      2598
Thr Gly Trp Phe Leu Gln Asn Gly Gly Cys Gly Tyr Val Leu Arg Pro
            685                 690                 695

tct ata atg cga gat gaa gtt tct tac ttc agc gca aat aca aag ggc      2646
Ser Ile Met Arg Asp Glu Val Ser Tyr Phe Ser Ala Asn Thr Lys Gly
        700                 705                 710

att cta cct ggg gtg tct cct cta gct ctt cat atc aag atc atc agt      2694
Ile Leu Pro Gly Val Ser Pro Leu Ala Leu His Ile Lys Ile Ile Ser
    715                 720                 725

ggt cag aat ttc cca aag ccc aag gga gct tgt gcc aaa ggg gat gtc      2742
Gly Gln Asn Phe Pro Lys Pro Lys Gly Ala Cys Ala Lys Gly Asp Val
730                 735                 740                 745

ata gat ccc tat gtt tgt ata gag ata cac gga att cca gcg gat tgt      2790
Ile Asp Pro Tyr Val Cys Ile Glu Ile His Gly Ile Pro Ala Asp Cys
                750                 755                 760

tcg gaa caa aga act aaa act gta cag caa aac agt gat aat cct att      2838
Ser Glu Gln Arg Thr Lys Thr Val Gln Gln Asn Ser Asp Asn Pro Ile
            765                 770                 775

ttt gat gaa act ttt gag ttc caa gta aac cta cct gag ctg gcc atg      2886
Phe Asp Glu Thr Phe Glu Phe Gln Val Asn Leu Pro Glu Leu Ala Met
        780                 785                 790
```

```
atc cgt ttt gtt gtt ctg gat gat gac tac att ggg gat gag ttt ata     2934
Ile Arg Phe Val Val Leu Asp Asp Asp Tyr Ile Gly Asp Glu Phe Ile
    795                 800                 805

ggg caa tat acg ata cca ttt gaa tgt ttg cag cct gga tat cgg cat     2982
Gly Gln Tyr Thr Ile Pro Phe Glu Cys Leu Gln Pro Gly Tyr Arg His
810                 815                 820                 825

gtt ccc ctg cgt tct ttt gtg ggt gac atc atg gag cac gta acc ctt     3030
Val Pro Leu Arg Ser Phe Val Gly Asp Ile Met Glu His Val Thr Leu
                830                 835                 840

ttt gtc cac ata gca ata act aat cga agt gga gga gga aag gca cag     3078
Phe Val His Ile Ala Ile Thr Asn Arg Ser Gly Gly Gly Lys Ala Gln
            845                 850                 855

aag cgc agt ctt tca gtg aga atg ggg aag aaa gtt cgg gaa tat acc     3126
Lys Arg Ser Leu Ser Val Arg Met Gly Lys Lys Val Arg Glu Tyr Thr
        860                 865                 870

atg ctc agg aat atc ggt ctt aaa acc att gat gac atc ttt aaa ata     3174
Met Leu Arg Asn Ile Gly Leu Lys Thr Ile Asp Asp Ile Phe Lys Ile
    875                 880                 885

gcg gtt cat cca tta cga gaa gcc ata gat atg aga gaa aat atg cag     3222
Ala Val His Pro Leu Arg Glu Ala Ile Asp Met Arg Glu Asn Met Gln
890                 895                 900                 905

aat gca atc gtg tct att aag gaa cta tgt gga ctc cct cca att gcc     3270
Asn Ala Ile Val Ser Ile Lys Glu Leu Cys Gly Leu Pro Pro Ile Ala
                910                 915                 920

agt ctg aag cag tgc ctg tta act ctg tca tct cgg ctc atc acc agt     3318
Ser Leu Lys Gln Cys Leu Leu Thr Leu Ser Ser Arg Leu Ile Thr Ser
            925                 930                 935

gac aat act cct tca gtc tca ctt gtg atg aaa gac agc ttt cct tac     3366
Asp Asn Thr Pro Ser Val Ser Leu Val Met Lys Asp Ser Phe Pro Tyr
        940                 945                 950

ctg gag cct ctg ggt gca att cca gat gtg cag aaa aag atg ctg act     3414
Leu Glu Pro Leu Gly Ala Ile Pro Asp Val Gln Lys Lys Met Leu Thr
    955                 960                 965

gct tat gat ctg atg att caa gag agc cgg ttt ctc ata gaa atg gcg     3462
Ala Tyr Asp Leu Met Ile Gln Glu Ser Arg Phe Leu Ile Glu Met Ala
970                 975                 980                 985

gac aca gtc cag gaa aag att gta cag tgt cag aaa gca ggg atg  gag    3510
Asp Thr Val Gln Glu Lys Ile Val Gln Cys Gln Lys Ala Gly Met  Glu
                990                 995                 1000

ttc cat gaa gaa  ctt cat aat ttg ggg  gca aaa gaa ggc ttg  aag      3555
Phe His Glu Glu  Leu His Asn Leu Gly  Ala Lys Glu Gly Leu  Lys
            1005                 1010                 1015

gga aga aaa ctc  aac aaa gca act gag  agc ttt gct tgg aac  att      3600
Gly Arg Lys Leu  Asn Lys Ala Thr Glu  Ser Phe Ala Trp Asn  Ile
            1020                 1025                 1030

aca gta ttg aag  ggc caa gga gat ctg  ttg aag aat gcc aag  aat      3645
Thr Val Leu Lys  Gly Gln Gly Asp Leu  Leu Lys Asn Ala Lys  Asn
            1035                 1040                 1045

gaa gct ata gaa  aac atg aag cag atc  cag ctg gca tgc ctg  tcc      3690
Glu Ala Ile Glu  Asn Met Lys Gln Ile  Gln Leu Ala Cys Leu  Ser
            1050                 1055                 1060

tgt gga ctg agt  aaa gcc ccc agc agc  agt gct gag gcc aag  agc      3735
Cys Gly Leu Ser  Lys Ala Pro Ser Ser  Ser Ala Glu Ala Lys  Ser
            1065                 1070                 1075

aag cgc agc ctg  gaa gcc ata gag gag  aag gaa agt agt gag  gag      3780
Lys Arg Ser Leu  Glu Ala Ile Glu Glu  Lys Glu Ser Ser Glu  Glu
            1080                 1085                 1090

aat ggg aag ctg  tga ctctgggcat tatcgacacg ttcacccatc ttatcaagga    3835
Asn Gly Lys Leu
            1095
```

ctctggtttc tcattcttgt tttctttctt taaatgtttt ataagttcac aaaatggtgc 3895 cctatatggg gtattggaca tagatatttt cacaatgtca gtatttcagt gtagttaatt 3955 tatctaaatt aaagccttta gtatcagtgt tttaaattct gagacatgtg tcaacacccc 4015 tgtgtggatg cctgtggaag agtgtgtgtg tgtgtgtgtg tgtgtgtgtg tggcagagag 4075 agagaaagag agagagagag agaaattctg ttaaaatcta ttctgtgttg cattattcat 4135 ttagtgagtt attccttgat cattttggga caattgtttt aatctgaaat tctaaagagc 4195 acttactgta acctgttgct gtgtttaatt tgacttctct gcctttgaca tttaatttag 4255 tgatcttagc atagcttatt attgaaggaa gccaaattta tcaaagcata gatgttttgg 4315 tagattaaat atagattaga aaaattccta agaatcagag tagaaataaa agtgaatgaa 4375 agattaaaca gatgatgaga atttctaaaa agattagcaa ggtcatttct tcagtcagaa 4435 aactttaaaa aatatttatt aaataaaatc aatttttagg aagttttctg tagtcattta 4495 ctaaacatat gatttcacta gaaaagctga tcataagtga atttatacct acctgtgtgg 4555 tactctgaaa cacactgaaa gctctgttgc aattaggatt ttgatgtgac aataatattg 4615 ttgtataatt tcgagatttg taggaaggtc tcattcttcc aagctgagag tctagcactc 4675 attttctata acagatatgg cagcttagag gtgttggctt tgtttggatg taatttaggg 4735 tactaaattt aaatttaaag atattgttca aacaatatca tatcatcaca ttgagctgat 4795 ataaattctg tgggtccgat aatatctttg tgataattta agagctaacc agttaccaca 4855 catctatgat ataaccctaa cacacacaga aaagcataca tgcaaaaaga aatgactaat 4915 tagggtacat ttataattgc atctaggtaa tttttaccct aatgtcttca taaagtactt 4975 gagtgtaatg tttgttacct ccaacagaac taaatgttct atggttatga aagaatatat 5035 ttatttaaag cattgctttt attttgaaaa gcttcttaat taatttgatt aacaaatatg 5095 ctaatttggg gaaacctaga gaagataatt gttgaaattt tgcaaatata aacatctcct 5155 atagcttctg tgttatttct gacttcttaa cactattatg tttatgttgc acattactga 5215 aagagtaaag atatgaaaaa aacacttatt gttttctttt attgtgaatt gaaaaagcaa 5275 agctaatgaa aatgggttac tacatcaaaa atatcttaaa gagtttgcta tttccatgga 5335 ccagatatga tgaaattatt ccctgggttt aaaactgggc actcgaggag gaggtacctg 5395 aagtcatttg aaggcaagtt tccaatgatg ctacaatggc ctgaaaaaat ttctttaccc 5455 tctgttatat ttaacttgct ggtaggagga atagtggaat gcaggtgtta agccctttgt 5515 ggtgaaaaag aggttctata gacagaaaca aaacccacct tacatcagct gattggttga 5575 ttttactagt gtacctcttc atctacttga attctatttg gtaaatccat gtctttactg 5635 gatatacagt taggtgggaa gaggagataa aggatgacaa actctcaaac aatatttata 5695 catttattta ctccagggtc aaatccaatc cttggaagta gcttctctag tttattttat 5755 ttgtcccaga gctctactca cacttaggac ccacccaaaa attctcaaaa acgtaatatg 5815 gattctgcct catctgatgc tatttctggc agtgggttgt cagccatact ctgcttcatt 5875 ccactgggtg tccttgctag atggggagtg agatgtggag cagggaggag ctttggattc 5935 tgggagtgga ggtggcaagg gaaaagtctc ctagtctcct gtgatgttcc tgcctccaga 5995 tagaatagca aaaacaaaca attttttttt gtgtattatg cctccatgac attgttacat 6055 tctatgagga gcatctgtct cctttctaga cttgaactgt ggtagaaaaa gcccccttct 6115 ctcttctatc tacttagatt tggtgatgct aggaatgtag tgttttagat attaattcta 6175 tttttattta ttcattttta catcaccaat aggatctgag gtggagatgg cgggtattat 6235 cactggcatt ttacaggtga gaaagcccaa agccactgag gtaattaatg gaataattga 6295 ttttgaactt gggtctgtct gatttcatgt gcaagattat atacttagtg attttgattt 6355 taagtttatt cttaacattt taaaccagac tattaactct tacctttata accacagata 6415 caaagaactg tatcatttat tttctgaata taaaatatta atggtcaata taaaaataca 6475 aaaatagaga actatataca acagaaaagc aaaattaccc actaataaca ttttgattta 6535 tatcccttta gacactgttt agagtttata catatatgta aatatgcttg tattttaaca 6595 aaattgagat attatataaa ctgtttgtag cagggtgttt aaaattttaa caatatgtta 6655 tggatatctt tctgtgtcaa taaatgtgta tttacattag a 6696

<210> SEQ ID NO 47
<211> LENGTH: 1095
<212> TYPE: PRT
<213> ORGANISM: Homo sapiens

<400> SEQUENCE: 47

Met Ala Glu Gly Ala Ala Gly Arg Glu Asp Pro Ala Pro Pro Asp Ala
1 5 10 15

Ala Gly Gly Glu Asp Asp Pro Arg Val Gly Pro Asp Ala Ala Gly Asp
20 25 30

Cys Val Thr Ala Ala Ser Gly Gly Arg Met Arg Asp Arg Arg Ser Gly
35 40 45

Val Ala Leu Pro Gly Ala Ala Gly Thr Pro Ala Asp Ser Glu Ala Gly
50 55 60

Leu Leu Glu Ala Ala Arg Ala Thr Pro Arg Arg Ser Ser Ile Ile Lys
65 70 75 80

Asp Pro Ser Asn Gln Lys Cys Gly Gly Arg Lys Lys Thr Val Ser Phe
85 90 95

Ser Ser Met Pro Ser Glu Lys Lys Ile Ser Ser Ala Asn Asp Cys Ile
100 105 110

Ser Phe Met Gln Ala Gly Cys Glu Leu Lys Lys Val Arg Pro Asn Ser
115 120 125

Arg Ile Tyr Asn Arg Phe Phe Thr Leu Asp Thr Asp Leu Gln Ala Leu
130 135 140

Arg Trp Glu Pro Ser Lys Lys Asp Leu Glu Lys Ala Lys Leu Asp Ile
145 150 155 160

Ser Ala Ile Lys Glu Ile Arg Leu Gly Lys Asn Thr Glu Thr Phe Arg
165 170 175

Asn Asn Gly Leu Ala Asp Gln Ile Cys Glu Asp Cys Ala Phe Ser Ile
180 185 190

Leu His Gly Glu Asn Tyr Glu Ser Leu Asp Leu Val Ala Asn Ser Ala
195 200 205

Asp Val Ala Asn Ile Trp Val Ser Gly Leu Arg Tyr Leu Val Ser Arg
210 215 220

Ser Lys Gln Pro Leu Asp Phe Met Glu Gly Asn Gln Asn Thr Pro Arg
225 230 235 240

Phe Met Trp Leu Lys Thr Val Phe Glu Ala Ala Asp Val Asp Gly Asn
245 250 255

Gly Ile Met Leu Glu Asp Thr Ser Val Glu Leu Ile Lys Gln Leu Asn
260 265 270

Pro Thr Leu Lys Glu Ala Lys Ile Arg Leu Lys Phe Lys Glu Ile Gln
275 280 285

```
Lys Ser Lys Glu Lys Leu Thr Thr Arg Val Thr Glu Glu Glu Phe Cys
    290                 295                 300

Glu Ala Phe Cys Glu Leu Cys Thr Arg Pro Glu Val Tyr Phe Leu Leu
305                 310                 315                 320

Val Gln Ile Ser Lys Asn Lys Glu Tyr Leu Asp Ala Asn Asp Leu Met
                325                 330                 335

Leu Phe Leu Glu Ala Glu Gln Gly Val Thr His Ile Thr Glu Asp Ile
            340                 345                 350

Cys Leu Asp Ile Ile Arg Arg Tyr Glu Leu Ser Glu Glu Gly Arg Gln
        355                 360                 365

Lys Gly Phe Leu Ala Ile Asp Gly Phe Thr Gln Tyr Leu Leu Ser Ser
    370                 375                 380

Glu Cys Asp Ile Phe Asp Pro Glu Gln Lys Lys Val Ala Gln Asp Met
385                 390                 395                 400

Thr Gln Pro Leu Ser His Tyr Tyr Ile Asn Ala Ser His Asn Thr Tyr
                405                 410                 415

Leu Ile Glu Asp Gln Phe Arg Gly Pro Ala Asp Ile Asn Gly Tyr Ile
            420                 425                 430

Arg Ala Leu Lys Met Gly Cys Arg Ser Val Glu Leu Asp Val Ser Asp
        435                 440                 445

Gly Ser Asp Asn Glu Pro Ile Leu Cys Asn Arg Asn Asn Met Thr Thr
    450                 455                 460

His Val Ser Phe Arg Ser Val Ile Glu Val Ile Asn Lys Phe Ala Phe
465                 470                 475                 480

Val Ala Ser Glu Tyr Pro Leu Ile Leu Cys Leu Gly Asn His Cys Ser
                485                 490                 495

Leu Pro Gln Gln Lys Val Met Ala Gln Gln Met Lys Lys Val Phe Gly
            500                 505                 510

Asn Lys Leu Tyr Thr Glu Ala Pro Leu Pro Ser Glu Ser Tyr Leu Pro
        515                 520                 525

Ser Pro Glu Lys Leu Lys Arg Met Ile Ile Val Lys Gly Lys Lys Leu
    530                 535                 540

Pro Ser Asp Pro Asp Val Leu Glu Gly Glu Val Thr Asp Glu Asp Glu
545                 550                 555                 560

Glu Ala Glu Met Ser Arg Arg Met Ser Val Asp Tyr Asn Gly Glu Gln
                565                 570                 575

Lys Gln Ile Arg Leu Cys Arg Glu Leu Ser Asp Leu Val Ser Ile Cys
            580                 585                 590

Lys Ser Val Gln Tyr Arg Asp Phe Glu Leu Ser Met Lys Ser Gln Asn
        595                 600                 605

Tyr Trp Glu Met Cys Ser Phe Ser Glu Thr Glu Ala Ser Arg Ile Ala
    610                 615                 620

Asn Glu Tyr Pro Glu Asp Phe Val Asn Tyr Asn Lys Lys Phe Leu Ser
625                 630                 635                 640

Arg Ile Tyr Pro Ser Ala Met Arg Ile Asp Ser Ser Asn Leu Asn Pro
                645                 650                 655

Gln Asp Phe Trp Asn Cys Gly Cys Gln Ile Val Ala Met Asn Phe Gln
            660                 665                 670

Thr Pro Gly Pro Met Met Asp Leu His Thr Gly Trp Phe Leu Gln Asn
        675                 680                 685

Gly Gly Cys Gly Tyr Val Leu Arg Pro Ser Ile Met Arg Asp Glu Val
    690                 695                 700
```

```
Ser Tyr Phe Ser Ala Asn Thr Lys Gly Ile Leu Pro Gly Val Ser Pro
705                 710                 715                 720

Leu Ala Leu His Ile Lys Ile Ile Ser Gly Gln Asn Phe Pro Lys Pro
                725                 730                 735

Lys Gly Ala Cys Ala Lys Gly Asp Val Ile Asp Pro Tyr Val Cys Ile
            740                 745                 750

Glu Ile His Gly Ile Pro Ala Asp Cys Ser Glu Gln Arg Thr Lys Thr
        755                 760                 765

Val Gln Gln Asn Ser Asp Asn Pro Ile Phe Asp Glu Thr Phe Glu Phe
    770                 775                 780

Gln Val Asn Leu Pro Glu Leu Ala Met Ile Arg Phe Val Val Leu Asp
785                 790                 795                 800

Asp Asp Tyr Ile Gly Asp Glu Phe Ile Gly Gln Tyr Thr Ile Pro Phe
                805                 810                 815

Glu Cys Leu Gln Pro Gly Tyr Arg His Val Pro Leu Arg Ser Phe Val
            820                 825                 830

Gly Asp Ile Met Glu His Val Thr Leu Phe Val His Ile Ala Ile Thr
        835                 840                 845

Asn Arg Ser Gly Gly Gly Lys Ala Gln Lys Arg Ser Leu Ser Val Arg
    850                 855                 860

Met Gly Lys Lys Val Arg Glu Tyr Thr Met Leu Arg Asn Ile Gly Leu
865                 870                 875                 880

Lys Thr Ile Asp Asp Ile Phe Lys Ile Ala Val His Pro Leu Arg Glu
                885                 890                 895

Ala Ile Asp Met Arg Glu Asn Met Gln Asn Ala Ile Val Ser Ile Lys
            900                 905                 910

Glu Leu Cys Gly Leu Pro Pro Ile Ala Ser Leu Lys Gln Cys Leu Leu
        915                 920                 925

Thr Leu Ser Ser Arg Leu Ile Thr Ser Asp Asn Thr Pro Ser Val Ser
    930                 935                 940

Leu Val Met Lys Asp Ser Phe Pro Tyr Leu Glu Pro Leu Gly Ala Ile
945                 950                 955                 960

Pro Asp Val Gln Lys Lys Met Leu Thr Ala Tyr Asp Leu Met Ile Gln
                965                 970                 975

Glu Ser Arg Phe Leu Ile Glu Met Ala Asp Thr Val Gln Glu Lys Ile
            980                 985                 990

Val Gln Cys Gln Lys Ala Gly Met  Glu Phe His Glu Glu  Leu His Asn
        995                 1000                1005

Leu Gly  Ala Lys Glu Gly Leu  Lys Gly Arg Lys Leu  Asn Lys Ala
    1010                1015                1020

Thr Glu  Ser Phe Ala Trp Asn  Ile Thr Val Leu Lys  Gly Gln Gly
    1025                1030                1035

Asp Leu  Leu Lys Asn Ala Lys  Asn Glu Ala Ile Glu  Asn Met Lys
    1040                1045                1050

Gln Ile  Gln Leu Ala Cys Leu  Ser Cys Gly Leu Ser  Lys Ala Pro
    1055                1060                1065

Ser Ser  Ser Ala Glu Ala Lys  Ser Lys Arg Ser Leu  Glu Ala Ile
    1070                1075                1080

Glu Glu  Lys Glu Ser Ser Glu  Glu Asn Gly Lys Leu
    1085                1090                1095
```

<210> SEQ ID NO 48
<211> LENGTH: 3118
<212> TYPE: DNA

```
<213> ORGANISM: Homo sapiens
<220> FEATURE:
<221> NAME/KEY: CDS
<222> LOCATION: (340)..(1686)

<400> SEQUENCE: 48

tctcattgca ttgcgcagag ctcagccatc tttctcatcc gtcaggcatt cctgagaaag     60

agggccactc tacctctctt gctgccagcc ttcactccag caaggagggt gctgggtgac    120

ctgagcccac atagccccga gcacccgaag cacacacagc agagtcctct ggactttgag    180

gaagaaccca cagcaggagg aagtcagcag ggagtggctg tgtgaaacct gggaccactt    240

ctgccttcct acgtggcagt ggctcagagt tatttgagtg ctgtcaaact gagctgattg    300

ctgccctagt attagatcag tccatagaaa gtgggagca atg gca ctg aca ctg      354
                                           Met Ala Leu Thr Leu
                                           1               5

cta gag gat tgg tgc aag ggg atg gac atg gac ccc aga aag gcc ctg      402
Leu Glu Asp Trp Cys Lys Gly Met Asp Met Asp Pro Arg Lys Ala Leu
                10                  15                  20

ctg att gta ggc atc ccc atg gag tgt agt gag gtg gaa att cag gac      450
Leu Ile Val Gly Ile Pro Met Glu Cys Ser Glu Val Glu Ile Gln Asp
            25                  30                  35

act gtg aag gca ggc tta cag ccc ctg tgc gca tac agg gtc cta ggg      498
Thr Val Lys Ala Gly Leu Gln Pro Leu Cys Ala Tyr Arg Val Leu Gly
        40                  45                  50

aga atg ttc agg agg gaa gac aat gcc aag gca gtc ttc att gaa ctg      546
Arg Met Phe Arg Arg Glu Asp Asn Ala Lys Ala Val Phe Ile Glu Leu
    55                  60                  65

gct gac act gtc aat tac act act ctg ccc agt cac ata cca gga aag      594
Ala Asp Thr Val Asn Tyr Thr Thr Leu Pro Ser His Ile Pro Gly Lys
70                  75                  80                  85

ggt ggc tcc tgg gaa gtg gtg gta aaa ccc cgt aac cca gat gat gag      642
Gly Gly Ser Trp Glu Val Val Val Lys Pro Arg Asn Pro Asp Asp Glu
                90                  95                  100

ttt ctc agt aga ctg aac tac ttc ctg aaa gat gag ggc cga agt atg      690
Phe Leu Ser Arg Leu Asn Tyr Phe Leu Lys Asp Glu Gly Arg Ser Met
            105                 110                 115

aca gat gtg gcc aga gcc ctg gga tgt tgc agc ctc cct gcc gag agc      738
Thr Asp Val Ala Arg Ala Leu Gly Cys Cys Ser Leu Pro Ala Glu Ser
        120                 125                 130

ctg gat gca gag gtc atg ccc caa gtt aga tcc cca cct tta gag cct      786
Leu Asp Ala Glu Val Met Pro Gln Val Arg Ser Pro Pro Leu Glu Pro
    135                 140                 145

ccg aaa gaa agt atg tgg tac agg aaa ctg aaa gtg ttt tcg gga act      834
Pro Lys Glu Ser Met Trp Tyr Arg Lys Leu Lys Val Phe Ser Gly Thr
150                 155                 160                 165

gct tcc cct agc cca ggc gaa gag acc ttt gaa gac tgg cta gag cag      882
Ala Ser Pro Ser Pro Gly Glu Glu Thr Phe Glu Asp Trp Leu Glu Gln
                170                 175                 180

gtc act gag ata atg ccc ata tgg caa gtg tct gag gtg gag aag agg      930
Val Thr Glu Ile Met Pro Ile Trp Gln Val Ser Glu Val Glu Lys Arg
            185                 190                 195

cgg cgt ttg ctg gag agc tta cgt ggg cct gct ctg tca atc atg cgg      978
Arg Arg Leu Leu Glu Ser Leu Arg Gly Pro Ala Leu Ser Ile Met Arg
        200                 205                 210

gtg ctc cag gcc aac aat gac tcc ata act gtg gag cag tgc ctt gac     1026
Val Leu Gln Ala Asn Asn Asp Ser Ile Thr Val Glu Gln Cys Leu Asp
    215                 220                 225

gcc cta aag cag atc ttt ggg gat aaa gag gac ttt aga gcc tct cag     1074
Ala Leu Lys Gln Ile Phe Gly Asp Lys Glu Asp Phe Arg Ala Ser Gln
```

```
230                 235                 240                 245

ttt agg ttt ctg cag acc tct ccg aag att gga gag aaa gtc tcc act      1122
Phe Arg Phe Leu Gln Thr Ser Pro Lys Ile Gly Glu Lys Val Ser Thr
                250                 255                 260

ttc ctg ctg cgc tta gag ccc ctg ctg cag aaa gcc gtg cac aag agc      1170
Phe Leu Leu Arg Leu Glu Pro Leu Leu Gln Lys Ala Val His Lys Ser
            265                 270                 275

ccc ttg tca gtg cgc agc aca gac atg att cgt ctg aaa cat ctc tta      1218
Pro Leu Ser Val Arg Ser Thr Asp Met Ile Arg Leu Lys His Leu Leu
        280                 285                 290

gct cgg gtc gcc atg acc ccc gcc ctc agg ggc aag ctg gag ctc ttg      1266
Ala Arg Val Ala Met Thr Pro Ala Leu Arg Gly Lys Leu Glu Leu Leu
    295                 300                 305

gat cag cga ggg tgt cct ccc aat ttt ctg gag tta atg aag ctc att      1314
Asp Gln Arg Gly Cys Pro Pro Asn Phe Leu Glu Leu Met Lys Leu Ile
310                 315                 320                 325

cga gat gaa gaa gag tgg gag aac act gag gca gtg atg aag aat aag      1362
Arg Asp Glu Glu Glu Trp Glu Asn Thr Glu Ala Val Met Lys Asn Lys
                330                 335                 340

gag aag cca tca ggg aga ggc cgg ggg gcc tcc ggt aga cag gca aga      1410
Glu Lys Pro Ser Gly Arg Gly Arg Gly Ala Ser Gly Arg Gln Ala Arg
            345                 350                 355

gca gaa gcc agt gtc tct gca cct cag gcc acc gtg cag gca agg tct      1458
Ala Glu Ala Ser Val Ser Ala Pro Gln Ala Thr Val Gln Ala Arg Ser
        360                 365                 370

ttt agc gac agc agc ccc cag acc ata cag gga ggc tta ccc cca tta      1506
Phe Ser Asp Ser Ser Pro Gln Thr Ile Gln Gly Gly Leu Pro Pro Leu
    375                 380                 385

gtg aaa cgc agg cgg ctg tta ggc agt gaa agc act agg gga gaa gac      1554
Val Lys Arg Arg Arg Leu Leu Gly Ser Glu Ser Thr Arg Gly Glu Asp
390                 395                 400                 405

cat ggc cag gcc acg tat ccc aag gct gaa aac cag act cca ggc agg      1602
His Gly Gln Ala Thr Tyr Pro Lys Ala Glu Asn Gln Thr Pro Gly Arg
                410                 415                 420

gag ggg cca cag gct gca gga gag gag ttg gga aac gag gca ggg gct      1650
Glu Gly Pro Gln Ala Ala Gly Glu Glu Leu Gly Asn Glu Ala Gly Ala
            425                 430                 435

ggg gcc atg agc cat ccc aag ccc tgg gaa aca tag gctcagaaga           1696
Gly Ala Met Ser His Pro Lys Pro Trp Glu Thr
        440                 445

ccgaagcact ccttcccctg gcaggcagca gggacatttg aacaagggga aggggcagct    1756

tacactaaca gggaacttga ctggggcaga gggacaggga agccaggtcg agatcaagcc    1816

cccttacttt ccaccagctg gaagggactt caccaaccaa gaccaaatag catctggttc    1876

agtgggggcc gggcccatag cccctaacag gtacaggaga cacaagcggg gaaccactac    1936

acttagcaca tggggtgcct gggcttcaga tggggacccc agcgaagcag gggctgaaga    1996

aggtgtggct gggggctctg gcctggtcct ctggacaccc ccaaatatct accctgtgga    2056

ctttgagctg agcatgccca ctggcaccca ggccacgtgg gacctggagg agcctgcctg    2116

gggcctgcct ctgccagaag gagccagggc tgctgaggaa gagctgtggg gcagaagtga    2176

agccccgcag gggaggccac agggtccagc ctgtctttag gatcatctac actgcatgag    2236

gggagcccca ggaaggcagc attcataagc ccctgcacca gtgaggaaga gaaagaggag    2296

gagaattaag aagaggatga tcgggaggag gaagaggaga ataaggagga gcaggaggaa    2356

gagggggagg agaaggagga agagggggag gaggaagagg ggaaggagga ggaagaagtg    2416

taagaagaga agagaggatg tgttgggggt gggtagttgt ttttggtttg cgtcatcatc    2476
```

```
aggcccgggc tctgctcact gctgttccgt gtcaagaact ccacctctgc tttgccggtg   2536

tagatctcgg ccagtggctg cttgttctct tggggatgtg tgtgttttta tctgagcagc   2596

tcctttccag agtaccccag cgcagttcca ggagacggtg ggaaggaggc atggcagacg   2656

ctcaccttgt gactgtgacc tcgactgcag gaggaccaac cagacacggg aaggagcagg   2716

gctgcctgag gctccccagg aagctttgtg ctttggcgtt ccacccctgc tgttactcgt   2776

gactcagttt cctcaacttg gtggggtgtt ccctgctatg ttttccagca tcctgtgact   2836

gtcctgtgca gtctataggg cagggccctg ccccagcggg tgggctcagg agggggttcc   2896

ctgaagcgag tacacattgc cagagcccac catcctggca agaggtggat cctggggccc   2956

tatggaagga gggatgtggt ggggggggcc acactgaggg aggggccggg gacttgtgac   3016

ctgtagtggc tgtttgcagt ttctctctgt gttagattcc cttttcttca gcagtttcag   3076

ttcatgtttc tcttcagtaa attttgttca gtgttccaaa aa                      3118


<210> SEQ ID NO 49
<211> LENGTH: 448
<212> TYPE: PRT
<213> ORGANISM: Homo sapiens

<400> SEQUENCE: 49

Met Ala Leu Thr Leu Leu Glu Asp Trp Cys Lys Gly Met Asp Met Asp
1               5                   10                  15

Pro Arg Lys Ala Leu Leu Ile Val Gly Ile Pro Met Glu Cys Ser Glu
            20                  25                  30

Val Glu Ile Gln Asp Thr Val Lys Ala Gly Leu Gln Pro Leu Cys Ala
        35                  40                  45

Tyr Arg Val Leu Gly Arg Met Phe Arg Arg Glu Asp Asn Ala Lys Ala
    50                  55                  60

Val Phe Ile Glu Leu Ala Asp Thr Val Asn Tyr Thr Thr Leu Pro Ser
65                  70                  75                  80

His Ile Pro Gly Lys Gly Gly Ser Trp Glu Val Val Val Lys Pro Arg
                85                  90                  95

Asn Pro Asp Asp Glu Phe Leu Ser Arg Leu Asn Tyr Phe Leu Lys Asp
            100                 105                 110

Glu Gly Arg Ser Met Thr Asp Val Ala Arg Ala Leu Gly Cys Cys Ser
        115                 120                 125

Leu Pro Ala Glu Ser Leu Asp Ala Glu Val Met Pro Gln Val Arg Ser
    130                 135                 140

Pro Pro Leu Glu Pro Pro Lys Glu Ser Met Trp Tyr Arg Lys Leu Lys
145                 150                 155                 160

Val Phe Ser Gly Thr Ala Ser Pro Ser Pro Gly Glu Glu Thr Phe Glu
                165                 170                 175

Asp Trp Leu Glu Gln Val Thr Glu Ile Met Pro Ile Trp Gln Val Ser
            180                 185                 190

Glu Val Glu Lys Arg Arg Arg Leu Leu Glu Ser Leu Arg Gly Pro Ala
        195                 200                 205

Leu Ser Ile Met Arg Val Leu Gln Ala Asn Asn Asp Ser Ile Thr Val
    210                 215                 220

Glu Gln Cys Leu Asp Ala Leu Lys Gln Ile Phe Gly Asp Lys Glu Asp
225                 230                 235                 240

Phe Arg Ala Ser Gln Phe Arg Phe Leu Gln Thr Ser Pro Lys Ile Gly
                245                 250                 255
```

```
Glu Lys Val Ser Thr Phe Leu Leu Arg Leu Glu Pro Leu Leu Gln Lys
            260                 265                 270

Ala Val His Lys Ser Pro Leu Ser Val Arg Ser Thr Asp Met Ile Arg
        275                 280                 285

Leu Lys His Leu Leu Ala Arg Val Ala Met Thr Pro Ala Leu Arg Gly
    290                 295                 300

Lys Leu Glu Leu Leu Asp Gln Arg Gly Cys Pro Pro Asn Phe Leu Glu
305                 310                 315                 320

Leu Met Lys Leu Ile Arg Asp Glu Glu Glu Trp Glu Asn Thr Glu Ala
                325                 330                 335

Val Met Lys Asn Lys Glu Lys Pro Ser Gly Arg Gly Arg Gly Ala Ser
            340                 345                 350

Gly Arg Gln Ala Arg Ala Glu Ala Ser Val Ser Ala Pro Gln Ala Thr
        355                 360                 365

Val Gln Ala Arg Ser Phe Ser Asp Ser Ser Pro Gln Thr Ile Gln Gly
    370                 375                 380

Gly Leu Pro Pro Leu Val Lys Arg Arg Arg Leu Leu Gly Ser Glu Ser
385                 390                 395                 400

Thr Arg Gly Glu Asp His Gly Gln Ala Thr Tyr Pro Lys Ala Glu Asn
                405                 410                 415

Gln Thr Pro Gly Arg Glu Gly Pro Gln Ala Ala Gly Glu Glu Leu Gly
            420                 425                 430

Asn Glu Ala Gly Ala Gly Ala Met Ser His Pro Lys Pro Trp Glu Thr
        435                 440                 445


<210> SEQ ID NO 50
<211> LENGTH: 8861
<212> TYPE: DNA
<213> ORGANISM: Homo sapiens
<220> FEATURE:
<221> NAME/KEY: CDS
<222> LOCATION: (135)..(818)

<400> SEQUENCE: 50

agtgctgatg ttggagccgg ttagcgaacc ccaagagtgc agagtgtgga gcgtggagcg      60

ccgggactgt gcacgcttga ccggaagccc agaccagtgc ggtcctagcc agagagaaag     120

gacatttgcc aaca atg aga cac gaa gcg ccc atg cag atg gcc tct gcc       170
                Met Arg His Glu Ala Pro Met Gln Met Ala Ser Ala
                1               5                   10

caa gat gcc agg tac ggc cag aaa gac tcc tct gat cag aac ttt gac       218
Gln Asp Ala Arg Tyr Gly Gln Lys Asp Ser Ser Asp Gln Asn Phe Asp
        15                  20                  25

tac atg ttc aaa tta ctc atc atc ggc aat agc agt gtg ggg aaa aca       266
Tyr Met Phe Lys Leu Leu Ile Ile Gly Asn Ser Ser Val Gly Lys Thr
    30                  35                  40

tct ttt cta ttc cgt tat gca gat gac tcc ttt aca tct gca ttc gtc       314
Ser Phe Leu Phe Arg Tyr Ala Asp Asp Ser Phe Thr Ser Ala Phe Val
45                  50                  55                  60

agc aca gtt ggg atc gat ttc aaa gta aaa act gta ttc aaa aat gaa       362
Ser Thr Val Gly Ile Asp Phe Lys Val Lys Thr Val Phe Lys Asn Glu
                65                  70                  75

aag aga atc aag ctt cag att tgg gac aca gca ggc cag gaa aga tac       410
Lys Arg Ile Lys Leu Gln Ile Trp Asp Thr Ala Gly Gln Glu Arg Tyr
            80                  85                  90

agg act atc acc aca gcc tat tat cgt gga gcc atg ggc ttt att tta       458
Arg Thr Ile Thr Thr Ala Tyr Tyr Arg Gly Ala Met Gly Phe Ile Leu
        95                  100                 105
```

```
atg tat gac att aca aat gaa gaa tcc ttc aat gca gta caa gat tgg      506
Met Tyr Asp Ile Thr Asn Glu Glu Ser Phe Asn Ala Val Gln Asp Trp
    110                 115                 120

tca act caa atc aaa aca tac tct tgg gac aat gcc caa gtt att ctg      554
Ser Thr Gln Ile Lys Thr Tyr Ser Trp Asp Asn Ala Gln Val Ile Leu
125                 130                 135                 140

gtt ggg aac aag tgt gac atg gaa gac gag cgg gtc atc tca act gag      602
Val Gly Asn Lys Cys Asp Met Glu Asp Glu Arg Val Ile Ser Thr Glu
                145                 150                 155

cga ggt caa cat tta gga gaa cag ctt ggg ttt gag ttt ttt gaa aca      650
Arg Gly Gln His Leu Gly Glu Gln Leu Gly Phe Glu Phe Phe Glu Thr
            160                 165                 170

agt gcc aag gac aac att aat gtc aag cag aca ttt gag cgc ctt gtg      698
Ser Ala Lys Asp Asn Ile Asn Val Lys Gln Thr Phe Glu Arg Leu Val
        175                 180                 185

gat atc atc tgc gac aaa atg tca gag agt ttg gag act gat cct gcc      746
Asp Ile Ile Cys Asp Lys Met Ser Glu Ser Leu Glu Thr Asp Pro Ala
    190                 195                 200

atc act gct gca aag cag aac acg aga ctc aag gaa act cct cct cca      794
Ile Thr Ala Ala Lys Gln Asn Thr Arg Leu Lys Glu Thr Pro Pro Pro
205                 210                 215                 220

ccg cag ccc aac tgt gcc tgc tag tgtccccgtg cacacaggca gctccagggg     848
Pro Gln Pro Asn Cys Ala Cys
                225

gctctggttg ccaacaaaca gcatttgtaa atggtctatt agccttcatt tatactgcct    908

aacaattatt tgaaggaata aattgatgtc aatggctcgt acgcattcaa ttcttgggag    968

ctttcctgtt taatatgtgg caaatatgtg atcttaaatt tataaggact atccatctat   1028

aaacatctgg tacctgcatg tgacttgtta tttatttgtc tgctaggctc tttttgtttc   1088

aaatttgttc tcagactact tctgggacat cagactataa tctcactaca actggctttt   1148

gtcccattga ttcaaattat gctattcact tgtaggaatg atgaccaagg aattgcttgt   1208

gtgtgtgtgt gtgtgtgtgt gtgtgcacgc atgcccgcat gcgtgcagag gaagaagtca   1268

caagacttca tttgctttac tcttagttga aaatcaaatg gaagtttttc tcatgattag   1328

ggacgctgtc acgagtctgg tcagtttact gttgggaact gtgtctttat ttcactgtta   1388

ttaataactg agatcattgg cctataaaga aattgaaatg ttgtttttaa ggtccttgca   1448

atttcctaa gtcattaata ttacctgact ggggctattt aacaataatc ttcgtttaca   1508

catttaaata agcaagtatc tacccaggac tgctttttcc actgatcctt cccaattctg   1568

tgaatattca acatcattga acagattgag acatatctac tgaatgccag ttatgcaaca   1628

agcattttaa ccaagaaggg tatgagtagc tatggaattc caaggtccaa gccccccttat   1688

ttttcaatga cttgccttcc ccaaccccca taatgcacac caccaccacc atcactttct   1748

ggaaccatca ccaactcttg gactagagct tatgttgaag cttgttaggg ctcctctttc   1808

cgtaggatgt agacttgcct ccccaaacac ggccatcttc tcaaacctca gctaagttct   1868

tttacctgtt tagatgctat ttaaatcaga tttcaaaggg tccccagttg agaaaaagga   1928

aaattttaat ctttaatcat ctttttaagt ccagatgttc ataaattcta aagcatattc   1988

ctattacgtg aatgcttaag ttacacagga aacattctat aactgtagta tttcaatttc   2048

agaaatattt aggatccata gcaatttaaa agagggagga aaccactgga gcattctaat   2108

tttgtatcac aaacttccta aaggacctat atgaataaag agaaaacaac aaatcctacc   2168

agctgtacag agagcaacag ggaaatttgg cctctgtatc actgtccagc attatttaaa   2228

gctaggattt aggaaggaag caggaattat ttggcagatt tggaaggata gtttcgttaa   2288
```

```
gtgaactttc tactttttg gtggttatgt caaagaattt ttttcctctt ctcaaaaata   2348
gagaggcttc ccatgaaagt attggatgca aatgaaacag gcatacatct aaagatatct   2408
ttggagaata aatccttaca agtcacagaa ctaggtcaca cacattagta agtcaaaagt   2468
tggaaattag gggagagagc atttggaatg ctttaagcat ttccatgtta tttctcacct   2528
tcctagttga agatccacta atcagtagta catttctact ttggtgccct acaaagcaaa   2588
ccttagcata gtaaagacaa gaaaacatta atgttttatt agtttttaat ggggcaacca   2648
acttcaaaat cacaggaatt acagtgacgg gagagaaaga agcaggaggc ataaaaacag   2708
atttgtttgt agcagtagtc tgtttgtaca atgttataat atttctgtaa cttgggccag   2768
aatgtggcca tgttaaatga tatagctatt aagctcactt ttacaatcta aaaggaacta   2828
ataaagccag gaaacccttc tcatcctcct tcacagccct catcccacac atagatgtaa   2888
aaagcttaga aagaatattc tgatggcttt ttcagaagga aggaccttga tgtgtgtatt   2948
gtggtaaaat gaaaagcaaa atgagacagt atttaaaagt gaaagagcag agttttgctc   3008
tgctgaaaac cccttccctg aagaactgat tgctgttgaa gttaattggc ccttagatgg   3068
gaagccctaa gccaagctcc cacttacaca gtgtcaaaca tcccgaagtg gaaacatttt   3128
atgccagtca ggggagagac aggcaacaat agcccaaatg tcattgccaa gaaacatctg   3188
atactttcta atttctaaac cccaatggaa gtgaggcctt tttcattgat tctcagttct   3248
gaaactccca ccctgttagg atttccattc caaataattc aatgagaggt ttccagagaa   3308
acagtcacag agctcaagag aaagaacact taaatgctcc tgctgtaatt gcatcaaaaa   3368
atccgggttt taacatcaaa tttggcaaat ggtgggacca acccaaggtt aactaagtgg   3428
gctttcattg gcattgagct atgttactta taaattataa cactatagtt ccaaggtttt   3488
tcagcctttt ggccaacaca cacacacaca cacacacaca cacacacaca cactatacca   3548
tcatctatca atagtctaaa tacataaata aatgcaggtc atttttatca atggcctaac   3608
taaatttata tttaaaagaa caagactttt aaaaagtaca tactcctgtt ggtttgtaag   3668
ttatacacat ttatctcttg tctttgattt aattaaatta gtgttttaag tatgaattta   3728
ttttcctttg ctactcatta cctgaccact ttcactcctc tagataccct taggaataaa   3788
cctgaactgt tccaaatcga ttcttccaag agctttggtg ttggtacctt cctttctttt   3848
cctaatgcaa ctgaaaaatt agactgaaaa ttatttgact taaatagcca tcctcagagt   3908
gaatcagcat ttcagttttt ggagatgggg atggaagtag aaggtgcaca aagcgtccta   3968
agatggcagt ttgaatgtta gcatcgcatc tacatgctca taagaggaat tgcttcagga   4028
caatgaatca gttcattgtt gctgccccca gtgaacagct ccaactgcct tgatgaactt   4088
ctaatgactg tgaaagctag gaggttcttc tagttcctcc ttagggtcac ttgaagttca   4148
gtattttttt gctgcctggt aactaagtgc taagattttt acttggaaag aaaactatga   4208
caatgccttc agttgtagca gaaagttgtg gcattgtgat aataaacaaa atctacaaag   4268
ttacaaccca aattatacaa gacatcaaaa cactcagtaa acaaatatat atatttcacc   4328
tacttaaatc ttattcatat taattatagg ccttttgttt agtacactgg ttattttta    4388
aggaaccaat ttaaactttc aattttaaat acatctatgc tgacgataga ctttcgggta   4448
tatacaacct tcttcttctc ttttaaaagt taaatacatt ccactattaa ctgaacttcc   4508
atgaagcaac attaatttta gagcatggta gtccataatc agtggttcat tgtgatgtgc   4568
tttatccaac atgtatctta gtgcatggtt gaggatgtac tatgtgatat tttagttaac   4628
```

```
agtgtggcat ttgtgggact atattaaaag catatccaaa ctaccaagct ataccaagct   4688
gaggtaggta acacctgcat gtgaaaaact gtgatatgaa tcttatttat aaaaaagtca   4748
taactaaaac ccttctagac caaaaagtta ctgtgtgttt gttaataatc ttcatagtac   4808
tactggaatg ctcaatcagt tatttttggt gtggcatact tcagagctgg cctgtccgtc   4868
tgaagaaccc tttctctcac aattacagtt tgcatgacta gaacccggaa ctctgttcct   4928
ttgcgtgtat agtcacttag tgtgctgtcc gggtgccaca tgagcaacta cacccatgtg   4988
gcctttctgt cactccctgg aaaatgcaac ctctacagct ctgctcagct ctgcctgtgt   5048
gcattgatta ccttcgcttt agtagtttgc ctgtaaaatg gtgaagtctt tctgatatgc   5108
tgaacctttg agccagcttt tgggagttct tcatatttta ggtgaatttt tgaccaaagt   5168
caattaaaga cataaacctg ttttatatca tggaatttac tgggccaaat taagtaaaag   5228
atgaagttta tgaccagaat aaaaaagcct ttacccctgc acagcactgt atctaaaggg   5288
ctctaggttg tagaaatata gtacccccta acagggaaaa accaagttgg gggatttatc   5348
taaaatgtat ctacctattg ttactggtat ttcacaaata atttttttct taaaaatatt   5408
tacagaaatg cttgacactc cggtcaaata atatttccct ttgatagatt gaaatatttg   5468
cttttagatt acacatacag tgctgccctt ctcaacagtc actcacacgc tcactcgcct   5528
gtacaaaggt atcaggcaaa cactgatact tttttttaag aaggcaaaat tccatctatg   5588
gtgctttctc agtgctaggg aaaagggagc ttttactatg ttccagctat aactcacatc   5648
ttacttataa ggtccataaa atcggttctt cacactgatt tcgtttgatt agtctgtgca   5708
tgtaattaat ttcctccaaa cagagagagt ggaggggaaa taaattttgc aagcattcta   5768
gataacagaa atgagtcatt ttaaaacctc actcagagct cgagtgttaa gatcagacca   5828
tctagctagt ggacaaattg aactttctat ttgcagttct cttttacttt ctgactttct   5888
tttaaattac tgcagttttt caaaacacta tcctcatgga atgacaggac caagaataga   5948
aaatgagact caaatttcac catttacttc ccatcagcaa ccattactgg tggagtttca   6008
aacagtcatt acttgctgaa atgaggtttg aggttacctg tgtatttcat tcacctgtgt   6068
taatatttcc ttcatcgtgg acaagtgaga gttggctgtg gctttatttc ttgaggcaaa   6128
ttattttgca ttcatgttat ttggggctag gtattgctta ggttcgtgaa tgctgttctt   6188
acagacacag atggtacctg agcccctcag acacctgccc tttcagggac gtgagcatga   6248
cttacatctg tcaagtggtt ccatacttct tgtaaaagta aagtttgggt attgtttgct   6308
gtatcaatat gatggctttc catgcattgt ctcattatcc ctaggatacg tgctaaagga   6368
aaactgtcct gtaattcctg ttaatatatt gttaatgtca gacgtgatgt gataccgtta   6428
gactgtccaa atgtacaaca atttaatggt gtttgtagaa ctgatatgtc ttaaatgttg   6488
catgaaatat gttataaaaa tagatttgtt ttctattttc aacacctcag aattgagggt   6548
tcatgggcca ataagtgcaa tatttaatga ctcactcagt gtatataaac tagtatgaaa   6608
gagtgaatta taatgaatgt gtgagatgct ttgatagctg tgtgacttat tcaaatgatt   6668
ttcttgtagc tgtatttgtc tagtggtgca atttatacag taaatatctt attggtgtca   6728
tgtaaaaccc ctctgtgcct acttcaaaat actttttttct tataaaacca aacatttagt   6788
atctggaaat atgtgtcaat tttatctctt agaattgtgg attttattgt caagacagaa   6848
tggctgttca tttattttat aaaagcatct ccttctataa ctcaaaattt tctttaagtg   6908
tcatataaaa gtgtacattt tacttttaag caactaattt agatacctaa gaaaaactat   6968
gtgcattagg aaaagtcatg tttttcttct cagaaaggtt gatcacatga catgtctact   7028
```

aagaatttc acctctgtac ttgtatgtat attttattgt tactcaatct tgtattttat 7088 ttacaaattc aacactgtca accctgggaa ttctaaaata ccaatgtatt tttaggttgt 7148 agctaatgtt gtattcactt tcaattctca gttgtccaca ctggtgatat aagaggaaca 7208 aatcagaatc attaaatact ttgtaatgcc atcataaact catatattca tcctcaaact 7268 cccttgttta atgctaattg gtggcctgga acttcactga gatgcaaaat caagaactga 7328 agcctagttg ctagataacg aaaagctata aatgtttatg tatgtgaatt ttaaattaga 7388 ataaccgtct taaactccta cttgccattt ctaaggcaaa gcattcattt taatattgta 7448 ctttgccttt tcattcagtt agtggagtaa gtcatgaaac ccttaggaag aaaaacaagt 7508 tatgacttat tcactaaaat tgatgcaaga cagttggttc tagatgacca tggccatgtg 7568 ttcatcatat aaaaccttca gttctctcta tggtgcttgg ctggagattg acatgtgagg 7628 atgtgccaat catattaaat ggatttggtc tatgtgggtg atatgtggcc tgaatgtaac 7688 tgtgatagac tgaaatttgt tcttagctct caaaatccac tgaagaagtc aagtgaaggt 7748 gggtaaaata gggagattag tgacaacttt gtgccaaatt ttttaaaaaa tggaagcagg 7808 tagccaatat tagaatgata atttaagggt gtggttgaat tttagttagt tgtcacatag 7868 ttattgaacc tcatatgctc agtgctgtgg gaatcaaaca tggaagaggt atggctcctg 7928 cccctaatga gaacaagggg gaaaaatcca gatataatct aaatgctagg ttatgtcagg 7988 gtataggaac acagagaatg gggacctgt aagaactgga agagtcagag agggctccat 8048 tgaagaggtc aaacataatt ccggaaagaa ttaggtagtg aggagattgt gccaggaaaa 8108 taagtgggaa aggccacagt tatgtttcct ttgaatggaa gagagacaaa gctatcagct 8168 atagatcatt gttttcttaa gacagccaaa ctggcccttt gaaaccattc aaattacccc 8228 agtttagctc cctacctttt agtctccgtg aggaagacaa gctgttgcat tatcatattc 8288 ctctgtgctg agcagctcaa gactcagcca caatatgcaa attgctttaa tgccatatta 8348 cggcagttga tttagacatt tgccagtgca ccaaaccatg agagattgtc cgacctaatg 8408 ccacctggca gatgtgtacc cagagatttt tctgtagctc catgtttccc ataaagggca 8468 ttggaaatgc acagatgaag atcttccttt ggaaccaggc acatttggcc ccttctcagt 8528 gactgcactg tggaactctt cttaagaaaa tattgaaaac agcttaatgc tttcatatag 8588 tgaccgacat ttagttgaaa actactgctg catagcaaat attgtgactc ttcatgtgtc 8648 cacaggagct cttgtgtggg tttaaagcta tgaagtgtat tcacattgtg aagttttaat 8708 tatctttatt gaaattaatt gtgtaaaaat ggtatgtgct ctattaggta ttcagtttgt 8768 atgtgaattc tataaagaaa gtggtttttg ttctttgagt ttgttttatt tcttgaagat 8828 tacaataaat atctaagaga ctatattcct gaa 8861

<210> SEQ ID NO 51
<211> LENGTH: 227
<212> TYPE: PRT
<213> ORGANISM: Homo sapiens

<400> SEQUENCE: 51

Met Arg His Glu Ala Pro Met Gln Met Ala Ser Ala Gln Asp Ala Arg
1               5                   10                  15

Tyr Gly Gln Lys Asp Ser Ser Asp Gln Asn Phe Asp Tyr Met Phe Lys
            20                  25                  30

Leu Leu Ile Ile Gly Asn Ser Ser Val Gly Lys Thr Ser Phe Leu Phe
        35                  40                  45

```
Arg Tyr Ala Asp Asp Ser Phe Thr Ser Ala Phe Val Ser Thr Val Gly
    50                  55                  60

Ile Asp Phe Lys Val Lys Thr Val Phe Lys Asn Glu Lys Arg Ile Lys
65                  70                  75                  80

Leu Gln Ile Trp Asp Thr Ala Gly Gln Glu Arg Tyr Arg Thr Ile Thr
                85                  90                  95

Thr Ala Tyr Tyr Arg Gly Ala Met Gly Phe Ile Leu Met Tyr Asp Ile
            100                 105                 110

Thr Asn Glu Glu Ser Phe Asn Ala Val Gln Asp Trp Ser Thr Gln Ile
        115                 120                 125

Lys Thr Tyr Ser Trp Asp Asn Ala Gln Val Ile Leu Val Gly Asn Lys
    130                 135                 140

Cys Asp Met Glu Asp Glu Arg Val Ile Ser Thr Glu Arg Gly Gln His
145                 150                 155                 160

Leu Gly Glu Gln Leu Gly Phe Glu Phe Phe Glu Thr Ser Ala Lys Asp
                165                 170                 175

Asn Ile Asn Val Lys Gln Thr Phe Glu Arg Leu Val Asp Ile Ile Cys
            180                 185                 190

Asp Lys Met Ser Glu Ser Leu Glu Thr Asp Pro Ala Ile Thr Ala Ala
        195                 200                 205

Lys Gln Asn Thr Arg Leu Lys Glu Thr Pro Pro Pro Pro Gln Pro Asn
    210                 215                 220

Cys Ala Cys
225


<210> SEQ ID NO 52
<211> LENGTH: 4176
<212> TYPE: DNA
<213> ORGANISM: Homo sapiens
<220> FEATURE:
<221> NAME/KEY: CDS
<222> LOCATION: (137)..(1210)

<400> SEQUENCE: 52

ccttttcttc gtagcctcca agggagctgg aacaaaaaac gaaaccaaaa cctgcctgct      60

cgctcctctc cccatcgcct gcgttccgct ggttgtgggc tttctgcggc cgctgagggc     120

gcgtctcccc tccgcc atg gca tca gtt ttg aat gtc aag gaa tcc aaa gct     172
                  Met Ala Ser Val Leu Asn Val Lys Glu Ser Lys Ala
                  1               5                   10

cct gaa aga acg gtt gta gtt gct ggt ctt cca gtt gac ctt ttt agt       220
Pro Glu Arg Thr Val Val Val Ala Gly Leu Pro Val Asp Leu Phe Ser
        15                  20                  25

gat caa tta ttg gcc gta tta gtg aag agc cac ttc caa gac att aag       268
Asp Gln Leu Leu Ala Val Leu Val Lys Ser His Phe Gln Asp Ile Lys
    30                  35                  40

aat gag ggc gga gat gtt gaa gat gtg ata tat ccg aca aga acc aag       316
Asn Glu Gly Gly Asp Val Glu Asp Val Ile Tyr Pro Thr Arg Thr Lys
45                  50                  55                  60

gga gtt gca tat gta ata ttc aaa gaa aaa aaa gtt gca gag aat gtc       364
Gly Val Ala Tyr Val Ile Phe Lys Glu Lys Lys Val Ala Glu Asn Val
                65                  70                  75

atc aga caa aag aaa cac tgg cta gca agg aag act aga cat gct gaa       412
Ile Arg Gln Lys Lys His Trp Leu Ala Arg Lys Thr Arg His Ala Glu
            80                  85                  90

ctc aca gtc tct ctc aga gtc tct cat ttt ggt gac aag atc ttc agc       460
Leu Thr Val Ser Leu Arg Val Ser His Phe Gly Asp Lys Ile Phe Ser
        95                  100                 105
```

```
tct gta aat gcc atc ctt gat ctt tct gtt ttt gga aaa gaa gtt act      508
Ser Val Asn Ala Ile Leu Asp Leu Ser Val Phe Gly Lys Glu Val Thr
    110                 115                 120

cta gaa act ctg gta aaa gac ctg aaa aaa aaa atc ccg agt tta agc      556
Leu Glu Thr Leu Val Lys Asp Leu Lys Lys Lys Ile Pro Ser Leu Ser
125                 130                 135                 140

ttc agt cct ttg aaa ccc aat gga aga atc tcc gtg gaa gga tca ttt      604
Phe Ser Pro Leu Lys Pro Asn Gly Arg Ile Ser Val Glu Gly Ser Phe
                145                 150                 155

ctg gct gtc aag agg ctc aga gaa tct ttg cta gca aga gca tgt tct      652
Leu Ala Val Lys Arg Leu Arg Glu Ser Leu Leu Ala Arg Ala Cys Ser
            160                 165                 170

ctc tta gaa aaa gac aga aat ttt acc agt gag gag aga aag tgg aat      700
Leu Leu Glu Lys Asp Arg Asn Phe Thr Ser Glu Glu Arg Lys Trp Asn
        175                 180                 185

aga caa aat ccc cag agg aat cta cag aga agt aat aac tct ttg gca      748
Arg Gln Asn Pro Gln Arg Asn Leu Gln Arg Ser Asn Asn Ser Leu Ala
    190                 195                 200

tca gtc agg acc tta gta cct gag act gct aga agt gga gaa atg ctt      796
Ser Val Arg Thr Leu Val Pro Glu Thr Ala Arg Ser Gly Glu Met Leu
205                 210                 215                 220

gtg ctt gac aca gat gtt ttt ctt tac ctg aaa cac aag tgt gga tct      844
Val Leu Asp Thr Asp Val Phe Leu Tyr Leu Lys His Lys Cys Gly Ser
                225                 230                 235

tat gaa agc aca ctg aaa aaa ttc cac att ctg agt cag gag aaa gtg      892
Tyr Glu Ser Thr Leu Lys Lys Phe His Ile Leu Ser Gln Glu Lys Val
            240                 245                 250

gat ggt gaa atc acc aca att tgt cta aaa agc att caa gtt ggt tct      940
Asp Gly Glu Ile Thr Thr Ile Cys Leu Lys Ser Ile Gln Val Gly Ser
        255                 260                 265

cag cca aac aat gca aaa cat gta aaa gag ctc att gag gaa tgg tca      988
Gln Pro Asn Asn Ala Lys His Val Lys Glu Leu Ile Glu Glu Trp Ser
    270                 275                 280

cat gct ctt tac tta aag ctt aga aaa gag aca ttt att ttg gaa gga     1036
His Ala Leu Tyr Leu Lys Leu Arg Lys Glu Thr Phe Ile Leu Glu Gly
285                 290                 295                 300

aag gaa aat aga gag aaa aga atg atc aaa agg gca tgt gaa caa tta     1084
Lys Glu Asn Arg Glu Lys Arg Met Ile Lys Arg Ala Cys Glu Gln Leu
                305                 310                 315

agt tcg aga tac ctt gaa gtc ctg att aac ctt tat agg aca cac att     1132
Ser Ser Arg Tyr Leu Glu Val Leu Ile Asn Leu Tyr Arg Thr His Ile
            320                 325                 330

gac att ata gga tct tct tct gac act tac ctg ttt aaa aaa ggg gtc     1180
Asp Ile Ile Gly Ser Ser Ser Asp Thr Tyr Leu Phe Lys Lys Gly Val
        335                 340                 345

atg aaa tta ata ggg caa aag gtt agt taa taaaatctca gcaatatagt       1230
Met Lys Leu Ile Gly Gln Lys Val Ser
    350                 355

cataagggct gctttctctt gctgagcagt gaccattgcc atgaatgagg ctagctttac   1290

acaccgtatc tcatgaatcc ttatagtcat ccttctttgt cagtgttgac tatcctcatg   1350

ttacagcgga agaaactagg atttggagaa gttaaaacac ttttctgaag ttatccagtt   1410

gacaaagaat gaggctgtgg cttagcccag tctatctgat tacacagata atatctaagg   1470

aataaaactt tgaaaaaaac tcaccaaact tttttttttt tttttttgag atggagtctc   1530

gctctgttgt ccaggctgga gtgcagtggc gtgatctcgg ctcactgcaa cgtccacctc   1590

ctgggttcac accattctcc tgcctcaacc tctggagtag ctgggactac aggtgcccac   1650
```

caccacgccc ggctaatctt tttgtatttt tttagtagag atggggtttc accgtgttag 1710
tcaggatggt ctccatctcc tgaccttgtg atccacccgc ctcggcctcc caaagtgctg 1770
ggattacagg cgtgagccac tgcgcccagc aaactcacca aactttgaag gaatcttact 1830
ttctctgtaa ctccaaatta ttagagaata ataattatta agaagtagcc ttaacatatg 1890
agaaatttga aaggtgatta ttatgccatg ggcaatttct taacatttac agtttgtgtt 1950
tactccgtgt agaattagaa tactggcaaa aatcactggg gaaactactt agatggaaag 2010
catatcttat gcaggtaatc attatttgac taaattctat tgtttcaagg ctgctggcca 2070
cataggatgt ttttactatt tttttagcct aagtgcttac ataaaatggt gattctttta 2130
taattgtgca agttgataat attaattgag tcattcttgt cacatccaac taaaacagac 2190
tcaagaagct agggggaaaa agtacttggg acacataata ttgctccaag aatgtaattc 2250
tctgtgagcc tggctactga aactgcttgc tgtaacctga gaccagtttt gtctatagct 2310
gctgagataa cttgctgtaa ctctaggact aattttacct atggccattg cccaccagtt 2370
ggagcttgcc agctccccag ggctttacta ataccaatga actttctctt aagatcacaa 2430
gttggccggg cgtggtgact catacctgta atcccagcac tttgggaggc cgaggcgggt 2490
ggatcacaag gtcaggagat tgagaccatc ctggctaaca tggtaaaacc ccatctctac 2550
taaaaataca aaaattagcc gggcatggtg gtgggcgcct gtagtcccac ctactcggga 2610
ggctagaggc tgaggcagga gaatggcgtg aacccgggag gtggagcttg cagtgagcca 2670
agactgcact actgcactcc agcctgggtg acagagcgag actccgtctc aaaaaaaaaa 2730
aaaaaaaaaa aagaaagacc acaagtaaca ttcttagttt taaataaaac cctcaacctt 2790
ctctttgttt gttggacata ctaaagatca cctagaattg aaattctttc ttctcaaaac 2850
attaaattta gttttgtgtc tacattttca ttttgacttt gacatgcatg gtgtcagaag 2910
tgggatacaa agctgactca cctcatggag aatcattggc ctttggagtt atggcatgag 2970
gtacccatgt tggggccctt tgaacccctt acaccccccac cactttcaca ggtaatcctt 3030
tctccctcca gtaagtatct cttggacaga actctcagat atggttcgag ttctgtttta 3090
tttgggatat gattagggag aggtctttcc ccctcttgtt tggtagatct gttgggtaga 3150
attattttcc ccctgttgac ctcagctgcg aggtttggac cttgaggctt ggatgaggga 3210
atttttccct ttctttggag aaggcttatc attcttactg gtaagcatgt attttatttt 3270
ctgtcctgtc ttgtatttat ttggcctttg tgtattcagt gcttgcattt acttggcttt 3330
tgcatagttg acattaaatc agagcaccca cgaaatgagc tctcaaagtt caaaggcatg 3390
ccagaatatt ttctggaact ccagctagta acatattcaa acattacagg gatcatttag 3450
tctgtttttc ttaaaactga actaaaagat ggaggctata aaatcataca ctccaaataa 3510
gatatgcata tttcattgat atcttgaggc taaaaaaaaa taaaaacaaa aacaaaacac 3570
attcaggata caaatattgc cttgttaaaa aatactgtct caaaggtggc tgaaactttc 3630
ttttctagac ctttcccctc cccttcttac agtatcccct ctttatcctt ctctaaacag 3690
ctattctaac atactactta aataaaaaca cttgaaaacc agcagatata aaacaaagtc 3750
attttgacct tcctactgtt ttttttttaa agcaaagatt aaattcccat gtaaaacctt 3810
cctccctata caaaaaagaa tagcagcatt tttatcttca atgacaaaga attgagtcca 3870
agaaaatact gtataaacct tgttaaaaat cactcttgtc ttttggtcct actcacataa 3930
ttcagcacac tttcacagtt aactattttt tgttcaattt agtgcactgg tgagtgactc 3990
aaactgcttt atcccaaatt tgatttacag cctttataag attgcctatt aaaaaagctt 4050
aaagcttatc cttagcccat tttgtcagaa aaataatttg catctaatca tttttataaa 4110
ctggtgaatt tacgtgtttt actatatcat gactaaaatt ctaaaataaa agttttaata 4170
tcttta 4176

<210> SEQ ID NO 53
<211> LENGTH: 357
<212> TYPE: PRT
<213> ORGANISM: Homo sapiens

<400> SEQUENCE: 53

Met Ala Ser Val Leu Asn Val Lys Glu Ser Lys Ala Pro Glu Arg Thr
1 5 10 15

Val Val Val Ala Gly Leu Pro Val Asp Leu Phe Ser Asp Gln Leu Leu
20 25 30

Ala Val Leu Val Lys Ser His Phe Gln Asp Ile Lys Asn Glu Gly Gly
35 40 45

Asp Val Glu Asp Val Ile Tyr Pro Thr Arg Thr Lys Gly Val Ala Tyr
50 55 60

Val Ile Phe Lys Glu Lys Lys Val Ala Glu Asn Val Ile Arg Gln Lys
65 70 75 80

Lys His Trp Leu Ala Arg Lys Thr Arg His Ala Glu Leu Thr Val Ser
85 90 95

Leu Arg Val Ser His Phe Gly Asp Lys Ile Phe Ser Ser Val Asn Ala
100 105 110

Ile Leu Asp Leu Ser Val Phe Gly Lys Glu Val Thr Leu Glu Thr Leu
115 120 125

Val Lys Asp Leu Lys Lys Lys Ile Pro Ser Leu Ser Phe Ser Pro Leu
130 135 140

Lys Pro Asn Gly Arg Ile Ser Val Glu Gly Ser Phe Leu Ala Val Lys
145 150 155 160

Arg Leu Arg Glu Ser Leu Leu Ala Arg Ala Cys Ser Leu Leu Glu Lys
165 170 175

Asp Arg Asn Phe Thr Ser Glu Glu Arg Lys Trp Asn Arg Gln Asn Pro
180 185 190

Gln Arg Asn Leu Gln Arg Ser Asn Asn Ser Leu Ala Ser Val Arg Thr
195 200 205

Leu Val Pro Glu Thr Ala Arg Ser Gly Glu Met Leu Val Leu Asp Thr
210 215 220

Asp Val Phe Leu Tyr Leu Lys His Lys Cys Gly Ser Tyr Glu Ser Thr
225 230 235 240

Leu Lys Lys Phe His Ile Leu Ser Gln Glu Lys Val Asp Gly Glu Ile
245 250 255

Thr Thr Ile Cys Leu Lys Ser Ile Gln Val Gly Ser Gln Pro Asn Asn
260 265 270

Ala Lys His Val Lys Glu Leu Ile Glu Glu Trp Ser His Ala Leu Tyr
275 280 285

Leu Lys Leu Arg Lys Glu Thr Phe Ile Leu Glu Gly Lys Glu Asn Arg
290 295 300

Glu Lys Arg Met Ile Lys Arg Ala Cys Glu Gln Leu Ser Ser Arg Tyr
305 310 315 320

Leu Glu Val Leu Ile Asn Leu Tyr Arg Thr His Ile Asp Ile Ile Gly
325 330 335

Ser Ser Ser Asp Thr Tyr Leu Phe Lys Lys Gly Val Met Lys Leu Ile

```
            340                 345                 350

Gly Gln Lys Val Ser
        355


<210> SEQ ID NO 54
<211> LENGTH: 1638
<212> TYPE: DNA
<213> ORGANISM: Homo sapiens
<220> FEATURE:
<221> NAME/KEY: CDS
<222> LOCATION: (269)..(1222)

<400> SEQUENCE: 54

attcaggtac caggtagccc caaggaggag ctgccgacct ggcagggaac aaccaagact      60

ggggttaaat ctcacagcct gcaagtggaa gagaagaact tgaacccagg tccaactttt     120

gcgccacagc aggctgcctc ttggtcctga caggaagtca caacttggcc ctgacttcct     180

atcctaggga aggggccggc tggagaggcc aggacagaga aagcagatcc cttctttttc     240

caaggactct gtgtcttcca taggcaac atg tca gaa ggg gtg ggc acg ttc       292
                               Met Ser Glu Gly Val Gly Thr Phe
                               1               5

cgc atg gta cct gaa gag gaa cag gag ctc cgt gcc caa ctg gag cag      340
Arg Met Val Pro Glu Glu Glu Gln Glu Leu Arg Ala Gln Leu Glu Gln
    10                  15                  20

ctc aca acc aag gac cat gga cct gtc ttt ggc ccg tgc agc cag ctg      388
Leu Thr Thr Lys Asp His Gly Pro Val Phe Gly Pro Cys Ser Gln Leu
25                  30                  35                  40

ccc cgc cac acc ttg cag aag gcc aag gat gag ctg aac gag aga gag      436
Pro Arg His Thr Leu Gln Lys Ala Lys Asp Glu Leu Asn Glu Arg Glu
                45                  50                  55

gag acc cgg gag gag gca gtg cga gag ctg cag gag atg gtg cag gcg      484
Glu Thr Arg Glu Glu Ala Val Arg Glu Leu Gln Glu Met Val Gln Ala
            60                  65                  70

cag gcg gcc tcg ggg gag gag ctg gcg gtg gcc gtg gcg gag agg gtg      532
Gln Ala Ala Ser Gly Glu Glu Leu Ala Val Ala Val Ala Glu Arg Val
        75                  80                  85

caa gag aag gac agc ggc ttc ttc ctg cgc ttc atc cgc gca cgg aag      580
Gln Glu Lys Asp Ser Gly Phe Phe Leu Arg Phe Ile Arg Ala Arg Lys
    90                  95                  100

ttc aac gtg ggc cgt gcc tat gag ctg ctc aga ggc tat gtg aat ttc      628
Phe Asn Val Gly Arg Ala Tyr Glu Leu Leu Arg Gly Tyr Val Asn Phe
105                 110                 115                 120

cgg ctg cag tac cct gag ctc ttt gac agc ctg tcc cca gag gct gtc      676
Arg Leu Gln Tyr Pro Glu Leu Phe Asp Ser Leu Ser Pro Glu Ala Val
                125                 130                 135

cgc tgc acc att gaa gct ggc tac cct ggt gtc ctc tct agt cgg gac      724
Arg Cys Thr Ile Glu Ala Gly Tyr Pro Gly Val Leu Ser Ser Arg Asp
            140                 145                 150

aag tat ggc cga gtg gtc atg ctc ttc aac att gag aac tgg caa agt      772
Lys Tyr Gly Arg Val Val Met Leu Phe Asn Ile Glu Asn Trp Gln Ser
        155                 160                 165

caa gaa atc acc ttt gat gag atc ttg cag gca tat tgc ttc atc ctg      820
Gln Glu Ile Thr Phe Asp Glu Ile Leu Gln Ala Tyr Cys Phe Ile Leu
    170                 175                 180

gag aag ctg ctg gag aat gag gaa act caa atc aat ggc ttc tgc atc      868
Glu Lys Leu Leu Glu Asn Glu Glu Thr Gln Ile Asn Gly Phe Cys Ile
185                 190                 195                 200

att gag aac ttc aag ggc ttt acc atg cag cag gct gct agt ctc cgg      916
Ile Glu Asn Phe Lys Gly Phe Thr Met Gln Gln Ala Ala Ser Leu Arg
                205                 210                 215
```

```
act tca gat ctc agg aag atg gtg gac atg ctc cag gat tcc ttc cca      964
Thr Ser Asp Leu Arg Lys Met Val Asp Met Leu Gln Asp Ser Phe Pro
            220                 225                 230

gcc cgg ttc aaa gcc atc cac ttc atc cac cag cca tgg tac ttc acc     1012
Ala Arg Phe Lys Ala Ile His Phe Ile His Gln Pro Trp Tyr Phe Thr
        235                 240                 245

acg acc tac aat gtg gtc aag ccc ttc ttg aag agc aag ctg ctt gag     1060
Thr Thr Tyr Asn Val Val Lys Pro Phe Leu Lys Ser Lys Leu Leu Glu
    250                 255                 260

agg gtc ttt gtc cac ggg gat gac ctt tct ggt ttc tac cag gag atc     1108
Arg Val Phe Val His Gly Asp Asp Leu Ser Gly Phe Tyr Gln Glu Ile
265                 270                 275                 280

gat gag aac atc ctg ccc tct gac ttc ggg ggc acg ctg ccc aag tat     1156
Asp Glu Asn Ile Leu Pro Ser Asp Phe Gly Gly Thr Leu Pro Lys Tyr
                285                 290                 295

gat ggc aag gcc gtt gct gag cag ctc ttt ggc ccc cag gcc caa gct     1204
Asp Gly Lys Ala Val Ala Glu Gln Leu Phe Gly Pro Gln Ala Gln Ala
            300                 305                 310

gag aac aca gcc ttc tga aaacatctcc tgccagctga actgtagtta            1252
Glu Asn Thr Ala Phe
        315

gaatctctgg gcctctcctc aactgtcctg gacccaaggc taggaaaggg ctgcttgaga   1312

tgactgtggt cccccccttag actccctaag cccgagtgag ctcaggtgtc accctgttct   1372

caagttgggg gatgggtaat aaaggagggg gaattccctt gaacaagaag aactggggat   1432

agttatattt ccacctgccc ttgaagcttt aagacagtga tttttgtgta aggttgtatt   1492

tcaaagactc gaattcattt tctcagtcat ttcctttgta acagagtttt acgacttaga   1552

gtctgtgaaa acaggcaagg agcccgggtt aaaatatccc cctattcgcc cccaaaatgc   1612

aataaaagaa gataaaagag agagga                                        1638
```

<210> SEQ ID NO 55
<211> LENGTH: 317
<212> TYPE: PRT
<213> ORGANISM: Homo sapiens

<400> SEQUENCE: 55

```
Met Ser Glu Gly Val Gly Thr Phe Arg Met Val Pro Glu Glu Glu Gln
1               5                   10                  15

Glu Leu Arg Ala Gln Leu Glu Gln Leu Thr Thr Lys Asp His Gly Pro
            20                  25                  30

Val Phe Gly Pro Cys Ser Gln Leu Pro Arg His Thr Leu Gln Lys Ala
        35                  40                  45

Lys Asp Glu Leu Asn Glu Arg Glu Glu Thr Arg Glu Glu Ala Val Arg
    50                  55                  60

Glu Leu Gln Glu Met Val Gln Ala Gln Ala Ala Ser Gly Glu Glu Leu
65                  70                  75                  80

Ala Val Ala Val Ala Glu Arg Val Gln Glu Lys Asp Ser Gly Phe Phe
                85                  90                  95

Leu Arg Phe Ile Arg Ala Arg Lys Phe Asn Val Gly Arg Ala Tyr Glu
            100                 105                 110

Leu Leu Arg Gly Tyr Val Asn Phe Arg Leu Gln Tyr Pro Glu Leu Phe
        115                 120                 125

Asp Ser Leu Ser Pro Glu Ala Val Arg Cys Thr Ile Glu Ala Gly Tyr
    130                 135                 140

Pro Gly Val Leu Ser Ser Arg Asp Lys Tyr Gly Arg Val Val Met Leu
```

```
145                 150                 155                 160

Phe Asn Ile Glu Asn Trp Gln Ser Gln Glu Ile Thr Phe Asp Glu Ile
                165                 170                 175

Leu Gln Ala Tyr Cys Phe Ile Leu Glu Lys Leu Leu Glu Asn Glu Glu
            180                 185                 190

Thr Gln Ile Asn Gly Phe Cys Ile Ile Glu Asn Phe Lys Gly Phe Thr
        195                 200                 205

Met Gln Gln Ala Ala Ser Leu Arg Thr Ser Asp Leu Arg Lys Met Val
    210                 215                 220

Asp Met Leu Gln Asp Ser Phe Pro Ala Arg Phe Lys Ala Ile His Phe
225                 230                 235                 240

Ile His Gln Pro Trp Tyr Phe Thr Thr Thr Tyr Asn Val Val Lys Pro
                245                 250                 255

Phe Leu Lys Ser Lys Leu Leu Glu Arg Val Phe Val His Gly Asp Asp
            260                 265                 270

Leu Ser Gly Phe Tyr Gln Glu Ile Asp Glu Asn Ile Leu Pro Ser Asp
        275                 280                 285

Phe Gly Gly Thr Leu Pro Lys Tyr Asp Gly Lys Ala Val Ala Glu Gln
    290                 295                 300

Leu Phe Gly Pro Gln Ala Gln Ala Glu Asn Thr Ala Phe
305                 310                 315


<210> SEQ ID NO 56
<211> LENGTH: 9563
<212> TYPE: DNA
<213> ORGANISM: Homo sapiens
<220> FEATURE:
<221> NAME/KEY: CDS
<222> LOCATION: (343)..(1821)

<400> SEQUENCE: 56

gcactgaggc gctgcggcgg cggtggtggc ggtggcagcg gtggcggctg ctcgtcctag      60

cctggcgggg gcgggggtct ggaagatggg ggcgggtgga acaacgggcc ggtgaggagc     120

agccgccgcc gtctccgccg tcgctggggc agctgccgcg gtggtcgcct ctggcagtgc     180

cgctagcttt caggcagtcg cctctcctcc cgacatcccg ccttgaggag gctgaggcgg     240

aatcgcggct ggcggcgggg ggacggaccg gccctgcagt ggccgcagtg acagcccgga     300

cccggccctc cgcccgctct cgcctcggcg cccgcagcca cg atg aac cgg ggc        354
                                               Met Asn Arg Gly
                                               1

ggc ggc agc ccg tcg gcc gcc gcc aac tac ctg ctc tgt acc aac tgc       402
Gly Gly Ser Pro Ser Ala Ala Ala Asn Tyr Leu Leu Cys Thr Asn Cys
5                   10                  15                  20

cgg aaa gtg ctg cgg aag gat aaa aga atc aga gtg tct caa ccc ttg       450
Arg Lys Val Leu Arg Lys Asp Lys Arg Ile Arg Val Ser Gln Pro Leu
                25                  30                  35

aca aga gga cca agt gcc ttt att cca gag aag gaa gtt gtc caa gca       498
Thr Arg Gly Pro Ser Ala Phe Ile Pro Glu Lys Glu Val Val Gln Ala
            40                  45                  50

aac aca gtg gat gaa cgt act aac ttt ctt gtg gaa gaa tac tct aca       546
Asn Thr Val Asp Glu Arg Thr Asn Phe Leu Val Glu Glu Tyr Ser Thr
        55                  60                  65

tcc ggt cgt ctg gac aac atc aca cag gtc atg agt tta cac act cag       594
Ser Gly Arg Leu Asp Asn Ile Thr Gln Val Met Ser Leu His Thr Gln
    70                  75                  80

tac ctg gag tct ttc ttg cgg agc cag ttt tac atg ttg cgc atg gat       642
Tyr Leu Glu Ser Phe Leu Arg Ser Gln Phe Tyr Met Leu Arg Met Asp
```

```
85                  90                  95                  100

ggt ccc ctt cct cta cca tac agg cac tat att gca ata atg gct gca      690
Gly Pro Leu Pro Leu Pro Tyr Arg His Tyr Ile Ala Ile Met Ala Ala
            105                 110                 115

gct aga cat cag tgt tct tac tta ata aac atg cat gtg gat gaa ttt      738
Ala Arg His Gln Cys Ser Tyr Leu Ile Asn Met His Val Asp Glu Phe
            120                 125                 130

tta aag act gga ggt att gct gag tgg ttg aat ggt ttg gaa tat gtg      786
Leu Lys Thr Gly Gly Ile Ala Glu Trp Leu Asn Gly Leu Glu Tyr Val
        135                 140                 145

cca caa aga ctg aaa aat ctt aat gaa att aat aag ctg cta gca cat      834
Pro Gln Arg Leu Lys Asn Leu Asn Glu Ile Asn Lys Leu Leu Ala His
    150                 155                 160

cga cct tgg ctg atc aca aaa gag cac att cag aaa ctt gtc aaa act      882
Arg Pro Trp Leu Ile Thr Lys Glu His Ile Gln Lys Leu Val Lys Thr
165                 170                 175                 180

gga gaa aat aat tgg tct ctg cct gaa ctg gta cat gct gtg gtc ctc      930
Gly Glu Asn Asn Trp Ser Leu Pro Glu Leu Val His Ala Val Val Leu
            185                 190                 195

ctg gca cat tat cat gct ttg gca agc ttt gtt ttt ggt agt ggt atc      978
Leu Ala His Tyr His Ala Leu Ala Ser Phe Val Phe Gly Ser Gly Ile
            200                 205                 210

aat cca gag aga gat cca gaa atc tcc aat gga ttc agg cta ata tca     1026
Asn Pro Glu Arg Asp Pro Glu Ile Ser Asn Gly Phe Arg Leu Ile Ser
        215                 220                 225

gtc aac aat ttc tgc gtt tgt gat ctt gct aat gac aac aac ata gag     1074
Val Asn Asn Phe Cys Val Cys Asp Leu Ala Asn Asp Asn Asn Ile Glu
    230                 235                 240

aat gca tct ctt tca ggc agc aac ttt ggg att gtg gat tct cta agt     1122
Asn Ala Ser Leu Ser Gly Ser Asn Phe Gly Ile Val Asp Ser Leu Ser
245                 250                 255                 260

gag cta gag gcc tta atg gaa agg atg aaa aga ctt caa gaa gaa agg     1170
Glu Leu Glu Ala Leu Met Glu Arg Met Lys Arg Leu Gln Glu Glu Arg
            265                 270                 275

gaa gat gaa gag gcg tct caa gaa gaa atg agc act cgt ttt gaa aag     1218
Glu Asp Glu Glu Ala Ser Gln Glu Glu Met Ser Thr Arg Phe Glu Lys
            280                 285                 290

gag aag aaa gaa agt ctt ttt gtg gtc tct gga gat act ttt cat tca     1266
Glu Lys Lys Glu Ser Leu Phe Val Val Ser Gly Asp Thr Phe His Ser
        295                 300                 305

ttt cct cat tca gat ttt gag gat gac atg att ata aca tct gat gtc     1314
Phe Pro His Ser Asp Phe Glu Asp Asp Met Ile Ile Thr Ser Asp Val
    310                 315                 320

tct cga tat att gaa gac cct ggt ttt ggg tat gaa gac ttt gcc aga     1362
Ser Arg Tyr Ile Glu Asp Pro Gly Phe Gly Tyr Glu Asp Phe Ala Arg
325                 330                 335                 340

cga gga gaa gag cat ttg cca aca ttc cga gct cag gac tat acc tgg     1410
Arg Gly Glu Glu His Leu Pro Thr Phe Arg Ala Gln Asp Tyr Thr Trp
            345                 350                 355

gaa aat cat ggg ttc tcc ctg gtg aac aga ctt tat tct gac att gga     1458
Glu Asn His Gly Phe Ser Leu Val Asn Arg Leu Tyr Ser Asp Ile Gly
            360                 365                 370

cat ctt ctt gat gaa aag ttt cgg atg gtc tac aat ctc aca tat aac     1506
His Leu Leu Asp Glu Lys Phe Arg Met Val Tyr Asn Leu Thr Tyr Asn
        375                 380                 385

act atg gcc acc cat gag gat gtt gac aca acc atg ctg cgc aga gct     1554
Thr Met Ala Thr His Glu Asp Val Asp Thr Thr Met Leu Arg Arg Ala
    390                 395                 400

tta ttt aac tat gtt cac tgt atg ttt gga atc agg tat gat gac tat     1602
```

```
Leu Phe Asn Tyr Val His Cys Met Phe Gly Ile Arg Tyr Asp Asp Tyr
405                 410                 415                 420

gat tat gga gaa gtt aat caa tta ctt gaa aga agc ctg aag gtt tac     1650
Asp Tyr Gly Glu Val Asn Gln Leu Leu Glu Arg Ser Leu Lys Val Tyr
                425                 430                 435

att aag aca gtg acc tgc tat cct gag aga act aca aaa cgc atg tat     1698
Ile Lys Thr Val Thr Cys Tyr Pro Glu Arg Thr Thr Lys Arg Met Tyr
            440                 445                 450

gat agt tac tgg cgg cag ttc aaa cac tca gaa aaa gtt cat gtc aat     1746
Asp Ser Tyr Trp Arg Gln Phe Lys His Ser Glu Lys Val His Val Asn
        455                 460                 465

cta ctt tta atg gaa gca cga atg caa gct gaa ctt ctt tat gct ctt     1794
Leu Leu Leu Met Glu Ala Arg Met Gln Ala Glu Leu Leu Tyr Ala Leu
    470                 475                 480

cgt gcc ata act cgg cat ttg acc tga agtatcaccc aaggaaaatg           1841
Arg Ala Ile Thr Arg His Leu Thr
485                 490

tcatacatgt gtaaagacct ttcacataag ataaacattg aagctatttg tgatatagca   1901

tcaaaaatta ttcagttctc tagtgtcaaa gtttagccgt ttgttttttt tttttgttt    1961

tttgcggctg taatgtgcaa tgatgtgttt tattttcctt gatgcttaac attactaaca   2021

attgcaaaaa taatactgag gagcactact ttgcattgtt tgtagttgga gttttggata   2081

ctgatcataa atcatgaatc tggcgtatta atgcttaact tcagcgcctt tgggttgtgt   2141

gtatgtgtat tttttctccc cccaccccgc ccttttttt ttaagaataa ggacaagtgc    2201

ttacaatctg ctcaagcaat tgtttttcag atattggaat tcagcaaaga gtgacctctc   2261

tggccattct aaaactttaa tgttgtgtcc taaatctggt ggaggaaaag catgcgctgt   2321

tgaaccaagc tgctcactgg acacatattt gtgtccccag gagattattt gtcaggcact   2381

gtttttttatt tgtttgtttg ttcatttatt gttgttttac tgctattggc gataacatga  2441

aatgtgatac agctattgcc cataatttaa tgtgaaatta atcatgatga attctatagc   2501

atgctactga aatgccaaat tcagctattt tctttctctt ctaaaatgga agtttcagtt   2561

ttccatatca gatgtatata agtggaatta taacacaatc ctatcactga cagtaatcct   2621

cagtcacctt aaataatcag tgctcacagt gctgcttaca gttcatttag ttggcacata   2681

taaacctgta cccacacaag actgaccaaa aattttcttt gcacattttt cctttctcat   2741

agttttttc tatatttcgt taagcaaagg aaggttaata tgcctatttt tcctgttagg    2801

cttttagaaa ttattttcca tgacttttgt tcttataata ggttagacag tttatttttc   2861

aaaggtaaaa attgtgtttc tatgcattaa tgtgattgaa ctacaaaaac agagtgcaat   2921

atgttcaaaa aatactcaac taaactttcc ccctgtcata tcactgcaaa agtgtccttt   2981

taaacagagc cataaagaaa tttttttcaa atttctttat tgcacaggct tttttcagtt   3041

ttacctttct gggattgaac aatgttcctt tcataatgcc aaagcattcc cttccccaga   3101

aaaatctcct tggacaactg gtttaaaaac gttattaagt catagggggag gaataagcgg  3161

ccaaaaagtc acatttttgc attggtttac gttgcttgat tagactatct tcagagagca   3221

cattatgtgt ttatagcttt aatttgtatt atgtcaatga accagtgaag tgcctaaaga   3281

gatgcttaca actatccagt aggacacaac tgcactgctt tttaaacact ttttggttag   3341

ttaagggtga cttgaattgt acacatacat gctaattttt gaaaacttat ccatttttca   3401

tagtaaataa tatagataaa attttctgtt agagttcccg caaatatttc attttagact   3461

tacttgtgat ataagattta acttttcttt tgtgaaagaa tcgtgaacta gtgtttcatg   3521
```

aaatcatttt cctcttccat ttatcatcct cctctggtac aatatattgg gttgctttct 3581
tttagatttt gttccagata ggaaaacaaa tatgactgta tacttattaa cataaggtag 3641
ttctgcattt ttggattcca ggatcctgtt tgaaatcttc catgtgagga aaaaattact 3701
aatattttta aagacagggt ggtttattta aagagattat tcagagaact tgtgccatat 3761
ctcgtctgtt ttattgcata tgccatatgt taacttttat tcaatattac attatgtaga 3821
tatgtaatac aaagaaaata tttaggagaa tggcaaaaca caaatggcaa cataaatgtc 3881
catttgactt acctaacttc acaactttca agttgaggat gtcatttatt cttgaatttg 3941
ttttttttact agatgctttc aattaatagc cctatatttt tgtgcaggcg aactgtataa 4001
caggataaaa aatgatttgt atgtattgaa aaggaggaga aattctcaca gaacaccata 4061
tgagctttag accaaaaggg gaaacaaggt ttaagtaact aaaatggcca cttagtttgt 4121
gtttattttt ttccctggaa atgtaagtag ttggagttta ggctatggaa atattagtgc 4181
ctttaataga tctctttcct tgcaaagttt ctttttagct cagcattgat ctatcttatc 4241
aataggaaaa taagttgact tggaactata aacaaaaaca acaccatata tttatgaacc 4301
tcagtgaacc agcctagaaa aattgacttc tgcaggtgct aaagcaccta ctaatacgca 4361
gcatgcacag catttcaggt tgtgaatacc attttacaac gagtttgctg ttaactctct 4421
ttatccaatg caaacttgaa attctgatgc ggttttccag ggtggtattt tttcagagta 4481
ttgaatttac tatttagtaa tttatagtat agctttttat attaaaatgt gatattttta 4541
aaagagatat ctggttcaat tggtataatg acgtgattat gcaatatgct gatctacacc 4601
ttgcgctcac attgtgccaa acttaaatgt gcaagtgtac gtgagaaaag cacatgtgaa 4661
tgtgaattct ttaattcttt gcttattatg ttaaaattag tcttcatagt ccactgatgt 4721
gtatgcttga ataatgtcta tttactttgg aatttcaaga tttccagctt caatggtaat 4781
ttataatttc tcagatcacc ttaagaaata ttgagatact ctcccacctg aaaataatct 4841
gttctttaac ccacctgact atgggagtag ccaggcaggt gcctcactgg cttcttcaga 4901
cgaggcttcc tcaggtggat atatgactat taggggaaaa gaggcttttg agacagctta 4961
ttacctcctt cccctttttg aactaagtac attgtctcag tcccagtatg aatttgtccc 5021
atttggggta tttttaaaat aaaagatggc taacatggaa tctggggcat agccttggcc 5081
tttaattatg gttgtaagcc caaataatgg cagagaaaca cagggctgtt tttacaacag 5141
aaaactcaat ataagtttta tataagaatc ctataaaatt tgaaccagag ctcctattta 5201
gttgttataa tgtctcctaa agatcttaaa tgcttctaaa agctaattat tattccagag 5261
caactttttc cttttccccc ttataaagtt tttttttaaa tccaaaatct tagatttctg 5321
tgccacagca aaataaaatg atcaacaatt aaagatctgt acttaaaata gtacaccatt 5381
tttagtggag ggagggtgca tgcctatatg atggtaagat tcttttgaac tctaaggaca 5441
attcctcatg gaaaaaataa atttcagtgc atattataaa aatgatttgc actgtgttag 5501
caaaataagg tgttttaggt tgtattttaa agacaattct aaatcatttc tctggaaagc 5561
aagaccttaa attcttctct ttaatagaac tgcttttatg caaagagatg gtcttaacat 5621
ggactaaaca gtacataaca ataatgtttg ttatgtaaat agtatatcac atttgcttag 5681
tagcacaatt caacagcagg ctgaaagtcg tggctcctct gctcagattg agttttaagt 5741
tacctaattt atgtaatcag aatctattct aggtggccgt caacgtaaac tgtgtttccc 5801
tattatatcc ctctggagac tgagaatcaa attaaatagt ctttcttcaa agcagtactg 5861
taacatgaat gtatttatct cagtcaacag aacttatatg cccactgtat gtggagctta 5921

```
tttcaatgct aatttggctt agttagcaga cctagaatct gcccaggtga gacctagaac   5981
aaaaatagct ggggtgaaat ggataagaga ggtagaggta tatgtcaagg cagagcccta   6041
tgaggaagga agagttttca aagaatatga ggaacatagt gctgagagtg tggctgcctt   6101
cagcaccgta cacctaatct agagaaaata tttcccatgt gggaggtcct gtctgcattc   6161
agtccaccct tttctgcctg cttcttcctc caagtgcctc aacctctaca tgctcactct   6221
cctccccttc cctcagccca tcttggtcta agcagctttc acaatccaaa ccaaacatca   6281
ccagccaccc gctgataagt caccagcatt tactttcctg agttactttt tctccattca   6341
ttgagactat ggattcatcc caactccttc taaatccctc aaccatccag ctatattttg   6401
gctaaccttt gccctagaca ctctaccaga tgttaatgca gtatcaagtg taaattgtgt   6461
caccctattc tgttctaccc ttttccctgc tgccgaaata tcttgctctc ctctacctca   6521
tccccaaaga gcctataaat tcagagtatc caacctttc atggattcac tcactgttgt   6581
tcagtaatac aacttccata ttttaaataa atcataaaag atttttgcct tctatcaaag   6641
taggaaactt tatatttata catgatacag aaattgaact atttctatcg ttcagaattt   6701
agcatataac aggattttaa agtgattgaa ttgccatcct aacttggatt tgtattaggt   6761
tatgaatgaa tactgttgtt agtccaagct atttgaatgt aaagttaaaa ttctccagca   6821
atccagaatg acttgtaacc cttcagtgga atgggaaatt tctggtatgc aaatagggtg   6881
gtgttccaga catttgtttt attggtggtg tttgggcctt gaaacacatt tctaatagaa   6941
tgacatatgg caaagggtat ttagatggtc ctatgggatc acagaagccc atatgattta   7001
aaatatagat aaaataacac aaaattgggt acataagggt ttaaccaggc tttcctgggt   7061
tagactaagc ctctaacctc tgttcctatc ctgttcttat gggaggaaaa aaaatgttcc   7121
atgggatgaa aagaaaatgc attgactttg tagtctttat tctcctagcc gcacttcggg   7181
tatatccaga aggaagagga aatgcaaaga ggaagaagat gtaatagttc ttctctccag   7241
ctaggtgcac ttgaggttgt tcataaatgt aaaattatgt caggtttcta acatgggaca   7301
ctgcacacag ttgtctgacc tgatgaacca tcccatttga aagtatagat tattattatt   7361
tcttgtagta tttggttgtt ttccatctca ttcatgaaca actcaacctg atagtagtat   7421
ccaataaatg cctttcaggg ctcaggaatg aattgacatc ctagttaaga aatgagactt   7481
aataatggag actgaatgag gcggtttgta ttaaattata tgccatgaag tgttcatttt   7541
agctttaacc taattatgac tgtaccacca tgaagtacag aatgaaaaat tatatatatg   7601
gggggaaac agaatgaata tctgattctt ttgaatgctt gtggaaatct ttgagatcgt   7661
gcagggcata ccacaaaata gcctttagaa cagataccca attttacagt tcataggaca   7721
acatcaaaca ttagtaagtc taaataagat gaatagaatt tttgttatgt aaattttgct   7781
agaacagtct attttcttgc acccctcaag ttaacctctt aaaaaaatga atgtataatt   7841
tctaccgaaa gaatatcaga gagaatctct ctggcctata gtgttaaaat attgttcaca   7901
aatcctgatt agttaagtgc atacattatg aaacttacag aataaaactt attatacatc   7961
tctttcttaa attaatatct ttacacattt tcaactggct ccccaagtct gataaggaag   8021
gattaaaaga aaaaagaaat gtattagttg ggtggccaag gagtttcctt tgtaatgttg   8081
agagacttcc gctttctgaa tttcgctggt tctctaaggt aaaagagtta aatagtaccc   8141
ttgttcacca aggaaagtga tccaaactat atatctagtg cagatatttc ctttgcatta   8201
tttagtcttc tctggagaga aaatacagtt tccccttcct ctttctcttc acatttactc   8261
```

```
ttttcaaccc aaaataagag acatagaaag caaaccacag ccagtttggc atcttctcag   8321

tgctactagt ataggcacat acacatacac agtctcagca aggttataaa gaaccctgtc   8381

aggtccactt gcaacatggc cttgctactt ggattagctc ctttaagcct gaaaataact   8441

ttcctggtca tggaagaact ggacgcatct tttaacttat gaaatagaag ttgaacttga   8501

aaactctttt taaaaaatcc tggttttgca ggacagctac ataatgaatg tatatattaa   8561

gactgtagct gaattgcaca tgaaatcaga ttgccaactt cttgactttc aatgttagac   8621

atttatcctt aagttgtgag cgatatatgt agcatgctgt gaaatgtctg ttatagctct   8681

ttaattcatc agtattaata cagaattatc atttgcgttt cttggtactt tttattcaat   8741

gtaatcagaa gctgtgatgt tttgcctttg tagtcctgtg ctttgttact gtaatttttt   8801

tttttttttt acgaagcacg tgactggact aatgtaaggc agatgacgtg atctttaaga   8861

ctgctatata tatcagtctc ttactctata aggttttaaa ttagaataag cttttatcaa   8921

atagataatt gatgcaattt aggattcacg caagtttcag tgtcaaatgg cggtcttata   8981

gtttcaattc tgaaaatagc aaacttaata aacagccact ttaaacttgt tctggcaaac   9041

cagaccctgc tgtagatata gtctaaggta gttaaccata taagcctttt caactcttaa   9101

tgccctccac atgaatcagc agttaagaag gttctagaac ccatgaaagc ttttgtatgt   9161

attactaggt tttgttttc ttatgtttgc tgattttaca gttctgacta aagctgacct    9221

aaatggatca gtttatgtgt aatattctag tgctttaatg actctttttt tctttggagg   9281

gagggtaaca ttatttggac agatgcagaa ggaactgtta gtgagtcaag acaaacacat   9341

ctgaaataaa ggaactgtgt attaacatgt taacaattca taactgcact ttttatgaca   9401

ttttgaaaat ctatttatag gtacagaaca atgggttttg ttaaactgta tcacatttat   9461

acttgcagaa atttatttca ttgttattag taggaatttt attggttcaa taaaattggc   9521

aaaactgaac accaatcatt tgcctacttt gtttatactg ga                      9563
```

<210> SEQ ID NO 57
<211> LENGTH: 492
<212> TYPE: PRT
<213> ORGANISM: Homo sapiens

<400> SEQUENCE: 57

```
Met Asn Arg Gly Gly Gly Ser Pro Ser Ala Ala Ala Asn Tyr Leu Leu
1               5                   10                  15

Cys Thr Asn Cys Arg Lys Val Leu Arg Lys Asp Lys Arg Ile Arg Val
            20                  25                  30

Ser Gln Pro Leu Thr Arg Gly Pro Ser Ala Phe Ile Pro Glu Lys Glu
        35                  40                  45

Val Val Gln Ala Asn Thr Val Asp Glu Arg Thr Asn Phe Leu Val Glu
    50                  55                  60

Glu Tyr Ser Thr Ser Gly Arg Leu Asp Asn Ile Thr Gln Val Met Ser
65                  70                  75                  80

Leu His Thr Gln Tyr Leu Glu Ser Phe Leu Arg Ser Gln Phe Tyr Met
                85                  90                  95

Leu Arg Met Asp Gly Pro Leu Pro Leu Pro Tyr Arg His Tyr Ile Ala
            100                 105                 110

Ile Met Ala Ala Ala Arg His Gln Cys Ser Tyr Leu Ile Asn Met His
        115                 120                 125

Val Asp Glu Phe Leu Lys Thr Gly Gly Ile Ala Glu Trp Leu Asn Gly
    130                 135                 140
```

```
Leu Glu Tyr Val Pro Gln Arg Leu Lys Asn Leu Asn Glu Ile Asn Lys
145                 150                 155                 160

Leu Leu Ala His Arg Pro Trp Leu Ile Thr Lys Glu His Ile Gln Lys
                165                 170                 175

Leu Val Lys Thr Gly Glu Asn Asn Trp Ser Leu Pro Glu Leu Val His
            180                 185                 190

Ala Val Val Leu Leu Ala His Tyr His Ala Leu Ala Ser Phe Val Phe
        195                 200                 205

Gly Ser Gly Ile Asn Pro Glu Arg Asp Pro Glu Ile Ser Asn Gly Phe
    210                 215                 220

Arg Leu Ile Ser Val Asn Asn Phe Cys Val Cys Asp Leu Ala Asn Asp
225                 230                 235                 240

Asn Asn Ile Glu Asn Ala Ser Leu Ser Gly Ser Asn Phe Gly Ile Val
                245                 250                 255

Asp Ser Leu Ser Glu Leu Glu Ala Leu Met Glu Arg Met Lys Arg Leu
            260                 265                 270

Gln Glu Glu Arg Glu Asp Glu Glu Ala Ser Gln Glu Glu Met Ser Thr
        275                 280                 285

Arg Phe Glu Lys Glu Lys Lys Glu Ser Leu Phe Val Val Ser Gly Asp
    290                 295                 300

Thr Phe His Ser Phe Pro His Ser Asp Phe Glu Asp Asp Met Ile Ile
305                 310                 315                 320

Thr Ser Asp Val Ser Arg Tyr Ile Glu Asp Pro Gly Phe Gly Tyr Glu
                325                 330                 335

Asp Phe Ala Arg Arg Gly Glu Glu His Leu Pro Thr Phe Arg Ala Gln
            340                 345                 350

Asp Tyr Thr Trp Glu Asn His Gly Phe Ser Leu Val Asn Arg Leu Tyr
        355                 360                 365

Ser Asp Ile Gly His Leu Leu Asp Glu Lys Phe Arg Met Val Tyr Asn
    370                 375                 380

Leu Thr Tyr Asn Thr Met Ala Thr His Glu Asp Val Asp Thr Thr Met
385                 390                 395                 400

Leu Arg Arg Ala Leu Phe Asn Tyr Val His Cys Met Phe Gly Ile Arg
                405                 410                 415

Tyr Asp Asp Tyr Asp Tyr Gly Glu Val Asn Gln Leu Leu Glu Arg Ser
            420                 425                 430

Leu Lys Val Tyr Ile Lys Thr Val Thr Cys Tyr Pro Glu Arg Thr Thr
        435                 440                 445

Lys Arg Met Tyr Asp Ser Tyr Trp Arg Gln Phe Lys His Ser Glu Lys
    450                 455                 460

Val His Val Asn Leu Leu Leu Met Glu Ala Arg Met Gln Ala Glu Leu
465                 470                 475                 480

Leu Tyr Ala Leu Arg Ala Ile Thr Arg His Leu Thr
                485                 490
```

<210> SEQ ID NO 58
<211> LENGTH: 4672
<212> TYPE: DNA
<213> ORGANISM: Homo sapiens
<220> FEATURE:
<221> NAME/KEY: CDS
<222> LOCATION: (48)..(1064)

<400> SEQUENCE: 58

```
ctccctgccc acctcctgca gcctcctgcg ccccgccgag ctggcgg atg gag ctg       56
                                                    Met Glu Leu
```

```
                                                  1

cgc agc ggg agc gtg ggc agc cag gcg gtg gcg cgg agg atg gat ggg      104
Arg Ser Gly Ser Val Gly Ser Gln Ala Val Ala Arg Arg Met Asp Gly
    5                   10                  15

gac agc cga gat ggc ggc ggc ggc aag gac gcc acc ggg tcg gag gac      152
Asp Ser Arg Asp Gly Gly Gly Gly Lys Asp Ala Thr Gly Ser Glu Asp
20                  25                  30                  35

tac gag aac ctg ccg act agc gcc tcc gtg tcc acc cac atg aca gca      200
Tyr Glu Asn Leu Pro Thr Ser Ala Ser Val Ser Thr His Met Thr Ala
                40                  45                  50

gga gcg atg gcc ggg atc ctg gag cac tcg gtc atg tac ccg gtg gac      248
Gly Ala Met Ala Gly Ile Leu Glu His Ser Val Met Tyr Pro Val Asp
            55                  60                  65

tcg gtg aag aca cga atg cag agt ttg agt cca gat ccc aaa gcc cag      296
Ser Val Lys Thr Arg Met Gln Ser Leu Ser Pro Asp Pro Lys Ala Gln
        70                  75                  80

tac aca agt atc tac gga gcc ctc aag aaa atc atg cgg acc gaa ggc      344
Tyr Thr Ser Ile Tyr Gly Ala Leu Lys Lys Ile Met Arg Thr Glu Gly
    85                  90                  95

ttc tgg agg ccc ttg cga ggc gtc aac gtc atg atc atg ggt gca ggg      392
Phe Trp Arg Pro Leu Arg Gly Val Asn Val Met Ile Met Gly Ala Gly
100                 105                 110                 115

ccg gcc cat gcc atg tat ttt gcc tgc tat gaa aac atg aaa agg act      440
Pro Ala His Ala Met Tyr Phe Ala Cys Tyr Glu Asn Met Lys Arg Thr
                120                 125                 130

tta aat gac gtt ttc cac cac caa gga aac agc cac cta gcc aac ggg      488
Leu Asn Asp Val Phe His His Gln Gly Asn Ser His Leu Ala Asn Gly
            135                 140                 145

ata gct ggg agt atg gcc acc ctg ctc cac gat gcg gta atg aat cca      536
Ile Ala Gly Ser Met Ala Thr Leu Leu His Asp Ala Val Met Asn Pro
        150                 155                 160

gca gaa gtg gtg aag cag cgc ttg cag atg tac aac tcg cag cac cgg      584
Ala Glu Val Val Lys Gln Arg Leu Gln Met Tyr Asn Ser Gln His Arg
    165                 170                 175

tca gca atc agc tgc atc cgg acg gtg tgg agg acc gag ggg ttg ggg      632
Ser Ala Ile Ser Cys Ile Arg Thr Val Trp Arg Thr Glu Gly Leu Gly
180                 185                 190                 195

gcc ttc tac cgg agc tac acc acg cag ctg acc atg aac atc ccc ttc      680
Ala Phe Tyr Arg Ser Tyr Thr Thr Gln Leu Thr Met Asn Ile Pro Phe
                200                 205                 210

cag tcc atc cac ttc atc acc tat gag ttc ctg cag gag cag gtc aac      728
Gln Ser Ile His Phe Ile Thr Tyr Glu Phe Leu Gln Glu Gln Val Asn
            215                 220                 225

ccc cac cgg acc tac aac ccg cag tcc cac atc atc tca ggc ggg ctg      776
Pro His Arg Thr Tyr Asn Pro Gln Ser His Ile Ile Ser Gly Gly Leu
        230                 235                 240

gcc ggg gcc ctc gcc gcg gcc gcc acg acc ccc ctg gac gtc tgt aag      824
Ala Gly Ala Leu Ala Ala Ala Ala Thr Thr Pro Leu Asp Val Cys Lys
    245                 250                 255

acc ctt ctg aac act cag gag aac gtg gcc ctc tcg ctg gcc aac atc      872
Thr Leu Leu Asn Thr Gln Glu Asn Val Ala Leu Ser Leu Ala Asn Ile
260                 265                 270                 275

agc ggc cgg ctg tcg ggt atg gcc aat gcc ttc cgg acg gtg tac cag      920
Ser Gly Arg Leu Ser Gly Met Ala Asn Ala Phe Arg Thr Val Tyr Gln
                280                 285                 290

ctc aac ggc ctg gcc ggc tac ttc aaa ggc atc cag gcg cgt gtc atc      968
Leu Asn Gly Leu Ala Gly Tyr Phe Lys Gly Ile Gln Ala Arg Val Ile
            295                 300                 305

tac cag atg ccc tcc acc gcc att tct tgg tct gtc tat gag ttc ttc     1016
```

```
Tyr Gln Met Pro Ser Thr Ala Ile Ser Trp Ser Val Tyr Glu Phe Phe
        310                 315                 320

aag tac ttt ctc acc aag cgc cag ctg gaa aat cga gct cca tac taa     1064
Lys Tyr Phe Leu Thr Lys Arg Gln Leu Glu Asn Arg Ala Pro Tyr
    325                 330                 335

aggaagggat catagaatct tttcttaaag tcattctctg cctgcatcca gccccttgcc   1124

ctctcctcac acgtagatca ttttttttt gcagggtgct gcctatgggc cctctgctcc   1184

ccaatgcctt agagagagga ggggacggca cggccgctca ccggaaggct gtgtgcgggg   1244

acatccgagg tggtggtgga caggaaggac ttgggaaggg gagcgagaaa ttgctttttc   1304

tcttcctccc tgggcagaat gtagcttttc tgcttcactg tggcagcctc ctccctggat   1364

ccttagatcc cagaggaggg aagaaaattt gcagtgactg aaaacagtaa aaaaaaaaaa   1424

aaaaaaaaaa aaaaaaaaaa aaaaaaaaaa aaatttatgt atataaaagt tgcattacac   1484

agtacaaaat agatggataa tgtttatcct ttatttttct atgtagaagt ttttgaattt   1544

gtgtgtgtgc ttgtgcgtgt ctacacctag tattacggct gggactctcc agctgttttt   1604

gttgttgtta tgtttttaag agggttgaat tcttccatca ggtgaacgaa aaaggcaaca   1664

aagtaataaa tcagtgaatg tggccggcag ctgtgtttag cccctccaga tggaagtttc   1724

acttgaatgt aaaataataa agtttatatt ttgaatttct cttttcatgg gggaaaaaag   1784

gtacgttaaa aaaatcaaaa taatgatatg tcacttgcag ctaccttttt ttttctttta   1844

aattcaatca gccaccttca tgtgcctttt tcctttgtct ttccccaaaa ttccaggacc   1904

agagatctgg ccctggccta ttttctcttg ctgtgtacac acacgcacac atgctgggtg   1964

gcaggatctc gcccgctgga gggtggtgga gcccagtaga attggggtga ctgggcataa   2024

acctgctgag actgcttcct tccctggttg tgagtgatgt gaatgcctgc cttccccggt   2084

cagcacttag aagcccttga taggcagcat ttggcgactt gtggggcagg tgtttgggat   2144

aaatcctacc ttcatcctag gacttatttc tgcatcagcc ttttaactca ggcacttcag   2204

gtaacgtgat ctatgtgtgt tttgactgaa tctcatctcc tgtgtttccc tgtgcagtct   2264

agggaagcat gtctccagtc tttgtccctg tcttgtccca accattaatt ctcatgtcac   2324

agcttctcac tgcatgtgac aagagccagg cctatctgct agggccctgc ggctgaggtc   2384

tgacctggac cctcatgccc gagtcggaag acccctctcc agaagccatt ctgcatcctt   2444

gtctgctctg cgtcacccga gaacacaggc ttcgcagcct cgctttctga aatggtgtgt   2504

gccgagtcag attgccgctc agagaaaata caagcccgtt ttccctagct gtgccatttg   2564

gtgctctgcc aggctgccgt gcaagggaat accgacgaga cgagctgcac tgtctctgat   2624

ttggagccct caccggagct tgtctttaaa aatgagcagg aagctcatgt atgtttgcat   2684

ttcagtgagc cgggtcctga cctgccgcca cccatcacgg tcagcgtggt gcatcttacc   2744

gaggaggcgc aggcctggat tcttttgagt ggtgctactg cctaggaagt aacacgtgga   2804

gaatttccat cttgggacca tgcacacagt gccttgggga gtagattttg ccctaatagc   2864

gatgaagaat tttatcagtc agtggagttc ctttttcaga tcagggatgg gaaagagcca   2924

aactgggtac ctcccacgtg tgccccgtga acagcccttt gcagctgggc tgtggggctt   2984

ggctgctgcc ctgtcccatc tggcagttaa cgccttctcc ctgctctgcc ccccactccc   3044

caaaaccagt tgcagcctca acccacatgg ggatgtagaa agccgtaaag tccacgctac   3104

tgttgaaaat gtttacatct ccgctctcaa cctgccttgg gttcgtgtta aatggtgtta   3164

aattctgcaa atggagggga aaaaaatcaa attctaaatt tcaaagtaga atttaaagca   3224
```

```
aatttgtaaa aaaattatcc taccacccct tttggtccac ttaagatatg ccacgctgaa   3284
gcaaggtatt tcctactgga ttttgctttc actggtgttt agaaaataaa cttgatttct   3344
ctaggagcac tcctttggtt agagggatgc aagaaggaga ggtgaaggtg gcgtgtggtg   3404
gctcatgcct gtaatcccag cactttgggg aggccgaggc aggcggatca cttgaggcca   3464
gcagtttgag accagcctgg ccaacatgat gaaaccccat ctctactaaa aatacaaaaa   3524
attagctggg catggtggca ggcacctgta atcccagtta cttgggaggc tgaggcagga   3584
gaattgcttg aacccaggag gtggaggttg cagtgagctg agattgtgcc actgcacttc   3644
agcctgggcg acagagtgac tctgtcaaaa aggaaaggca aaaaccggac cctggagctc   3704
tgtgggccct gattgcaggc ccctccctgt gtgatgaggg atgagtcagc ttggggagcc   3764
acttggccag cctgcatgcc tggtcatcag gaggttgaga aaagccttga aagttgtgaa   3824
gcactgagca gatacaagtg tttgttaatt ttgtagaaat taactttccc atctggcctt   3884
tatctccaaa gttggtattg ttgctccacg cagactgcag tccggtttct tattgtgact   3944
ttgacaatgc aaagtgcaaa ataggaagag gcctccccac cccactatcc caccctggtg   4004
accaattcag tgtaaccttt gcacgtactc agtcattggt gtctttggag tgacatctgc   4064
agccagttag tgccacctga gtacagcact cgtactttta catgatgtgt gtgtgagtag   4124
ctcttctgtc caaaccatga tttgaggttc aactacctgt agatcaaagc tttattttag   4184
aacgataaac tgatttttc caaatgggtg aaatcttctc cccatgacta tgttttctta    4244
actttgcatt gaatctattt actgggttac attctatgtg tagtttgctt tcttcatttt   4304
tttttctttt aaaatgctca tgtcttattc caagcacctt cctccaaagt ccccataaag   4364
ctgcatctcc aacacattgt tatgccaata aggttttatt taactttatt taaggatgat   4424
tgtgtctttg aatgacaaat gtactgctgc ttcctacctg caagacgaac aatgtatgtt   4484
tcaagggtga gcaagtgtta tttcttaaat ttctcaaatg cctgtagtaa ctattgtttc   4544
tgcctctcaa ttgttgccag ctctttgaag aaggggagaa ttgtgtgttt ttgtgtgggg   4604
atgtttctga tatgctgcta cagttgcaaa acactggagc tagagaaaat aaagtactga   4664
tcttcgaa                                                            4672
```

<210> SEQ ID NO 59
<211> LENGTH: 338
<212> TYPE: PRT
<213> ORGANISM: Homo sapiens

<400> SEQUENCE: 59

```
Met Glu Leu Arg Ser Gly Ser Val Gly Ser Gln Ala Val Ala Arg Arg
1               5                   10                  15

Met Asp Gly Asp Ser Arg Asp Gly Gly Gly Gly Lys Asp Ala Thr Gly
            20                  25                  30

Ser Glu Asp Tyr Glu Asn Leu Pro Thr Ser Ala Ser Val Ser Thr His
        35                  40                  45

Met Thr Ala Gly Ala Met Ala Gly Ile Leu Glu His Ser Val Met Tyr
    50                  55                  60

Pro Val Asp Ser Val Lys Thr Arg Met Gln Ser Leu Ser Pro Asp Pro
65                  70                  75                  80

Lys Ala Gln Tyr Thr Ser Ile Tyr Gly Ala Leu Lys Lys Ile Met Arg
                85                  90                  95

Thr Glu Gly Phe Trp Arg Pro Leu Arg Gly Val Asn Val Met Ile Met
            100                 105                 110
```

```
Gly Ala Gly Pro Ala His Ala Met Tyr Phe Ala Cys Tyr Glu Asn Met
        115                 120                 125

Lys Arg Thr Leu Asn Asp Val Phe His His Gln Gly Asn Ser His Leu
    130                 135                 140

Ala Asn Gly Ile Ala Gly Ser Met Ala Thr Leu Leu His Asp Ala Val
145                 150                 155                 160

Met Asn Pro Ala Glu Val Val Lys Gln Arg Leu Gln Met Tyr Asn Ser
                165                 170                 175

Gln His Arg Ser Ala Ile Ser Cys Ile Arg Thr Val Trp Arg Thr Glu
            180                 185                 190

Gly Leu Gly Ala Phe Tyr Arg Ser Tyr Thr Thr Gln Leu Thr Met Asn
        195                 200                 205

Ile Pro Phe Gln Ser Ile His Phe Ile Thr Tyr Glu Phe Leu Gln Glu
    210                 215                 220

Gln Val Asn Pro His Arg Thr Tyr Asn Pro Gln Ser His Ile Ile Ser
225                 230                 235                 240

Gly Gly Leu Ala Gly Ala Leu Ala Ala Ala Ala Thr Thr Pro Leu Asp
                245                 250                 255

Val Cys Lys Thr Leu Leu Asn Thr Gln Glu Asn Val Ala Leu Ser Leu
            260                 265                 270

Ala Asn Ile Ser Gly Arg Leu Ser Gly Met Ala Asn Ala Phe Arg Thr
        275                 280                 285

Val Tyr Gln Leu Asn Gly Leu Ala Gly Tyr Phe Lys Gly Ile Gln Ala
    290                 295                 300

Arg Val Ile Tyr Gln Met Pro Ser Thr Ala Ile Ser Trp Ser Val Tyr
305                 310                 315                 320

Glu Phe Phe Lys Tyr Phe Leu Thr Lys Arg Gln Leu Glu Asn Arg Ala
                325                 330                 335

Pro Tyr


<210> SEQ ID NO 60
<211> LENGTH: 4944
<212> TYPE: DNA
<213> ORGANISM: Homo sapiens
<220> FEATURE:
<221> NAME/KEY: CDS
<222> LOCATION: (128)..(2170)

<400> SEQUENCE: 60

ctatgtctga tagcatttga ccctattgct tttagcctcc cggctttata tctatatata      60

cacaggtata tgtgtatatt ttatataatt gttctccgtt cgttgatatc aaagacagtt     120

gaaggaa atg aat ttt gaa act tca cgg tgt gcc acc cta cag tac tgc      169
        Met Asn Phe Glu Thr Ser Arg Cys Ala Thr Leu Gln Tyr Cys
        1               5                   10

cct gac cct tac atc cag cgt ttc gta gaa acc cca gct cat ttc tct      217
Pro Asp Pro Tyr Ile Gln Arg Phe Val Glu Thr Pro Ala His Phe Ser
15                  20                  25                  30

tgg aaa gaa agt tat tac cga tcc acc atg tcc cag agc aca cag aca      265
Trp Lys Glu Ser Tyr Tyr Arg Ser Thr Met Ser Gln Ser Thr Gln Thr
                35                  40                  45

aat gaa ttc ctc agt cca gag gtt ttc cag cat atc tgg gat ttt ctg      313
Asn Glu Phe Leu Ser Pro Glu Val Phe Gln His Ile Trp Asp Phe Leu
            50                  55                  60

gaa cag cct ata tgt tca gtt cag ccc att gac ttg aac ttt gtg gat      361
Glu Gln Pro Ile Cys Ser Val Gln Pro Ile Asp Leu Asn Phe Val Asp
        65                  70                  75
```

-continued

```
gaa cca tca gaa gat ggt gcg aca aac aag att gag att agc atg gac      409
Glu Pro Ser Glu Asp Gly Ala Thr Asn Lys Ile Glu Ile Ser Met Asp
    80                  85                  90

tgt atc cgc atg cag gac tcg gac ctg agt gac ccc atg tgg cca cag      457
Cys Ile Arg Met Gln Asp Ser Asp Leu Ser Asp Pro Met Trp Pro Gln
95                  100                 105                 110

tac acg aac ctg ggg ctc ctg aac agc atg gac cag cag att cag aac      505
Tyr Thr Asn Leu Gly Leu Leu Asn Ser Met Asp Gln Gln Ile Gln Asn
                115                 120                 125

ggc tcc tcg tcc acc agt ccc tat aac aca gac cac gcg cag aac agc      553
Gly Ser Ser Ser Thr Ser Pro Tyr Asn Thr Asp His Ala Gln Asn Ser
            130                 135                 140

gtc acg gcg ccc tcg ccc tac gca cag ccc agc tcc acc ttc gat gct      601
Val Thr Ala Pro Ser Pro Tyr Ala Gln Pro Ser Ser Thr Phe Asp Ala
        145                 150                 155

ctc tct cca tca ccc gcc atc ccc tcc aac acc gac tac cca ggc ccg      649
Leu Ser Pro Ser Pro Ala Ile Pro Ser Asn Thr Asp Tyr Pro Gly Pro
    160                 165                 170

cac agt ttc gac gtg tcc ttc cag cag tcg agc acc gcc aag tcg gcc      697
His Ser Phe Asp Val Ser Phe Gln Gln Ser Ser Thr Ala Lys Ser Ala
175                 180                 185                 190

acc tgg acg tat tcc act gaa ctg aag aaa ctc tac tgc caa att gca      745
Thr Trp Thr Tyr Ser Thr Glu Leu Lys Lys Leu Tyr Cys Gln Ile Ala
                195                 200                 205

aag aca tgc ccc atc cag atc aag gtg atg acc cca cct cct cag gga      793
Lys Thr Cys Pro Ile Gln Ile Lys Val Met Thr Pro Pro Pro Gln Gly
            210                 215                 220

gct gtt atc cgc gcc atg cct gtc tac aaa aaa gct gag cac gtc acg      841
Ala Val Ile Arg Ala Met Pro Val Tyr Lys Lys Ala Glu His Val Thr
        225                 230                 235

gag gtg gtg aag cgg tgc ccc aac cat gag ctg agc cgt gaa ttc aac      889
Glu Val Val Lys Arg Cys Pro Asn His Glu Leu Ser Arg Glu Phe Asn
    240                 245                 250

gag gga cag att gcc cct cct agt cat ttg att cga gta gag ggg aac      937
Glu Gly Gln Ile Ala Pro Pro Ser His Leu Ile Arg Val Glu Gly Asn
255                 260                 265                 270

agc cat gcc cag tat gta gaa gat ccc atc aca gga aga cag agt gtg      985
Ser His Ala Gln Tyr Val Glu Asp Pro Ile Thr Gly Arg Gln Ser Val
                275                 280                 285

ctg gta cct tat gag cca ccc cag gtt ggc act gaa ttc acg aca gtc     1033
Leu Val Pro Tyr Glu Pro Pro Gln Val Gly Thr Glu Phe Thr Thr Val
            290                 295                 300

ttg tac aat ttc atg tgt aac agc agt tgt gtt gga ggg atg aac cgc     1081
Leu Tyr Asn Phe Met Cys Asn Ser Ser Cys Val Gly Gly Met Asn Arg
        305                 310                 315

cgt cca att tta atc att gtt act ctg gaa acc aga gat ggg caa gtc     1129
Arg Pro Ile Leu Ile Ile Val Thr Leu Glu Thr Arg Asp Gly Gln Val
    320                 325                 330

ctg ggc cga cgc tgc ttt gag gcc cgg atc tgt gct tgc cca gga aga     1177
Leu Gly Arg Arg Cys Phe Glu Ala Arg Ile Cys Ala Cys Pro Gly Arg
335                 340                 345                 350

gac agg aag gcg gat gaa gat agc atc aga aag cag caa gtt tcg gac     1225
Asp Arg Lys Ala Asp Glu Asp Ser Ile Arg Lys Gln Gln Val Ser Asp
                355                 360                 365

agt aca aag aac ggt gat ggt acg aag cgc ccg ttt cgt cag aac aca     1273
Ser Thr Lys Asn Gly Asp Gly Thr Lys Arg Pro Phe Arg Gln Asn Thr
            370                 375                 380

cat ggt atc cag atg aca tcc atc aag aaa cga aga tcc cca gat gat     1321
His Gly Ile Gln Met Thr Ser Ile Lys Lys Arg Arg Ser Pro Asp Asp
        385                 390                 395
```

```
gaa ctg tta tac tta cca gtg agg ggc cgt gag act tat gaa atg ctg      1369
Glu Leu Leu Tyr Leu Pro Val Arg Gly Arg Glu Thr Tyr Glu Met Leu
    400                 405                 410

ttg aag atc aaa gag tcc ctg gaa ctc atg cag tac ctt cct cag cac      1417
Leu Lys Ile Lys Glu Ser Leu Glu Leu Met Gln Tyr Leu Pro Gln His
415                 420                 425                 430

aca att gaa acg tac agg caa cag caa cag cag cag cac cag cac tta      1465
Thr Ile Glu Thr Tyr Arg Gln Gln Gln Gln Gln Gln His Gln His Leu
                435                 440                 445

ctt cag aaa cag acc tca ata cag tct cca tct tca tat ggt aac agc      1513
Leu Gln Lys Gln Thr Ser Ile Gln Ser Pro Ser Ser Tyr Gly Asn Ser
            450                 455                 460

tcc cca cct ctg aac aaa atg aac agc atg aac aag ctg cct tct gtg      1561
Ser Pro Pro Leu Asn Lys Met Asn Ser Met Asn Lys Leu Pro Ser Val
        465                 470                 475

agc cag ctt atc aac cct cag cag cgc aac gcc ctc act cct aca acc      1609
Ser Gln Leu Ile Asn Pro Gln Gln Arg Asn Ala Leu Thr Pro Thr Thr
    480                 485                 490

att cct gat ggc atg gga gcc aac att ccc atg atg ggc acc cac atg      1657
Ile Pro Asp Gly Met Gly Ala Asn Ile Pro Met Met Gly Thr His Met
495                 500                 505                 510

cca atg gct gga gac atg aat gga ctc agc ccc acc cag gca ctc cct      1705
Pro Met Ala Gly Asp Met Asn Gly Leu Ser Pro Thr Gln Ala Leu Pro
                515                 520                 525

ccc cca ctc tcc atg cca tcc acc tcc cac tgc aca ccc cca cct ccg      1753
Pro Pro Leu Ser Met Pro Ser Thr Ser His Cys Thr Pro Pro Pro Pro
            530                 535                 540

tat ccc aca gat tgc agc att gtc agt ttc tta gcg agg ttg ggc tgt      1801
Tyr Pro Thr Asp Cys Ser Ile Val Ser Phe Leu Ala Arg Leu Gly Cys
        545                 550                 555

tca tca tgt ctg gac tat ttc acg acc cag ggg ctg acc acc atc tat      1849
Ser Ser Cys Leu Asp Tyr Phe Thr Thr Gln Gly Leu Thr Thr Ile Tyr
    560                 565                 570

cag att gag cat tac tcc atg gat gat ctg gca agt ctg aaa atc cct      1897
Gln Ile Glu His Tyr Ser Met Asp Asp Leu Ala Ser Leu Lys Ile Pro
575                 580                 585                 590

gag caa ttt cga cat gcg atc tgg aag ggc atc ctg gac cac cgg cag      1945
Glu Gln Phe Arg His Ala Ile Trp Lys Gly Ile Leu Asp His Arg Gln
                595                 600                 605

ctc cac gaa ttc tcc tcc cct tct cat ctc ctg cgg acc cca agc agt      1993
Leu His Glu Phe Ser Ser Pro Ser His Leu Leu Arg Thr Pro Ser Ser
            610                 615                 620

gcc tct aca gtc agt gtg ggc tcc agt gag acc cgg ggt gag cgt gtt      2041
Ala Ser Thr Val Ser Val Gly Ser Ser Glu Thr Arg Gly Glu Arg Val
        625                 630                 635

att gat gct gtg cga ttc acc ctc cgc cag acc atc tct ttc cca ccc      2089
Ile Asp Ala Val Arg Phe Thr Leu Arg Gln Thr Ile Ser Phe Pro Pro
    640                 645                 650

cga gat gag tgg aat gac ttc aac ttt gac atg gat gct cgc cgc aat      2137
Arg Asp Glu Trp Asn Asp Phe Asn Phe Asp Met Asp Ala Arg Arg Asn
655                 660                 665                 670

aag caa cag cgc atc aaa gag gag ggg gag tga gcctcaccat gtgagctctt    2190
Lys Gln Gln Arg Ile Lys Glu Glu Gly Glu
                675                 680

cctatccctc tcctaactgc cagcccccta aaagcactcc tgcttaatct tcaaagcctt    2250

ctccctagct cctccccttc ctcttgtctg atttcttagg ggaaggagaa gtaagaggct    2310

acctcttacc taacatctga cctggcatct aattctgatt ctggctttaa gccttcaaaa    2370
```

```
ctatagcttg cagaactgta gctgccatgg ctaggtagaa gtgagcaaaa aagagttggg   2430
tgtctcctta agctgcagag atttctcatt gacttttata aagcatgttc acccttatag   2490
tctaagacta tatatataaa tgtataaata tacagtatag atttttgggt ggggggcatt   2550
gagtattgtt taaaatgtaa tttaaatgaa agaaaattga gttgcactta ttgaccattt   2610
tttaatttac ttgttttgga tggcttgtct atactccttc ccttaagggg tatcatgtat   2670
ggtgataggt atctagagct taatgctaca tgtgagtgac gatgatgtac agattctttc   2730
agttctttgg attctaaata catgccacat caaacctttg agtagatcca tttccattgc   2790
ttattatgta ggtaagactg tagatatgta ttcttttctc agtgttggta tattttatat   2850
tactgacatt tcttctagtg atgatggttc acgttggggt gatttaatcc agttataaga   2910
agaagttcat gtccaaacgt cctctttagt tttggttgg gaatgaggaa aattcttaaa   2970
aggcccatag cagccagttc aaaaacaccc gacgtcatgt atttgagcat atcagtaacc   3030
cccttaaatt taataccaga taccttatct tacaatattg attgggaaaa catttgctgc   3090
cattacagag gtattaaaac taaatttcac tactagattg actaactcaa atacacattt   3150
gctactgttg taagaattct gattgatttg attgggatga atgccatcta tctagttcta   3210
acagtgaagt tttactgtct attaatattc agggtaaata ggaatcattc agaaatgttg   3270
agtctgtact aaacagtaag atatctcaat gaaccataaa ttcaactttg taaaaatctt   3330
ttgaagcata gataatattg tttggtaaat gtttcttttg tttggtaaat gtttctttta   3390
aagaccctcc tattctataa aactctgcat gtagaggctt gtttaccttt ctctctctaa   3450
ggtttacaat aggagtggtg atttgaaaaa tataaaatta tgagattggt tttcctgtgg   3510
cataaattgc atcactgtat cattttcttt tttaaccggt aagagtttca gtttgttgga   3570
aagtaactgt gagaacccag tttcccgtcc atctccctta gggactaccc atagacatga   3630
aaggtcccca cagagcaaga gataagtctt tcatggctgc tgttgcttaa accacttaaa   3690
cgaagagttc ccttgaaact ttgggaaaac atgttaatga caatattcca gatctttcag   3750
aaatataaca cattttttg catgcatgca aatgagctct gaaatcttcc catgcattct   3810
ggtcaagggc tgtcattgca cataagcttc cattttaatt ttaaagtgca aaagggccag   3870
cgtggctcta aaaggtaatg tgtggattgc ctctgaaaag tgtgtatata ttttgtgtga   3930
aattgcatac tttgtatttt gattattttt tttttcttct tgggatagtg ggatttccag   3990
aaccacactt gaaacctttt tttatcgttt ttgtattttc atgaaaatac catttagtaa   4050
gaataccaca tcaaataaga aataatgcta caattttaag aggggaggga agggaaagtt   4110
tttttttatt attttttaa aattttgtat gttaaagaga atgagtcctt gatttcaaag   4170
ttttgttgta cttaaatggt aataagcact gtaaacttct gcaacaagca tgcagctttg   4230
caaacccatt aaggggaaga atgaaagctg ttccttggtc ctagtaagaa gacaaactgc   4290
ttcccttact ttgctgaggg tttgaataaa cctaggactt ccgagctatg tcagtactat   4350
tcaggtaaca ctagggcctt ggaaattcct gtactgtgtc tcatggattt ggcactagcc   4410
aaagcgaggc acccttactg gcttacctcc tcatggcagc ctactctcct tgagtgtatg   4470
agtagccagg gtaaggggta aaaggatagt aagcatagaa accactagaa agtgggctta   4530
atggagttct tgtggcctca gctcaatgca gttagctgaa gaattgaaaa gtttttgttt   4590
ggagacgttt ataaacagaa atggaaagca gagttttcat taaatccttt taccttttt    4650
ttttcttggt aatcccctaa aataacagta tgtgggatat tgaatgttaa agggatattt   4710
ttttctatta tttttataat tgtacaaaat taagcaaatg ttaaaagttt tatatgcttt   4770
```

attaatgttt tcaaaaggta ttatacatgt gatacatttt ttaagcttca gttgcttgtc 4830
ttctggtact ttctgttatg ggcttttggg gagccagaag ccaatctaca atctcttttt 4890
gtttgccagg acatgcaata aaatttaaaa aataaataaa aactaattaa gaaa 4944

<210> SEQ ID NO 61
<211> LENGTH: 680
<212> TYPE: PRT
<213> ORGANISM: Homo sapiens

<400> SEQUENCE: 61

Met Asn Phe Glu Thr Ser Arg Cys Ala Thr Leu Gln Tyr Cys Pro Asp
1 5 10 15

Pro Tyr Ile Gln Arg Phe Val Glu Thr Pro Ala His Phe Ser Trp Lys
20 25 30

Glu Ser Tyr Tyr Arg Ser Thr Met Ser Gln Ser Thr Gln Thr Asn Glu
35 40 45

Phe Leu Ser Pro Glu Val Phe Gln His Ile Trp Asp Phe Leu Glu Gln
50 55 60

Pro Ile Cys Ser Val Gln Pro Ile Asp Leu Asn Phe Val Asp Glu Pro
65 70 75 80

Ser Glu Asp Gly Ala Thr Asn Lys Ile Glu Ile Ser Met Asp Cys Ile
85 90 95

Arg Met Gln Asp Ser Asp Leu Ser Asp Pro Met Trp Pro Gln Tyr Thr
100 105 110

Asn Leu Gly Leu Leu Asn Ser Met Asp Gln Gln Ile Gln Asn Gly Ser
115 120 125

Ser Ser Thr Ser Pro Tyr Asn Thr Asp His Ala Gln Asn Ser Val Thr
130 135 140

Ala Pro Ser Pro Tyr Ala Gln Pro Ser Ser Thr Phe Asp Ala Leu Ser
145 150 155 160

Pro Ser Pro Ala Ile Pro Ser Asn Thr Asp Tyr Pro Gly Pro His Ser
165 170 175

Phe Asp Val Ser Phe Gln Gln Ser Ser Thr Ala Lys Ser Ala Thr Trp
180 185 190

Thr Tyr Ser Thr Glu Leu Lys Lys Leu Tyr Cys Gln Ile Ala Lys Thr
195 200 205

Cys Pro Ile Gln Ile Lys Val Met Thr Pro Pro Pro Gln Gly Ala Val
210 215 220

Ile Arg Ala Met Pro Val Tyr Lys Lys Ala Glu His Val Thr Glu Val
225 230 235 240

Val Lys Arg Cys Pro Asn His Glu Leu Ser Arg Glu Phe Asn Glu Gly
245 250 255

Gln Ile Ala Pro Pro Ser His Leu Ile Arg Val Glu Gly Asn Ser His
260 265 270

Ala Gln Tyr Val Glu Asp Pro Ile Thr Gly Arg Gln Ser Val Leu Val
275 280 285

Pro Tyr Glu Pro Pro Gln Val Gly Thr Glu Phe Thr Thr Val Leu Tyr
290 295 300

Asn Phe Met Cys Asn Ser Ser Cys Val Gly Gly Met Asn Arg Arg Pro
305 310 315 320

Ile Leu Ile Ile Val Thr Leu Glu Thr Arg Asp Gly Gln Val Leu Gly
325 330 335

Arg Arg Cys Phe Glu Ala Arg Ile Cys Ala Cys Pro Gly Arg Asp Arg

```
            340                 345                 350

Lys Ala Asp Glu Asp Ser Ile Arg Lys Gln Gln Val Ser Asp Ser Thr
        355                 360                 365

Lys Asn Gly Asp Gly Thr Lys Arg Pro Phe Arg Gln Asn Thr His Gly
    370                 375                 380

Ile Gln Met Thr Ser Ile Lys Lys Arg Arg Ser Pro Asp Asp Glu Leu
385                 390                 395                 400

Leu Tyr Leu Pro Val Arg Gly Arg Glu Thr Tyr Glu Met Leu Leu Lys
                405                 410                 415

Ile Lys Glu Ser Leu Glu Leu Met Gln Tyr Leu Pro Gln His Thr Ile
            420                 425                 430

Glu Thr Tyr Arg Gln Gln Gln Gln Gln Gln His Gln His Leu Leu Gln
        435                 440                 445

Lys Gln Thr Ser Ile Gln Ser Pro Ser Ser Tyr Gly Asn Ser Ser Pro
    450                 455                 460

Pro Leu Asn Lys Met Asn Ser Met Asn Lys Leu Pro Ser Val Ser Gln
465                 470                 475                 480

Leu Ile Asn Pro Gln Gln Arg Asn Ala Leu Thr Pro Thr Thr Ile Pro
                485                 490                 495

Asp Gly Met Gly Ala Asn Ile Pro Met Met Gly Thr His Met Pro Met
            500                 505                 510

Ala Gly Asp Met Asn Gly Leu Ser Pro Thr Gln Ala Leu Pro Pro Pro
        515                 520                 525

Leu Ser Met Pro Ser Thr Ser His Cys Thr Pro Pro Pro Pro Tyr Pro
    530                 535                 540

Thr Asp Cys Ser Ile Val Ser Phe Leu Ala Arg Leu Gly Cys Ser Ser
545                 550                 555                 560

Cys Leu Asp Tyr Phe Thr Thr Gln Gly Leu Thr Thr Ile Tyr Gln Ile
                565                 570                 575

Glu His Tyr Ser Met Asp Asp Leu Ala Ser Leu Lys Ile Pro Glu Gln
            580                 585                 590

Phe Arg His Ala Ile Trp Lys Gly Ile Leu Asp His Arg Gln Leu His
        595                 600                 605

Glu Phe Ser Ser Pro Ser His Leu Leu Arg Thr Pro Ser Ser Ala Ser
    610                 615                 620

Thr Val Ser Val Gly Ser Ser Glu Thr Arg Gly Glu Arg Val Ile Asp
625                 630                 635                 640

Ala Val Arg Phe Thr Leu Arg Gln Thr Ile Ser Phe Pro Pro Arg Asp
                645                 650                 655

Glu Trp Asn Asp Phe Asn Phe Asp Met Asp Ala Arg Arg Asn Lys Gln
            660                 665                 670

Gln Arg Ile Lys Glu Glu Gly Glu
        675                 680


<210> SEQ ID NO 62
<211> LENGTH: 7501
<212> TYPE: DNA
<213> ORGANISM: Homo sapiens
<220> FEATURE:
<221> NAME/KEY: CDS
<222> LOCATION: (297)..(4265)

<400> SEQUENCE: 62

gggcagaccc tggagatcgg gctcgcggcg ccttccatcg tggctccgcg ctggggcttg      60

cggagcacgc ttcccgcccc tcggagcccg cgggcccggc cgccccgccc ccgggcgccc     120
```

```
tgagcgagca ggcggggagg gcggggaggg tccgcgcgtt ggtggtgctc gcctcgcagc    180

tgcgcccgcc ggcttcagca ccttccgctg tccgccgctg cagccgcctc ctcctccagg    240

tgctgactat tctgatgccg agtttccaat tgccttgatt aaagtagaaa cattct atg    299
                                                              Met
                                                              1

gct tgg atg act tac att tca aat tgg ttt gag caa gat gat tgg tat      347
Ala Trp Met Thr Tyr Ile Ser Asn Trp Phe Glu Gln Asp Asp Trp Tyr
            5                   10                  15

gaa gga cta caa aga gca aac atg tcc cag gta agg caa gtg gga ttg      395
Glu Gly Leu Gln Arg Ala Asn Met Ser Gln Val Arg Gln Val Gly Leu
        20                  25                  30

ctg gct gct gga tgt cag cca tgg aac aag gat gta tgt gct gcc agt      443
Leu Ala Ala Gly Cys Gln Pro Trp Asn Lys Asp Val Cys Ala Ala Ser
    35                  40                  45

gga gac agg ttt gca tat tgt gcg acc ctg gct atc tat att tat cag      491
Gly Asp Arg Phe Ala Tyr Cys Ala Thr Leu Ala Ile Tyr Ile Tyr Gln
50                  55                  60                  65

ttg gat cac cgt tat aat gaa ttc aaa ctt cac gca att atg tct gaa      539
Leu Asp His Arg Tyr Asn Glu Phe Lys Leu His Ala Ile Met Ser Glu
                70                  75                  80

cat aaa aaa aca atc aca gca att tct tgg tgt cca cat aat cct gat      587
His Lys Lys Thr Ile Thr Ala Ile Ser Trp Cys Pro His Asn Pro Asp
            85                  90                  95

ctg ttt gca agt ggc agt act gat aat tta gtg atc att tgg aat gtt      635
Leu Phe Ala Ser Gly Ser Thr Asp Asn Leu Val Ile Ile Trp Asn Val
        100                 105                 110

gca gaa caa aaa gtc att gct aaa ctc gac agt aca aaa ggg atc cct      683
Ala Glu Gln Lys Val Ile Ala Lys Leu Asp Ser Thr Lys Gly Ile Pro
    115                 120                 125

gct tct ctt agt tgg tgc tgg aat gca gag gat gtg gtg gca ttt gtt      731
Ala Ser Leu Ser Trp Cys Trp Asn Ala Glu Asp Val Val Ala Phe Val
130                 135                 140                 145

tcc cac aga ggc cca ctg ttc att tgg acc atc tca gga cca gat agt      779
Ser His Arg Gly Pro Leu Phe Ile Trp Thr Ile Ser Gly Pro Asp Ser
                150                 155                 160

gga gtg att gta cac aaa gat gct cat agc ttc ttg tct gat atc tgt      827
Gly Val Ile Val His Lys Asp Ala His Ser Phe Leu Ser Asp Ile Cys
            165                 170                 175

atg ttc aga tgg cat aca cac caa aag ggg aaa gtt gtg ttt ggt cat      875
Met Phe Arg Trp His Thr His Gln Lys Gly Lys Val Val Phe Gly His
        180                 185                 190

att gat gga agt cta tca att ttt cat cca ggt aat aaa aat cag aaa      923
Ile Asp Gly Ser Leu Ser Ile Phe His Pro Gly Asn Lys Asn Gln Lys
    195                 200                 205

cat gtt ttg aga cca gaa tct ctt gaa ggg aca gat gaa gag gat cca      971
His Val Leu Arg Pro Glu Ser Leu Glu Gly Thr Asp Glu Glu Asp Pro
210                 215                 220                 225

gtt acg gcc ttg gaa tgg gac cca cta tct act gat tat ctt cta gtg     1019
Val Thr Ala Leu Glu Trp Asp Pro Leu Ser Thr Asp Tyr Leu Leu Val
                230                 235                 240

gtt aat ttg cat tat gga att cgc ctg gta gat tct gaa tca ctt tct     1067
Val Asn Leu His Tyr Gly Ile Arg Leu Val Asp Ser Glu Ser Leu Ser
            245                 250                 255

tgc ata aca aca ttt aat ctt ccc agt gca gca gct tct gta cag tgc     1115
Cys Ile Thr Thr Phe Asn Leu Pro Ser Ala Ala Ala Ser Val Gln Cys
        260                 265                 270

tta gcc tgg gtt ccc agt gct cct ggg atg ttt ata act gga gat tct     1163
Leu Ala Trp Val Pro Ser Ala Pro Gly Met Phe Ile Thr Gly Asp Ser
```

```
    275                 280                 285

caa gtg ggt gtt tta cgc att tgg aat gtt tca aga aca aca cct att      1211
Gln Val Gly Val Leu Arg Ile Trp Asn Val Ser Arg Thr Thr Pro Ile
290                 295                 300                 305

gat aat ctt aaa tta aag aaa aca gga ttt cac tgc tta cat gta ctt      1259
Asp Asn Leu Lys Leu Lys Lys Thr Gly Phe His Cys Leu His Val Leu
                310                 315                 320

aat tct cct cca aga aaa aag ttt tca gtc caa tct cca acc aaa aat      1307
Asn Ser Pro Pro Arg Lys Lys Phe Ser Val Gln Ser Pro Thr Lys Asn
            325                 330                 335

cat tat aca tcc tca aca agc gaa gca gtt cca ccc cca act tta aca      1355
His Tyr Thr Ser Ser Thr Ser Glu Ala Val Pro Pro Pro Thr Leu Thr
        340                 345                 350

cag aat caa gca ttt tct ctt cct cct ggt cat gca gtg tgt tgt ttc      1403
Gln Asn Gln Ala Phe Ser Leu Pro Pro Gly His Ala Val Cys Cys Phe
    355                 360                 365

ttg gat ggt gga gtt gga ctt tat gat atg gga gct aag aag tgg gat      1451
Leu Asp Gly Gly Val Gly Leu Tyr Asp Met Gly Ala Lys Lys Trp Asp
370                 375                 380                 385

ttt ctt aga gac ttg gga cat gtg gaa act atc ttt gac tgc aaa ttc      1499
Phe Leu Arg Asp Leu Gly His Val Glu Thr Ile Phe Asp Cys Lys Phe
                390                 395                 400

aaa cct gac gat cct aat ctt tta gca aca gct tca ttt gat ggc act      1547
Lys Pro Asp Asp Pro Asn Leu Leu Ala Thr Ala Ser Phe Asp Gly Thr
            405                 410                 415

ata aaa gtc tgg gat ata aac aca tta aca gca gtg tac aca tcc ccg      1595
Ile Lys Val Trp Asp Ile Asn Thr Leu Thr Ala Val Tyr Thr Ser Pro
        420                 425                 430

ggt aat gaa ggt gtt att tat tcc ctt tct tgg gct cca ggt ggt tta      1643
Gly Asn Glu Gly Val Ile Tyr Ser Leu Ser Trp Ala Pro Gly Gly Leu
    435                 440                 445

aat tgt att gct ggg gga act tcc cga aat ggt gct ttt att tgg aat      1691
Asn Cys Ile Ala Gly Gly Thr Ser Arg Asn Gly Ala Phe Ile Trp Asn
450                 455                 460                 465

gtt caa aag ggc aaa att ata caa cga ttt aat gag cat gga aca aat      1739
Val Gln Lys Gly Lys Ile Ile Gln Arg Phe Asn Glu His Gly Thr Asn
                470                 475                 480

gga ata ttc tgc att gcc tgg agt cat aaa gat tct aaa aga ata gca      1787
Gly Ile Phe Cys Ile Ala Trp Ser His Lys Asp Ser Lys Arg Ile Ala
            485                 490                 495

acc tgc agc agt gat ggt ttc tgt att att cga aca att gat ggt aaa      1835
Thr Cys Ser Ser Asp Gly Phe Cys Ile Ile Arg Thr Ile Asp Gly Lys
        500                 505                 510

gtg cta cac aaa tat aaa cat cca gct gca gtg ttt ggt tgt gat tgg      1883
Val Leu His Lys Tyr Lys His Pro Ala Ala Val Phe Gly Cys Asp Trp
    515                 520                 525

agc caa aac aat aaa gac atg ata gcc act ggc tgt gaa gac aca aat      1931
Ser Gln Asn Asn Lys Asp Met Ile Ala Thr Gly Cys Glu Asp Thr Asn
530                 535                 540                 545

gtt cgt gtt tat tat gta gcc acc agc tca gat caa cca ttg aaa gta      1979
Val Arg Val Tyr Tyr Val Ala Thr Ser Ser Asp Gln Pro Leu Lys Val
                550                 555                 560

ttt agt ggg cat aca gca aaa gtg ttt cat gtt aaa tgg tct cct ctg      2027
Phe Ser Gly His Thr Ala Lys Val Phe His Val Lys Trp Ser Pro Leu
            565                 570                 575

aga gag gga att ctt tgc agt ggt tct gat gat ggt acc gtt cga atc      2075
Arg Glu Gly Ile Leu Cys Ser Gly Ser Asp Asp Gly Thr Val Arg Ile
        580                 585                 590

tgg gat tat act cag gat gct tgc atc aat att ctt aat gga cac act      2123
```

```
Trp Asp Tyr Thr Gln Asp Ala Cys Ile Asn Ile Leu Asn Gly His Thr
    595                 600                 605

gca cct gtg aga gga tta atg tgg aat act gag att cca tat ctg ctc      2171
Ala Pro Val Arg Gly Leu Met Trp Asn Thr Glu Ile Pro Tyr Leu Leu
610                 615                 620                 625

ata tct ggc agc tgg gac tat act ata aaa gta tgg gac act cga gaa      2219
Ile Ser Gly Ser Trp Asp Tyr Thr Ile Lys Val Trp Asp Thr Arg Glu
                630                 635                 640

gga act tgt gtg gat act gtg tat gat cac ggt gca gat gta tat ggt      2267
Gly Thr Cys Val Asp Thr Val Tyr Asp His Gly Ala Asp Val Tyr Gly
            645                 650                 655

tta acc tgc cat ccc agt cgc ccc ttc act atg gcc tct tgc tcc cgt      2315
Leu Thr Cys His Pro Ser Arg Pro Phe Thr Met Ala Ser Cys Ser Arg
        660                 665                 670

gac tct aca gtg aga ctc tgg tca tta aca gcc tta gtc act cct gta      2363
Asp Ser Thr Val Arg Leu Trp Ser Leu Thr Ala Leu Val Thr Pro Val
    675                 680                 685

caa ata aat att ctg gca gac aga tct tgg gaa gaa att att ggg aac      2411
Gln Ile Asn Ile Leu Ala Asp Arg Ser Trp Glu Glu Ile Ile Gly Asn
690                 695                 700                 705

act gat tat gct ata gaa cca ggc act cct cct cta ctg tgt ggt aaa      2459
Thr Asp Tyr Ala Ile Glu Pro Gly Thr Pro Pro Leu Leu Cys Gly Lys
                710                 715                 720

gtg tca aga gat att aga cag gaa ata gaa aaa cta act gct aat tct      2507
Val Ser Arg Asp Ile Arg Gln Glu Ile Glu Lys Leu Thr Ala Asn Ser
            725                 730                 735

caa gtg aaa aaa cta aga tgg ttc tca gaa tgt tta tct cct cca ggt      2555
Gln Val Lys Lys Leu Arg Trp Phe Ser Glu Cys Leu Ser Pro Pro Gly
        740                 745                 750

ggc agt gac aat tta tgg aac ttg gtt gct gtg ata aaa gga cag gat      2603
Gly Ser Asp Asn Leu Trp Asn Leu Val Ala Val Ile Lys Gly Gln Asp
    755                 760                 765

gat agc tta ctt cct cag aac tac tgc aaa gga ata atg cac ttg aaa      2651
Asp Ser Leu Leu Pro Gln Asn Tyr Cys Lys Gly Ile Met His Leu Lys
770                 775                 780                 785

cat ctg att aaa ttt aga aca tct gaa gct caa gaa cta aca aca gtc      2699
His Leu Ile Lys Phe Arg Thr Ser Glu Ala Gln Glu Leu Thr Thr Val
                790                 795                 800

aag atg tct aaa ttt ggt ggt ggt att ggt gta cct gct aaa gag gaa      2747
Lys Met Ser Lys Phe Gly Gly Gly Ile Gly Val Pro Ala Lys Glu Glu
            805                 810                 815

aga ctg aag gaa gct gct gaa atc cac ttg aga tta gga caa att cag      2795
Arg Leu Lys Glu Ala Ala Glu Ile His Leu Arg Leu Gly Gln Ile Gln
        820                 825                 830

aga tac tgt gaa ctt atg gtt gaa ctt gga gag tgg gac aaa gcc ctg      2843
Arg Tyr Cys Glu Leu Met Val Glu Leu Gly Glu Trp Asp Lys Ala Leu
    835                 840                 845

tca att gca cca gga gtc tct gtg aaa tac tgg aag aag tta atg cag      2891
Ser Ile Ala Pro Gly Val Ser Val Lys Tyr Trp Lys Lys Leu Met Gln
850                 855                 860                 865

agg aga gct gac caa tta atc cag gaa gat aag gat gat gtc att cca      2939
Arg Arg Ala Asp Gln Leu Ile Gln Glu Asp Lys Asp Asp Val Ile Pro
                870                 875                 880

tac tgc ata gcc att ggt gat gtg aaa aag cta gtc cat ttt ttc atg      2987
Tyr Cys Ile Ala Ile Gly Asp Val Lys Lys Leu Val His Phe Phe Met
            885                 890                 895

tca aga ggt cag ctt aaa gaa gct ctg ctt gtt gca cag gct gct tgt      3035
Ser Arg Gly Gln Leu Lys Glu Ala Leu Leu Val Ala Gln Ala Ala Cys
        900                 905                 910
```

```
gaa gga aat atg cag ccc tta cat gtt tcc gtg cct aaa gga gct tca     3083
Glu Gly Asn Met Gln Pro Leu His Val Ser Val Pro Lys Gly Ala Ser
    915                 920                 925

tat tct gat gat atc tac aag gaa gac ttt aat gaa ctc ctg cac aaa     3131
Tyr Ser Asp Asp Ile Tyr Lys Glu Asp Phe Asn Glu Leu Leu His Lys
930                 935                 940                 945

gtc agt aaa gaa ctg gca gaa tgg tat ttt caa gat ggt cga gca gta     3179
Val Ser Lys Glu Leu Ala Glu Trp Tyr Phe Gln Asp Gly Arg Ala Val
                950                 955                 960

cta gcc gca tgt tgc cat ctt gcc ata gat aat att gag ctt gct atg     3227
Leu Ala Ala Cys Cys His Leu Ala Ile Asp Asn Ile Glu Leu Ala Met
            965                 970                 975

gca tac ctg att cgc gga aat gaa ctg gag ttg gca gtc tgt gtg ggc     3275
Ala Tyr Leu Ile Arg Gly Asn Glu Leu Glu Leu Ala Val Cys Val Gly
        980                 985                 990

aca gta cta gga gag tct gca  gca cca gca acc cac  tat gcc tta gaa   3323
Thr Val Leu Gly Glu Ser Ala  Ala Pro Ala Thr His  Tyr Ala Leu Glu
    995                 1000                1005

tta  ctg gcg aga aag tgc  atg atg att tca gta  tgc ttt cca tgt      3368
Leu  Leu Ala Arg Lys Cys  Met Met Ile Ser Val  Cys Phe Pro Cys
1010                 1015                 1020

gtt  gga tac agt gtc ccc  ttt tgt tac gtt aac  agg aat ttg gca      3413
Val  Gly Tyr Ser Val Pro  Phe Cys Tyr Val Asn  Arg Asn Leu Ala
1025                 1030                 1035

gct  gat ctt ctt ctg atg  att cct gat aat gaa  cta cat tta ata      3458
Ala  Asp Leu Leu Leu Met  Ile Pro Asp Asn Glu  Leu His Leu Ile
1040                 1045                 1050

aaa  ctc tgt gct ttc tac  cca gga tgt act gaa  gag ata aat gac      3503
Lys  Leu Cys Ala Phe Tyr  Pro Gly Cys Thr Glu  Glu Ile Asn Asp
1055                 1060                 1065

ctt  cat gat aag tgt aag  cta ccc aca gtg gaa  gaa tgt atg cag      3548
Leu  His Asp Lys Cys Lys  Leu Pro Thr Val Glu  Glu Cys Met Gln
1070                 1075                 1080

tta  gct gag aca gcc cgt  gca gat gac aat ata  ttt gaa act gta      3593
Leu  Ala Glu Thr Ala Arg  Ala Asp Asp Asn Ile  Phe Glu Thr Val
1085                 1090                 1095

aaa  tat tac ttg tta agt  caa gaa cct gaa aaa  gcc ctt cct att      3638
Lys  Tyr Tyr Leu Leu Ser  Gln Glu Pro Glu Lys  Ala Leu Pro Ile
1100                 1105                 1110

ggt  att agc ttt gtt aaa  gaa tac atc agt agc  tca gac tgg act      3683
Gly  Ile Ser Phe Val Lys  Glu Tyr Ile Ser Ser  Ser Asp Trp Thr
1115                 1120                 1125

ttg  gat acc ata tac cct  gtt ctt gac cta ctg  agc tat att cgt      3728
Leu  Asp Thr Ile Tyr Pro  Val Leu Asp Leu Leu  Ser Tyr Ile Arg
1130                 1135                 1140

act  gaa aaa tta ctc ttg  cat acg tgt act gaa  gct cga aat gag      3773
Thr  Glu Lys Leu Leu Leu  His Thr Cys Thr Glu  Ala Arg Asn Glu
1145                 1150                 1155

ttg  ctg ata tta tgt ggt  tac att ggt gca tta  ctg gct atc aga      3818
Leu  Leu Ile Leu Cys Gly  Tyr Ile Gly Ala Leu  Leu Ala Ile Arg
1160                 1165                 1170

aga  cag tac caa agc att  gtt cca gca ctt tat  gag tac aca agt      3863
Arg  Gln Tyr Gln Ser Ile  Val Pro Ala Leu Tyr  Glu Tyr Thr Ser
1175                 1180                 1185

cag  cta tta aaa cgt cgg  gag gtg tca gta cct  tta aaa att gaa      3908
Gln  Leu Leu Lys Arg Arg  Glu Val Ser Val Pro  Leu Lys Ile Glu
1190                 1195                 1200

tat  ctt tct gag gaa ttg  gat gca tgg aga gct  tgc aca cag tcc      3953
Tyr  Leu Ser Glu Glu Leu  Asp Ala Trp Arg Ala  Cys Thr Gln Ser
1205                 1210                 1215
```

```
acc  aac aga tca tta gaa  gac tct ccg tat aca  ccc cct tct gat      3998
Thr  Asn Arg Ser Leu Glu  Asp Ser Pro Tyr Thr  Pro Pro Ser Asp
1220                 1225                 1230

tca  caa aga atg att tat  gca act tta tta aag  aga cta aaa gaa      4043
Ser  Gln Arg Met Ile Tyr  Ala Thr Leu Leu Lys  Arg Leu Lys Glu
1235                 1240                 1245

gag  tca ctg aaa gga att  att gga cca gat tat  gtg act gga tca      4088
Glu  Ser Leu Lys Gly Ile  Ile Gly Pro Asp Tyr  Val Thr Gly Ser
1250                 1255                 1260

aat  ctt cca agt cat tct  gat att cac att tct  tgt ctt acg gga      4133
Asn  Leu Pro Ser His Ser  Asp Ile His Ile Ser  Cys Leu Thr Gly
1265                 1270                 1275

tta  aaa atc cag ggc cct  gtg ttt ttc ctt gaa  gac ggg aaa tct      4178
Leu  Lys Ile Gln Gly Pro  Val Phe Phe Leu Glu  Asp Gly Lys Ser
1280                 1285                 1290

gct  atc tcc ttg aat gat  gct ttg atg tgg gca  aag gtg aat cca      4223
Ala  Ile Ser Leu Asn Asp  Ala Leu Met Trp Ala  Lys Val Asn Pro
1295                 1300                 1305

ttc  tca cct tta ggg act  gga ata cga ctc aat  cca ttc tga          4265
Phe  Ser Pro Leu Gly Thr  Gly Ile Arg Leu Asn  Pro Phe
1310                 1315                 1320

tagaagattt ttgtccatgc ttgatttttt tttttaaaga aaaactttca tgggttagca   4325

ttaccttaat ctttgttgct caagtgccag aggttgggag aaggattgca ggttgggaga   4385

ggtgggaaat agcagtgaat tttagtcatt aacttcaaaa tatatatata tatataattt   4445

aaaggaaaaa taggtgcctc ctttataaac agtaatagct acgtttggga aggaggaaac   4505

atttaaatta taaaggactg aataatctaa aaagcatata aaagtttcac acagcataaa   4565

agataccaaa atatcatatg gttgaaatat tgaaacatat taaattgtgc aacacctaga   4625

atagtgctag acatacagta agtacttaat ggatatttga atgattgaat atcttgaaat   4685

gttgaaatgt aaggtgtgca cagtgatctt caacttaaca aacacttacg ttctccttta   4745

taaaatgcat agtaaaccac taacgttagc tgttttaata aaagttttca gttataagtt   4805

tagtaaatat taataaatgg atacacattc aaaatacttt taaaaaaaag aaaatgttac   4865

cagttttttt atctgaagtt taactgtccc attgtaaagg tgtaagttat ataggcttga   4925

aaaaaattgg cgggtaaaaa tcacaaaatg cagtcgaata tatatatgaa aacttgcatt   4985

aggtgataaa gtgactattt taagagattc agcatgcatg gatattagtt ttgattaatg   5045

tgtacaataa tttacacagt atactctagt caatttatgt taactttatt taaaacacaa   5105

tttatttggc cgggcacggt ggctcacacc tgtaatctca gcactttggc aggccaaggc   5165

aggtggatca cctgaggtca ggagttcatg accagcctgg ccagcatggt aaaaccctgt   5225

ctccactaaa aatacaaaaa ttagccaggc atggtggcgg gcacctgtaa tcccagttac   5285

ttgggaagct gaggcaggag aatcccttga acctgggagg cagaggttcc agtgagccaa   5345

gatcgcacca ctgcactcca gcctgggcaa caaagagcga aactctgtct caaaaaacaa   5405

accaacaaaa accacaattg atttgatgaa aattagtttt aagtaaatgt ttgtaaatag   5465

atattggttg aatttttgga tatattatgt tgatttaact tttaaaatgt tgtttaaaag   5525

tgtgaagcta tgaaaagcct gataatgtga ctacagatat ttcagttgga ctagaattct   5585

gactttgaaa cttattaaat taatgcatac tggaagtact ttgatactca agttgtttca   5645

caagatttat aatatagatg gttttgtttg actaaagaat aatctcatat aactagaata   5705

cttgtggctt ttattatctt taaacttgtt gcatttaaaa tatttttaaa accttcttaa   5765
```

caaaacttct taaaactgga aaaaatatat attatgtatc tatgtatcat atttatcaca 5825 tgaccacttt tgattcctta aaaagacatt acaggcttaa attccatttt attaaaaaaa 5885 aaaaattgcc tgtaatccca gcacttcagg aggccgagat gggcagatct tgaggtcggt 5945 agatggagac catcctggcc aacatggtga aaccctgtct ctactaaaaa tacaaaaatt 6005 agctgggtgt ggtggtgtgt acctgtagtc ccagctaccc aggaagctaa ggcaggagaa 6065 tcgcttgaat ccaggaggcg gaggttgcag tgagctgaga tcgcactact gcactccagc 6125 ctgggcgaca gagcaagacc accatctcca aaaattatat atataaaaat aattaatatt 6185 atagaagaga atatacacaa ctcagagatg caatggataa tataaaaaga gtacctgaga 6245 tgtatttttt taaactctta gagatatctg taactcaaat ttttcttagg tgaggaggat 6305 tattaactgg cacatatgta ctaaaaaccc ctcacttaaa aatggcagtc tcaatcctac 6365 tgtcattctt tttattttaa aataaataaa taagcctatc tttttgtgct tacatactta 6425 aaaggatatc attaagtata taaacaatca ttacttctgt atttttaatg aatgcaggaa 6485 aataatattt ttatgtataa aagatgaaga aaaaattttg caagtcttta agcacataaa 6545 tacaacagaa tagccaccca atttctgtct gaaatctaaa ttggatggat ttgaccatca 6605 ttctattatc tttgatttct acaatgtcta tatcttatta cctataacta ttaatttttc 6665 atagaattat aaatgtcatt tgactatgtc aatctgtata tattgtacct taatatgaaa 6725 aacaaatttt ttaattcata aaagtatttt tattagattt catatgcatg aaacccaagc 6785 aaattatatg aatttatttt actatttgaa aatgttcata ttaccaataa tgtggacaaa 6845 ttactttgca ggtttaaata tgcctctgta aaggaagagt ctcattagac aatgattttt 6905 aaagcattgg aaaaatattt tgcctgtaaa agttagtaac taggtggttc acaaaattac 6965 aacatcaaaa tagttacatc ttgtgaaaat atatgatttt tatgtcaatc aagacaaatg 7025 aaatatatat gtatgtgtat atatatacat gtatgtatga aatatatata tgtgcgtgtg 7085 tgtgtgtata tatatatata tatatatata tttctatgaa attgtccaga tgtgttcagg 7145 aacatgattg cattagagca atgactgtat tttgttgtcc ttataacatt tatattattt 7205 cagttttaag tcaaaaggta ttctgaatat aataaaagcc tcacaaatta tttgtaaaat 7265 ttagtagttc atatttagta tatcagtaat atagaagaca tctttatagt caactcttaa 7325 ttaatgctta ttgtaccaaa tctttgagat atttgtacat aaatgaaata tgtactttca 7385 tgctaaaatt atatatcatg actgtgctat aatttggcat gtcattatct agatttatat 7445 gtatgtacgt atttcaggtc cttgaaattt taataaatat tacagttaaa tcctga 7501

<210> SEQ ID NO 63
<211> LENGTH: 1322
<212> TYPE: PRT
<213> ORGANISM: Homo sapiens

<400> SEQUENCE: 63

Met Ala Trp Met Thr Tyr Ile Ser Asn Trp Phe Glu Gln Asp Asp Trp
1 5 10 15

Tyr Glu Gly Leu Gln Arg Ala Asn Met Ser Gln Val Arg Gln Val Gly
20 25 30

Leu Leu Ala Ala Gly Cys Gln Pro Trp Asn Lys Asp Val Cys Ala Ala
35 40 45

Ser Gly Asp Arg Phe Ala Tyr Cys Ala Thr Leu Ala Ile Tyr Ile Tyr
50 55 60

Gln Leu Asp His Arg Tyr Asn Glu Phe Lys Leu His Ala Ile Met Ser

```
65                  70                  75                  80

Glu His Lys Lys Thr Ile Thr Ala Ile Ser Trp Cys Pro His Asn Pro
                85                  90                  95

Asp Leu Phe Ala Ser Gly Ser Thr Asp Asn Leu Val Ile Ile Trp Asn
            100                 105                 110

Val Ala Glu Gln Lys Val Ile Ala Lys Leu Asp Ser Thr Lys Gly Ile
        115                 120                 125

Pro Ala Ser Leu Ser Trp Cys Trp Asn Ala Glu Asp Val Val Ala Phe
    130                 135                 140

Val Ser His Arg Gly Pro Leu Phe Ile Trp Thr Ile Ser Gly Pro Asp
145                 150                 155                 160

Ser Gly Val Ile Val His Lys Asp Ala His Ser Phe Leu Ser Asp Ile
                165                 170                 175

Cys Met Phe Arg Trp His Thr His Gln Lys Gly Lys Val Val Phe Gly
            180                 185                 190

His Ile Asp Gly Ser Leu Ser Ile Phe His Pro Gly Asn Lys Asn Gln
        195                 200                 205

Lys His Val Leu Arg Pro Glu Ser Leu Glu Gly Thr Asp Glu Glu Asp
    210                 215                 220

Pro Val Thr Ala Leu Glu Trp Asp Pro Leu Ser Thr Asp Tyr Leu Leu
225                 230                 235                 240

Val Val Asn Leu His Tyr Gly Ile Arg Leu Val Asp Ser Glu Ser Leu
                245                 250                 255

Ser Cys Ile Thr Thr Phe Asn Leu Pro Ser Ala Ala Ala Ser Val Gln
            260                 265                 270

Cys Leu Ala Trp Val Pro Ser Ala Pro Gly Met Phe Ile Thr Gly Asp
        275                 280                 285

Ser Gln Val Gly Val Leu Arg Ile Trp Asn Val Ser Arg Thr Thr Pro
    290                 295                 300

Ile Asp Asn Leu Lys Leu Lys Lys Thr Gly Phe His Cys Leu His Val
305                 310                 315                 320

Leu Asn Ser Pro Pro Arg Lys Lys Phe Ser Val Gln Ser Pro Thr Lys
                325                 330                 335

Asn His Tyr Thr Ser Ser Thr Ser Glu Ala Val Pro Pro Pro Thr Leu
            340                 345                 350

Thr Gln Asn Gln Ala Phe Ser Leu Pro Pro Gly His Ala Val Cys Cys
        355                 360                 365

Phe Leu Asp Gly Gly Val Gly Leu Tyr Asp Met Gly Ala Lys Lys Trp
    370                 375                 380

Asp Phe Leu Arg Asp Leu Gly His Val Glu Thr Ile Phe Asp Cys Lys
385                 390                 395                 400

Phe Lys Pro Asp Asp Pro Asn Leu Leu Ala Thr Ala Ser Phe Asp Gly
                405                 410                 415

Thr Ile Lys Val Trp Asp Ile Asn Thr Leu Thr Ala Val Tyr Thr Ser
            420                 425                 430

Pro Gly Asn Glu Gly Val Ile Tyr Ser Leu Ser Trp Ala Pro Gly Gly
        435                 440                 445

Leu Asn Cys Ile Ala Gly Gly Thr Ser Arg Asn Gly Ala Phe Ile Trp
    450                 455                 460

Asn Val Gln Lys Gly Lys Ile Ile Gln Arg Phe Asn Glu His Gly Thr
465                 470                 475                 480

Asn Gly Ile Phe Cys Ile Ala Trp Ser His Lys Asp Ser Lys Arg Ile
                485                 490                 495
```

```
Ala Thr Cys Ser Ser Asp Gly Phe Cys Ile Ile Arg Thr Ile Asp Gly
            500                 505                 510

Lys Val Leu His Lys Tyr Lys His Pro Ala Ala Val Phe Gly Cys Asp
        515                 520                 525

Trp Ser Gln Asn Asn Lys Asp Met Ile Ala Thr Gly Cys Glu Asp Thr
    530                 535                 540

Asn Val Arg Val Tyr Tyr Val Ala Thr Ser Ser Asp Gln Pro Leu Lys
545                 550                 555                 560

Val Phe Ser Gly His Thr Ala Lys Val Phe His Val Lys Trp Ser Pro
                565                 570                 575

Leu Arg Glu Gly Ile Leu Cys Ser Gly Ser Asp Asp Gly Thr Val Arg
            580                 585                 590

Ile Trp Asp Tyr Thr Gln Asp Ala Cys Ile Asn Ile Leu Asn Gly His
        595                 600                 605

Thr Ala Pro Val Arg Gly Leu Met Trp Asn Thr Glu Ile Pro Tyr Leu
    610                 615                 620

Leu Ile Ser Gly Ser Trp Asp Tyr Thr Ile Lys Val Trp Asp Thr Arg
625                 630                 635                 640

Glu Gly Thr Cys Val Asp Thr Val Tyr Asp His Gly Ala Asp Val Tyr
                645                 650                 655

Gly Leu Thr Cys His Pro Ser Arg Pro Phe Thr Met Ala Ser Cys Ser
            660                 665                 670

Arg Asp Ser Thr Val Arg Leu Trp Ser Leu Thr Ala Leu Val Thr Pro
        675                 680                 685

Val Gln Ile Asn Ile Leu Ala Asp Arg Ser Trp Glu Glu Ile Ile Gly
    690                 695                 700

Asn Thr Asp Tyr Ala Ile Glu Pro Gly Thr Pro Pro Leu Leu Cys Gly
705                 710                 715                 720

Lys Val Ser Arg Asp Ile Arg Gln Glu Ile Glu Lys Leu Thr Ala Asn
                725                 730                 735

Ser Gln Val Lys Lys Leu Arg Trp Phe Ser Glu Cys Leu Ser Pro Pro
            740                 745                 750

Gly Gly Ser Asp Asn Leu Trp Asn Leu Val Ala Val Ile Lys Gly Gln
        755                 760                 765

Asp Asp Ser Leu Leu Pro Gln Asn Tyr Cys Lys Gly Ile Met His Leu
    770                 775                 780

Lys His Leu Ile Lys Phe Arg Thr Ser Glu Ala Gln Glu Leu Thr Thr
785                 790                 795                 800

Val Lys Met Ser Lys Phe Gly Gly Gly Ile Gly Val Pro Ala Lys Glu
                805                 810                 815

Glu Arg Leu Lys Glu Ala Ala Glu Ile His Leu Arg Leu Gly Gln Ile
            820                 825                 830

Gln Arg Tyr Cys Glu Leu Met Val Glu Leu Gly Glu Trp Asp Lys Ala
        835                 840                 845

Leu Ser Ile Ala Pro Gly Val Ser Val Lys Tyr Trp Lys Lys Leu Met
    850                 855                 860

Gln Arg Arg Ala Asp Gln Leu Ile Gln Glu Asp Lys Asp Asp Val Ile
865                 870                 875                 880

Pro Tyr Cys Ile Ala Ile Gly Asp Val Lys Lys Leu Val His Phe Phe
                885                 890                 895

Met Ser Arg Gly Gln Leu Lys Glu Ala Leu Leu Val Ala Gln Ala Ala
            900                 905                 910
```

```
Cys Glu Gly Asn Met Gln Pro Leu His Val Ser Val Pro Lys Gly Ala
        915                 920                 925

Ser Tyr Ser Asp Asp Ile Tyr Lys Glu Asp Phe Asn Glu Leu Leu His
    930                 935                 940

Lys Val Ser Lys Glu Leu Ala Glu Trp Tyr Phe Gln Asp Gly Arg Ala
945                 950                 955                 960

Val Leu Ala Ala Cys Cys His Leu Ala Ile Asp Asn Ile Glu Leu Ala
                965                 970                 975

Met Ala Tyr Leu Ile Arg Gly Asn Glu Leu Glu Leu Ala Val Cys Val
            980                 985                 990

Gly Thr Val Leu Gly Glu Ser Ala  Ala Pro Ala Thr His  Tyr Ala Leu
        995                 1000                 1005

Glu Leu  Leu Ala Arg Lys Cys  Met Met Ile Ser Val  Cys Phe Pro
    1010                 1015                 1020

Cys Val  Gly Tyr Ser Val Pro  Phe Cys Tyr Val Asn  Arg Asn Leu
    1025                 1030                 1035

Ala Ala  Asp Leu Leu Leu Met  Ile Pro Asp Asn Glu  Leu His Leu
    1040                 1045                 1050

Ile Lys  Leu Cys Ala Phe Tyr  Pro Gly Cys Thr Glu  Glu Ile Asn
    1055                 1060                 1065

Asp Leu  His Asp Lys Cys Lys  Leu Pro Thr Val Glu  Glu Cys Met
    1070                 1075                 1080

Gln Leu  Ala Glu Thr Ala Arg  Ala Asp Asp Asn Ile  Phe Glu Thr
    1085                 1090                 1095

Val Lys  Tyr Tyr Leu Leu Ser  Gln Glu Pro Glu Lys  Ala Leu Pro
    1100                 1105                 1110

Ile Gly  Ile Ser Phe Val Lys  Glu Tyr Ile Ser Ser  Ser Asp Trp
    1115                 1120                 1125

Thr Leu  Asp Thr Ile Tyr Pro  Val Leu Asp Leu Leu  Ser Tyr Ile
    1130                 1135                 1140

Arg Thr  Glu Lys Leu Leu Leu  His Thr Cys Thr Glu  Ala Arg Asn
    1145                 1150                 1155

Glu Leu  Leu Ile Leu Cys Gly  Tyr Ile Gly Ala Leu  Leu Ala Ile
    1160                 1165                 1170

Arg Arg  Gln Tyr Gln Ser Ile  Val Pro Ala Leu Tyr  Glu Tyr Thr
    1175                 1180                 1185

Ser Gln  Leu Leu Lys Arg Arg  Glu Val Ser Val Pro  Leu Lys Ile
    1190                 1195                 1200

Glu Tyr  Leu Ser Glu Glu Leu  Asp Ala Trp Arg Ala  Cys Thr Gln
    1205                 1210                 1215

Ser Thr  Asn Arg Ser Leu Glu  Asp Ser Pro Tyr Thr  Pro Pro Ser
    1220                 1225                 1230

Asp Ser  Gln Arg Met Ile Tyr  Ala Thr Leu Leu Lys  Arg Leu Lys
    1235                 1240                 1245

Glu Glu  Ser Leu Lys Gly Ile  Ile Gly Pro Asp Tyr  Val Thr Gly
    1250                 1255                 1260

Ser Asn  Leu Pro Ser His Ser  Asp Ile His Ile Ser  Cys Leu Thr
    1265                 1270                 1275

Gly Leu  Lys Ile Gln Gly Pro  Val Phe Phe Leu Glu  Asp Gly Lys
    1280                 1285                 1290

Ser Ala  Ile Ser Leu Asn Asp  Ala Leu Met Trp Ala  Lys Val Asn
    1295                 1300                 1305

Pro Phe  Ser Pro Leu Gly Thr  Gly Ile Arg Leu Asn  Pro Phe
```

1310 1315 1320

<210> SEQ ID NO 64
<211> LENGTH: 5454
<212> TYPE: DNA
<213> ORGANISM: Homo sapiens

<400> SEQUENCE: 64
aggcatttcc ggcccagggg gcttggctcc ccgcggcacg ggatttagcg ttcgcgctcc 60
ttcccttccc gtggtcgagc cgagtcctga cctgagggct gcatcaagat cttgtcattc 120
cacatcgtgg tttcctttga ggatgtggct gtacccctct cccaggagga gtgggactgt 180
ctgatccctg ctcagagggg cctctacaag gatgtgatga tggggaccta tgggaaccta 240
ctctcattag taggtgaatg gttaagcaaa ctgtggtaca tccataccat gggatacgac 300
tcaacaatca aaaggaactg cccagacttc accacgatgc aatatatgca tgacttcaag 360
cttccaaacc tgatgtcatc tccaggctgg agcgggggga cgaaccatag acccctcaca 420
tcctgagaac tcaggggagc tggagctgga ggcacaagag agaaggctgt gattctagga 480
ttgaaaaaga ggaaatgatt ccaaagcagg acatttctga agaattggaa tcccagagag 540
caaaatcaga agatcatgta aggaatattt ttaaggaaac tgaagagatg agtaaaactg 600
agggaaagtt agagaattgc tggagaaaat atgcagtaga aggagttaag aactcattct 660
cccagaagag caatttcaga gaaattacca tgaggtatgt gaaaaccctc tctagagaga 720
atggccagaa gttcaatgct gttggagaaa actgcattac agactcaaat cctgccaaac 780
atcttagagg gtctagagag gagagtctcc atccaagtgt gtcaagtgta gaaaacttgc 840
aacaacatga ggacctcatt aacctccaga gtttccaatt aggagaaaga gcctatcaga 900
cagatgtgtt agtgaaagtg cccagacaga gctcagttct tagtgagaat cagaggatga 960
ataatccaga gagatggttt gagagtactg ggtgtggaaa aacttacaat cagaacagag 1020
cttttaacca gcaccagaga tttcatagtg gagagaagac ctatgagcac aatgaatgtg 1080
gaaaagcttt cagttggccc tctatcctca gtaaacatca gagaatccac actggtaaga 1140
aactctacac atgtgaggat tgtggcaaat ctttcagtgt tcactcatac tttattcagc 1200
attgtaaaat tcacactaga gaaaaaccct atgagtgtat taaatgtggg aaagctttta 1260
gtacacattc atcttatgtt caacatctaa aaattcatac aggagagaaa catcatgagt 1320
gtaatcagtg tgggaaagcc tttagtcata gctctaatct aattcatcat cagagaattc 1380
atagtggaga gaaaccttac aagtgcaaag aatgtgggaa agccttcaac agacaatcaa 1440
accttattca gcatcagaga attcattctg gagagaaacc ttatgactgt aaggagtgtg 1500
gcaaagcctt cagtacacaa ttatttctca ttcagcatca gagaattcat acaggagaaa 1560
agccctatga atgtaatgaa tgtgcaaaat cctttagcct gaaccgaact cttactgtcc 1620
atcagagaat tcacactgga gagaaacctt ataggtgtaa tgaatgtggg aaatccttta 1680
gtcaatgctc acaagttatt caacataaga gaattcacac tggagagaaa ccttatatct 1740
gcaatgagtg tggaaaatca tttggtgctc gtctatccct tatccagcat cagagaattc 1800
acactggaga gaaaccttat ggttgtagtg tgtgtgggaa aacctttagt caaaagggac 1860
atcttattca gcatcagtga attcacacag gagagaaacc ctatgaatgt agtgagtgtg 1920
gaaaagcttt cagccagagt tttaatctta ttcaccatca aagaacacac aatggtgaga 1980
agtcctatga atgtaatgaa tgtgataaag ccttcagttt gctttcttcc cttgttcaac 2040
atcagagaat acataatgga gacaaaccct atgagtgtca caaatgtggg aaggccttta 2100
gccaggggtc acaccttatt cagcatcaga ggagtcacat tggtgagaaa ccctatgagt 2160
gtaatgagtg tgggaaaacc tttgggcaga tatccaccct aattaagcat gagagaacac 2220
acaatggaga gaagccctat gagtgcagtg actgtgggaa ggccttcagc cagagtgcac 2280
accttatcca ccatcaaaga attcacactg gagagaatcc ctatgagtgc agtgaatgtg 2340
ggaaggcctt caatgtttgt tcctctctca ttcagcatca cagaattcat actggtgaga 2400
aaccttatga atgtagtgac tgtggcaagg cgttcagtca gcattcacaa tttatccaac 2460
atcagagaat tcacactgga gagaaaccct acatgtgcaa tgagtgtgag aaatccttca 2520
gtgcatgctt atcccttatc caacacaaga gaattcacac tggagagaaa ccctatgtat 2580
gtgccaaatg tggaaaatcc ttctgacaaa gctctcacct tattcaacat cagagaattc 2640
acagtgggga gcaacctcat acgtgtaatc gatgtgaaaa aaccttcagt tagagaataa 2700
ctcttagtag tcatgagaaa atccatacaa ttcacattag agagcaagtc tatgaatgta 2760
gtaagtgtgg ggaactctag cgcacagtca tctttcattc aacattgtac agttcacagt 2820
ggagagtaac tgattagtct ataaattctt cacagttata cattatatga gagtcatact 2880
cgtgagaaat gagtcacttt atggttttcc ttttggagat tcagctctta agggatttca 2940
ctctcccagt gagctgctaa ctaaaggcag gctgctgaag tatatagcag caatcccaca 3000
atagcacacc ttgcttcaga ttcagaggat gagccccctt cttgagccct gtagatatgt 3060
gaaacttaat tatttagatg catttcatgg caccagaccc taaggtacag ttaggtattt 3120
cactggagac cacttacttt gctttgcttt gctttttttt tttttttttt ttgtatgatt 3180
tatttcaact tcaaagaaag tagttgagat ccttgcactt ccaagtgtga tggaaccagg 3240
ctagggtttt ctttgtttgt ttgggcctct tcaaaacgtt tttattctgt tataaggaat 3300
atgatacctt aagcttcaat tcacagggaa gagaaacatg attataagca aaagtttgtc 3360
aaggaataag gtgagtcttt gtgtagatta aaatagttga gaccttgcta aaaagtcaga 3420
taacactgta atccacctcc aggtttccaa gagttaagac gctgccagca aggagcttgc 3480
agtcttgtag ctggcccaat atatccaact aattcaaaat gggaaattgt acattttact 3540
taaacaggat ttggtagatg ggtcttctag atatgttgtc atgaagaaaa atcaggaaaa 3600
tgtccaaggg tgggagcctg tggcttatgg cttcacttac ccatcacaga tagctatgtt 3660
acactgcaag aacagagttc atggcttttc ctgaggtggc tggaaacctt aatctcctga 3720
agttaagtca aaacttaaat gtcaattcac ccagctctct tgcctgcagg ctgatccagg 3780
gacttagagc ttgttaccca gttacaactt cttctagaga agaactttta agaaggaagc 3840
aaaaagaaat tcagtttccc ccaaggatct cttctttgag gttccatcaa gagatgacaa 3900
aaggaggctg ggcgcggtgt ctcacacctg taatcccagc actttgggag gctgaagtgg 3960
gcagatcacg aggtcaagag atcaagacca tcctggccaa catggtgaaa ccacatttct 4020
acaaaatgca aaaattagct gggcatggtg gtgcacgcct gtagtcccag ctacttggga 4080
ggctgaggca ggagaattgc ttgaacccag gaggcggagg tagcagtgag ccaagattgc 4140
accactgcat tccagcatgg ccacaaagca agactccaaa aaatatatat atatatgaca 4200
aaagggttag gaagcttttc ctctgaggcc cacgattaca caaccaaatc agaaaataat 4260
attttttttg ttttaaacct gtttacataa gatggaggtg tttacttaac taagaacctc 4320
ggtatttact caaatccggt tttgggtttt atggctaaaa catttctcca gattaacctt 4380
atcagtttgg aatatgtttt tattttccat taaatatttc atccaaatca tactgaattt 4440

```
tatttatcat ggcttttaat gttctctatt caagtcaaat ttctgtttcc taattacttg   4500

gcttggtgat ggcattaata ttggttggga gctagatggt ctctgctcta tttgatgatt   4560

ggcatagagc aatcatacac ttggtacttc ctagcatttt tttttgagac agtatcatgc   4620

tgtatcatgt tgcacagggt ggagtgcagt ggtgcagtca tagctcactg taaccttgaa   4680

ctcctgggct caagtgattc ccctgcctca acttcatgag tagcagggac tacagctgtg   4740

taccaccaca ccggcctctc ctggcttctt aaccacttac attaaaattg agaggagaaa   4800

ggcattttca gtttctttag ttaataaaaa gaagccattt ctggaggagt tttatgcctg   4860

taccagcaga ggttcagcct tccaggaatc tcatcatgat ccatactgct gacacaggcc   4920

tttgtcacct gaagcattct taaaataagg agactgacat taaacaggac aattgtgaac   4980

tccactttgt aagcatcata catatcttac aactcattct gaagactcct ttattcttgc   5040

tcttcccaga gagctactgt gtttagtcat gctcactgca ctcacaagag aaaaagagta   5100

agtggcatat ttgcaggtgt tgatggttac aagagcattt ttactttttc ctccatgttt   5160

gttctgcagc atttccattg atgcatgcta ttgtagactt cttaggttga ccttggcctt   5220

gacctccacc actagctcat gacccaaaac tgaagatgtg catcagaaag ggacagattt   5280

ggtctttctg ctgtaaaaga tattctgcct tagtgcctgc taatttgttg tgcatagtcc   5340

tgtgctgcca atcttcccca ccaattgtta aggttaatgt gtgttttata tgtgtattca   5400

caaacattaa aatgtaatca gtggattcca aaaaaaaaaa aaaaaaaaaa aaaa         5454
```

<210> SEQ ID NO 65
<211> LENGTH: 3061
<212> TYPE: DNA
<213> ORGANISM: Homo sapiens
<220> FEATURE:
<221> NAME/KEY: CDS
<222> LOCATION: (303)..(1949)

<400> SEQUENCE: 65

```
gcgcacggcg aatccaccgg taccgtggtg gaagcgcgcc ctgggctgcc gggggcgcgg     60

ccgcggtggc acttggaccc gaggaggcgg caggtgagag gttccggagc tttccaggcg    120

ctctggggtc cagcaggagc tggtgcccgg gccggttggg tctcaggcct gagaagaacg    180

cagacgtctc gcctcatcgt cgctctgtgg ctttaccggc gtgagactac atttcccgcc    240

ggccctcgcg gcgtgcgctt tctggcgccc cctttctgct tccagcctca tagcccaggt    300

gc atg gac ccc tta gct cta ccg tcg cag gac tct gcc ctt ccc caa       347
   Met Asp Pro Leu Ala Leu Pro Ser Gln Asp Ser Ala Leu Pro Gln
   1               5                   10                  15

gag agg aac cag aag gag gac cta tca gcc ctt gaa att cta aaa gtc      395
Glu Arg Asn Gln Lys Glu Asp Leu Ser Ala Leu Glu Ile Leu Lys Val
               20                  25                  30

atg tcc ctt ggg tca gaa ttg ttc agg gat gtg gcc ata gtc ttc tcc      443
Met Ser Leu Gly Ser Glu Leu Phe Arg Asp Val Ala Ile Val Phe Ser
            35                  40                  45

caa gaa gaa tgg cag tgg ttg gca cct gct cag agg gat ttg tac aga      491
Gln Glu Glu Trp Gln Trp Leu Ala Pro Ala Gln Arg Asp Leu Tyr Arg
        50                  55                  60

gac gtg atg ttg gag acc tac agc aac ctg gtc tca ctg ggt ctt gcc      539
Asp Val Met Leu Glu Thr Tyr Ser Asn Leu Val Ser Leu Gly Leu Ala
    65                  70                  75

gtt tcc aaa cct gat gtg atc tcc ttc cta gag caa ggc aaa gag ccc      587
Val Ser Lys Pro Asp Val Ile Ser Phe Leu Glu Gln Gly Lys Glu Pro
80                  85                  90                  95
```

-continued

```
tgg atg gtg gag aga gtg gtg tct gga ggc ctg tgt cca gta ttg gag      635
Trp Met Val Glu Arg Val Val Ser Gly Gly Leu Cys Pro Val Leu Glu
                100                 105                 110

tcc aga tat gat acc aag gaa tta ttt cca aag cag cat gtt tat gaa      683
Ser Arg Tyr Asp Thr Lys Glu Leu Phe Pro Lys Gln His Val Tyr Glu
            115                 120                 125

gtc gaa tca ccc caa tgg gag ata atg gaa agc ctt aca agt tat ggt      731
Val Glu Ser Pro Gln Trp Glu Ile Met Glu Ser Leu Thr Ser Tyr Gly
        130                 135                 140

ctt gag tgt tca agt ttc caa gat gat tgg gaa tgc aga aac cag ttt      779
Leu Glu Cys Ser Ser Phe Gln Asp Asp Trp Glu Cys Arg Asn Gln Phe
    145                 150                 155

gac aga caa cag gga aat cca gac aga cat ttc cat cag atg atc atc      827
Asp Arg Gln Gln Gly Asn Pro Asp Arg His Phe His Gln Met Ile Ile
160                 165                 170                 175

aga cat gaa gaa atg ccc act ttt gac cag cat gca tcc ctt act ttt      875
Arg His Glu Glu Met Pro Thr Phe Asp Gln His Ala Ser Leu Thr Phe
                180                 185                 190

tat cag aaa att cat act aga gaa aaa cct ttt ggg tat aat aaa tgt      923
Tyr Gln Lys Ile His Thr Arg Glu Lys Pro Phe Gly Tyr Asn Lys Cys
            195                 200                 205

aga aaa gac ttc tgg caa aag gaa ctc ctt att aat cat caa gga att      971
Arg Lys Asp Phe Trp Gln Lys Glu Leu Leu Ile Asn His Gln Gly Ile
        210                 215                 220

tat act aat gag aaa ccc tat aaa tgt aag gaa tgt ggg aag gcc ttt     1019
Tyr Thr Asn Glu Lys Pro Tyr Lys Cys Lys Glu Cys Gly Lys Ala Phe
    225                 230                 235

aaa tat ggc tca cga cta att caa cat gag aat att cat tct ggt aag     1067
Lys Tyr Gly Ser Arg Leu Ile Gln His Glu Asn Ile His Ser Gly Lys
240                 245                 250                 255

aaa cca tat gaa tgt aag gaa tgt gga aag gcc ttc aat tct ggt tca     1115
Lys Pro Tyr Glu Cys Lys Glu Cys Gly Lys Ala Phe Asn Ser Gly Ser
                260                 265                 270

aat ttt ata caa cat cag aga gtt cat act ggt gag aaa ccg tat gaa     1163
Asn Phe Ile Gln His Gln Arg Val His Thr Gly Glu Lys Pro Tyr Glu
            275                 280                 285

tgt aaa gat tgt gag aag gcc ttt agt cga agc tca cag ttg att gaa     1211
Cys Lys Asp Cys Glu Lys Ala Phe Ser Arg Ser Ser Gln Leu Ile Glu
        290                 295                 300

cat cag cga act cac aca ggc gag aaa ccc tat cag tgt aag gaa tgt     1259
His Gln Arg Thr His Thr Gly Glu Lys Pro Tyr Gln Cys Lys Glu Cys
    305                 310                 315

ggc aag gcc ttc aat cgg atc tca cat ctt aaa gta cat tat aga att     1307
Gly Lys Ala Phe Asn Arg Ile Ser His Leu Lys Val His Tyr Arg Ile
320                 325                 330                 335

cat act ggt gaa aaa ccc tat gca tgc aag gaa tgt ggg aaa acc ttt     1355
His Thr Gly Glu Lys Pro Tyr Ala Cys Lys Glu Cys Gly Lys Thr Phe
                340                 345                 350

agt cat cgt tct cag ttg att caa cat cag act gtt cat act ggc agg     1403
Ser His Arg Ser Gln Leu Ile Gln His Gln Thr Val His Thr Gly Arg
            355                 360                 365

aaa ctc tat gaa tgt aag gaa tgt ggg aag gct ttt aat caa ggc tca     1451
Lys Leu Tyr Glu Cys Lys Glu Cys Gly Lys Ala Phe Asn Gln Gly Ser
        370                 375                 380

act ctt ata cga cat cag aga att cat acc ggt gag aaa ccc tat gag     1499
Thr Leu Ile Arg His Gln Arg Ile His Thr Gly Glu Lys Pro Tyr Glu
    385                 390                 395

tgc aaa gta tgt gga aag gcc ttt aga gtg agc tca caa ctc aag caa     1547
Cys Lys Val Cys Gly Lys Ala Phe Arg Val Ser Ser Gln Leu Lys Gln
400                 405                 410                 415
```

```
cat cag aga att cac act gga gag aaa ccc tac caa tgt aag gta tgt     1595
His Gln Arg Ile His Thr Gly Glu Lys Pro Tyr Gln Cys Lys Val Cys
                420                 425                 430

ggt agg gcc ttc aaa cgg gtc tca cat ctt act gta cat tac aga att     1643
Gly Arg Ala Phe Lys Arg Val Ser His Leu Thr Val His Tyr Arg Ile
            435                 440                 445

cat aca ggt gaa aag cca tat gaa tgt aag gaa tgt ggg aag gct ttt     1691
His Thr Gly Glu Lys Pro Tyr Glu Cys Lys Glu Cys Gly Lys Ala Phe
        450                 455                 460

agt cat tgc tca caa ttg att cat cat cag gtt att cac act gag aaa     1739
Ser His Cys Ser Gln Leu Ile His His Gln Val Ile His Thr Glu Lys
    465                 470                 475

aag ccc tat gaa tat aag gaa tgt gag aag acc ttg agt cat gat tca     1787
Lys Pro Tyr Glu Tyr Lys Glu Cys Glu Lys Thr Leu Ser His Asp Ser
480                 485                 490                 495

act acc gtt caa cct cag aga atg cat aat aga gaa aca cat gtg aat     1835
Thr Thr Val Gln Pro Gln Arg Met His Asn Arg Glu Thr His Val Asn
                500                 505                 510

ata ata aat gta gaa aag cct tcc atc agc agt tac ccc tta cta atc     1883
Ile Ile Asn Val Glu Lys Pro Ser Ile Ser Ser Tyr Pro Leu Leu Ile
            515                 520                 525

atc aga gaa ttt atg ttg gca agc aac cat atg aat gga agt aat ggg     1931
Ile Arg Glu Phe Met Leu Ala Ser Asn His Met Asn Gly Ser Asn Gly
        530                 535                 540

gaa agc cca tta gcc tag gctaattgtg actgtgactt acttctccct           1979
Glu Ser Pro Leu Ala
    545

cttggagaaa gacttgaaga atgtaatgcc agtgacaatg ccttcattca gaggtaagcc   2039

tttatcctaa gtctgaaaat tcatatcaaa gaaaatttta tggatgtaaa ttgttcagat   2099

cataattgtc aaaaatgctg ggaaaggttg ggagaaattt tatttctaac acattccaga   2159

accacatttt ctaaccacag tgtagtaatt ttatcaagag caaaagttat agttttctta   2219

caagttaaaa aaacagccag attatcattt gcttaacaaa gaaatcatgc aattaccata   2279

aatggtaatg aaaagaatga attgagagtt taacatgcca agagatgtga aatgtggcca   2339

aagagatgtg agggtaaggg gaaagccaaa gctacactgg aggaattttt atagcctttg   2399

aatgcatgca tatacatgaa aatctgaaag ataaactcat atgcactaaa catgctattc   2459

aagtctacca aacatccagg cagtgaaaga agaaagtaac agaaaatgat gaaataaaga   2519

gaccatctta caataatctc agtttttgtt tctttctgat ccagaaataa tctaaattta   2579

ggagaatatt tcttaatttc cacattgtta cattgtttta tgtgactggc acagacaacc   2639

attggttgtc atcccagcag ccatacccaa ttccccttgt tattggcagc atctgtgtct   2699

tgccttggac tctgagaata tcagatgcta attttccagt ctcctgtgca gcacagtatg   2759

gccagtatct cccagtgttg ctcagtggaa tctgccgggg cttctgggaa agattttcct   2819

cattcagaag agacaggttt atcatgaaga cttcctcctc tctcacttcc tgcttttaaa   2879

catttttata taagaacatg atgcctgaag ctgctgcagc tgtcttggaa ccaagaagag   2939

aaaaaagtgg acctcagaga agctgaccca gagcctgaga agactcagct actaggccaa   2999

ttctggaact gcctttttga tgccttgtta tctgagaaaa ataaaacttg attgctcagt   3059

ta                                                                  3061
```

<210> SEQ ID NO 66
<211> LENGTH: 548
<212> TYPE: PRT

<213> ORGANISM: Homo sapiens

<400> SEQUENCE: 66

Met Asp Pro Leu Ala Leu Pro Ser Gln Asp Ser Ala Leu Pro Gln Glu
1 5 10 15

Arg Asn Gln Lys Glu Asp Leu Ser Ala Leu Glu Ile Leu Lys Val Met
20 25 30

Ser Leu Gly Ser Glu Leu Phe Arg Asp Val Ala Ile Val Phe Ser Gln
35 40 45

Glu Glu Trp Gln Trp Leu Ala Pro Ala Gln Arg Asp Leu Tyr Arg Asp
50 55 60

Val Met Leu Glu Thr Tyr Ser Asn Leu Val Ser Leu Gly Leu Ala Val
65 70 75 80

Ser Lys Pro Asp Val Ile Ser Phe Leu Glu Gln Gly Lys Glu Pro Trp
85 90 95

Met Val Glu Arg Val Val Ser Gly Gly Leu Cys Pro Val Leu Glu Ser
100 105 110

Arg Tyr Asp Thr Lys Glu Leu Phe Pro Lys Gln His Val Tyr Glu Val
115 120 125

Glu Ser Pro Gln Trp Glu Ile Met Glu Ser Leu Thr Ser Tyr Gly Leu
130 135 140

Glu Cys Ser Ser Phe Gln Asp Asp Trp Glu Cys Arg Asn Gln Phe Asp
145 150 155 160

Arg Gln Gln Gly Asn Pro Asp Arg His Phe His Gln Met Ile Ile Arg
165 170 175

His Glu Glu Met Pro Thr Phe Asp Gln His Ala Ser Leu Thr Phe Tyr
180 185 190

Gln Lys Ile His Thr Arg Glu Lys Pro Phe Gly Tyr Asn Lys Cys Arg
195 200 205

Lys Asp Phe Trp Gln Lys Glu Leu Leu Ile Asn His Gln Gly Ile Tyr
210 215 220

Thr Asn Glu Lys Pro Tyr Lys Cys Lys Glu Cys Gly Lys Ala Phe Lys
225 230 235 240

Tyr Gly Ser Arg Leu Ile Gln His Glu Asn Ile His Ser Gly Lys Lys
245 250 255

Pro Tyr Glu Cys Lys Glu Cys Gly Lys Ala Phe Asn Ser Gly Ser Asn
260 265 270

Phe Ile Gln His Gln Arg Val His Thr Gly Glu Lys Pro Tyr Glu Cys
275 280 285

Lys Asp Cys Glu Lys Ala Phe Ser Arg Ser Ser Gln Leu Ile Glu His
290 295 300

Gln Arg Thr His Thr Gly Glu Lys Pro Tyr Gln Cys Lys Glu Cys Gly
305 310 315 320

Lys Ala Phe Asn Arg Ile Ser His Leu Lys Val His Tyr Arg Ile His
325 330 335

Thr Gly Glu Lys Pro Tyr Ala Cys Lys Glu Cys Gly Lys Thr Phe Ser
340 345 350

His Arg Ser Gln Leu Ile Gln His Gln Thr Val His Thr Gly Arg Lys
355 360 365

Leu Tyr Glu Cys Lys Glu Cys Gly Lys Ala Phe Asn Gln Gly Ser Thr
370 375 380

Leu Ile Arg His Gln Arg Ile His Thr Gly Glu Lys Pro Tyr Glu Cys
385 390 395 400

-continued

```
Lys Val Cys Gly Lys Ala Phe Arg Val Ser Ser Gln Leu Lys Gln His
                405                 410                 415

Gln Arg Ile His Thr Gly Glu Lys Pro Tyr Gln Cys Lys Val Cys Gly
            420                 425                 430

Arg Ala Phe Lys Arg Val Ser His Leu Thr Val His Tyr Arg Ile His
        435                 440                 445

Thr Gly Glu Lys Pro Tyr Glu Cys Lys Glu Cys Gly Lys Ala Phe Ser
    450                 455                 460

His Cys Ser Gln Leu Ile His His Gln Val Ile His Thr Glu Lys Lys
465                 470                 475                 480

Pro Tyr Glu Tyr Lys Glu Cys Glu Lys Thr Leu Ser His Asp Ser Thr
                485                 490                 495

Thr Val Gln Pro Gln Arg Met His Asn Arg Glu Thr His Val Asn Ile
            500                 505                 510

Ile Asn Val Glu Lys Pro Ser Ile Ser Ser Tyr Pro Leu Leu Ile Ile
        515                 520                 525

Arg Glu Phe Met Leu Ala Ser Asn His Met Asn Gly Ser Asn Gly Glu
    530                 535                 540

Ser Pro Leu Ala
545
```